US009272021B2

(12) United States Patent
Scheiflinger et al.

(10) Patent No.: US 9,272,021 B2
(45) Date of Patent: Mar. 1, 2016

(54) TREATMENT OF COAGULATION DISEASE BY ADMINISTRATION OF RECOMBINANT VWF

(75) Inventors: Friedrich Scheiflinger, Vienna (AT); Peter Turecek, Klosterneuburg (AT); Bruce Ewenstein, Brookline, MA (US); Wing Yen Wong, Simi Valley, CA (US); Tobias M. Suiter, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 97 days.

(21) Appl. No.: 13/493,926

(22) Filed: Jun. 11, 2012

(65) Prior Publication Data

US 2012/0316116 A1  Dec. 13, 2012

Related U.S. Application Data

(60) Provisional application No. 61/495,884, filed on Jun. 10, 2011, provisional application No. 61/511,901, filed on Jul. 26, 2011, provisional application No. 61/523,790, filed on Aug. 15, 2011.

(51) Int. Cl.
*A61K 38/36* (2006.01)
*A61P 7/02* (2006.01)
*A61K 38/37* (2006.01)

(52) U.S. Cl.
CPC ............... *A61K 38/36* (2013.01); *A61K 38/37* (2013.01)

(58) Field of Classification Search
None
See application file for complete search history.

(56) References Cited

U.S. PATENT DOCUMENTS

| | | | |
|---|---|---|---|
| 5,972,885 A * | 10/1999 | Spira et al. | 514/13.5 |
| 6,531,577 B1 | 3/2003 | Kaergaard et al. | |
| 6,864,403 B1 | 3/2005 | Cahoon et al. | |
| 7,335,634 B2 | 2/2008 | Walter et al. | |
| 8,173,597 B2 | 5/2012 | Schwarz et al. | |
| 2005/0239171 A1* | 10/2005 | Mitterer et al. | 435/69.6 |
| 2010/0099603 A1 | 4/2010 | Schnecker et al. | |
| 2010/0286047 A1 | 11/2010 | Kronthaler | |
| 2012/0035110 A1 | 2/2012 | Grillberger et al. | |

FOREIGN PATENT DOCUMENTS

| | | | |
|---|---|---|---|
| WO | WO 86/06095 A1 | | 10/1986 |
| WO | WO 2005/012354 A1 | | 2/2006 |
| WO | WO 2006/071801 | * | 7/2006 |
| WO | WO 2008/151817 | * | 12/2008 |
| WO | WO 2009/066400 A2 | | 7/2009 |
| WO | WO 2009/156137 A1 | | 12/2009 |
| WO | WO 2012/006581 A1 | | 1/2012 |

OTHER PUBLICATIONS

Michiels et al, Intravenous DDAVP and factor VIII-von Willebrand factor concentrate for the treatment and prophylaxis of bleedings in patients With von Willebrand disease type 1, 2 and 3 (Clin Appl Thromb Hemost. Jan. 2007;13(1):14-34).*
Andersson, L.-O. et al., "Isolation and characterization of human factor VIII Molecular forms in commercial factor VIII concentrate, cryoprecipitate, and plasma," Proc. Natl. Acad. Sci. USA, May 1986, vol. 83, pp. 2979-2983.
Brown, J.E. et al., "An Elisa Test for the Binding of von Willebrand Antigen to Collagen," *Thrombosis Research*, 1986, vol. 43, pp. 303-311.
Castaman, G. et al., "von Willebrand's disease in the year 2003: towards the complete identification of gene defects for correct diagnosis and treatment," *Haematological/Journal of Hematology*, Jan. 2003, vol. 88, No. 1, pp. 94-108.
Cumming, A.M. et al., "Analysis of von Willebrand factor multimers using a commercially available enhanced chemiluminescence kit," *J. Clin. Pathol.*, 1993, vol. 46, pp. 470-473.
Denis, C.V. et al., "Clearance of von Willebrand factor," *Thromb. Haemost.*, 2008, vol. 99, pp. 271-278.
Favaloro, E.J. et al., "Laboratory Assays for von Willebrand Factor: Relative Contribution to the Diagnosis of von Wilebrand's Diease," *Pathology*, 1997, vol. 29, pp. 385-391.
Favaloro, E.J., "Collagen Binding Assay for von Willebrand Factor (VWF:CBA): Detection of von Willebrands Disease (VWD), and Discrimination of VWD Subtypes, Depends on Collagen Source," *Thromb. Haemost.*, 2000, vol. 83, pp. 127-135.
Fijnvandraat, K. et al., "Inter-individual variation in half-life of infused recombinant factor VIII is related to pre-infusion von Willebrand factor antigen levels," *British Journal of Haematology*, 1995, vol. 91, pp. 474-476.
MacFarlane, D.E. et al., A Method for Assaying von Willebrand Factor (Ristocetin Cofactor), *Thrombos. Diathes. Haemorrh. (Stuttg.)*, 1975, vol. 34, pp. 306-308.
Turecek, P.L. et al., "Comparative Study on Collagen-Binding Enzyme-Linked Immunosorbent Assay and Ristocetin Cofactor Activity Assays for Detection of Functional Activity of von Willebrand Factor," *Seminars in Thrombosis and Hemostasis*, 2002, vol. 28, No. 2, pp. 149-160.
Turecek, P.L. et al., "PEG Modified rVWF Prolongs the Survival of Native rFVIII in Hemophilia a Knock-Out Mice," *Blood*, 2006, vol. 108: Abstract 1002, 1 page.
Turecek, P.L. et al., "Biochemical and Functional Characterization of Chemically Modified Recombinant von Willebrand Factor (rVWF) as a Carrier Prolonging Survival of RFVIII in Hemophilia a Knock-Out Mice," *J. Thromb. Haemost.*, Aug. 2007; vol. 5 Supplement 2: O-M-018, 3 pages.
Turecek, P.L. et al., "Structure and Function of a Recombinant von Willebrand Factor Drug Candidate," *Seminars in Thrombosis and Hemostasis*, 2010, vol. 36, No. 5, pp. 510-521.

(Continued)

*Primary Examiner* — Karlheinz R Skowronek
*Assistant Examiner* — Sergio Coffa
(74) *Attorney, Agent, or Firm* — Morgan Lewis & Bockius LLP

(57) ABSTRACT

The present invention provides methods of treating coagulation disease, including hemophilia and von Willebrand disease by administering recombinant von Willebrand Factor alone or in combination with Factor VIII.

32 Claims, 23 Drawing Sheets

(56) References Cited

OTHER PUBLICATIONS

Van Wezel, A.L., "Growth of Cell-strains and Primary Cells on Micro-carriers in Homogeneous Culture," *Nature*, Oct. 7, 1967, vol. 216, pp. 64-65.

Weiss, H.J. et al., "Quantitative Assay of Plasma Factor Deficient i von Willebrand's Disease that is Necessary for Platelet Aggregation, Relationship to Factor VIII Procoagulant Activity and Antigen Content," *The Journal of Clinical Investigation*, Nov. 1973, vol. 52, pp. 2708-2716.

Wen, L.T. et al., "Chemiluminographic Detection of von Willebrand Factor Multimeric Composition," *Journal of Clinical Laboratory Analysis*, 1993, vol. 7, pp. 317-323.

Fischer, B.E. et al., "Structural Analysis of Recombinant von Willebrand Factor Produced at Industrial Scale Fermentation of Transformed CHO Cells Co-Expressing Recombinant Furin," *FEBS Letters*, Nov. 20, 1995, vol. 375, pp. 259-262.

Fischer, B.E., "Recombinint von Willebrand factor: potential therapeutic use," *Journal of Thrombosis and Thrombolysis*, Jan. 1, 1999, vol. 6, pp. 197-205.

International Search Report mailed Sep. 7, 2012, for International Patent Application No. PCT/US2012/041957, 6 pages.

Schlokat, E. et al., "Production of Highly Homogenous and Structurally Intact Recombinant von Willebrand Factor Multimers by Furin-Mediated Propeptide Removal in Vitro," Dec. 1, 1996, vol. 24, Part 3, pp. 257-267.

Turecek, P.L. et al., "In Vivo Characterization of Recombinant von Willebrand Factor in Dogs with von Willebrand Disease," *Blood*, Nov. 1, 1997, vol. 90, No. 9, pp. 3555-3567.

Turecek, P.L. et al., "Biochemical and Functional Characterization of a Serum-Free rVWF Drug Candidate," *Blood*, Nov. 1, 2006, vol. 108, No. 11, p. 303A., Abstract.

Varadi, K. et al., "In Vivo Cleavage of Recombonant VWF Upon Intravenous Administration in Preclinical and Clinical Setting," *Blood*, Nov. 1, 2011, vol. 118, No. 21, p. 549.

\* cited by examiner

FIG. 4

| COHORT | # of patents | Gender (Female/Male) | Age (years) Median (range) | Weight (kg) Median | Ethnicity |
|---|---|---|---|---|---|
| 1 (Type 3) | 3 | 1/2 | 38 (26-44) | 130 | Caucasian |
| 2 (Type 3) | 5 | 2/3 | 26 (21-39) | 86.2 | Caucasian |
| 3 (Type 3) | 5 | 0/5 | 34 (19-55) | 79 | 4 Caucasian 1 Asian |
| 4A (Type 3) (50 IU/kg VWF:RCo) | 22 | 11/11 | 33 (18-60) | 74.8 | Caucasian |
| 4B (Severe Type 1) | 3 | 2/1 | 25 (19-47) | 82.1 | Caucasian |
| Total | 32* | 15/17 | 33 (18-60) | 81.1 | 31 Caucasian 1 Asian |

*Six subjects from cohort 1-3 were re-enrolled in cohort 4A

FIG. 8

| Cohort | rVWF/rFVIII | pdVWF/pdFVIII |
|---|---|---|
| Cohort 1 (Type 3) n=3 | Hypertension** | |
| Cohort 2 (Type 3) n=5 | Tremor, generalized pruritus | |
| Cohort 4A (Type 3) n=22 | Nausea, sP-selectin increase, dizziness, psychomotor hyperactivity, hypertension** | Low titer anti-VWF Ab, dizziness (n=2), headache |

*All reported related adverse events were mild, no related adverse events were reported for cohort 3 and 4B
**Same patient

FIG. 9

Patient 1
02-0001

| Time (hours) | VWF:RCo (IU/mL) | VWF:Ag (IU/mL) | FVIII activity (IU/mL) | VWF:CBA (IU/mL) |
|---|---|---|---|---|
| screening | <0.007 | <0.01 | 0.03 | <0.01 |
| 0 | <0.007 | <0.01 | 0.03 | <0.01 |
| 0.25 | 0.043 | 0.05 | 0.10 | 0.04 |
| 0.5 | 0.036 | 0.06 | 0.08 | 0.04 |
| 1 | 0.036 | 0.05 | 0.09 | 0.04 |
| 3 | 0.030 | 0.05 | 0.11 | 0.03 |
| 6 | 0.028 | 0.04 | 0.13 | 0.03 |
| 9 | 0.021 | 0.03 | 0.13 | 0.02 |
| 12 | 0.020 | 0.04 | 0.13 | 0.02 |
| 24 | <0.007 | 0.03 | 0.12 | <0.01 |
| 28 | <0.007 | 0.02 | 0.09 | <0.01 |
| 32 | <0.007 | 0.03 | 0.08 | <0.01 |
| 48 | <0.007 | 0.02 | 0.07 | <0.01 |
| 72 | <0.007 | 0.01 | 0.05 | <0.01 |
| 96 | <0.007 | 0.01 | 0.04 | <0.01 |

Manual Test Baxter (VWF:RCo); Data from the Central Laboratory (VWF:Ag, FVIII activity, VWF:CBA)

Patient 2
02-0002

| Time (hours) | VWF:RCo (IU/mL) | VWF:Ag (IU/mL) | FVIII activity (IU/mL) | VWF:CBA (IU/mL) |
|---|---|---|---|---|
| screening | <0.007 | <0.01 | 0.03 | <0.01 |
| 0 | <0.007 | <0.01 | 0.03 | <0.01 |
| 0.25 | 0.044 | 0.04 | 0.12 | 0.04 |
| 0.5 | 0.041 | 0.04 | 0.13 | 0.04 |
| 1 | 0.041 | 0.03 | 0.14 | 0.05 |
| 3 | 0.031 | 0.02 | 0.18 | 0.02 |
| 6 | 0.022 | 0.02 | 0.16 | 0.02 |
| 9 | 0.015 | 0.01 | 0.14 | 0.01 |
| 12 | 0.007 | 0.01 | 0.08 | <0.01 |
| 24 | <0.007 | 0.02 | 0.08 | <0.01 |
| 28 | <0.007 | 0.02 | 0.07 | <0.01 |
| 32 | <0.007 | 0.01 | 0.05 | <0.01 |
| 48 | <0.007 | 0.01 | 0.03 | <0.01 |
| 72 | <0.007 | <0.01 | | <0.01 |
| 96 | <0.007 | <0.01 | | <0.01 |

Manual Test Baxter (VWF:RCo); Data from the Central Laboratory (VWF:Ag, FVIII activity, VWF:CBA)

Patient 3
07-0001

| Time (hours) | VWF:RCo (IU/mL) | VWF:Ag (IU/mL) | FVIII activity (IU/mL) | VWF:CBA (IU/mL) |
|---|---|---|---|---|
| screening | <0.007 | <0.01 | 0.02 | <0.01 |
| 0 | <0.007 | <0.01 | 0.02 | <0.01 |
| 0.25 | 0.044 | 0.05 | 0.08 | 0.04 |
| 0.5 | 0.037 | 0.05 | 0.09 | 0.04 |
| 1 | 0.033 | 0.05 | 0.11 | 0.04 |
| 3 | 0.029 | 0.04 | 0.13 | 0.04 |
| 6 | 0.026 | 0.04 | 0.12 | 0.03 |
| 9 | 0.022 | 0.03 | 0.12 | 0.03 |
| 12 | 0.015 | 0.03 | 0.12 | 0.02 |
| 24 | 0.007 | 0.02 | 0.04 | <0.01 |
| 28 | <0.007 | 0.02 | 0.12 | <0.01 |
| 32 | <0.007 | 0.02 | 0.06 | <0.01 |
| 48 | <0.007 | <0.01 | 0.04 | <0.01 |
| 72 | <0.007 | <0.01 | 0.02 | <0.01 |
| 96 | <0.007 | <0.01 | | <0.01 |

Manual Test Baxter (VWF:RCo); Data from the Central Laboratory (VWF:Ag, FVIII activity, VWF:CBA)

FIG. 16

| Cohort | Investigational Product | Parameter | N | Median | 90% CI for Median | Mean | SD | CV (%) | GM |
|---|---|---|---|---|---|---|---|---|---|
| Cohort 2 | r(VWF/FVIII | AUC₀₋₉₆hrs [h*U/dL] | 5 | 1880.01 | 988.16; 3010.68 | 1860.05 | 942.5 | 50.67 | 1677.47 |
| | | AUC₀₋ᵢₙf [h*U/dL] | 5 | 1508.83 | 1056.99; 3072.84 | 1953.47 | 965.19 | 49.49 | 1766.01 |
| | | AUMC₀₋ᵢₙf [h²*U/dL] | 5 | 64518.47 | 33186.37; 126406.0 | 72917.08 | 41521.23 | 56.94 | 63274.8 |
| | | T₁/₂ [hours] | 5 | 22.86 | 17.81; 24.48 | 21.93 | 2.54 | 11.56 | 21.8 |
| | | MRT [hours] | 5 | 35.91 | 27.51; 42.73 | 36.22 | 6.08 | 16.78 | 35.79 |
| | | CL [mL/kg/hours] | 5 | 0.53 | 0.24; 0.71 | 0.47 | 0.21 | 44.92 | 0.43 |
| | | Vss [mL/kg] | 5 | 17.12 | 9.26; 24 | 16.63 | 6.91 | 41.52 | 15.4 |
| | | Cmax [U/dL] | 5 | 34 | 32; 98 | 51.8 | 28.99 | 55.96 | 46.39 |
| | | Tmax [hours] | 5 | 12.22 | 6.03; 48.07 | 21.15 | 17.1 | 80.87 | 16.27 |
| | | IR [(U/dL)/(U VWF:RCo/kg)] | 5 | 4.53 | 3.96; 13.11 | 6.86 | 3.93 | 57.33 | 6.11 |
| | | Tₐₗₚₕₐ [hours] | 1 | 32.57 | NA | 32.57 | NA | NA | 32.57 |
| | | Tᵦₑₜₐ [hours] | 1 | 3207.83 | NA | 3207.83 | NA | NA | 3207.83 |

FIG. 18

| Cohort | Investigational Product | Parameter | N | Median | 90% CI for Median | Mean | SD | CV (%) | GM |
|---|---|---|---|---|---|---|---|---|---|
| Cohort 3 | rVWF/rFVIII | AUC₀₋₃₆ₕᵣₛ [h*U/dL] | 4 | 2745.17 | 2093.62; 3639.65 | 2805.91 | 635.05 | 22.63 | 2752.8 |
| | | AUC₀₋ᵢₙf [h*U/dL] | 4 | 2858.66 | 2172.08; 3947.87 | 2959.32 | 740.27 | 25.01 | 2892.1 |
| | | AUMC₀₋ᵢₙf [h*²U/dL] | 4 | 100089.53 | 71254.38; 168025.02 | 109864.62 | 47247.29 | 43.01 | 102450.3 |
| | | T₁/₂ [hours] | 4 | 20.72 | 14.43; 25.93 | 20.46 | 5.19 | 25.36 | 19.94 |
| | | MRT [hours] | 4 | 37.53 | 29.97; 43.16 | 36.05 | 8.21 | 22.77 | 35.3 |
| | | Cl [mL/kg/hours] | 4 | 0.7 | 0.53; 0.95 | 0.72 | 0.18 | 25.34 | 0.7 |
| | | Vss [mL/kg] | 4 | 25.32 | 18.9; 31.12 | 25.16 | 5.82 | 23.11 | 24.65 |
| | | Cmax [U/dL] | 4 | 57 | 42; 66 | 55.5 | 11.09 | 19.98 | 54.63 |
| | | Tmax [hours] | 4 | 16.45 | 6.1; 28.48 | 16.87 | 10.9 | 64.6 | 13.95 |
| | | IR [(U/dL)/(U VWF:RCo/kg)] | 4 | 2.84 | 2.04; 3.31 | 2.75 | 0.58 | 20.9 | 2.71 |
| | | Talpha [hours] | 0 | NA | | | | | |
| | | Tbeta [hours] | 0 | NA | | | | | |

FIG. 20

| Cohort | Investigational Product | Parameter | N | Median | 90% CI for Median | Mean | SD | CV (%) | GM |
|---|---|---|---|---|---|---|---|---|---|
| Cohort 4A | rVWF/FVIII | AUC$_{0-\infty/dose}$ [h*U/dL] | 19 | 4895.34 | 4049.13; 5239.58 | 4882.21 | 1993.76 | 40.84 | 4462.04 |
| | | AUC$_{0-inf}$ [h*U/dL] | 19 | 5287.34 | 4323.1; 5913.43 | 5375.56 | 2380.4 | 44.28 | 4520.61 |
| | | AUMC$_{0-inf}$ [h²*U/dL] | 19 | 198560.36 | 157848.13; 259996.51 | 233248.57 | 157945.3 | 67.72 | 153532.14 |
| | | T$_{1/2}$ [hours] | 18 | 24.39 | 21.41; 25.78 | 24.3 | 6.47 | 26.64 | 23.48 |
| | | MRT [hours] | 19 | 39.56 | 36.69; 43.32 | 38.92 | 12.43 | 31.93 | 34.06 |
| | | CL [mL/kg/hours] | 19 | 0.95 | 0.85; 1.16 | 1.57 | 2.67 | 169.59 | 1.04 |
| | | V$_{ss}$ [mL/kg] | 19 | 37.27 | 32.42; 38.84 | 37.12 | 11.63 | 31.34 | 35.28 |
| | | C$_{max}$ [U/dL] | 19 | 90 | 83; 99 | 94.53 | 22.68 | 24 | 92.07 |
| | | T$_{max}$ [hours] | 19 | 12.3 | 8.73; 24.22 | 15.94 | 11.01 | 69.07 | 9.14 |
| | | IR [(U/dL)/(U VWF:RCo/kg)] | 19 | 1.83 | 1.74; 2.01 | 2.07 | 0.82 | 39.39 | 1.97 |
| | | T$_{apex}$ [hours] | 1 | 36.66 | NA | 36.66 | NA | NA | 36.66 |
| | | T$_{last}$ [hours] | 1 | 182.27 | NA | 182.27 | NA | NA | 182.27 |
| | pdVWF/FVIII | AUC$_{0-\infty/dose}$ [h*U/dL] | 17 | 3061.61 | 2911.05; 4270.87 | 3185.02 | 1218.32 | 38.28 | 2943.65 |
| | | AUC$_{0-inf}$ [h*U/dL] | 17 | 3209.44 | 3026.55; 4394.81 | 3361.13 | 1350.1 | 40.17 | 3092.1 |
| | | AUMC$_{0-inf}$ [h²*U/dL] | 17 | 100993.49 | 83515.77; 149051.17 | 110375.88 | 72364.04 | 61.13 | 99239.4 |
| | | T$_{1/2}$ [hours] | 17 | 18.07 | 17.52; 21.59 | 19.1 | 5.13 | 26.84 | 18.46 |
| | | MRT [hours] | 17 | 30.33 | 27.68; 38.41 | 32.7 | 7.47 | 22.83 | 31.94 |
| | | CL [mL/kg/hours] | 17 | 1.71 | 1.56; 2.37 | 1.89 | 0.75 | 39.96 | 1.75 |
| | | V$_{ss}$ [mL/kg] | 17 | 59.01 | 45.8; 67.85 | 58.24 | 17.15 | 29.44 | 55.94 |
| | | C$_{max}$ [U/dL] | 17 | 71 | 58; 80 | 70.59 | 15.87 | 22.48 | 68.92 |
| | | T$_{max}$ [hours] | 17 | 6.63 | 3.25; 12.08 | 9.83 | 9.6 | 97.74 | 5.96 |
| | | IR [(U/dL)/(U VWF:RCo/kg)] | 17 | 1.17 | 1.14; 1.5 | 1.31 | 0.33 | 24.99 | 1.27 |
| | | T$_{apex}$ [hours] | 5 | 26.03 | 0.66; 42.02 | 20.5 | 18.95 | 92.42 | 7.05 |
| | | T$_{last}$ [hours] | 5 | 81.94 | 24.3; 668.45 | 291.55 | 337.7 | 115.83 | 121.36 |

TREATMENT OF COAGULATION DISEASE BY ADMINISTRATION OF RECOMBINANT VWF

CROSS-REFERENCES TO RELATED APPLICATIONS

The present application claims the benefit of U.S. Patent Application No. 61/495,884, filed Jun. 10, 2011, U.S. Patent Application No. 61/511,901, filed Jul. 26, 2011, and U.S. Patent Application No. 61/523,790, filed Aug. 15, 2011, the disclosures of which are expressly incorporated herein by reference in their entireties for all purposes.

BACKGROUND OF THE INVENTION

Coagulation diseases, such as von Willebrand Disease (VWD) and Hemophilia, generally result from a deficiency in the coagulation cascade. "von Willebrand Disease" refers to the group of diseases caused by a deficiency of von Willebrand factor. Von Willebrand factor helps blood platelets clump together and stick to the blood vessel wall, which is necessary for normal blood clotting. Hemophilia A refers to a deficiency of Factor VIII activity, whereas Hemophilia B refers to a Factor IX deficiency. Current treatment for these coagulopathies includes a replacement therapy using pharmaceutical preparations comprising the normal coagulation factor.

Replacement therapy in VWD and Hemophilia A patients involves the repeated administration of preparations containing normal coagulation factors via intravenous infusion, which can constitute a heavy load on the life of these patients, particularly when venous access is difficult to achieve. It would be advantageous if the frequency of infusions could be reduced. One potentially viable therapy is to stabilize Factor VIII through its association with a second molecule, such as von Willebrand Factor (VWF), with the result that plasma half-life of Factor VIII is increased.

VWF is a glycoprotein circulating in plasma as a series of multimers ranging in size from about 500 to 20,000 kD. The full length of cDNA of VWF has been cloned; the propolypeptide corresponds to amino acid residues 23 to 764 of the full length prepro-VWF (Eikenboom et al (1995) Haemophilia 1, 77 90). Multimeric forms of VWF are composed of 250 kD polypeptide subunits linked together by disulfide bonds. VWF mediates the initial platelet adhesion to the sub-endothelium of the damaged vessel wall, with the larger multimers exhibiting enhanced hemostatic activity. Multimerized VWF binds to the platelet surface glycoprotein Gp1bα, through an interaction in the A1 domain of VWF, facilitating platelet adhesion. Other sites on VWF mediate binding to the blood vessel wall. Thus, VWF forms a bridge between the platelet and the vessel wall that is essential to platelet adhesion and primary hemostasis under conditions of high shear stress. Normally, endothelial cells secrete large polymeric forms of VWF and those forms of VWF that have a lower molecular weight arise from proteolytic cleavage. The multimers of exceptionally large molecular masses are stored in the Weibel-Pallade bodies of the endothelial cells and liberated upon stimulation by agonists such as thrombin and histamine.

That FVIII pharmacokinetics are a function of VWF levels is supported by several previous observations. Reduction of FVIII binding activity in von Willebrand Disease (VWD), due to either reduced VWF protein levels or lowered FVIII binding affinity, results in reduced steady-state levels of endogenous FVIII (summarized in Castaman et al., Disorders of Hemostasis 88(1):94-108 (2003), and improving survival of VWF has been proposed as a viable strategy for improving FVIII stability (Denis et al., Thromb Haemost. 2008 February; 99(2):271-8; Turecek et al., Blood, 2006, 108(11): Abstract 1002). Among severe Hemophilia A patients, a correlation between pre-infusion VWF levels and the half-life of infused FVIII has been demonstrated by Fijnvandraat and colleagues (Fijnvandraat, et al., Br J Haematol. 1995 October; 91(2):474-6). In that study, patients with 200-300% of average VWF levels were seen to have a FVIII half-life of 15-29 hours compared to a mean of 12.5 hours in patients with normal VWF levels. In another study, patients with blood group O were demonstrated to have significantly lower VWF levels and shorter FVIII half-lives (15.3 hours) compared with those with blood group A (19.7 hours) (Vlot, et al. Thromb Haemost. 2000 January; 83(1):65-9). Chemically modified VWF has been shown to prolong survival of rFVIII (Turecek et al., J. Thromb. Haemost. 2007 Jul. 9; 5(2) abstract available at: http/www.blackwellpublishing.com/isth2007/abstract.asp?id=64898). As such, co-administration of rVWF and rFVIII is a viable strategy for the treatment of coagulation diseases such as von Willebrand Disease and Hemophilia A.

BRIEF SUMMARY OF THE INVENTION

Accordingly, the present invention provides methods and combinations for treating coagulation disease by administering recombinant von Willebrand Factor (rVWF) alone or in combination with recombinant Factor VIII (rFVIII) to a subject in need thereof, with the result that the in-vivo half-life of Factor VIII is increased.

In one aspect, the present invention provides a method for treating Von Willebrand Disease or Hemophilia A in a subject in need thereof, the method comprising: administering to the subject recombinant Von Willebrand Factor (rVWF) such that Factor VIII half-life is extended as compared to a subject administered plasma derived Von Willebrand Factor, wherein the rVWF is a high molecular weight VWF multimer composition comprising at least 20% VWF decamers or higher order multimers, and wherein the rVWF has a higher specific activity than plasma derived Von Willebrand Factor.

In further embodiments and in accordance with the above, methods of the invention include co-administering to the subject recombinant Von Willebrand Factor (rVWF) and recombinant Factor VIII (rFVIII).

In further embodiments and in accordance with any of the above, the rVWF and rFVIII are administered together in a single composition.

In further embodiments and in accordance with any of the above, the subject is administered between 1.0 IU/kg VWF:RCo and 150 IU/kg VWF:RCo per dose.

In further embodiments and in accordance with any of the above, the subject is administered between 2 IU/kg VWF:RCo and 50 IU/kg VWF:RCo per dose.

In further embodiments and in accordance with any of the above, the subject is administered between 5 IU/kg VWF:RCo and 40 IU/kg VWF:RCo per dose.

In further embodiments and in accordance with any of the above, the subject is administered between 10 IU/kg VWF:RCo and 20 IU/kg VWF:RCo per dose.

In further embodiments and in accordance with any of the above, the rVWF used in methods of the invention is matured in vitro by treatment with Furin.

In further embodiments and in accordance with any of the above, the rVWF is produced through expression in a Chinese Hamster Ovary (CHO cell culture).

In further embodiments and in accordance with any of the above, the rFVIII and rVWF are produced through expression in the same cell culture.

In further embodiments, and in accordance with any of the above, the subject is administered rVWF no more than once every other day.

In further embodiments and in accordance with any of the above, the subject is administered rVWF no more than twice a week.

In further aspects and in accordance with any of the above, the high molecular weight VWF multimer composition maintains the at least 20% VWF decamers or higher order multimers for at least 3 hours post-administration.

In further embodiments and in accordance with any of the above, the Factor VIII half-life is extended by about 5 hours.

In further embodiments and in accordance with any of the above, the Factor VIII half-life is extended for at least 12 hours.

In further embodiments and in accordance with any of the above, the Factor VIII half-life is extended for at least 24 hours.

In further embodiments and in accordance with any of the above, the Factor VIII half-life is extended for at least 36 hours.

In further embodiments and in accordance with any of the above, the Factor VIII half-life is extended for at least 48 hours.

In further embodiments and in accordance with any of the above, wherein the Factor VIII half-life is extended for at least 72 hours.

In further embodiments and in accordance with any of the above, the ratio of FVIII procoagulant activity (IU FVIII:C) to rVWF Ristocetin cofactor activity (IU rVWF:RCo) administered to the subject is between 2:1 and 1:4.

In further embodiments and in accordance with any of the above, the ratio of FVIII procoagulant activity (IU FVIII:C) to rVWF Ristocetin cofactor activity (IU rVWF:RCo) administered to the subject is between 3:2 and 1:3.

In further embodiments and in accordance with any of the above, the ratio of FVIII procoagulant activity (IU FVIII:C) to rVWF Ristocetin cofactor activity (IU rVWF:RCo) administered to the subject is between 1:1 and 1:2.

In further embodiments and in accordance with any of the above, 23 the ratio of FVIII procoagulant activity (IU FVIII:C) to rVWF Ristocetin cofactor activity (IU rVWF:RCo) administered to the subject is about 3:4.

In further embodiments and in accordance with any of the above, the rVWF has a specific activity of about 20-150 mU/µg.

In further embodiments and in accordance with any of the above, the high molecular weight VWF multimer composition comprises at least 30% VWF decamers or higher order multimers.

In further embodiments and in accordance with any of the above, the high molecular weight VWF multimer composition comprises at least 40% VWF decamers or higher order multimers.

In further embodiments and in accordance with any of the above, the high molecular weight VWF multimer composition comprises at least 50% VWF decamers or higher order multimers.

In further embodiments and in accordance with any of the above, the high molecular weight VWF multimer composition comprises at least 60% VWF decamers or higher order multimers.

In further embodiments and in accordance with any of the above, the high molecular weight VWF multimer composition comprises at least 70% VWF decamers or higher order multimers.

In further aspects and in accordance with any of the above, the present invention provides a method for treating Hemophilia A or Von Willebrand Disease in a subject in need thereof, the method comprising: administering to the subject recombinant Von Willebrand Factor (rVWF) such that Factor VIII half-life is extended as compared to a subject administered plasma derived Von Willebrand Factor, wherein: (a) the rVWF has a higher specific activity than plasma derived Von Willebrand Factor, wherein the specific activity of rVWF is about 20-150 mU/µg; and (b) the FVIII half-life is at least 1.5 times higher as compared to FVIII half-life in a subject administered plasma derived Von Willebrand Factor.

In further aspects and in accordance with any of the above, the present invention provides a method for treating Hemophilia A or Von Willebrand Disease in a subject in need thereof, the method comprising: administering to the subject recombinant Von Willebrand Factor (rVWF) such that Factor VIII half-life is extended as compared to a subject administered plasma derived Von Willebrand Factor, wherein: (a) the rVWF is a high molecular weight VWF multimer composition comprising at least 20% VWF decamers or higher order multimers, (b) the rVWF has a higher specific activity than plasma derived Von Willebrand Factor, wherein the specific activity of rVWF is at least about 20-150 mU/µg; and (c) the FVIII half-life is at least 1.5 times higher as compared to FVIII half-life in a subject administered plasma derived Von Willebrand Factor.

In further embodiments and in accordance with any of the above, the level of Factor VIII procoagulant activity (FVIII:C) in the plasma of the subject 24 hours post-administration of the rVWF is at least 90% of the level of FVIII:C activity present in the plasma 1 hour post-administration.

In further embodiments and in accordance with any of the above, the level of Factor VIII procoagulant activity (FVIII:C) in the plasma of the subject 24 hours post-administration is at least 100% of the level of FVIII:C activity present in the plasma 1 hour post-administration.

In further embodiments and in accordance with any of the above, the level of Factor VIII procoagulant activity (FVIII:C) in the plasma of the subject 36 hours post-administration is at least 80% of the level of FVIII:C activity present in the plasma 1 hour post-administration.

In further embodiments and in accordance with any of the above, the level of Factor VIII procoagulant activity (FVIII:C) in the plasma of the subject 48 hours post-administration is at least 50% of the level of FVIII:C activity present in the plasma 1 hour post-administration.

In further embodiments and in accordance with any of the above, the higher order rVWF multimers are stable for at least 6 hours post-administration.

In further embodiments and in accordance with any of the above, the higher order rVWF multimers are stable for at least 12 hours post-administration.

In further embodiments and in accordance with any of the above, the higher order rVWF multimers are stable for at least 18 hours post-administration.

In further embodiments and in accordance with any of the above, the higher order rVWF multimers are stable for at least 24 hours post-administration.

In further embodiments and in accordance with any of the above, the higher order rVWF multimers are stable for at least 36 hours post-administration.

In further embodiments and in accordance with any of the above, the higher order rVWF multimers are stable for at least 48 hours post-administration.

In further embodiments and in accordance with any of the above, the higher order rVWF multimers are stable for at least 72 hours post-administration.

In further aspects and in accordance with any of the above, the present invention provides a method for treating Hemophilia A or Von Willebrand Disease in a subject in need thereof, the method comprising: administering to the subject recombinant Von Willebrand Factor (rVWF).

In further embodiments and in accordance with any of the above, the method comprises co-administering to the subject recombinant Factor VIII (rFVIII) and recombinant Von Willebrand Factor (rVWF).

In further embodiments and in accordance with any of the above, the rFVIII and rVWF are administered together in a single composition.

In further embodiments and in accordance with any of the above, the ratio of rFVIII procoagulant activity (IU rFVIII:C) to rVWF Ristocetin cofactor activity (IU rVWF:RCo) administered to the subject is between 2:1 and 1:4.

In further embodiments and in accordance with any of the above, the ratio of rFVIII procoagulant activity (IU rFVIII:C) to rVWF Ristocetin cofactor activity (IU rVWF:RCo) administered to the subject is between 3:2 and 1:3.

In further embodiments and in accordance with any of the above, the ratio of rFVIII procoagulant activity (IU rFVIII:C) to rVWF Ristocetin cofactor activity (IU rVWF:RCo) administered to the subject is between 1:1 and 1:2.

In further embodiments and in accordance with any of the above, the ratio of rFVIII procoagulant activity (IU rFVIII:C) to rVWF Ristocetin cofactor activity (IU rVWF:RCo) administered to the subject is about 3:4.

In further embodiments and in accordance with any of the above, the rVWF is matured in vitro by treatment with Furin.

In further embodiments and in accordance with any of the above, the rVWF is expressed in mammalian cell culture.

In further embodiments and in accordance with any of the above, the rFVIII is expressed in mammalian cell culture.

In further embodiments and in accordance with any of the above, the mammalian culture comprises CHO cells.

In further embodiments and in accordance with any of the above, the rFVIII and rVWF are co-expressed in the same culture.

In further embodiments and in accordance with any of the above, the rFVIII and rVWF are co-purified.

In further embodiments and in accordance with any of the above, the rFVIII and rVWF are purified separately.

In further embodiments and in accordance with any of the above, a rFVIII/rVWF complex is reconstituted prior to administration.

In further embodiments and in accordance with any of the above, rVWF is treated with Furin prior to reconstituting the rFVIII/rVWF complex.

In further embodiments and in accordance with any of the above, the reconstituted rFVIII/rVWF complex is treated with Furin.

In further embodiments and in accordance with any of the above, the Furin is recombinant Furin.

In further embodiments and in accordance with any of the above, the subject is administered rVWF no more than once daily.

In further embodiments and in accordance with any of the above, the subject is administered rVWF no more than once every other day.

In further embodiments and in accordance with any of the above, the subject is co-administered rVWF no more than once every third day.

In further embodiments and in accordance with any of the above, the subject is administered rVWF no more than once every fourth day.

In further embodiments and in accordance with any of the above, the subject is administered between 1.5 IU/kg FVIII:C and 150 IU/kg FVIII:C per dose.

In further embodiments and in accordance with any of the above, the subject is administered between 10 IU/kg FVIII:C and 100 IU/kg FVIII:C per dose.

In further embodiments and in accordance with any of the above, the subject is administered between 25 IU/kg FVIII:C and 75 IU/kg FVIII:C per dose.

In further embodiments and in accordance with any of the above, the subject is administered between 40 IU/kg FVIII:C and 60 IU/kg FVIII:C per dose.

In further embodiments and in accordance with any of the above, the level of Factor VIII procoagulant activity (FVIII:C) in the plasma of the subject 24 hours post-administration is at least 90% of the level of FVIII:C activity present in the plasma 1 hour post-administration.

In further embodiments and in accordance with any of the above, the level of Factor VIII procoagulant activity (FVIII:C) in the plasma of the subject 24 hours post-administration is at least 100% of the level of FVIII:C activity present in the plasma 1 hour post-administration.

In further embodiments and in accordance with any of the above, the level of Factor VIII procoagulant activity (FVIII:C) in the plasma of the subject 36 hours post-administration is at least 80% of the level of FVIII:C activity present in the plasma 1 hour post-administration.

In further embodiments and in accordance with any of the above, the level of Factor VIII procoagulant activity (FVIII:C) in the plasma of the subject 48 hours post-administration is at least 50% of the level of FVIII:C activity present in the plasma 1 hour post-administration.

In further embodiments and in accordance with any of the above, the rVWF administered to the subject has a HMW VWF multimer composition comprising at least 10% VWF decamers or higher order multimers.

In further embodiments and in accordance with any of the above, the rVWF administered to the subject has a HMW VWF multimer composition comprising at least 20% VWF decamers or higher order multimers.

In further embodiments and in accordance with any of the above, the rVWF administered to the subject has a HMW VWF multimer composition comprising at least 30% VWF decamers or higher order multimers.

In further embodiments and in accordance with any of the above, the rVWF administered to the subject has a HMW VWF multimer composition comprising at least 40% VWF decamers or higher order multimers.

In further embodiments and in accordance with any of the above, the rVWF administered to the subject has a HMW VWF multimer composition comprising at least 50% VWF decamers or higher order multimers.

In further embodiments and in accordance with any of the above, higher order rVWF multimers are stable in vitro for at least 3 hours post-administration.

In further embodiments and in accordance with any of the above, higher order rVWF multimers are stable in vitro for at least 6 hours post-administration.

In further embodiments and in accordance with any of the above, wherein higher order rVWF multimers are stable in vitro for at least 12 hours post-administration.

In further embodiments and in accordance with any of the above, wherein higher order rVWF multimers are stable in vitro for at least 18 hours post-administration.

In further embodiments and in accordance with any of the above, higher order rVWF multimers are stable in vitro for at least 24 hours post-administration.

In further embodiments and in accordance with any of the above, higher order rVWF multimers are stable in vitro for at least 36 hours post-administration.

In further embodiments and in accordance with any of the above, wherein higher order rVWF multimers are stable in vitro for at least 48 hours post-administration.

In further embodiments and in accordance with any of the above, higher order rVWF multimers are stable in vitro for at least 72 hours post-administration.

In further embodiments and in accordance with any of the above, endogenous FVIII activity is stabilized for at least 12 hours.

In further embodiments and in accordance with any of the above, endogenous FVIII activity is stabilized for at least 24 hours.

In further embodiments and in accordance with any of the above, endogenous FVIII activity is stabilized for at least 36 hours.

In further embodiments and in accordance with any of the above, endogenous FVIII activity is stabilized for at least 48 hours.

In further embodiments and in accordance with any of the above, endogenous FVIII activity is stabilized for at least 72 hours.

In further embodiments and in accordance with any of the above, wherein co-administered rFVIII activity is stabilized for at least 12 hours.

In further embodiments and in accordance with any of the above, co-administered rFVIII activity is stabilized for at least 24 hours.

In further embodiments and in accordance with any of the above, co-administered rFVIII activity is stabilized for at least 36 hours.

In further embodiments and in accordance with any of the above, co-administered rFVIII activity is stabilized for at least 48 hours.

In further embodiments and in accordance with any of the above, co-administered rFVIII activity is stabilized for at least 72 hours.

In further embodiments and in accordance with any of the above, co-administered rFVIII activity is stabilized by extending the half-life of the rFVIII in vivo.

In further embodiments and in accordance with any of the above, FVIII half-life is extended by about five hours as compared to a patient administered pdFVIII.

In further embodiments and in accordance with any of the above, at least 1% of the co-administered rFVIII activity is maintained for at least 36 hours in a patient administered said rFVIII.

In further embodiments and in accordance with any of the above, at least 1% of the co-administered rFVIII activity is maintained for at least 48 hours in a patient administered said rFVIII.

In further embodiments and in accordance with any of the above, at least 1% of the co-administered rFVIII activity is maintained for at least 72 hours in a patient administered said rFVIII.

In further embodiments and in accordance with any of the above, at least 1% of the co-administered rFVIII activity is maintained for at least 90 hours in a patient administered said rFVIII.

In further embodiments and in accordance with any of the above, at least 1% of the co-administered rFVIII activity is maintained for at least 120 hours in a patient administered said rFVIII.

In further embodiments and in accordance with any of the above, at least 1% of the co-administered rFVIII activity is maintained for at least 168 hours in a patient administered said rFVIII.

BRIEF DESCRIPTION OF THE DRAWINGS

FIG. 4. Table summarizing patient demographics for the study.

FIG. 8. Summary of adverse events from the study.

FIG. 9. rVWF PK parameters data from the study.

FIG. 16. Summary of pharmacokinetic parameters for Factor VIII procoagulant activity (FVIII:C) for patients in Cohort 2.

FIG. 18. Summary of pharmacokinetic parameters for Factor VIII procoagulant activity (FVIII:C) for patients in Cohort 3.

FIG. 20. Summary of pharmacokinetic parameters for Factor VIII procoagulant activity (FVIII:C) for patients in Cohort 4A.

DETAILED DESCRIPTION OF THE INVENTION

Overview

The present invention provides compositions and methods for treating coagulation disease in a subject by administering recombinant von Willebrand Factor (rVWF) alone or in combination with Factor VIII (which can be recombinant or plasma derived). In some aspects, the compositions and methods of the present invention are used for treating coagulation diseases such as von Willebrand Disease (VWD) or Hemophilia A.

Figure 7:
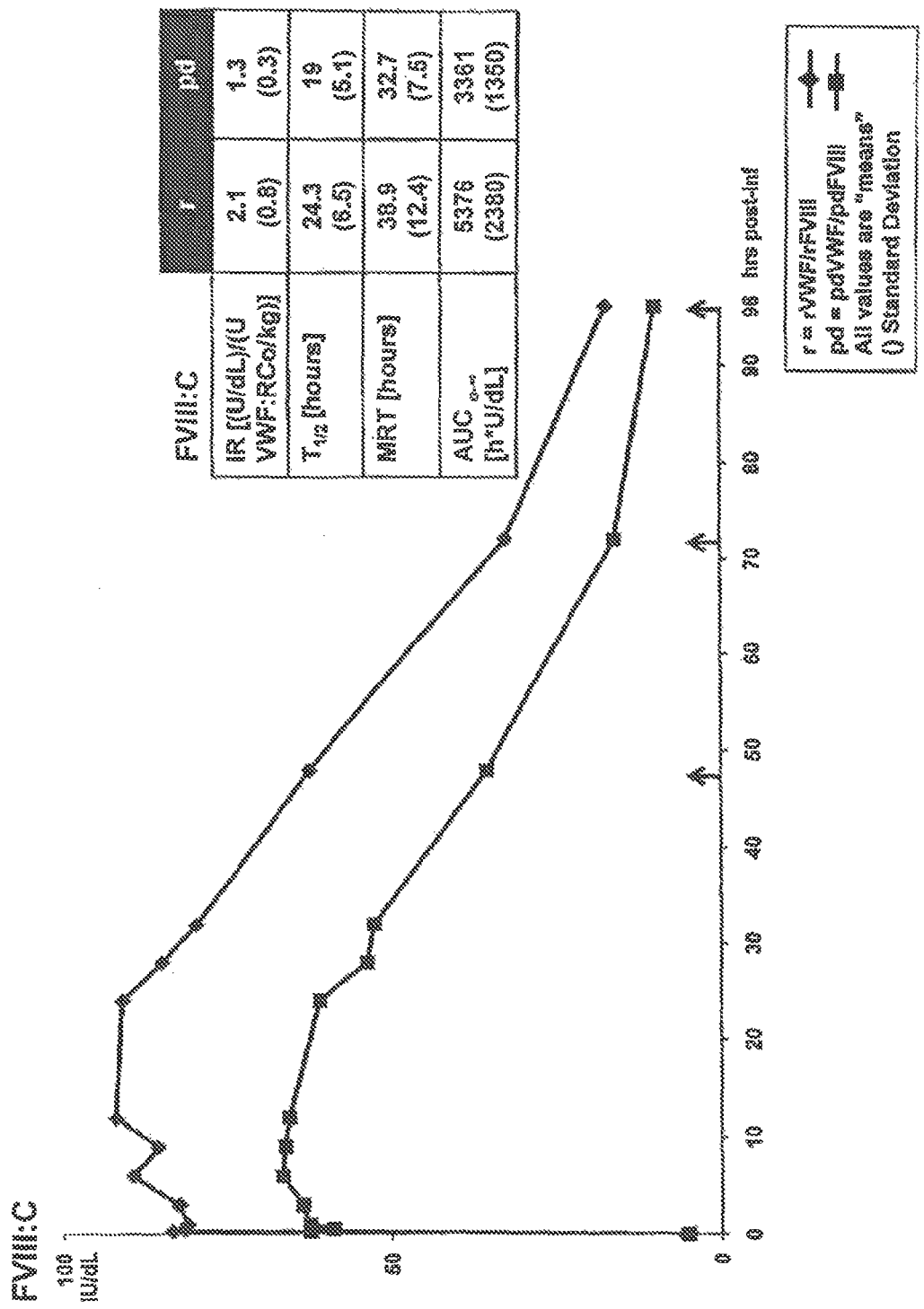
FIG. 7. Pharmacokinetic data of rVWF/rFVIII and pdVWF/pdFVIII treatment of Cohort 4A.
Figure 21:
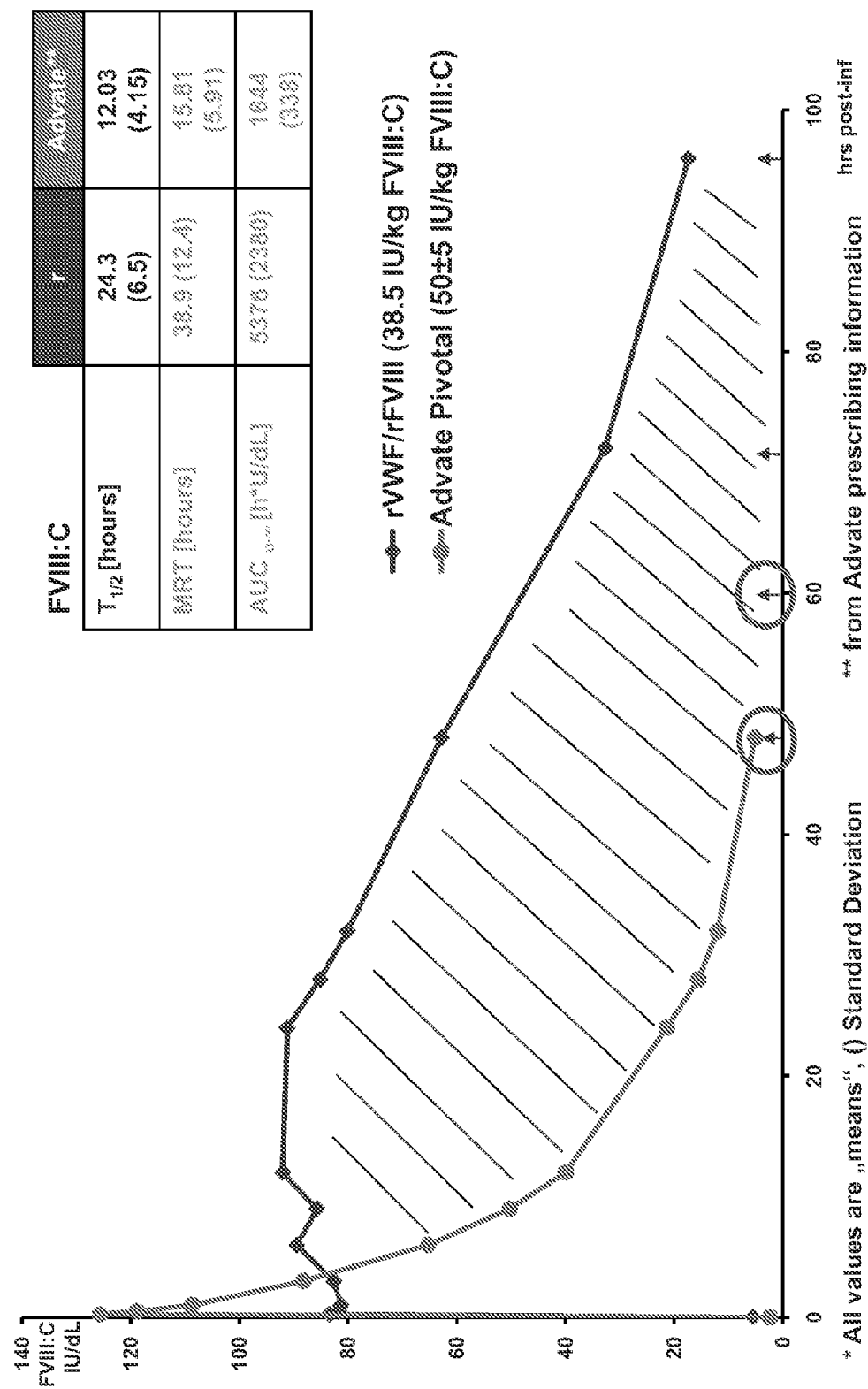
FIG. 21. Pharmacokinetic data of FVIII:C comparing co-administered rVWF and rFVIII to Advate Pivotal.

In one aspect, rVWF administered to the subject provides increased stability for in vivo Factor VIII (FVIII) activity as compared to FVIII stability due to administered plasma derived VWF, allowing for lower doses and/or frequency of treatment than in traditional treatments for coagulation diseases. Increased stability of FVIII activity and levels of FVIII can be measured using methods known in the art and described herein, including standard assays such as one-stage clotting assays, chromogenic assays, and immunoassays (see for example Lippi et al., Blood Coagulation & Fibrinolysis, 2009, 20(1): 1-3 and Chandler et al., Am J. Clin. Pathol., 2003, 120:34-39, each of which is hereby incorporated by reference in its entirety for all purposes and in particular for all teachings related to assays of FVIII level and activity). As shown in FIG. 20, average FVIII half-life was increased by rVWF by 5.2 hours over the half-life for patients receiving pdVWF. FIGS. 2 and 7 also show increases in FVIII activity in patients administered rVWF as compared to those administered pdVWF: FIG. 2 shows that average FVIII half-life was increased by 4.7 hours for patients administered rVWF as compared to patients administered pdVWF, and the data from Cohort 4A in FIG. 7 shows an increase in FVIII half-life of 5.3 hours for patients administered rVWF as compared to patients administered pdVWF. In addition, as shown in FIG. 21, the half-life of plasma FVIII is increased by 12.27 hours in VWD patients receiving rVWF in combination with rFVIII as compared to patients receiving FVIII (i.e., Advate) alone.

In a further aspect, the administration of rVWF stabilizes endogenous and/or co-administered FVIII activity, with the result that the in vivo half-life and/or activity of FVIII is increased. In embodiments in which rVWF and FVIII are co-administered, the rVWF and FVIII can be administered to the subject together in a single composition. In further embodiments, neither rVWF nor FVIII are modified with a water soluble polymer. In other embodiments, either the rVWF or FVIII or both are modified with a water soluble polymer. As will be appreciated, in embodiments in which rVWF is co-administered with FVIII, the FVIII may be recombinant or plasma derived.

In further aspects and in accordance with any of the above, the rVWF administered to the subject is a high molecular weight multimer composition comprising decamers or higher order multimers of rVWF. As discussed above, the use of rVWF compositions of the invention provide therapeutic flexibility to dose (or re-dose) with or without FVIII (recombinant or plasma derived). In further embodiments, the rVWF administered to the subject is a high molecular weight VWF multimer composition comprising at least 20% VWF decamers or higher order multimers. In specific embodiments, the rVWF administered to subjects is not modified with a water soluble polymer.

In still further aspects, the rVWF administered to the subject has a higher specific activity than pdVWF.

In a still further aspect, the rVWF alone or in combination with pdFVIII or rFVIII is administered to the subject no more than twice a week.

In a yet further aspect, the rVWF is processed with Furin prior to administration to the subject. In certain embodiments, the rVWF is processed with recombinant Furin.

In further aspects, the rVWF of use in the present invention is produced in accordance with methods known in the art and described for example in US 2012/0035110, filed Jul. 8, 2011 and U.S. Pat. No. 8,173,597, issued May 8, 2012, each of which is hereby incorporated by reference in its entirety for all purposes and in particular for all teachings related to rVWF compositions and methods for producing those compositions.

In accordance with any of the above, rVWF alone or in combination with FVIII is used to treat patients with coagulation diseases, such as VWD and Hemophilia A. Patients with VWD have some level of FVIII, but the stability of that FVIII is generally compromised because these patients lack VWF. Treatment of VWD patients may in some embodiments involve an initial treatment with both rVWF and rFVIII followed by repeated administrations of rVWF alone. In other embodiments, the initial treatment may be with rVWF alone while subsequent repeated administrations are with both rVWF and rFVIII, or the initial and subsequent repeat administrations may all include a co-administration of both rVWF and rFVIII. Similarly, Hemophilia A patients (who lack FVIII) may receive an initial treatment of both rVWF and rFVIII, and subsequent repeat treatments may comprise the administration of rFVIII alone or rVWF alone. In other embodiments, the initial treatment may be rFVIII alone while the subsequent repeat treatments involve co-administration of rVWF and rFVIII.

DEFINITIONS

As used herein. "rVWF" refers to recombinant VWF.

As used herein, "rFVIII" refers to recombinant FVIII.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, "recombinant VWF" includes VWF obtained via recombinant DNA technology. In certain embodiments, VWF proteins of the invention can comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF in the present invention can include all potential forms, including the monomeric and multimeric forms. It should also be understood that the present invention encompasses different forms of VWF to be used in combination. For example, the VWF of the present invention may include different multimers, different derivatives and both biologically active derivatives and derivatives not biologically active.

In the context of the present invention, the recombinant VWF embraces any member of the VWF family from, for example, a mammal such as a primate, human, monkey, rabbit, pig, rodent, mouse, rat, hamster, gerbil, canine, feline, and biologically active derivatives thereof. Mutant and variant VWF proteins having activity are also embraced, as are functional fragments and fusion proteins of the VWF proteins. Furthermore, the VWF of the invention may further comprise tags that facilitate purification, detection, or both. The VWF described herein may further be modified with a therapeutic moiety or a moiety suitable imaging in vitro or in vivo.

As used herein, "plasma-derived VWF (pdVWF)" includes all forms of the protein found in blood including the mature VWF obtained from a mammal having the property of in vivo-stabilizing, e.g. binding, of at least one FVIII molecule.

The term "highly multimeric VWF" or "high molecular weight VWF" refers to VWF comprising at least 10 subunits, or 12, 14, or 16 subunits, to about 20, 22, 24 or 26 subunits or more. The term "subunit" refers to a monomer of VWF. As is known in the art, it is generally dimers of VWF that polymerize to form the larger order multimers. (see Turecek et al., Semin. Thromb. Hemost. 2010, 36(5): 510-521 which is hereby incorporated by reference in its entirety for all purposes and in particular for all teachings regarding multimer analysis of VWF).

As used herein, the term "factor VIII" or "FVIII" refers to any form of factor VIII molecule with the typical characteristics of blood coagulation factor VIII, whether endogenous to a patient, derived from blood plasma, or produced through the use of recombinant DNA techniques, and including all modified forms of factor VIII. Factor VIII (FVIII) exists naturally and in therapeutic preparations as a heterogeneous distribution of polypeptides arising from a single gene product (see, e.g., Andersson et al., *Proc. Natl. Acad. Sci. USA*, 83:2979-2983 (1986)). Commercially available examples of therapeutic preparations containing Factor VIII include those sold under the trade names of HEMOFIL M, ADVATE, and RECOMBINATE (available from Baxter Healthcare Corporation, Deerfield, Ill., U.S.A.).

As used herein, "plasma FVIII activity" and "in vivo FVIII activity" are used interchangeably. The in vivo FVIII activity measured using standard assays may be endogenous FVIII activity, the activity of a therapeutically administered FVIII (recombinant or plasma derived), or both endogenous and administered FVIII activity. Similarly, "plasma FVIII" refers to endogenous FVIII or administered recombinant or plasma derived FVIII.

As used herein "von Willebrand Disease" refers to the group of diseases caused by a deficiency of von Willebrand factor. Von Willebrand factor helps blood platelets clump together and stick to the blood vessel wall, which is necessary for normal blood clotting. As described in further detail herein, there are several types of Von Willebrand disease.

As used herein, the terms "hemophilia" or "haemophilia" refer to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Common treatments for hemophilia include both prophylactic and on-demand administration of clotting factors, such as FVIII, FIX, including Bebulin®-VH, and FXI, as well as FEIBA-VH, desmopressin, and plasma infusions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. VWF is the predominant species present in a preparation is substantially purified. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

As used herein, "administering" (and all grammatical equivalents) includes intravenous administration, intramuscular administration, subcutaneous administration, oral administration, administration as a suppository, topical contact, intraperitoneal, intralesional, or intranasal administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, the terms "patient" and "subject" are used interchangeably and refer to a mammal (preferably human) that has a disease or has the potential of contracting a disease.

As used herein, the term "about" denotes an approximate range of plus or minus 10% from a specified value. For instance, the language "about 20%" encompasses a range of 18-22%.

As used herein, the term "half-life" refers to the period of time it takes for the amount of a substance undergoing decay (or clearance from a sample or from a patient) to decrease by half.

Compositions of the Invention

The present invention utilizes compositions comprising recombinant von Willebrand Factor (rVWF) for treatment of coagulation disease, such as VWD and Hemophilia A. In some embodiments, the present invention utilizes rVWF in combination with Factor VIII (FVIII). The co-administered FVIII may be recombinant (rFVIII) or plasma derived (pd-FVIII). In preferred aspects, the compositions of the present invention stabilize in vivo Factor VIII activity (also referred to herein as plasma Factor VIII activity) such that the in vivo half-life of Factor VIII is extended as compared to that in subjects that have not been administered rVWF or that have been administered pdVWF. Measuring the extent to which rVWF stabilizes FVIII activity (including extension of FVIII half-life) can be carried out using methods known in the art. The level of FVIII activity can be measured by, for instance, one-stage clotting assays, chromogenic assays, and immunoassays (see for example Lippi et al., Blood Coagulation & Fibrinolysis, 2009, 20(1): 1-3, European Pharmacopoeia (Ph. Eur., 3.sup.rd Ed. 1997: 2.7.4), and Chandler et al., Am J. Clin. Pathol., 2003, 120:34-39, each of which is hereby incorporated by reference in its entirety for all purposes and in particular for all teachings related to assays of FVIII level and activity).

In certain embodiments, VWF proteins of the invention may comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF useful for the present invention includes all potential forms, including the monomeric and multimeric forms. One particularly useful form of VWF are homo-multimers of at least two VWFs. The VWF proteins may be either a biologically active derivative, or when to be used solely as a stabilizer for FVIII the VWF may be of a form not biologically active. It should also be understood that the present invention encompasses different forms of VWF to be used in combination. For example, a composition useful for the present invention may include different multimers, different derivatives and both biologically active derivatives and derivatives not biologically active.

In primary hemostasis VWF serves as a bridge between platelets and specific components of the extracellular matrix, such as collagen. The biological activity of VWF in this process can be measured by different in vitro assays (Turecek et al., Semin. Thromb. Hemost. 28: 149-160, 2002). The ristocetin cofactor assay is based on the agglutination of fresh or formalin-fixed platelets induced by the antibiotic ristocetin in the presence of VWF. The degree of platelet agglutination depends on the VWF concentration and can be measured by the turbidimetric method, e.g. by use of an aggregometer (Weiss et al., J. Clin. Invest. 52: 2708-2716, 1973; Macfarlane et al., Thromb. Diath. Haemorrh. 34: 306-308, 1975). The second method is the collagen binding assay, which is based on ELISA technology (Brown et Bosak, Thromb. Res. 43: 303-311, 1986; Favaloro, Thromb. Haemost. 83: 127-135, 2000). A microtiter plate is coated with type I or III collagen. Then the VWF is bound to the collagen surface and subsequently detected with an enzyme-labeled polyclonal antibody. The last step is the substrate reaction, which can be photometrically monitored with an ELISA reader. As provided herein, the specific Ristocetin Cofactor activity of the VWF (VWF:RCo) of the present invention is generally described in terms of mU/μg of VWF, as measured using in vitro assays.

An advantage of the rVWF compositions of the present invention over pdVWF is that rVWF exhibits a higher specific activity than pdVWF. In some embodiments, the rVWF of the invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 115, 120, 125, 130, 135, 140, 145, 150 or more mU/μg. In one embodiment, rVWF used in the methods described herein has a specific activity of from 20 mU/μg to 150 mU/μg. In another embodiment, the VWF has a specific activity of from 30 mU/μg to 120 mU/μg. In another embodiment, the rVWF has a specific activity from 40 mU/μg to 90 mU/μg. In yet another embodiment, the rVWF has a specific activity selected from variations 1 to 133 found in Table 1.

TABLE 1

Exemplary embodiments for the specific activity of rVWF found in the compositions and used in the methods provided herein.

| (mU/μg) | |
|---|---|
| 20 | Var. 1 |
| 22.5 | Var. 2 |
| 25 | Var. 3 |
| 27.5 | Var. 4 |
| 30 | Var. 5 |
| 32.5 | Var. 6 |
| 35 | Var. 7 |
| 37.5 | Var. 8 |
| 40 | Var. 9 |
| 42.5 | Var. 10 |
| 45 | Var. 11 |
| 47.5 | Var. 12 |
| 50 | Var. 13 |
| 52.5 | Var. 14 |
| 55 | Var. 15 |
| 57.5 | Var. 16 |
| 60 | Var. 17 |
| 62.5 | Var. 18 |
| 65 | Var. 19 |
| 67.5 | Var. 20 |
| 70 | Var. 21 |
| 72.5 | Var. 22 |
| 75 | Var. 23 |
| 77.5 | Var. 24 |
| 80 | Var. 25 |
| 82.5 | Var. 26 |
| 85 | Var. 27 |
| 87.5 | Var. 28 |
| 90 | Var. 29 |
| 92.5 | Var. 30 |
| 95 | Var. 31 |
| 97.5 | Var. 32 |
| 100 | Var. 33 |
| 105 | Var. 34 |
| 110 | Var. 35 |
| 115 | Var. 36 |
| 120 | Var. 37 |
| 125 | Var. 38 |
| 130 | Var. 39 |
| 135 | Var. 40 |
| 140 | Var. 41 |
| 145 | Var. 42 |
| 150 | Var. 43 |
| 20-150 | Var. 44 |
| 20-140 | Var. 45 |
| 20-130 | Var. 46 |
| 20-120 | Var. 47 |
| 20-110 | Var. 48 |
| 20-100 | Var. 49 |
| 20-90 | Var. 50 |
| 20-80 | Var. 51 |
| 20-70 | Var. 52 |
| 20-60 | Var. 53 |
| 20-50 | Var. 54 |
| 20-40 | Var. 55 |
| 30-150 | Var. 56 |
| 30-140 | Var. 57 |
| 30-130 | Var. 58 |
| 30-120 | Var. 59 |
| 30-110 | Var. 60 |
| 30-100 | Var. 61 |
| 30-90 | Var. 62 |
| 30-80 | Var. 63 |
| 30-70 | Var. 64 |
| 30-60 | Var. 65 |
| 30-50 | Var. 66 |
| 30-40 | Var. 67 |
| 40-150 | Var. 68 |
| 40-140 | Var. 69 |
| 40-130 | Var. 70 |
| 40-120 | Var. 71 |
| 40-110 | Var. 72 |
| 40-100 | Var. 73 |
| 40-90 | Var. 74 |
| 40-80 | Var. 75 |
| 40-70 | Var. 76 |
| 40-60 | Var. 77 |
| 40-50 | Var. 78 |
| 50-150 | Var. 79 |
| 50-140 | Var. 80 |
| 50-130 | Var. 81 |

TABLE 1-continued

Exemplary embodiments for the specific activity of rVWF found in the compositions and used in the methods provided herein.

| (mU/µg) | |
|---|---|
| 50-120 | Var. 82 |
| 50-110 | Var. 83 |
| 50-100 | Var. 84 |
| 50-90 | Var. 85 |
| 50-80 | Var. 86 |
| 50-70 | Var. 87 |
| 50-60 | Var. 88 |
| 60-150 | Var. 89 |
| 60-140 | Var. 90 |
| 60-130 | Var. 91 |
| 60-120 | Var. 92 |
| 60-110 | Var. 93 |
| 60-100 | Var. 94 |
| 60-90 | Var. 95 |
| 60-80 | Var. 96 |
| 60-70 | Var. 97 |
| 70-150 | Var. 98 |
| 70-140 | Var. 99 |
| 70-130 | Var. 100 |
| 70-120 | Var. 101 |
| 70-110 | Var. 102 |
| 70-100 | Var. 103 |
| 70-90 | Var. 104 |
| 70-80 | Var. 105 |
| 80-150 | Var. 106 |
| 80-140 | Var. 107 |
| 80-130 | Var. 108 |
| 80-120 | Var. 109 |
| 80-110 | Var. 110 |
| 80-100 | Var. 111 |
| 80-90 | Var. 112 |
| 90-150 | Var. 113 |
| 90-140 | Var. 114 |
| 90-130 | Var. 115 |
| 90-120 | Var. 116 |
| 90-110 | Var. 117 |
| 90-100 | Var. 118 |
| 100-150 | Var. 119 |
| 100-140 | Var. 120 |
| 100-130 | Var. 121 |
| 100-120 | Var. 122 |
| 100-110 | Var. 123 |
| 110-150 | Var. 124 |
| 110-140 | Var. 125 |
| 110-130 | Var. 126 |
| 110-120 | Var. 127 |
| 120-150 | Var. 128 |
| 120-140 | Var. 129 |
| 120-130 | Var. 130 |
| 130-150 | Var. 131 |
| 130-140 | Var. 132 |
| 140-150 | Var. 133 |

Var. = Variation

The rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In further embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. As shown in the multimer analysis in FIG. 2 (bottom panel), application of ADAMTS13 will cleave the ultra-large rVWF multimers over time, but during production (generally through expression in cell culture), rVWF compositions of the present invention are generally not exposed to ADAMTS13 and retain their highly multimeric structure.

In one embodiment, a rVWF composition used in the methods described herein has a distribution of rVWF oligomers characterized in that 95% of the oligomers have between 6 subunits and 20 subunits. In other embodiments, the a rVWF composition has a distribution of rVWF oligomers characterized in that 95% of the oligomers have a range of subunits selected from variations 458 to 641 found in Table 2.

TABLE 2

Exemplary embodiments for the distribution of rVWF oligomers found in the compositions and used in the methods provided herein.

| Subunits | |
|---|---|
| 2-40 | Var. 458 |
| 2-38 | Var. 459 |
| 2-36 | Var. 460 |
| 2-34 | Var. 461 |
| 2-32 | Var. 462 |
| 2-30 | Var. 463 |
| 2-28 | Var. 464 |
| 2-26 | Var. 465 |
| 2-24 | Var. 466 |
| 2-22 | Var. 467 |
| 2-20 | Var. 468 |
| 2-18 | Var. 469 |
| 2-16 | Var. 470 |
| 2-14 | Var. 471 |
| 2-12 | Var. 472 |
| 2-10 | Var. 473 |
| 2-8 | Var. 474 |
| 4-40 | Var. 475 |
| 4-38 | Var. 476 |
| 4-36 | Var. 477 |
| 4-34 | Var. 478 |
| 4-32 | Var. 479 |
| 4-30 | Var. 480 |
| 4-28 | Var. 481 |
| 4-26 | Var. 482 |
| 4-24 | Var. 483 |
| 4-22 | Var. 484 |
| 4-20 | Var. 485 |
| 4-18 | Var. 486 |
| 4-16 | Var. 487 |
| 4-14 | Var. 488 |
| 4-12 | Var. 489 |
| 4-10 | Var. 490 |
| 4-8 | Var. 491 |
| 6-40 | Var. 492 |
| 6-38 | Var. 493 |
| 6-36 | Var. 494 |
| 6-34 | Var. 495 |
| 6-32 | Var. 496 |
| 6-30 | Var. 497 |
| 6-28 | Var. 498 |
| 6-26 | Var. 499 |
| 6-24 | Var. 500 |
| 6-22 | Var. 501 |
| 6-20 | Var. 502 |
| 6-18 | Var. 503 |
| 6-16 | Var. 504 |
| 6-14 | Var. 505 |
| 6-12 | Var. 506 |
| 6-10 | Var. 507 |
| 6-8 | Var. 508 |
| 8-40 | Var. 509 |
| 8-38 | Var. 510 |
| 8-36 | Var. 511 |
| 8-34 | Var. 512 |
| 8-32 | Var. 513 |
| 8-30 | Var. 514 |
| 8-28 | Var. 515 |
| 8-26 | Var. 516 |
| 8-24 | Var. 517 |
| 8-22 | Var. 518 |
| 8-20 | Var. 519 |
| 8-18 | Var. 520 |
| 8-16 | Var. 521 |
| 8-14 | Var. 522 |
| 8-12 | Var. 523 |
| 8-10 | Var. 524 |

TABLE 2-continued

Exemplary embodiments for the distribution of rVWF oligomers found in the compositions and used in the methods provided herein.

| Subunits | |
|---|---|
| 10-40 | Var. 525 |
| 10-38 | Var. 526 |
| 10-36 | Var. 527 |
| 10-34 | Var. 528 |
| 10-32 | Var. 529 |
| 10-30 | Var. 530 |
| 10-28 | Var. 531 |
| 10-26 | Var. 532 |
| 10-24 | Var. 533 |
| 10-22 | Var. 534 |
| 10-20 | Var. 535 |
| 10-18 | Var. 536 |
| 10-16 | Var. 537 |
| 10-14 | Var. 538 |
| 10-12 | Var. 539 |
| 12-40 | Var. 540 |
| 12-38 | Var. 541 |
| 12-36 | Var. 542 |
| 12-34 | Var. 543 |
| 12-32 | Var. 544 |
| 12-30 | Var. 545 |
| 12-28 | Var. 546 |
| 12-26 | Var. 547 |
| 12-24 | Var. 548 |
| 12-22 | Var. 549 |
| 12-20 | Var. 550 |
| 12-18 | Var. 551 |
| 12-16 | Var. 552 |
| 12-14 | Var. 553 |
| 14-40 | Var. 554 |
| 14-38 | Var. 555 |
| 14-36 | Var. 556 |
| 14-34 | Var. 557 |
| 14-32 | Var. 558 |
| 14-30 | Var. 559 |
| 14-28 | Var. 560 |
| 14-26 | Var. 561 |
| 14-24 | Var. 562 |
| 14-22 | Var. 563 |
| 14-20 | Var. 564 |
| 14-18 | Var. 565 |
| 14-16 | Var. 566 |
| 16-40 | Var. 567 |
| 16-38 | Var. 568 |
| 16-36 | Var. 569 |
| 16-34 | Var. 570 |
| 16-32 | Var. 571 |
| 16-30 | Var. 572 |
| 16-28 | Var. 573 |
| 16-26 | Var. 574 |
| 16-24 | Var. 575 |
| 16-22 | Var. 576 |
| 16-20 | Var. 577 |
| 16-18 | Var. 578 |
| 18-40 | Var. 579 |
| 18-38 | Var. 580 |
| 18-36 | Var. 581 |
| 18-34 | Var. 582 |
| 18-32 | Var. 583 |
| 18-30 | Var. 584 |
| 18-28 | Var. 585 |
| 18-26 | Var. 586 |
| 18-24 | Var. 587 |
| 18-22 | Var. 588 |
| 18-20 | Var. 589 |
| 20-40 | Var. 590 |
| 20-38 | Var. 591 |
| 20-36 | Var. 592 |
| 20-34 | Var. 593 |
| 20-32 | Var. 594 |
| 20-30 | Var. 595 |
| 20-28 | Var. 596 |
| 20-26 | Var. 597 |
| 20-24 | Var. 598 |
| 20-22 | Var. 599 |
| 22-40 | Var. 600 |
| 22-38 | Var. 601 |
| 22-36 | Var. 602 |
| 22-34 | Var. 603 |
| 22-32 | Var. 604 |
| 22-30 | Var. 605 |
| 22-28 | Var. 606 |
| 22-26 | Var. 607 |
| 22-24 | Var. 608 |
| 24-40 | Var. 609 |
| 24-38 | Var. 610 |
| 24-36 | Var. 611 |
| 24-34 | Var. 612 |
| 24-32 | Var. 613 |
| 24-30 | Var. 614 |
| 24-28 | Var. 615 |
| 24-26 | Var. 616 |
| 26-40 | Var. 617 |
| 26-38 | Var. 618 |
| 26-36 | Var. 619 |
| 26-34 | Var. 620 |
| 26-32 | Var. 621 |
| 26-30 | Var. 622 |
| 26-28 | Var. 623 |
| 28-40 | Var. 624 |
| 28-38 | Var. 625 |
| 28-36 | Var. 626 |
| 28-34 | Var. 627 |
| 28-32 | Var. 628 |
| 28-30 | Var. 629 |
| 30-40 | Var. 630 |
| 30-38 | Var. 631 |
| 30-36 | Var. 632 |
| 30-34 | Var. 633 |
| 30-32 | Var. 634 |
| 32-40 | Var. 635 |
| 32-38 | Var. 636 |
| 32-36 | Var. 637 |
| 32-34 | Var. 638 |
| 34-40 | Var. 639 |
| 36-38 | Var. 640 |
| 38-40 | Var. 641 |

Var. = Variation

In one embodiment, a rVWF composition can be characterized according to the percentage of rVWF molecules that are present in a particular higher order rVWF multimer or larger multimer. For example, in one embodiment, at least 20% of rVWF molecules in a rVWF composition used in the methods described herein are present in an oligomeric complex of at least 10 subunits. In another embodiment, at least 20% of rVWF molecules in a rVWF composition used in the methods described herein are present in an oligomeric complex of at least 12 subunits. In yet other embodiments, a rVWF composition used in the methods provided herein has a minimal percentage (e.g., has at least X %) of rVWF molecules present in a particular higher-order rVWF multimer or larger multimer (e.g., a multimer of at least Y subunits) according to any one of variations 134 to 457 found in Table 3 to Table 5.

TABLE 3

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 6 | 8 | 10 | 12 | 14 | 16 |
| Minimal Percentage of rVWF Molecules | 10% | Var. 134 | Var. 152 | Var. 170 | Var. 188 | Var. 206 | Var. 224 |
| | 15% | Var. 135 | Var. 153 | Var. 171 | Var. 189 | Var. 207 | Var. 225 |
| | 20% | Var. 136 | Var. 154 | Var. 172 | Var. 190 | Var. 208 | Var. 226 |
| | 25% | Var. 137 | Var. 155 | Var. 173 | Var. 191 | Var. 209 | Var. 227 |
| | 30% | Var. 138 | Var. 156 | Var. 174 | Var. 192 | Var. 210 | Var. 228 |
| | 35% | Var. 139 | Var. 157 | Var. 175 | Var. 193 | Var. 211 | Var. 229 |
| | 40% | Var. 140 | Var. 158 | Var. 176 | Var. 194 | Var. 212 | Var. 230 |
| | 45% | Var. 141 | Var. 159 | Var. 177 | Var. 195 | Var. 213 | Var. 231 |
| | 50% | Var. 142 | Var. 160 | Var. 178 | Var. 196 | Var. 214 | Var. 232 |
| | 55% | Var. 143 | Var. 161 | Var. 179 | Var. 197 | Var. 215 | Var. 233 |
| | 60% | Var. 144 | Var. 162 | Var. 180 | Var. 198 | Var. 216 | Var. 234 |
| | 65% | Var. 145 | Var. 163 | Var. 181 | Var. 199 | Var. 217 | Var. 235 |
| | 70% | Var. 146 | Var. 164 | Var. 182 | Var. 200 | Var. 218 | Var. 236 |
| | 75% | Var. 147 | Var. 165 | Var. 183 | Var. 201 | Var. 219 | Var. 237 |
| | 80% | Var. 148 | Var. 166 | Var. 184 | Var. 202 | Var. 220 | Var. 238 |
| | 85% | Var. 149 | Var. 167 | Var. 185 | Var. 203 | Var. 221 | Var. 239 |
| | 90% | Var. 150 | Var. 168 | Var. 186 | Var. 204 | Var. 222 | Var. 240 |
| | 95% | Var. 151 | Var. 169 | Var. 187 | Var. 205 | Var. 223 | Var. 241 |

Var. = Variation

TABLE 4

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 18 | 20 | 22 | 24 | 26 | 28 |
| Minimal Percentage of rVWF Molecules | 10% | Var. 242 | Var. 260 | Var. 278 | Var. 296 | Var. 314 | Var. 332 |
| | 15% | Var. 243 | Var. 261 | Var. 279 | Var. 297 | Var. 315 | Var. 333 |
| | 20% | Var. 244 | Var. 262 | Var. 280 | Var. 298 | Var. 316 | Var. 333 |
| | 25% | Var. 245 | Var. 263 | Var. 281 | Var. 299 | Var. 317 | Var. 335 |
| | 30% | Var. 246 | Var. 264 | Var. 282 | Var. 300 | Var. 318 | Var. 336 |
| | 35% | Var. 247 | Var. 265 | Var. 283 | Var. 301 | Var. 319 | Var. 337 |
| | 40% | Var. 248 | Var. 266 | Var. 284 | Var. 302 | Var. 320 | Var. 338 |
| | 45% | Var. 249 | Var. 267 | Var. 285 | Var. 303 | Var. 321 | Var. 339 |
| | 50% | Var. 250 | Var. 268 | Var. 286 | Var. 304 | Var. 322 | Var. 340 |
| | 55% | Var. 251 | Var. 269 | Var. 287 | Var. 305 | Var. 323 | Var. 341 |
| | 60% | Var. 252 | Var. 270 | Var. 288 | Var. 306 | Var. 324 | Var. 342 |
| | 65% | Var. 253 | Var. 271 | Var. 289 | Var. 307 | Var. 325 | Var. 343 |
| | 70% | Var. 254 | Var. 272 | Var. 290 | Var. 308 | Var. 326 | Var. 344 |
| | 75% | Var. 255 | Var. 273 | Var. 291 | Var. 309 | Var. 327 | Var. 345 |
| | 80% | Var. 256 | Var. 274 | Var. 292 | Var. 310 | Var. 328 | Var. 346 |
| | 85% | Var. 257 | Var. 275 | Var. 293 | Var. 311 | Var. 329 | Var. 347 |
| | 90% | Var. 258 | Var. 276 | Var. 294 | Var. 312 | Var. 330 | Var. 348 |
| | 95% | Var. 259 | Var. 277 | Var. 295 | Var. 313 | Var. 331 | Var. 349 |

Var. = Variation

TABLE 5

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 30 | 32 | 34 | 36 | 38 | 40 |
| Minimal Percentage of rVWF Molecules | 10% | Var. 350 | Var. 368 | Var. 386 | Var. 404 | Var. 422 | Var. 440 |
| | 15% | Var. 351 | Var. 369 | Var. 387 | Var. 405 | Var. 423 | Var. 441 |
| | 20% | Var. 352 | Var. 370 | Var. 388 | Var. 406 | Var. 424 | Var. 442 |
| | 25% | Var. 353 | Var. 371 | Var. 389 | Var. 407 | Var. 425 | Var. 443 |
| | 30% | Var. 354 | Var. 372 | Var. 390 | Var. 408 | Var. 426 | Var. 444 |
| | 35% | Var. 355 | Var. 373 | Var. 391 | Var. 409 | Var. 427 | Var. 445 |
| | 40% | Var. 356 | Var. 374 | Var. 392 | Var. 410 | Var. 428 | Var. 446 |

TABLE 5-continued

Exemplary embodiments for the percentage of rVWF molecules that are present in a particular higher order rVWF multimer or larger multimer found in the compositions and used in the methods provided herein.

| | Minimal Number of Subunits in rVWF Multimer | | | | | |
|---|---|---|---|---|---|---|
| | 30 | 32 | 34 | 36 | 38 | 40 |
| 45% | Var. 357 | Var. 375 | Var. 393 | Var. 411 | Var. 429 | Var. 447 |
| 50% | Var. 358 | Var. 376 | Var. 394 | Var. 412 | Var. 430 | Var. 448 |
| 55% | Var. 359 | Var. 377 | Var. 395 | Var. 413 | Var. 431 | Var. 449 |
| 60% | Var. 360 | Var. 378 | Var. 396 | Var. 414 | Var. 432 | Var. 450 |
| 65% | Var. 361 | Var. 379 | Var. 397 | Var. 415 | Var. 433 | Var. 451 |
| 70% | Var. 362 | Var. 380 | Var. 398 | Var. 416 | Var. 434 | Var. 452 |
| 75% | Var. 363 | Var. 381 | Var. 399 | Var. 417 | Var. 435 | Var. 453 |
| 80% | Var. 364 | Var. 382 | Var. 400 | Var. 418 | Var. 436 | Var. 454 |
| 85% | Var. 365 | Var. 383 | Var. 401 | Var. 419 | Var. 437 | Var. 455 |
| 90% | Var. 366 | Var. 384 | Var. 402 | Var. 420 | Var. 438 | Var. 456 |
| 95% | Var. 367 | Var. 385 | Var. 403 | Var. 421 | Var. 439 | Var. 457 |

Var. = Variation

In accordance with the above, the rVWF composition administered to the subject (with or without FVIII) generally comprises a significant percentage of high molecular weight (HMW) rVWF multimers. In further embodiments, the HMW rVWF multimer composition comprises at least 10%-80% rVWF decamers or higher order multimers. In further embodiments, the composition comprises about 10-95%, 20-90%, 30-85%, 40-80%, 50-75%, 60-70% decamers or higher order multimers. In further embodiments, the HMW rVWF multimer composition comprises at least about 10%, 20%, 30%, 40%, 50%, 60%, 70%, 80%, 90% decamers or higher order multimers.

Assessment of the number and percentage of rVWF multimers can be conducted using methods known in the art, including without limitation methods using electrophoresis and size exclusion chromatography methods to separate VWF multimers by size, for example as discussed by Cumming et al, (J Clin Pathol. 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabelled antibody against VWF followed by chemiluminescent detection (see for example Wen et al., (1993), J. Clin. Lab. Anal., 7: 317-323, which is hereby incorporated by reference in its entirety for all purposes and in particular for all teachings related to assessment of VWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In further embodiments, higher order rVWF multimers of the invention are stable for about 1 to about 90 hours post-administration. In still further embodiments, the higher order rVWF multimers are stable for about 5-80, 10-70, 15-60, 20-50, 25-40, 30-35 hours post-administration. In yet further embodiments, the higher order rVWF multimers are stable for at least 3, 6, 12, 18, 24, 36, 48, 72 hours post-administration. In certain embodiments the stability of the rVWF multimers is assessed in vitro.

In one embodiment, higher order rVWF multimers used in the compositions and methods provided herein have a half life of at least 12 hour post administration. In another embodiment, the higher order rVWF multimers have a half life of at least 24 hour post administration. In yet other embodiments, the higher order rVWF multimers have a half life selected from variations 642 to 1045 found in Table 6.

TABLE 6

Exemplary embodiments for the half-life of higher order rVWF multimers found in the compositions and used in the methods provided herein.

| Hours | |
|---|---|
| at least 1 | Var. 642 |
| at least 2 | Var. 643 |
| at least 3 | Var. 644 |
| at least 4 | Var. 645 |
| at least 5 | Var. 646 |
| at least 6 | Var. 647 |
| at least 7 | Var. 648 |
| at least 8 | Var. 649 |
| at least 9 | Var. 650 |
| at least 10 | Var. 651 |
| at least 11 | Var. 652 |
| at least 12 | Var. 653 |
| at least 14 | Var. 654 |
| at least 16 | Var. 655 |
| at least 18 | Var. 656 |
| at least 20 | Var. 657 |
| at least 22 | Var. 658 |
| at least 24 | Var. 659 |
| at least 27 | Var. 660 |
| at least 30 | Var. 661 |
| at least 33 | Var. 662 |
| at least 36 | Var. 663 |
| at least 39 | Var. 664 |
| at least 42 | Var. 665 |
| at least 45 | Var. 666 |
| at least 48 | Var. 667 |
| at least 54 | Var. 668 |
| at least 60 | Var. 669 |
| at least 66 | Var. 670 |
| at least 72 | Var. 671 |
| at least 78 | Var. 672 |
| at least 84 | Var. 673 |
| at least 90 | Var. 674 |
| 2-90 | Var. 675 |
| 2-84 | Var. 676 |
| 2-78 | Var. 677 |
| 2-72 | Var. 678 |
| 2-66 | Var. 679 |
| 2-60 | Var. 680 |
| 2-54 | Var. 681 |

TABLE 6-continued

Exemplary embodiments for the half-life of higher order rVWF multimers found in the compositions and used in the methods provided herein.

| Hours | |
|---|---|
| 2-48 | Var. 682 |
| 2-45 | Var. 683 |
| 2-42 | Var. 684 |
| 2-39 | Var. 685 |
| 2-36 | Var. 686 |
| 2-33 | Var. 687 |
| 2-30 | Var. 688 |
| 2-27 | Var. 689 |
| 2-24 | Var. 690 |
| 2-22 | Var. 691 |
| 2-20 | Var. 692 |
| 2-18 | Var. 693 |
| 2-16 | Var. 694 |
| 2-14 | Var. 695 |
| 2-12 | Var. 696 |
| 2-10 | Var. 697 |
| 2-8 | Var. 698 |
| 2-6 | Var. 699 |
| 2-4 | Var. 700 |
| 3-90 | Var. 701 |
| 3-84 | Var. 702 |
| 3-78 | Var. 703 |
| 3-72 | Var. 704 |
| 3-66 | Var. 705 |
| 3-60 | Var. 706 |
| 3-54 | Var. 707 |
| 3-48 | Var. 708 |
| 3-45 | Var. 709 |
| 3-42 | Var. 710 |
| 3-39 | Var. 711 |
| 3-36 | Var. 712 |
| 3-33 | Var. 713 |
| 3-30 | Var. 714 |
| 3-27 | Var. 715 |
| 3-24 | Var. 716 |
| 3-22 | Var. 717 |
| 3-20 | Var. 718 |
| 3-18 | Var. 719 |
| 3-16 | Var. 720 |
| 3-14 | Var. 721 |
| 3-12 | Var. 722 |
| 3-10 | Var. 723 |
| 3-8 | Var. 724 |
| 3-6 | Var. 725 |
| 3-4 | Var. 726 |
| 4-90 | Var. 727 |
| 4-84 | Var. 728 |
| 4-78 | Var. 729 |
| 4-72 | Var. 730 |
| 4-66 | Var. 731 |
| 4-60 | Var. 732 |
| 4-54 | Var. 733 |
| 4-48 | Var. 734 |
| 4-45 | Var. 735 |
| 4-42 | Var. 736 |
| 4-39 | Var. 737 |
| 4-36 | Var. 738 |
| 4-33 | Var. 739 |
| 4-30 | Var. 740 |
| 4-27 | Var. 741 |
| 4-24 | Var. 742 |
| 4-22 | Var. 743 |
| 4-20 | Var. 744 |
| 4-18 | Var. 745 |
| 4-16 | Var. 746 |
| 4-14 | Var. 747 |
| 4-12 | Var. 748 |
| 4-10 | Var. 749 |
| 4-8 | Var. 750 |
| 4-6 | Var. 751 |
| 6-90 | Var. 752 |
| 6-84 | Var. 753 |
| 6-78 | Var. 754 |
| 6-72 | Var. 755 |
| 6-66 | Var. 756 |
| 6-60 | Var. 757 |
| 6-54 | Var. 758 |
| 6-48 | Var. 759 |
| 6-45 | Var. 760 |
| 6-42 | Var. 761 |
| 6-39 | Var. 762 |
| 6-36 | Var. 763 |
| 6-33 | Var. 764 |
| 6-30 | Var. 765 |
| 6-27 | Var. 766 |
| 6-24 | Var. 767 |
| 6-22 | Var. 768 |
| 6-20 | Var. 769 |
| 6-18 | Var. 770 |
| 6-16 | Var. 771 |
| 6-14 | Var. 772 |
| 6-12 | Var. 773 |
| 6-10 | Var. 774 |
| 6-8 | Var. 775 |
| 8-90 | Var. 776 |
| 8-84 | Var. 777 |
| 8-78 | Var. 778 |
| 8-72 | Var. 779 |
| 8-66 | Var. 780 |
| 8-60 | Var. 781 |
| 8-54 | Var. 782 |
| 8-48 | Var. 783 |
| 8-45 | Var. 784 |
| 8-42 | Var. 785 |
| 8-39 | Var. 786 |
| 8-36 | Var. 787 |
| 8-33 | Var. 788 |
| 8-30 | Var. 789 |
| 8-27 | Var. 790 |
| 8-24 | Var. 791 |
| 8-22 | Var. 792 |
| 8-20 | Var. 793 |
| 8-18 | Var. 794 |
| 8-16 | Var. 795 |
| 8-14 | Var. 796 |
| 8-12 | Var. 797 |
| 8-10 | Var. 798 |
| 10-90 | Var. 799 |
| 10-84 | Var. 800 |
| 10-78 | Var. 801 |
| 10-72 | Var. 802 |
| 10-66 | Var. 803 |
| 10-60 | Var. 804 |
| 10-54 | Var. 805 |
| 10-48 | Var. 806 |
| 10-45 | Var. 807 |
| 10-42 | Var. 808 |
| 10-39 | Var. 809 |
| 10-36 | Var. 810 |
| 10-33 | Var. 811 |
| 10-30 | Var. 812 |
| 10-27 | Var. 813 |
| 10-24 | Var. 814 |
| 10-22 | Var. 815 |
| 10-20 | Var. 816 |
| 10-18 | Var. 817 |
| 10-16 | Var. 818 |
| 10-14 | Var. 819 |
| 10-12 | Var. 820 |
| 12-90 | Var. 821 |
| 12-84 | Var. 822 |
| 12-78 | Var. 823 |
| 12-72 | Var. 824 |
| 12-66 | Var. 825 |
| 12-60 | Var. 826 |
| 12-54 | Var. 827 |
| 12-48 | Var. 828 |
| 12-45 | Var. 829 |
| 12-42 | Var. 830 |
| 12-39 | Var. 831 |

TABLE 6-continued

Exemplary embodiments for the half-life of higher order rVWF multimers found in the compositions and used in the methods provided herein.

| Hours | |
|---|---|
| 12-36 | Var. 832 |
| 12-33 | Var. 833 |
| 12-30 | Var. 834 |
| 12-27 | Var. 835 |
| 12-24 | Var. 836 |
| 12-22 | Var. 837 |
| 12-20 | Var. 838 |
| 12-18 | Var. 839 |
| 12-16 | Var. 840 |
| 12-14 | Var. 841 |
| 14-90 | Var. 842 |
| 14-84 | Var. 843 |
| 14-78 | Var. 844 |
| 14-72 | Var. 845 |
| 14-66 | Var. 846 |
| 14-60 | Var. 847 |
| 14-54 | Var. 848 |
| 14-48 | Var. 849 |
| 14-45 | Var. 850 |
| 14-42 | Var. 851 |
| 14-39 | Var. 852 |
| 14-36 | Var. 853 |
| 14-33 | Var. 854 |
| 14-30 | Var. 855 |
| 14-27 | Var. 856 |
| 14-24 | Var. 857 |
| 14-22 | Var. 858 |
| 14-20 | Var. 859 |
| 14-18 | Var. 860 |
| 14-16 | Var. 861 |
| 16-90 | Var. 862 |
| 16-84 | Var. 863 |
| 16-78 | Var. 864 |
| 16-72 | Var. 865 |
| 16-66 | Var. 866 |
| 16-60 | Var. 867 |
| 16-54 | Var. 868 |
| 16-48 | Var. 869 |
| 16-45 | Var. 870 |
| 16-42 | Var. 871 |
| 16-39 | Var. 872 |
| 16-36 | Var. 873 |
| 16-33 | Var. 874 |
| 16-30 | Var. 875 |
| 16-27 | Var. 876 |
| 16-24 | Var. 877 |
| 16-22 | Var. 878 |
| 16-20 | Var. 879 |
| 16-18 | Var. 880 |
| 18-90 | Var. 881 |
| 18-84 | Var. 882 |
| 18-78 | Var. 883 |
| 18-72 | Var. 884 |
| 18-66 | Var. 885 |
| 18-60 | Var. 886 |
| 18-54 | Var. 887 |
| 18-48 | Var. 888 |
| 18-45 | Var. 889 |
| 18-42 | Var. 890 |
| 18-39 | Var. 891 |
| 18-36 | Var. 892 |
| 18-33 | Var. 893 |
| 18-30 | Var. 894 |
| 18-27 | Var. 895 |
| 18-24 | Var. 896 |
| 18-22 | Var. 897 |
| 18-20 | Var. 898 |
| 20-90 | Var. 899 |
| 20-84 | Var. 900 |
| 20-78 | Var. 901 |
| 20-72 | Var. 902 |
| 20-66 | Var. 903 |
| 20-60 | Var. 904 |
| 20-54 | Var. 905 |
| 20-48 | Var. 906 |
| 20-45 | Var. 907 |
| 20-42 | Var. 908 |
| 20-39 | Var. 909 |
| 20-36 | Var. 910 |
| 20-33 | Var. 911 |
| 20-30 | Var. 912 |
| 20-27 | Var. 913 |
| 20-24 | Var. 914 |
| 20-22 | Var. 915 |
| 22-90 | Var. 916 |
| 22-84 | Var. 917 |
| 22-78 | Var. 918 |
| 22-72 | Var. 919 |
| 22-66 | Var. 920 |
| 22-60 | Var. 921 |
| 22-54 | Var. 922 |
| 22-48 | Var. 923 |
| 22-45 | Var. 924 |
| 22-42 | Var. 925 |
| 22-39 | Var. 926 |
| 22-36 | Var. 927 |
| 22-33 | Var. 928 |
| 22-30 | Var. 929 |
| 22-27 | Var. 930 |
| 22-24 | Var. 931 |
| 24-90 | Var. 932 |
| 24-84 | Var. 933 |
| 24-78 | Var. 934 |
| 24-72 | Var. 935 |
| 24-66 | Var. 936 |
| 24-60 | Var. 937 |
| 24-54 | Var. 938 |
| 24-48 | Var. 939 |
| 24-45 | Var. 940 |
| 24-42 | Var. 941 |
| 24-39 | Var. 942 |
| 24-36 | Var. 943 |
| 24-33 | Var. 944 |
| 24-30 | Var. 945 |
| 24-27 | Var. 946 |
| 27-90 | Var. 947 |
| 27-84 | Var. 948 |
| 27-78 | Var. 949 |
| 27-72 | Var. 950 |
| 27-66 | Var. 951 |
| 27-60 | Var. 952 |
| 27-54 | Var. 953 |
| 27-48 | Var. 954 |
| 30-90 | Var. 955 |
| 30-84 | Var. 956 |
| 30-78 | Var. 957 |
| 30-72 | Var. 958 |
| 30-66 | Var. 959 |
| 30-60 | Var. 960 |
| 30-54 | Var. 961 |
| 30-48 | Var. 962 |
| 30-45 | Var. 963 |
| 30-42 | Var. 964 |
| 30-39 | Var. 965 |
| 30-36 | Var. 966 |
| 30-33 | Var. 967 |
| 33-90 | Var. 968 |
| 33-84 | Var. 969 |
| 33-78 | Var. 970 |
| 33-72 | Var. 971 |
| 33-66 | Var. 972 |
| 33-60 | Var. 973 |
| 33-54 | Var. 974 |
| 33-48 | Var. 975 |
| 33-45 | Var. 976 |
| 33-42 | Var. 977 |
| 33-29 | Var. 978 |
| 33-36 | Var. 979 |
| 36-90 | Var. 980 |
| 36-84 | Var. 981 |

TABLE 6-continued

Exemplary embodiments for the half-life of higher order rVWF multimers found in the compositions and used in the methods provided herein.

| Hours | |
|---|---|
| 36-78 | Var. 982 |
| 36-72 | Var. 983 |
| 36-66 | Var. 984 |
| 36-60 | Var. 985 |
| 36-54 | Var. 986 |
| 36-48 | Var. 987 |
| 36-45 | Var. 988 |
| 36-42 | Var. 989 |
| 36-39 | Var. 990 |
| 39-90 | Var. 991 |
| 39-84 | Var. 992 |
| 39-78 | Var. 993 |
| 39-72 | Var. 994 |
| 39-66 | Var. 995 |
| 39-60 | Var. 996 |
| 39-54 | Var. 997 |
| 39-48 | Var. 998 |
| 39-45 | Var. 999 |
| 39-42 | Var. 1000 |
| 42-90 | Var. 1001 |
| 42-84 | Var. 1002 |
| 42-78 | Var. 1003 |
| 42-72 | Var. 1004 |
| 42-66 | Var. 1005 |
| 42-60 | Var. 1006 |
| 42-54 | Var. 1007 |
| 42-48 | Var. 1008 |
| 42-45 | Var. 1009 |
| 45-90 | Var. 1010 |
| 45-84 | Var. 1011 |
| 45-78 | Var. 1012 |
| 45-72 | Var. 1013 |
| 45-66 | Var. 1014 |
| 45-60 | Var. 1015 |
| 45-54 | Var. 1016 |
| 45-48 | Var. 1017 |
| 48-90 | Var. 1018 |
| 48-84 | Var. 1019 |
| 48-78 | Var. 1020 |
| 48-72 | Var. 1021 |
| 48-66 | Var. 1022 |
| 48-60 | Var. 1023 |
| 48-54 | Var. 1024 |
| 54-90 | Var. 1025 |
| 54-84 | Var. 1026 |
| 54-78 | Var. 1027 |
| 54-72 | Var. 1028 |
| 54-66 | Var. 1029 |
| 54-60 | Var. 1030 |
| 60-90 | Var. 1031 |
| 60-84 | Var. 1032 |
| 60-78 | Var. 1033 |
| 60-72 | Var. 1034 |
| 60-66 | Var. 1035 |
| 66-90 | Var. 1036 |
| 66-84 | Var. 1037 |
| 66-78 | Var. 1038 |
| 66-72 | Var. 1039 |
| 72-90 | Var. 1040 |
| 72-84 | Var. 1041 |
| 72-78 | Var. 1042 |
| 78-90 | Var. 1043 |
| 78-84 | Var. 1044 |
| 84-90 | Var. 1045 |

Var. = Variation

Figure 22:
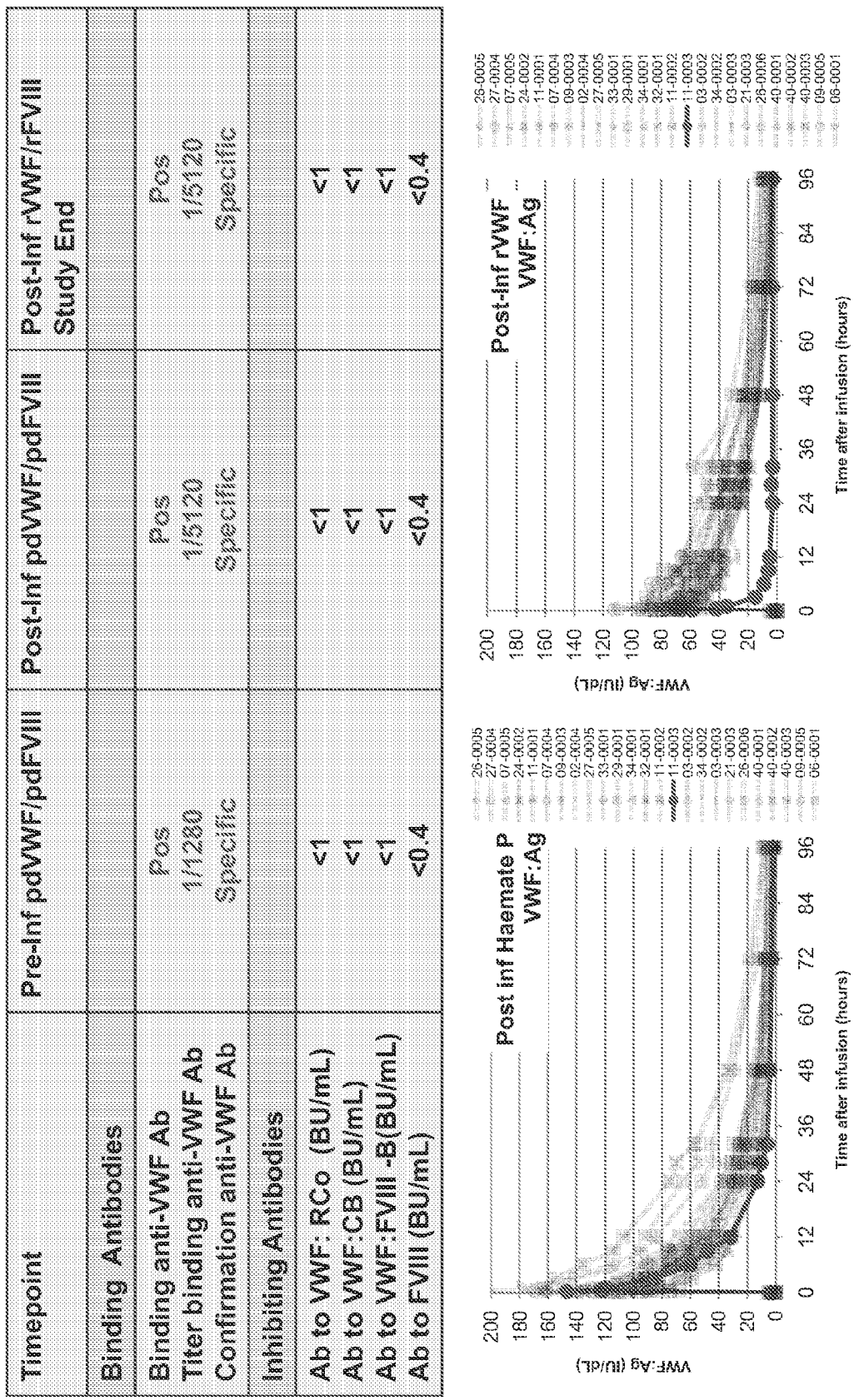
FIG. 22. Antibody summary for a subject receiving co-administered pdVWF/pdFVIII or rVWF/rFVIII.

In further aspects, rVWF of use in the present invention increases stability of plasma FVIII, which, as will be appreciated, may include pdFVII or rFVIII which has been administered to the patient or it may include FVIII endogenous to the patient, or any combination thereof. For example, as shown in FIG. 22, the half-life of plasma FVIII is increased in VWD patients receiving rVWF in combination with rFVIII as compared to patients receiving FVIII (i.e., Advate) alone. In further embodiments, rVWF increases half-life of FVIII by about 1.5-5-fold as compared to the half-life seen with patients receiving FVIII alone. In still further embodiments, rVWF increases half-life of FVIII by about 1.0-4.5, 1.5-4.0, 2.0-3.5, 2.5-3.0 fold. In one embodiment, administration of rVWF increases the stability of plasma FVIII, as compared to the administration of plasma-derived VWF, by an amount selected from variations 1046 to 1089 found in Table 7. In a specific embodiment, administration of a rVWF/FVIII complex increases the stability of plasma FVIII, as compared to the administration of plasma-derived VWF, by an amount selected from variations 1046 to 1089 found in Table 7.

TABLE 7

Exemplary embodiments for the increase in half-life experienced by plasma FVIII after administration of rVWF and rVWF/FVIII complexes, as compared to after administration of plasma-derived VWF and plasma-derived VWF/FVIII complexes.

| Increase in plasma FVIII half-life | |
|---|---|
| at least 1.5-fold | Var. 1046 |
| at least 2.0-fold | Var. 1047 |
| at least 2.5-fold | Var. 1048 |
| at least 3.0-fold | Var. 1049 |
| at least 3.5-fold | Var. 1050 |
| at least 4.0-fold | Var. 1051 |
| at least 4.5 fold | Var. 1052 |
| at least 5.0-fold | Var. 1053 |
| 1.5-fold | Var. 1054 |
| 2.0-fold | Var. 1055 |
| 2.5-fold | Var. 1056 |
| 3.0-fold | Var. 1057 |
| 3.5-fold | Var. 1058 |
| 4.0-fold | Var. 1059 |
| 4.5-fold | Var. 1060 |
| 5.0-fold | Var. 1061 |
| 1.5-5.0 fold | Var. 1062 |
| 1.5-4.5 fold | Var. 1063 |
| 1.5-4.0 fold | Var. 1064 |
| 1.5-3.5 fold | Var. 1065 |
| 1.5-3.0 fold | Var. 1066 |
| 1.5-2.5 fold | Var. 1067 |
| 1.5-2.0 fold | Var. 1068 |
| 2-5.0 fold | Var. 1069 |
| 2-4.5 fold | Var. 1070 |
| 2-4.0 fold | Var. 1071 |
| 2-3.5 fold | Var. 1072 |
| 2-3.0 fold | Var. |

TABLE 7-continued

Exemplary embodiments for the increase in half-life experienced by plasma FVIII after administration of rVWF and rVWF/FVIII complexes, as compared to after administration of plasma-derived VWF and plasma-derived VWF/FVIII complexes.

| Increase in plasma FVIII half-life | |
|---|---|
| 2-2.5 fold | Var. 1073 |
| 2.5-5.0 fold | Var. 1074 |
| 2.5-4.5 fold | Var. 1075 |
| 2.5-4.0 fold | Var. 1076 |
| 2.5-3.5 fold | Var. 1077 |
| 2.5-3.0 fold | Var. 1078 |
| 3-5.0 fold | Var. 1079 |
| 3-4.5 fold | Var. 1080 |
| 3-4.0 fold | Var. 1081 |
| 3-3.5 fold | Var. 1082 |
| 3.5-5.0 fold | Var. 1083 |
| 3.5-4.5 fold | Var. 1084 |
| 3.5-4.0 fold | Var. 1085 |
| 4-5.0 fold | Var. 1086 |
| 4-4.5 fold | Var. 1087 |
| 4.5-5.0 fold | Var. 1088 |
|  | Var. 1089 |

Var. = Variation

In still further embodiments, the increase in FVIII half-life is maintained at least 10, 20, 30, 40, 50, 60, 70, 80, 90, 100 hours after administration of rVWF. In yet further embodiments, the increase in FVIII half-life is maintained at least 5-125, 10-115, 15-105, 20-95, 25-85, 30-75, 35-65, 40-55 hours after administration of rVWF.

In one embodiment, the increase in the mean residence time (MRT) plasma FVIII is maintained for a time selected from variations 1090 to 1299 found in Table 8, after administration of rVWF. In a specific embodiment, the increase in the half life of plasma FVIII is maintained for a time selected from variations 1090 to 1299 found in Table 8, after administration of a rVWF/FVIII complex.

TABLE 8

Exemplary embodiments for the time plasma FVIII stability is maintained after administration of rVWF and rVWF/FVIII complexes.

| Hours | |
|---|---|
| at least 6 | Var. 1090 |
| at least 12 | Var. 1091 |
| at least 18 | Var. 1092 |
| at least 24 | Var. 1093 |
| at least 30 | Var. 1094 |
| at least 36 | Var. 1095 |
| at least 42 | Var. 1096 |
| at least 48 | Var. 1097 |
| at least 54 | Var. 1098 |
| at least 60 | Var. 1099 |
| at least 66 | Var. 1100 |
| at least 72 | Var. 1101 |
| at least 78 | Var. 1102 |
| at least 84 | Var. 1103 |
| at least 90 | Var. 1104 |
| at least 96 | Var. 1105 |
| at least 102 | Var. 1106 |
| at least 108 | Var. 1107 |
| at least 114 | Var. 1108 |
| at least 120 | Var. 1109 |
| 6-120 | Var. 1110 |
| 6-114 | Var. 1111 |
| 6-108 | Var. 1112 |
| 6-102 | Var. 1113 |
| 6-96 | Var. 1114 |
| 6-90 | Var. 1115 |
| 6-84 | Var. 1116 |
| 6-78 | Var. 1117 |
| 6-72 | Var. 1118 |
| 6-66 | Var. 1119 |
| 6-60 | Var. 1120 |
| 6-54 | Var. 1121 |
| 6-48 | Var. 1122 |
| 6-42 | Var. 1123 |
| 6-36 | Var. 1124 |
| 6-30 | Var. 1125 |
| 6-24 | Var. 1126 |
| 6-18 | Var. 1127 |
| 6-12 | Var. 1128 |
| 12-120 | Var. 1129 |
| 12-114 | Var. 1130 |
| 12-108 | Var. 1131 |
| 12-102 | Var. 1132 |
| 12-96 | Var. 1133 |
| 12-90 | Var. 1134 |
| 12-84 | Var. 1135 |
| 12-78 | Var. 1136 |
| 12-72 | Var. 1137 |
| 12-66 | Var. 1138 |
| 12-60 | Var. 1139 |
| 12-54 | Var. 1140 |
| 12-48 | Var. 1141 |
| 12-42 | Var. 1142 |
| 12-36 | Var. 1143 |
| 12-30 | Var. 1144 |
| 12-24 | Var. 1145 |
| 12-18 | Var. 1146 |
| 18-120 | Var. 1147 |
| 18-114 | Var. 1148 |
| 18-108 | Var. 1149 |
| 18-102 | Var. 1150 |
| 18-96 | Var. 1151 |
| 18-90 | Var. 1152 |
| 18-84 | Var. 1153 |
| 18-78 | Var. 1154 |
| 18-72 | Var. 1155 |
| 18-66 | Var. 1156 |
| 18-60 | Var. 1157 |
| 18-54 | Var. 1158 |
| 18-48 | Var. 1159 |
| 18-42 | Var. 1160 |
| 18-36 | Var. 1161 |
| 18-30 | Var. 1162 |
| 18-24 | Var. 1163 |
| 24-120 | Var. 1164 |
| 24-114 | Var. 1165 |
| 24-108 | Var. 1166 |
| 24-102 | Var. 1167 |
| 24-96 | Var. 1168 |
| 24-90 | Var. 1169 |
| 24-84 | Var. 1170 |
| 24-78 | Var. 1171 |
| 24-72 | Var. 1172 |
| 24-66 | Var. 1173 |
| 24-60 | Var. 1174 |

TABLE 8-continued

Exemplary embodiments for the time plasma FVIII stability is maintained after administration of rVWF and rVWF/FVIII complexes.

| Hours | |
|---|---|
| 24-54 | Var. 1175 |
| 24-48 | Var. 1176 |
| 24-42 | Var. 1177 |
| 24-36 | Var. 1178 |
| 24-30 | Var. 1179 |
| 30-120 | Var. 1180 |
| 30-114 | Var. 1181 |
| 30-108 | Var. 1182 |
| 30-102 | Var. 1183 |
| 30-96 | Var. 1184 |
| 30-90 | Var. 1185 |
| 30-84 | Var. 1186 |
| 30-78 | Var. 1187 |
| 30-72 | Var. 1188 |
| 30-66 | Var. 1189 |
| 30-60 | Var. 1190 |
| 30-54 | Var. 1191 |
| 30-48 | Var. 1192 |
| 30-42 | Var. 1193 |
| 30-36 | Var. 1194 |
| 36-120 | Var. 1195 |
| 36-114 | Var. 1196 |
| 36-108 | Var. 1197 |
| 36-102 | Var. 1198 |
| 36-96 | Var. 1199 |
| 36-90 | Var. 1200 |
| 36-84 | Var. 1201 |
| 36-78 | Var. 1202 |
| 36-72 | Var. 1203 |
| 36-66 | Var. 1204 |
| 36-60 | Var. 1205 |
| 36-54 | Var. 1206 |
| 36-48 | Var. 1207 |
| 36-42 | Var. 1208 |
| 42-120 | Var. 1209 |
| 42-114 | Var. 1210 |
| 42-108 | Var. 1211 |
| 42-102 | Var. 1212 |
| 42-96 | Var. 1213 |
| 42-90 | Var. 1214 |
| 42-84 | Var. 1215 |
| 42-78 | Var. 1216 |
| 42-72 | Var. 1217 |
| 42-66 | Var. 1218 |
| 42-60 | Var. 1219 |
| 42-54 | Var. 1220 |
| 42-48 | Var. 1221 |
| 48-120 | Var. 1222 |
| 48-114 | Var. 1223 |
| 48-108 | Var. 1224 |
| 48-102 | Var. 1225 |
| 48-96 | Var. 1226 |
| 48-90 | Var. 1227 |
| 48-84 | Var. 1228 |
| 48-78 | Var. 1229 |
| 48-72 | Var. 1230 |
| 48-66 | Var. 1231 |
| 48-60 | Var. 1232 |
| 48-54 | Var. 1233 |
| 54-120 | Var. 1234 |
| 54-114 | Var. 1235 |
| 54-108 | Var. 1236 |
| 54-102 | Var. 1237 |
| 54-96 | Var. 1238 |
| 54-90 | Var. 1239 |
| 54-84 | Var. 1240 |
| 54-78 | Var. 1241 |
| 54-72 | Var. 1242 |
| 54-66 | Var. 1243 |
| 54-60 | Var. 1244 |
| 60-120 | Var. 1245 |
| 60-114 | Var. 1246 |
| 60-108 | Var. 1247 |
| 60-102 | Var. 1248 |
| 60-96 | Var. 1249 |
| 60-90 | Var. 1250 |
| 60-84 | Var. 1251 |
| 60-78 | Var. 1252 |
| 60-72 | Var. 1253 |
| 60-66 | Var. 1254 |
| 66-120 | Var. 1255 |
| 66-114 | Var. 1256 |
| 66-108 | Var. 1257 |
| 66-102 | Var. 1258 |
| 66-96 | Var. 1259 |
| 66-90 | Var. 1260 |
| 66-84 | Var. 1261 |
| 66-78 | Var. 1262 |
| 66-72 | Var. 1263 |
| 72-120 | Var. 1264 |
| 72-114 | Var. 1265 |
| 72-108 | Var. 1266 |
| 72-102 | Var. 1267 |
| 72-96 | Var. 1268 |
| 72-90 | Var. 1269 |
| 72-84 | Var. 1270 |
| 72-78 | Var. 1271 |
| 78-120 | Var. 1272 |
| 78-114 | Var. 1273 |
| 78-108 | Var. 1274 |
| 78-102 | Var. 1275 |
| 78-96 | Var. 1276 |
| 78-90 | Var. 1277 |
| 78-84 | Var. 1278 |
| 84-120 | Var. 1279 |
| 84-114 | Var. 1280 |
| 84-108 | Var. 1281 |
| 84-102 | Var. 1282 |
| 84-96 | Var. 1283 |
| 84-90 | Var. 1284 |
| 90-120 | Var. 1285 |
| 90-114 | Var. 1286 |
| 90-108 | Var. 1287 |
| 90-102 | Var. 1288 |
| 90-96 | Var. 1289 |
| 96-120 | Var. 1290 |
| 96-114 | Var. 1291 |
| 96-108 | Var. 1292 |
| 96-102 | Var. 1293 |
| 102-120 | Var. 1294 |
| 102-114 | Var. 1295 |
| 102-108 | Var. 1296 |
| 108-120 | Var. 1297 |
| 108-114 | Var. 1298 |
| 114-120 | Var. 1299 |

Var. = Variation

In further aspects, the rVWF of the invention shows an increased effect on the stability of FVIII as compared to the effect of pdVWF. For example, as shown in FIG. 20, average FVIII half-life was increased by rVWF by 5.2 hours over the half-life for patients receiving pdVWF. In further embodiments, rVWF increases average FVIII half-life by about 1-15, 2-14, 3-13, 4-12, 5-11, 6-10, 5-9, 6-8 hours. In still further embodiments, rVWF increases FVIII half-life by about 10% to about 75% as compared to pdVWF. In yet further embodiments, rVWF increases FVIII half-life by about 10-80%, 15-65%, 20-60%, 25-55%, 30-50%, 35-45% as compared to pdVWF. In certain embodiments, the administration of rVWF increases the half life of FVIII by an amount selected from variations 1300 to 1643 found in Table 9, as compared to administration of plasma-derived VWF. In yet further embodiments, the average or percentage increase in FVIII half-life is maintained at least 10, 20, 30, 40, 50, 60, 70, 80, 90, 100 hours after administration of rVWF. In yet further embodiments, the increase in FVIII half-life is maintained at least 5-125, 10-115, 15-105, 20-95, 25-85, 30-75, 35-65, 40-55 hours after administration of rVWF.

TABLE 9

Exemplary embodiments for the increase in half-life experienced by plasma FVIII after administration of rVWF and rVWF/FVIII complexes.

| Increase in half life | |
|---|---|
| at least 1 hr | Var. 1300 |
| at least 2 hr | Var. 1301 |
| at least 3 hr | Var. 1302 |
| at least 4 hr | Var. 1303 |
| at least 5 hr | Var. 1304 |
| at least 6 hr | Var. 1305 |
| at least 7 hr | Var. 1306 |
| at least 8 hr | Var. 1307 |
| at least 9 hr | Var. 1308 |
| at least 10 hr | Var. 1309 |
| at least 11 hr | Var. 1310 |
| at least 12 hr | Var. 1311 |
| at least 13 hr | Var. 1312 |
| at least 14 hr | Var. 1313 |
| at least 15 hr | Var. 1314 |
| 1 hr | Var. 1315 |
| 2 hr | Var. 1316 |
| 3 hr | Var. 1317 |
| 4 hr | Var. 1318 |
| 5 hr | Var. 1319 |
| 6 hr | Var. 1320 |
| 7 hr | Var. 1321 |
| 8 hr | Var. 1322 |
| 9 hr | Var. 1323 |
| 10 hr | Var. 1324 |
| 11 hr | Var. 1325 |
| 12 hr | Var. 1326 |
| 13 hr | Var. 1327 |
| 14 hr | Var. 1328 |
| 15 hr | Var. 1329 |
| 1-15 hr | Var. 1330 |
| 1-14 hr | Var. 1331 |
| 1-13 hr | Var. 1332 |
| 1-12 hr | Var. 1333 |
| 1-11 hr | Var. 1334 |
| 1-10 hr | Var. 1335 |
| 1-9 hr | Var. 1336 |
| 1-8 hr | Var. 1337 |
| 1-7 hr | Var. 1338 |
| 1-6 hr | Var. 1339 |
| 1-5 hr | Var. 1340 |
| 1-4 hr | Var. 1341 |
| 1-3 hr | Var. 1342 |
| 1-2 hr | Var. 1343 |
| 2-15 hr | Var. 1344 |
| 2-14 hr | Var. 1345 |
| 2-13 hr | Var. 1346 |
| 2-12 hr | Var. 1347 |
| 2-11 hr | Var. 1348 |
| 2-10 hr | Var. 1349 |
| 2-9 hr | Var. 1350 |
| 2-8 hr | Var. 1351 |
| 2-7 hr | Var. 1352 |
| 2-6 hr | Var. 1353 |
| 2-5 hr | Var. 1354 |
| 2-4 hr | Var. 1355 |
| 2-3 hr | Var. 1356 |
| 3-15 hr | Var. 1357 |
| 3-14 hr | Var. 1358 |
| 3-13 hr | Var. 1359 |
| 3-12 hr | Var. 1360 |
| 3-11 hr | Var. 1361 |
| 3-10 hr | Var. 1362 |
| 3-9 hr | Var. 1363 |
| 3-8 hr | Var. 1364 |
| 3-7 hr | Var. 1365 |
| 3-6 hr | Var. 1366 |
| 3-5 hr | Var. 1367 |
| 3-4 hr | Var. 1368 |
| 4-15 hr | Var. 1369 |
| 4-14 hr | Var. 1370 |
| 4-13 hr | Var. 1371 |
| 4-12 hr | Var. 1372 |
| 4-11 hr | Var. 1373 |
| 4-10 hr | Var. 1374 |
| 4-9 hr | Var. 1375 |
| 4-8 hr | Var. 1376 |
| 4-7 hr | Var. 1377 |
| 4-6 hr | Var. 1378 |
| 4-5 hr | Var. 1379 |
| 5-15 hr | Var. 1380 |
| 5-14 hr | Var. 1381 |
| 5-13 hr | Var. 1382 |
| 5-12 hr | Var. 1383 |
| 5-11 hr | Var. 1384 |
| 5-10 hr | Var. 1385 |
| 5-9 hr | Var. 1386 |
| 5-8 hr | Var. 1387 |
| 5-7 hr | Var. 1388 |
| 5-6 hr | Var. 1389 |
| 6-15 hr | Var. 1390 |
| 6-14 hr | Var. 1391 |
| 6-13 hr | Var. 1392 |
| 6-12 hr | Var. 1393 |
| 6-11 hr | Var. 1394 |
| 6-10 hr | Var. 1395 |
| 6-9 hr | Var. 1396 |
| 6-8 hr | Var. 1397 |
| 6-7 hr | Var. 1398 |
| 7-15 hr | Var. 1399 |
| 7-14 hr | Var. 1400 |
| 7-13 hr | Var. 1401 |
| 7-12 hr | Var. 1402 |
| 7-11 hr | Var. 1403 |
| 7-10 hr | Var. 1404 |
| 7-9 hr | Var. 1405 |
| 7-8 hr | Var. 1406 |
| 8-15 hr | Var. 1407 |
| 8-14 hr | Var. 1408 |
| 8-13 hr | Var. 1409 |
| 8-12 hr | Var. 1410 |
| 8-11 hr | Var. 1411 |
| 8-10 hr | Var. 1412 |
| 8-9 hr | Var. 1413 |
| 9-15 hr | Var. 1414 |
| 9-14 hr | Var. 1415 |
| 9-13 hr | Var. 1416 |
| 9-12 hr | Var. 1417 |
| 9-11 hr | Var. 1418 |
| 9-10 hr | Var. 1419 |
| 10-15 hr | Var. 1420 |
| 10-14 hr | Var. 1421 |
| 10-13 hr | Var. 1422 |
| 10-12 hr | Var. 1423 |
| 10-11 hr | Var. 1424 |
| 11-15 hr | Var. 1425 |
| 11-14 hr | Var. 1426 |
| 11-13 hr | Var. 1427 |
| 11-12 hr | Var. 1428 |
| 12-15 hr | Var. 1429 |
| 12-14 hr | Var. 1430 |
| 12-13 hr | Var. 1431 |
| 13-15 hr | Var. 1432 |
| 13-14 hr | Var. 1433 |
| 14-15 hr | Var. 1434 |
| at least 10% | Var. 1435 |
| at least 15% | Var. 1436 |
| at least 20% | Var. 1437 |
| at least 25% | Var. 1438 |
| at least 30% | Var. 1439 |
| at least 35% | Var. 1440 |
| at least 40% | Var. 1441 |
| at least 45% | Var. 1442 |

TABLE 9-continued

Exemplary embodiments for the increase in half-life experienced by plasma FVIII after administration of rVWF and rVWF/FVIII complexes.

| Increase in half life | |
|---|---|
| at least 50% | Var. 1443 |
| at least 55% | Var. 1444 |
| at least 60% | Var. 1445 |
| at least 65% | Var. 1446 |
| at least 70% | Var. 1447 |
| at least 75% | Var. 1448 |
| at least 80% | Var. 1449 |
| at least 85% | Var. 1450 |
| at least 90% | Var. 1451 |
| at least 95% | Var. 1452 |
| at least 100% | Var. 1453 |
| 10% | Var. 1454 |
| 15% | Var. 1455 |
| 20% | Var. 1456 |
| 25% | Var. 1457 |
| 30% | Var. 1458 |
| 35% | Var. 1459 |
| 40% | Var. 1460 |
| 45% | Var. 1461 |
| 50% | Var. 1462 |
| 55% | Var. 1463 |
| 60% | Var. 1464 |
| 65% | Var. 1465 |
| 70% | Var. 1466 |
| 75% | Var. 1467 |
| 80% | Var. 1468 |
| 85% | Var. 1469 |
| 90% | Var. 1470 |
| 95% | Var. 1471 |
| 100% | Var. 1472 |
| 10-100% | Var. 1473 |
| 10-95% | Var. 1474 |
| 10-90% | Var. 1475 |
| 10-85% | Var. 1476 |
| 10-80% | Var. 1477 |
| 10-75% | Var. 1478 |
| 10-70% | Var. 1479 |
| 10-65% | Var. 1480 |
| 10-60% | Var. 1481 |
| 10-55% | Var. 1482 |
| 10-50% | Var. 1483 |
| 10-45% | Var. 1484 |
| 10-40% | Var. 1485 |
| 10-35% | Var. 1486 |
| 10-30% | Var. 1487 |
| 10-25% | Var. 1488 |
| 10-20% | Var. 1489 |
| 10-15% | Var. 1490 |
| 15-100% | Var. 1491 |
| 15-95% | Var. 1492 |
| 15-90% | Var. 1493 |
| 15-85% | Var. 1494 |
| 15-80% | Var. 1495 |
| 15-75% | Var. 1496 |
| 15-70% | Var. 1497 |
| 15-65% | Var. 1498 |
| 15-60% | Var. 1499 |
| 15-55% | Var. 1500 |
| 15-50% | Var. 1501 |
| 15-45% | Var. 1502 |
| 15-40% | Var. 1503 |
| 15-35% | Var. 1504 |
| 15-30% | Var. 1505 |
| 15-25% | Var. 1506 |
| 15-20% | Var. 1507 |
| 20-100% | Var. 1508 |
| 20-95% | Var. 1509 |
| 20-90% | Var. 1510 |
| 20-85% | Var. 1511 |
| 20-80% | Var. 1512 |
| 20-75% | Var. 1513 |
| 20-70% | Var. 1514 |
| 20-65% | Var. 1515 |
| 20-60% | Var. 1516 |
| 20-55% | Var. 1517 |
| 20-50% | Var. 1518 |
| 20-45% | Var. 1519 |
| 20-40% | Var. 1520 |
| 20-35% | Var. 1521 |
| 20-30% | Var. 1522 |
| 20-25% | Var. 1523 |
| 25-100% | Var. 1524 |
| 25-95% | Var. 1525 |
| 25-90% | Var. 1526 |
| 25-85% | Var. 1527 |
| 25-80% | Var. 1528 |
| 25-75% | Var. 1529 |
| 25-70% | Var. 1530 |
| 25-65% | Var. 1531 |
| 25-60% | Var. 1532 |
| 25-55% | Var. 1533 |
| 25-50% | Var. 1534 |
| 25-45% | Var. 1535 |
| 25-40% | Var. 1536 |
| 25-35% | Var. 1537 |
| 25-30% | Var. 1538 |
| 30-100% | Var. 1539 |
| 30-95% | Var. 1540 |
| 30-90% | Var. 1541 |
| 30-85% | Var. 1542 |
| 30-80% | Var. 1543 |
| 30-75% | Var. 1544 |
| 30-70% | Var. 1545 |
| 30-65% | Var. 1546 |
| 30-60% | Var. 1547 |
| 30-55% | Var. 1548 |
| 30-50% | Var. 1549 |
| 30-45% | Var. 1550 |
| 30-40% | Var. 1551 |
| 30-35% | Var. 1552 |
| 35-100% | Var. 1553 |
| 35-95% | Var. 1554 |
| 35-90% | Var. 1555 |
| 35-85% | Var. 1556 |
| 35-80% | Var. 1557 |
| 35-75% | Var. 1558 |
| 35-70% | Var. 1559 |
| 35-65% | Var. 1560 |
| 35-60% | Var. 1561 |
| 35-55% | Var. 1562 |
| 35-50% | Var. 1563 |
| 35-45% | Var. 1564 |
| 35-40% | Var. 1565 |
| 40-100% | Var. 1566 |
| 40-95% | Var. 1567 |
| 40-90% | Var. 1568 |
| 40-85% | Var. 1569 |
| 40-80% | Var. 1570 |
| 40-75% | Var. 1571 |
| 40-70% | Var. 1572 |
| 40-65% | Var. 1573 |
| 40-60% | Var. 1574 |
| 40-55% | Var. 1575 |
| 40-50% | Var. 1576 |
| 40-45% | Var. 1577 |
| 45-100% | Var. 1578 |
| 45-95% | Var. 1579 |
| 45-90% | Var. 1580 |
| 45-85% | Var. 1581 |
| 45-80% | Var. 1582 |
| 45-75% | Var. 1583 |
| 45-70% | Var. 1584 |
| 45-65% | Var. 1585 |
| 45-60% | Var. 1586 |
| 45-55% | Var. 1587 |
| 45-50% | Var. 1588 |
| 50-100% | Var. 1589 |
| 50-95% | Var. 1590 |

TABLE 9-continued

Exemplary embodiments for the increase in half-life experienced by plasma FVIII after administration of rVWF and rVWF/FVIII complexes.

| Increase in half life | |
|---|---|
| 50-90% | Var. 1591 |
| 50-85% | Var. 1592 |
| 50-80% | Var. 1593 |
| 50-75% | Var. 1594 |
| 50-70% | Var. 1595 |
| 50-65% | Var. 1596 |
| 50-60% | Var. 1597 |
| 50-55% | Var. 1598 |
| 55-100% | Var. 1599 |
| 55-95% | Var. 1600 |
| 55-90% | Var. 1601 |
| 55-85% | Var. 1602 |
| 55-80% | Var. 1603 |
| 55-75% | Var. 1604 |
| 55-70% | Var. 1605 |
| 55-65% | Var. 1606 |
| 55-60% | Var. 1607 |
| 60-100% | Var. 1608 |
| 60-95% | Var. 1609 |
| 60-90% | Var. 1610 |
| 60-85% | Var. 1611 |
| 60-80% | Var. 1612 |
| 60-75% | Var. 1613 |
| 60-70% | Var. 1614 |
| 60-65% | Var. 1615 |
| 65-100% | Var. 1616 |
| 65-95% | Var. 1617 |
| 65-90% | Var. 1618 |
| 65-85% | Var. 1619 |
| 65-80% | Var. 1620 |
| 65-75% | Var. 1621 |
| 65-70% | Var. 1622 |
| 70-100% | Var. 1623 |
| 70-95% | Var. 1624 |
| 70-90% | Var. 1625 |
| 70-85% | Var. 1626 |
| 70-80% | Var. 1627 |
| 70-75% | Var. 1628 |
| 75-100% | Var. 1629 |
| 75-95% | Var. 1630 |
| 75-90% | Var. 1631 |
| 75-85% | Var. 1632 |
| 75-80% | Var. 1633 |
| 80-100% | Var. 1634 |
| 80-95% | Var. 1635 |
| 80-90% | Var. 1636 |
| 80-85% | Var. 1637 |
| 85-100% | Var. 1638 |
| 85-95% | Var. 1639 |
| 85-90% | Var. 1640 |
| 90-100% | Var. 1641 |
| 90-95% | Var. 1642 |
| 95%-100% | Var. 1643 |

Var. = Variation

In still further aspects and in accordance with any of the above, the stabilization of FVIII activity by rVWF as compared to pdVWF can be measured by metrics in addition to FVIII half-life, including mean residence time (MRT) and area under curve (AUC). In exemplary embodiments, rVWF increases MRT by about 1-15 hours as compared to pdVWF. In further embodiments, rVWF increases MRT by about 1-25, 2-20, 3-15, 4-10, 5-9, 6-8 hours as compared to pdVWF. In still further embodiments, rVWF increases FVIII MRT by about 10-80%, 15-65%, 20-60%, 25-55%, 30-50%, 35-45% as compared to pdVWF. In yet further embodiments, the average or percentage increase in FVIII half-life is maintained at least 10, 20, 30, 40, 50, 60, 70, 80, 90, 100 hours after administration of rVWF. In certain embodiments, the administration of rVWF increases the MRT of FVIII by an amount selected from variations 1644 to 1987 found in Table 10, as compared to administration of plasma-derived VWF.

In yet further embodiments, the increase in MRT is maintained at least 5-125, 10-115, 15-105, 20-95, 25-85, 30-75, 35-65, 40-55 hours after administration of rVWF. In certain embodiments, the increase in MRT of FVIII caused by administration of rVWF is maintained for a time selected from variations 1090 to 1299 found in Table 8.

TABLE 10

Exemplary embodiments for the increase in FVIII mean residence time after administration of rVWF and rVWF/FVIII complexes, as compared to after administration of plasma-derived VWF and plasma-derived VWF/FVIII complexes.

| Increase in half life | |
|---|---|
| at least 1 hr | Var. 1644 |
| at least 2 hr | Var. 1645 |
| at least 3 hr | Var. 1646 |
| at least 4 hr | Var. 1647 |
| at least 5 hr | Var. 1648 |
| at least 6 hr | Var. 1649 |
| at least 7 hr | Var. 1650 |
| at least 8 hr | Var. 1651 |
| at least 9 hr | Var. 1652 |
| at least 10 hr | Var. 1653 |
| at least 11 hr | Var. 1654 |
| at least 12 hr | Var. 1655 |
| at least 13 hr | Var. 1656 |
| at least 14 hr | Var. 1657 |
| at least 15 hr | Var. 1658 |
| 1 hr | Var. 1659 |
| 2 hr | Var. 1660 |
| 3 hr | Var. 1661 |
| 4 hr | Var. 1662 |
| 5 hr | Var. 1663 |
| 6 hr | Var. 1664 |
| 7 hr | Var. 1665 |
| 8 hr | Var. 1666 |
| 9 hr | Var. 1667 |
| 10 hr | Var. 1668 |
| 11 hr | Var. 1669 |
| 12 hr | Var. 1670 |
| 13 hr | Var. 1671 |
| 14 hr | Var. 1672 |
| 15 hr | Var. 1673 |
| 1-15 hr | Var. 1674 |
| 1-14 hr | Var. 1675 |
| 1-13 hr | Var. 1676 |
| 1-12 hr | Var. 1677 |
| 1-11 hr | Var. 1678 |
| 1-10 hr | Var. 1679 |
| 1-9 hr | Var. 1680 |
| 1-8 hr | Var. 1681 |
| 1-7 hr | Var. 1682 |
| 1-6 hr | Var. 1683 |
| 1-5 hr | Var. 1684 |
| 1-4 hr | Var. 1685 |
| 1-3 hr | Var. 1686 |
| 1-2 hr | Var. 1687 |
| 2-15 hr | Var. 1688 |
| 2-14 hr | Var. 1689 |
| 2-13 hr | Var. 1690 |
| 2-12 hr | Var. 1691 |
| 2-11 hr | Var. 1692 |
| 2-10 hr | Var. 1693 |
| 2-9 hr | Var. 1694 |
| 2-8 hr | Var. 1695 |
| 2-7 hr | Var. 1696 |
| 2-6 hr | Var. 1697 |
| 2-5 hr | Var. 1698 |
| 2-4 hr | Var. 1699 |
| 2-3 hr | Var. 1700 |
| 3-15 hr | Var. 1701 |
| 3-14 hr | Var. 1702 |
| 3-13 hr | Var. 1703 |
| 3-12 hr | Var. 1704 |

TABLE 10-continued

Exemplary embodiments for the increase in FVIII mean residence time after administration of rVWF and rVWF/FVIII complexes, as compared to after administration of plasma-derived VWF and plasma-derived VWF/FVIII complexes.

| Increase in half life | |
|---|---|
| 3-11 hr | Var. 1705 |
| 3-10 hr | Var. 1706 |
| 3-9 hr | Var. 1707 |
| 3-8 hr | Var. 1708 |
| 3-7 hr | Var. 1709 |
| 3-6 hr | Var. 1710 |
| 3-5 hr | Var. 1711 |
| 3-4 hr | Var. 1712 |
| 4-15 hr | Var. 1713 |
| 4-14 hr | Var. 1714 |
| 4-13 hr | Var. 1715 |
| 4-12 hr | Var. 1716 |
| 4-11 hr | Var. 1717 |
| 4-10 hr | Var. 1718 |
| 4-9 hr | Var. 1719 |
| 4-8 hr | Var. 1720 |
| 4-7 hr | Var. 1721 |
| 4-6 hr | Var. 1722 |
| 4-5 hr | Var. 1723 |
| 5-15 hr | Var. 1724 |
| 5-14 hr | Var. 1725 |
| 5-13 hr | Var. 1726 |
| 5-12 hr | Var. 1727 |
| 5-11 hr | Var. 1728 |
| 5-10 hr | Var. 1729 |
| 5-9 hr | Var. 1730 |
| 5-8 hr | Var. 1731 |
| 5-7 hr | Var. 1732 |
| 5-6 hr | Var. 1733 |
| 6-15 hr | Var. 1734 |
| 6-14 hr | Var. 1735 |
| 6-13 hr | Var. 1736 |
| 6-12 hr | Var. 1737 |
| 6-11 hr | Var. 1738 |
| 6-10 hr | Var. 1739 |
| 6-9 hr | Var. 1740 |
| 6-8 hr | Var. 1741 |
| 6-7 hr | Var. 1742 |
| 7-15 hr | Var. 1743 |
| 7-14 hr | Var. 1744 |
| 7-13 hr | Var. 1745 |
| 7-12 hr | Var. 1746 |
| 7-11 hr | Var. 1747 |
| 7-10 hr | Var. 1748 |
| 7-9 hr | Var. 1749 |
| 7-8 hr | Var. 1750 |
| 8-15 hr | Var. 1751 |
| 8-14 hr | Var. 1752 |
| 8-13 hr | Var. 1753 |
| 8-12 hr | Var. 1754 |
| 8-11 hr | Var. 1755 |
| 8-10 hr | Var. 1756 |
| 8-9 hr | Var. 1757 |
| 9-15 hr | Var. 1758 |
| 9-14 hr | Var. 1759 |
| 9-13 hr | Var. 1760 |
| 9-12 hr | Var. 1761 |
| 9-11 hr | Var. 1762 |
| 9-10 hr | Var. 1763 |
| 10-15 hr | Var. 1764 |
| 10-14 hr | Var. 1765 |
| 10-13 hr | Var. 1766 |
| 10-12 hr | Var. 1767 |
| 10-11 hr | Var. 1768 |
| 11-15 hr | Var. 1769 |
| 11-14 hr | Var. 1770 |
| 11-13 hr | Var. 1771 |
| 11-12 hr | Var. 1772 |
| 12-15 hr | Var. 1773 |
| 12-14 hr | Var. 1774 |
| 12-13 hr | Var. 1775 |
| 13-15 hr | Var. 1776 |
| 13-14 hr | Var. 1777 |
| 14-15 hr | Var. 1778 |
| at least 10% | Var. 1779 |
| at least 15% | Var. 1780 |
| at least 20% | Var. 1781 |
| at least 25% | Var. 1782 |
| at least 30% | Var. 1783 |
| at least 35% | Var. 1784 |
| at least 40% | Var. 1785 |
| at least 45% | Var. 1786 |
| at least 50% | Var. 1787 |
| at least 55% | Var. 1788 |
| at least 60% | Var. 1789 |
| at least 65% | Var. 1790 |
| at least 70% | Var. 1791 |
| at least 75% | Var. 1792 |
| at least 80% | Var. 1793 |
| at least 85% | Var. 1794 |
| at least 90% | Var. 1795 |
| at least 95% | Var. 1796 |
| at least 100% | Var. 1797 |
| 10% | Var. 1798 |
| 15% | Var. 1799 |
| 20% | Var. 1800 |
| 25% | Var. 1801 |
| 30% | Var. 1802 |
| 35% | Var. 1803 |
| 40% | Var. 1804 |
| 45% | Var. 1805 |
| 50% | Var. 1806 |
| 55% | Var. 1807 |
| 60% | Var. 1808 |
| 65% | Var. 1809 |
| 70% | Var. 1810 |
| 75% | Var. 1811 |
| 80% | Var. 1812 |
| 85% | Var. 1813 |
| 90% | Var. 1814 |
| 95% | Var. 1815 |
| 100% | Var. 1816 |
| 10-100% | Var. 1817 |
| 10-95% | Var. 1818 |
| 10-90% | Var. 1819 |
| 10-85% | Var. 1820 |
| 10-80% | Var. 1821 |
| 10-75% | Var. 1822 |
| 10-70% | Var. 1823 |
| 10-65% | Var. 1824 |
| 10-60% | Var. 1825 |
| 10-55% | Var. 1826 |
| 10-50% | Var. 1827 |
| 10-45% | Var. 1828 |
| 10-40% | Var. 1829 |
| 10-35% | Var. 1830 |
| 10-30% | Var. 1831 |
| 10-25% | Var. 1832 |
| 10-20% | Var. 1833 |
| 10-15% | Var. 1834 |
| 15-100% | Var. 1835 |
| 15-95% | Var. 1836 |
| 15-90% | Var. 1837 |
| 15-85% | Var. 1838 |
| 15-80% | Var. 1839 |
| 15-75% | Var. 1840 |
| 15-70% | Var. 1841 |
| 15-65% | Var. 1842 |
| 15-60% | Var. 1843 |
| 15-55% | Var. 1844 |
| 15-50% | Var. 1845 |
| 15-45% | Var. 1846 |
| 15-40% | Var. 1847 |
| 15-35% | Var. 1848 |

TABLE 10-continued

Exemplary embodiments for the increase in FVIII mean residence time after administration of rVWF and rVWF/FVIII complexes, as compared to after administration of plasma-derived VWF and plasma-derived VWF/FVIII complexes.

| Increase in half life | |
|---|---|
| 15-30% | Var. 1849 |
| 15-25% | Var. 1850 |
| 15-20% | Var. 1851 |
| 20-100% | Var. 1852 |
| 20-95% | Var. 1853 |
| 20-90% | Var. 1854 |
| 20-85% | Var. 1855 |
| 20-80% | Var. 1856 |
| 20-75% | Var. 1857 |
| 20-70% | Var. 1858 |
| 20-65% | Var. 1859 |
| 20-60% | Var. 1860 |
| 20-55% | Var. 1861 |
| 20-50% | Var. 1862 |
| 20-45% | Var. 1863 |
| 20-40% | Var. 1864 |
| 20-35% | Var. 1865 |
| 20-30% | Var. 1866 |
| 20-25% | Var. 1867 |
| 25-100% | Var. 1868 |
| 25-95% | Var. 1869 |
| 25-90% | Var. 1870 |
| 25-85% | Var. 1871 |
| 25-80% | Var. 1872 |
| 25-75% | Var. 1873 |
| 25-70% | Var. 1874 |
| 25-65% | Var. 1875 |
| 25-60% | Var. 1876 |
| 25-55% | Var. 1877 |
| 25-50% | Var. 1878 |
| 25-45% | Var. 1879 |
| 25-40% | Var. 1880 |
| 25-35% | Var. 1881 |
| 25-30% | Var. 1882 |
| 30-100% | Var. 1883 |
| 30-95% | Var. 1884 |
| 30-90% | Var. 1885 |
| 30-85% | Var. 1886 |
| 30-80% | Var. 1887 |
| 30-75% | Var. 1888 |
| 30-70% | Var. 1889 |
| 30-65% | Var. 1890 |
| 30-60% | Var. 1891 |
| 30-55% | Var. 1892 |
| 30-50% | Var. 1893 |
| 30-45% | Var. 1894 |
| 30-40% | Var. 1895 |
| 30-35% | Var. 1896 |
| 35-100% | Var. 1897 |
| 35-95% | Var. 1898 |
| 35-90% | Var. 1899 |
| 35-85% | Var. 1900 |
| 35-80% | Var. 1901 |
| 35-75% | Var. 1902 |
| 35-70% | Var. 1903 |
| 35-65% | Var. 1904 |
| 35-60% | Var. 1905 |
| 35-55% | Var. 1906 |
| 35-50% | Var. 1907 |
| 35-45% | Var. 1908 |
| 35-40% | Var. 1909 |
| 40-100% | Var. 1910 |
| 40-95% | Var. 1911 |
| 40-90% | Var. 1912 |
| 40-85% | Var. 1913 |
| 40-80% | Var. 1914 |
| 40-75% | Var. 1915 |
| 40-70% | Var. 1916 |
| 40-65% | Var. 1917 |
| 40-60% | Var. 1918 |
| 40-55% | Var. 1919 |
| 40-50% | Var. 1920 |
| 40-45% | Var. 1921 |
| 45-100% | Var. 1922 |
| 45-95% | Var. 1923 |
| 45-90% | Var. 1924 |
| 45-85% | Var. 1925 |
| 45-80% | Var. 1926 |
| 45-75% | Var. 1927 |
| 45-70% | Var. 1928 |
| 45-65% | Var. 1929 |
| 45-60% | Var. 1930 |
| 45-55% | Var. 1931 |
| 45-50% | Var. 1932 |
| 50-100% | Var. 1933 |
| 50-95% | Var. 1934 |
| 50-90% | Var. 1935 |
| 50-85% | Var. 1936 |
| 50-80% | Var. 1937 |
| 50-75% | Var. 1938 |
| 50-70% | Var. 1939 |
| 50-65% | Var. 1940 |
| 50-60% | Var. 1941 |
| 50-55% | Var. 1942 |
| 55-100% | Var. 1943 |
| 55-95% | Var. 1944 |
| 55-90% | Var. 1945 |
| 55-85% | Var. 1946 |
| 55-80% | Var. 1947 |
| 55-75% | Var. 1948 |
| 55-70% | Var. 1949 |
| 55-65% | Var. 1950 |
| 55-60% | Var. 1951 |
| 60-100% | Var. 1952 |
| 60-95% | Var. 1953 |
| 60-90% | Var. 1954 |
| 60-85% | Var. 1955 |
| 60-80% | Var. 1956 |
| 60-75% | Var. 1957 |
| 60-70% | Var. 1958 |
| 60-65% | Var. 1959 |
| 65-100% | Var. 1960 |
| 65-95% | Var. 1961 |
| 65-90% | Var. 1962 |
| 65-85% | Var. 1963 |
| 65-80% | Var. 1964 |
| 65-75% | Var. 1965 |
| 65-70% | Var. 1966 |
| 70-100% | Var. 1967 |
| 70-95% | Var. 1968 |
| 70-90% | Var. 1969 |
| 70-85% | Var. 1970 |
| 70-80% | Var. 1971 |
| 70-75% | Var. 1972 |
| 75-100% | Var. 1973 |
| 75-95% | Var. 1974 |
| 75-90% | Var. 1975 |
| 75-85% | Var. 1976 |
| 75-80% | Var. 1977 |
| 80-100% | Var. 1978 |
| 80-95% | Var. 1979 |
| 80-90% | Var. 1980 |
| 80-85% | Var. 1981 |
| 85-100% | Var. 1982 |
| 85-95% | Var. 1983 |
| 85-90% | Var. 1984 |
| 90-100% | Var. 1985 |
| 90-95% | Var. 1986 |
| 95%-100% | Var. 1987 |

Var. = Variation

Further exemplary differences between pdVWF and rVWF are provided in the following table:

| pdVWF | rVWF |
|---|---|
| Synthesized in endothelial cells and megakaryocytes | Expressed in CHO cells |
| Post-translational modification of propeptide removal occurs intracellularly: during passage of the protein to the Golgi and post-Golgi compartments | Propeptide removal mediated in vitro through exposure of the pro-VWF to recombinant Furin |
| Glycosylation/ABO blood group glycans present | Fully glycosylated/ABO blood group gylcans absent |
| Consists of VWF subunits that have been exposed to plasma ADAMTS13<br>→ Ultra-large VWF multimers absent<br>→ Subunits cleaved at TYR$^{1605}$-MET$^{1606}$ | No exposure to ADAMTS13<br>→ Intact VWF subunits<br>→ Ultra-large VWF multimers present<br>→ Subunit cleavage occurs upon ADAMTS13 exposure |
| Plasma-derived VWF concentrates contain other proteins incl. ADAMTS13, hemagglutinins | Higher specific activity than pdVWF |

In some embodiments, the ratio of rFVIII procoagulant activity (IU rFVIII:C) to rVWF Ristocetin cofactor activity (IU rVWF:RCo) is between 3:1 and 1:5. In further embodiments, the ratio is between 2:1 and 1:4. In still further embodiments, the ratio is between 5:2 and 1:4. In further embodiments, the ratio is between 3:2 and 1:3. In still further embodiments, the ratio is about 1:1, 1:2, 1:3, 1:4, 1:5, 2:1, 2:3, 2:4, 2:5, 3:1, 3:2, 3:4, or 3:5. In further embodiments, the ratio is between 1:1 and 1:2. In yet further embodiments, the ratio is 1.1:1, 1.2:1, 1.3:1, 1.4:1, 1.5:1, 1.6:1, 1.7:1, 1.8:1, 1.9:1, or 2:1. In certain embodiments, the ratio of rFVIII procoagulant activity (IU rFVIII:C) to rVWF Ristocetin cofactor activity (IU rVWF:RCo) in a composition useful for a method described herein is selected from variations 1988 to 2140 found in Table 11.

TABLE 11

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 4:1 | Var. 1988 |
| 3:1 | Var. 1989 |
| 2:1 | Var. 1990 |
| 3:2 | Var. 1991 |
| 4:3 | Var. 1992 |
| 1:1 | Var. 1993 |
| 5:6 | Var. 1994 |
| 4:5 | Var. 1995 |
| 3:4 | Var. 1996 |
| 2:3 | Var. 1997 |
| 3:5 | Var. 1998 |
| 1:2 | Var. 1999 |
| 2:5 | Var. 2000 |
| 1:3 | Var. 2001 |
| 1:4 | Var. 2002 |
| 1:5 | Var. 2003 |
| 1:6 | Var. 2004 |
| 4:1-1:6 | Var. 2005 |
| 4:1-1:5 | Var. 2006 |
| 4:1-1:4 | Var. 2007 |
| 4:1-1:3 | Var. 2008 |
| 4:1-2:5 | Var. 2009 |
| 4:1-1:2 | Var. 2010 |
| 4:1-3:5 | Var. 2011 |
| 4:1-2:3 | Var. 2012 |
| 4:1-3:4 | Var. 2013 |
| 4:1-4:5 | Var. 2014 |
| 4:1-5:6 | Var. 2015 |
| 4:1-1:1 | Var. 2016 |
| 4:1-4:3 | Var. 2017 |
| 4:1-3:2 | Var. 2018 |
| 4:1-2:1 | Var. 2019 |
| 4:1-3:1 | Var. 2020 |
| 3:1-1:6 | Var. 2021 |
| 3:1-1:5 | Var. 2022 |
| 3:1-1:4 | Var. 2023 |
| 3:1-1:3 | Var. 2024 |
| 3:1-2:5 | Var. 2025 |
| 3:1-1:2 | Var. 2026 |
| 3:1-3:5 | Var. 2027 |
| 3:1-2:3 | Var. 2028 |
| 3:1-3:4 | Var. 2029 |
| 3:1-4:5 | Var. 2030 |
| 3:1-5:6 | Var. 2031 |
| 3:1-1:1 | Var. 2032 |
| 3:1-4:3 | Var. 2033 |
| 3:1-3:2 | Var. 2034 |
| 3:1-2:1 | Var. 2035 |
| 2:1-1:6 | Var. 2036 |
| 2:1-1:5 | Var. 2037 |
| 2:1-1:4 | Var. 2038 |

TABLE 11-continued

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 2:1-1:3 | Var. 2039 |
| 2:1-2:5 | Var. 2040 |
| 2:1-1:2 | Var. 2041 |
| 2:1-3:5 | Var. 2042 |
| 2:1-2:3 | Var. 2043 |
| 2:1-3:4 | Var. 2044 |
| 2:1-4:5 | Var. 2045 |
| 2:1-5:6 | Var. 2046 |
| 2:1-1:1 | Var. 2047 |
| 2:1-4:3 | Var. 2048 |
| 2:1-3:2 | Var. 2049 |
| 3:2-1:6 | Var. 2050 |
| 3:2-1:5 | Var. 2051 |
| 3:2-1:4 | Var. 2052 |
| 3:2-1:3 | Var. 2053 |
| 3:2-2:5 | Var. 2054 |
| 3:2-1:2 | Var. 2055 |
| 3:2-3:5 | Var. 2056 |
| 3:2-2:3 | Var. 2057 |
| 3:2-3:4 | Var. 2058 |
| 3:2-4:5 | Var. 2059 |
| 3:2-5:6 | Var. 2060 |
| 3:2-1:1 | Var. 2061 |
| 3:2-4:3 | Var. 2062 |
| 4:3-1:6 | Var. 2063 |
| 4:3-1:5 | Var. 2064 |
| 4:3-1:4 | Var. 2065 |
| 4:3-1:3 | Var. 2066 |
| 4:3-2:5 | Var. 2067 |
| 4:3-1:2 | Var. 2068 |
| 4:3-3:5 | Var. 2069 |
| 4:3-2:3 | Var. 2070 |
| 4:3-3:4 | Var. 2071 |
| 4:3-4:5 | Var. 2072 |
| 4:3-5:6 | Var. 2073 |
| 4:3-1:1 | Var. 2074 |
| 1:1-1:6 | Var. 2075 |
| 1:1-1:5 | Var. 2076 |
| 1:1-1:4 | Var. 2077 |
| 1:1-1:3 | Var. 2078 |
| 1:1-2:5 | Var. 2079 |
| 1:1-1:2 | Var. 2080 |
| 1:1-3:5 | Var. 2081 |
| 1:1-2:3 | Var. 2082 |
| 1:1-3:4 | Var. 2083 |
| 1:1-4:5 | Var. 2084 |
| 1:1-5:6 | Var. 2085 |
| 5:6-1:6 | Var. 2086 |
| 5:6-1:5 | Var. 2087 |
| 5:6-1:4 | Var. 2088 |
| 5:6-1:3 | Var. 2089 |
| 5:6-2:5 | Var. 2090 |
| 5:6-1:2 | Var. 2091 |
| 5:6-3:5 | Var. 2092 |
| 5:6-2:3 | Var. 2093 |
| 5:6-3:4 | Var. 2094 |
| 5:6-4:5 | Var. 2095 |
| 4:5-1:6 | Var. 2096 |
| 4:5-1:5 | Var. 2097 |
| 4:5-1:4 | Var. 2098 |
| 4:5-1:3 | Var. 2099 |
| 4:5-2:5 | Var. 2100 |
| 4:5-1:2 | Var. 2101 |
| 4:5-3:5 | Var. 2102 |
| 4:5-2:3 | Var. 2103 |
| 4:5-3:4 | Var. 2104 |
| 3:4-1:6 | Var. 2105 |
| 3:4-1:5 | Var. 2106 |
| 3:4-1:4 | Var. 2107 |
| 3:4-1:3 | Var. 2108 |
| 3:4-2:5 | Var. 2109 |
| 3:4-1:2 | Var. 2110 |

TABLE 11-continued

Exemplary embodiments for the ratio of rFVIII procoagulant activity
(IU rFVIII:C) to rVWF Ristocetin cofactor activity (IU rVWF:RCo)
in compositions and used in methods provided herein.

| (IU rFVIII:C) to (IU rVWF:RCo) | |
|---|---|
| 3:4-3:5 | Var. 2111 |
| 3:4-2:3 | Var. 2112 |
| 2:3-1:6 | Var. 2113 |
| 2:3-1:5 | Var. 2114 |
| 2:3-1:4 | Var. 2115 |
| 2:3-1:3 | Var. 2116 |
| 2:3-2:5 | Var. 2117 |
| 2:3-1:2 | Var. 2118 |
| 2:3-3:5 | Var. 2119 |
| 3:5-1:6 | Var. 2120 |
| 3:5-1:5 | Var. 2121 |
| 3:5-1:4 | Var. 2122 |
| 3:5-1:3 | Var. 2123 |
| 3:5-2:5 | Var. 2124 |
| 3:5-1:2 | Var. 2125 |
| 1:2-1:6 | Var. 2126 |
| 1:2-1:5 | Var. 2127 |
| 1:2-1:4 | Var. 2128 |
| 1:2-1:3 | Var. 2129 |
| 1:2-2:5 | Var. 2130 |
| 2:5-1:6 | Var. 2131 |
| 2:5-1:5 | Var. 2132 |
| 2:5-1:4 | Var. 2133 |
| 2:5-1:3 | Var. 2134 |
| 1:3-1:6 | Var. 2135 |
| 1:3-1:5 | Var. 2136 |
| 1:3-1:4 | Var. 2137 |
| 1:4-1:6 | Var. 2138 |
| 1:4-1:5 | Var. 2139 |
| 1:5-1:6 | Var. 2140 |

Var. = Variation

In specific aspects, the rVWF and/or the FVIII (recombinant or plasma derived) used in accordance with the present invention are not modified with any conjugation, post-translation or covalent modifications. In particular embodiments, the rVWF and/or FVIII of the present invention are not modified with a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

In other aspects, the rVWF and/or the FVIII (recombinant or plasma derived) used in accordance with the present invention are modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In one embodiment, the rVWF and/or FVIII proteins of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the rVWF and/or FVIII include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127:1011-8; Femandes and Gregonradis, Biochim Biophys Acta. 1997; 1341; 26-34). The generated Schiff Base can be stabilized by specific reduction with NaCNBH$_3$ to form a secondary amine. An alternative approach is the generation of terminal free amino groups on the polymer by reductive amination with NH$_4$Cl after prior oxidation. Bifunctional reagents can be used for linking two amino or two hydroxyl groups. For example a polymer containing an amino group can be coupled to an amino group of the coagulation protein with reagents like BS3 (Bis(sulfosuccinimidyl)suberate/Pierce, Rockford, Ill.). In addition heterobifunctional cross linking reagents like Sulfo-EMCS (N-ϵ-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PEG, 2,4,5-trichlorophenylcloroformate and P-nitrophenylcloroformate activated PEG, may be used in the conjugation of a coagulation protein.

In some aspects, the rVWF used in methods of the present invention has been matured in vitro with Furin. In further embodiments, the Furin is recombinant Furin.

In further aspects, the rVWF and/or rFVIII used in the methods of the present invention are produced by expression in a mammalian cell culture using methods known in the art.

In particular embodiments, the mammalian culture comprises CHO cells. In further embodiments, the rVWF and the rFVIII are co-expressed in the same culture. In such embodiments, the rVWF and the rFVIII are purified together (co-purified) or separately using methods known in the art. In other embodiments, the rVWF and the rFVIII are expressed in different cultures.

In an exemplary embodiment, the rVWF of the invention comprises rVWF protein isolated from a CHO cell expression system. In a further embodiment, the propeptide removal is mediated in vitro through exposure of the pro-VWF to Furin—in a still further embodiment, the Furin used for propeptide removal is recombinant Furin. In as yet further embodiment, fully glycosylated/ABO blood group glycans are absent.

In yet further embodiments, the rVWF used in methods and compositions of the present invention by expression in a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccharomyces* cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention.

In certain embodiments, the nucleic acid sequence comprising a sequence coding for VWF can be a vector. The vector can be delivered by a virus or can be a plasmid. The nucleic acid sequence coding for the protein can be a specific gene or a biologically functional part thereof. In one embodiment, the protein is at least a biologically active part of VWF.

A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some embodiments of the present invention, the nucleic acid sequence further comprises other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

In certain embodiments, the cell-culture methods of the invention may comprise the use of a microcarrier. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature 216:64-5 (1967)) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2008/0009040 and US 2007/0212770, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In certain embodiments, the culture of cells expressing VWF can be maintained for at least about 7 days, or at least about 14 days, 21 days, 28 days, or at least about 5 weeks, 6 weeks, 7 weeks, or at least about 2 months, or 3, 4, 5, 6, 7, 8, 9, 10, 11, 12, 13, 14, 15, 16, 17, 18 months or longer. The cell density at which a cell-culture is maintained at for production of a recombinant VWF protein will depend upon the culture-conditions and medium used for protein expression. One of skill in the art will readily be able to determine the optimal cell density for a cell-culture producing an VWF. In one embodiment, the culture is maintained at a cell density of between about $0.5 \times 10^6$ and $4 \times 10^7$ cells/ml for an extended period of time. In other embodiments, the cell density is maintained at a concentration of between about $1.0 \times 10^6$ and about $1.0 \times 10^7$ cells/ml for an extended period of time. In other embodiments, the cell density is maintained at a concentration of between about $1.0 \times 10^6$ and about $4.0 \times 10^6$ cells/ml for an extended period of time. In other embodiments, the cell density is maintained at a concentration of between about $1.0 \times 10^6$ and about $4.0 \times 10^6$ cells/ml for an extended period of time. In yet other embodiments, the cell density may be maintained at a concentration between about $2.0 \times 10^6$ and about $4.0 \times 10^6$, or between about $1.0 \times 10^6$ and about $2.5 \times 10^6$, or between about $1.5 \times 10^6$ and about $3.5 \times 10^6$, or any other similar range, for an extended period of time. After an appropriate time in cell culture, the rVWF can be isolated from the expression system using methods known in the art.

In a specific embodiment, the cell density of the continuous cell culture for production of rVWF is maintained at a concentration of no more than $2.5 \times 10^6$ cells/mL for an extended period. In other specific embodiments, the cell density is maintained at no more than $2.0 \times 10^6$ cells/mL, $1.5 \times 10^6$ cells/mL, $1.0 \times 10^6$ cells/mL, $0.5 \times 10^6$ cells/mL, or less. In one embodiment, the cell density is maintained at between $1.5 \times 10^6$ cells/mL and $2.5 \times 10^6$ cells/mL.

In one specific embodiment of the cell cultures described above, the cell culture solution comprises a medium supplement comprising copper. Such cell culture solutions are described for example in US 2012/0035110, filed Jul. 8, 2011, which is hereby incorporated by reference in its entirety for all purposes and in particular for all teachings related to cell culture methods and compositions for producing recombinant VWF.

In further embodiments, subsequent to purification (separately or together) from a mammalian cell culture, the rFVIII/rVWF complex is reconstituted prior to administration. In still further embodiments, the rVWF is treated with Furin prior to or subsequent to reconstitution of the rFVIII/rVWF complex. In further embodiments, the Furin is recombinant Furin.

In still further embodiments, the rVWF of the invention is not exposed to ADAMTS13, with the result that ultra large (i.e., comprising 10 or more subunits) are present in rVWF compositions of the invention.

In specific aspects, the rVWF and/or the rFVIII used in methods of the present invention are contained in a formulation containing a buffer, a sugar and/or a sugar alcohol (including without limitation trehalose and mannitol), a stabilizer (such as glycine), and a surfactant (such as Polysorbate 80). In further embodiments, for formulations containing rFVIII, the formulation may further include sodium, histidine, calcium, and glutathione.

In one aspect, the formulations comprising rVWF and/or rFVIII are lyophilized prior to administration. Lyophilization is carried out using techniques common in the art and should be optimized for the composition being developed [Tang et al., Pharm Res. 21:191-200. (2004) and Chang et al., Pharm Res. 13:243-9 (1996)].

Methods of preparing pharmaceutical formulations can include one or more of the following steps: adding a stabilizing agent as described herein to said mixture prior to lyophilizing, adding at least one agent selected from a bulking agent, an osmolarity regulating agent, and a surfactant, each of which as described herein, to said mixture prior to lyophilization. A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted recombinant VWF (with or without recombinant Factor VIII) compositions comprising the step of adding a diluent to a lyophilized recombinant VWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum *acacia*; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

In certain embodiments, compositions of the present invention are liquid formulations for administration with the use of a syringe or other storage vessel. In further embodiments, these liquid formulations are produced from lyophilized material described herein reconstituted as an aqueous solution.

In a further aspect, the compositions of the invention further comprise one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

Administration of Compositions of the Invention for Methods of Treating Disease

One of the advantages of administering rVWF to subjects to treat coagulation disease is that the higher specific activity of rVWF as compared to pdVWF allows flexibility in the amount of rVWF administered and the number of times the subject is re-dosed with rVWF (with or without co-administered FVIII). In addition, rVWF compositions provide the further flexibility of re-dosing with rVWF alone after an initial co-administration of rVWF and FVIII, without need for additional dosing with FVIII. As will be appreciated and as is discussed in further detail herein, the co-administered FVIII may be recombinant or plasma derived.

In one aspect, the administration of rVWF in accordance with the invention results in higher plasma FVIII levels and/or activity in the subject than is seen with a subject administered pdVWF. As discussed above, increases in FVIII levels and activity can be measured using methods standard in the art, thus allowing for determination of appropriate dosages for rVWF with or without FVIII.

Single or multiple administrations of rVWF (with or without FVIII) are carried out with the dose levels and pattern being selected by the treating physician. For the prevention or treatment of disease, the appropriate dosage depends on the type of disease to be treated (e.g., von Willebrand disease), the severity and course of the disease, whether drug is administered for preventive or therapeutic purposes, previous therapy, the patient's clinical history and response to the drug, and the discretion of the attending physician.

In further embodiments and in accordance with any of the above, treatment of coagulation diseases such as VWD or Hemophilia A may involve an initial treatment of rVWF alone or in combination with FVIII, followed by one or more repeat doses of rVWF alone, rVWF plus FVIII together, or FVIII alone. The nature of the initial and then the subsequent repeat administrations will depend in part on the disease being treated. For example, patients with VWD have some level of FVIII, but the stability of that FVIII is generally compromised because these patients lack VWF. Treatment of VWD patients may thus in some embodiments involve an initial treatment with both rVWF and rFVIII followed by repeated administrations of rVWF alone. In other embodiments, the initial treatment may be with rVWF alone while subsequent repeated administrations are with both rVWF and rFVIII. In still other embodiments, the initial and subsequent repeat administrations may all include a co-administration of both rVWF and rFVIII. Similarly, Hemophilia A patients (who lack FVIII) may receive an initial treatment of both rVWF and rFVIII, and subsequent repeat treatments may comprise the administration of rFVIII alone or rVWF alone. In other embodiments, the initial treatment may be rFVIII alone while the subsequent repeat treatments involve co-administration of rVWF and rFVIII.

In further aspects, rVWF is administered to a subject in doses ranging from 0.5 IU/kg-200 IU/kg. In some embodiments, rVWF is administered in doses ranging from 1-190, 5-180, 10-170, 15-160, 20-150, 25-140, 30-130, 35-120, 40-110, 45-100, 50-90, 55-80, or 60-70 IU/kg. In further embodiments and in accordance with any of the above, rVWF (with or without FVIII) is administered to a subject at doses of between about 1 IU/kg to about 150 IU/kg rVWF. In still further embodiments, the rVWF and rFVIII is administered at doses of between 1.5 IU/kg to 150 IU/kg, 2 IU/kg to 50 IU/kg, 5 IU/kg to 40 IU/kg, 10 IU/kg to 20 IU/kg, 10 IU/kg to 100 IU/kg, 25 IU/kg to 75 IU/kg, and 40 IU/kg to 75 IU/kg. In still further embodiments, rVWF is administered at 2, 5, 7.5, 10, 15, 20, 25, 30, 35, 40, 45, or 50 IU/kg. As will be appreciated and as is discussed further herein, appropriate dosages of rVWF (or rVWF together with FVIII) may be ascertained through use of established assays for determining blood level dosages in conjunction with appropriate dose-response data. In one embodiment, rVWF is administered to a subject in a dose selected from variations 2141 to 2338 in Table 12.

TABLE 12

Exemplary embodiments for the dosage of rVWF administered to a subject according to the methods provided herein.

| IU/kg | |
|---|---|
| About 0.5 | Var. 2141 |
| About 1 | Var. 2142 |
| About 2 | Var. 2143 |
| About 3 | Var. 2144 |
| About 4 | Var. 2145 |
| About 5 | Var. 2146 |
| About 10 | Var. 2147 |
| About 15 | Var. 2148 |
| About 20 | Var. 2149 |
| About 25 | Var. 2150 |
| About 30 | Var. 2151 |
| About 35 | Var. 2152 |
| About 40 | Var. 2153 |
| About 45 | Var. 2154 |
| About 50 | Var. 2155 |
| About 55 | Var. 2156 |
| About 60 | Var. 2157 |
| About 65 | Var. 2158 |
| About 70 | Var. 2159 |
| About 75 | Var. 2160 |
| About 80 | Var. 2161 |
| About 85 | Var. 2162 |
| About 90 | Var. 2163 |
| About 95 | Var. 2164 |
| About 100 | Var. 2165 |
| About 105 | Var. 2166 |
| About 110 | Var. 2167 |
| About 115 | Var. 2168 |
| About 120 | Var. 2169 |
| About 125 | Var. 2170 |
| About 130 | Var. 2171 |
| About 135 | Var. 2172 |
| About 140 | Var. 2173 |
| About 145 | Var. 2174 |
| About 150 | Var. 2175 |
| About 155 | Var. 2176 |
| About 160 | Var. 2177 |
| About 165 | Var. 2178 |
| About 170 | Var. 2179 |
| About 175 | Var. 2180 |
| About 180 | Var. 2181 |
| About 185 | Var. 2182 |
| About 190 | Var. 2183 |
| About 195 | Var. 2184 |
| About 200 | Var. 2185 |
| 0.5-200 | Var. 2186 |
| 0.5-175 | Var. 2187 |
| 0.5-150 | Var. 2188 |
| 0.5-125 | Var. 2189 |
| 0.5-100 | Var. 2190 |
| 0.5-75 | Var. 2191 |
| 0.5-50 | Var. 2192 |
| 0.5-40 | Var. 2193 |
| 0.5-30 | Var. 2194 |
| 0.5-25 | Var. 2195 |
| 0.5-20 | Var. 2196 |
| 0.5-15 | Var. 2197 |
| 0.5-10 | Var. 2198 |
| 0.5-7.5 | Var. 2199 |
| 0.5-5 | Var. 2200 |
| 0.5-2.5 | Var. 2201 |
| 0.5-1 | Var. 2202 |
| 1-200 | Var. 2203 |
| 1-175 | Var. 2204 |
| 1-150 | Var. 2205 |
| 1-125 | Var. 2206 |

TABLE 12-continued

Exemplary embodiments for the dosage of rVWF administered to a subject according to the methods provided herein.

| IU/kg | |
|---|---|
| 1-100 | Var. 2207 |
| 1-75 | Var. 2208 |
| 1-50 | Var. 2209 |
| 1-40 | Var. 2210 |
| 1-30 | Var. 2211 |
| 1-25 | Var. 2212 |
| 1-20 | Var. 2213 |
| 1-15 | Var. 2214 |
| 1-10 | Var. 2215 |
| 1-7.5 | Var. 2216 |
| 1-5 | Var. 2217 |
| 1-2.5 | Var. 2218 |
| 2.5-200 | Var. 2219 |
| 2.5-175 | Var. 2220 |
| 2.5-150 | Var. 2221 |
| 2.5-125 | Var. 2222 |
| 2.5-100 | Var. 2223 |
| 2.5-75 | Var. 2224 |
| 2.5-50 | Var. 2225 |
| 2.5-40 | Var. 2226 |
| 2.5-30 | Var. 2227 |
| 2.5-25 | Var. 2228 |
| 2.5-20 | Var. 2229 |
| 2.5-15 | Var. 2230 |
| 2.5-10 | Var. 2231 |
| 2.5-7.5 | Var. 2232 |
| 2.5-5 | Var. 2233 |
| 5-200 | Var. 2234 |
| 5-175 | Var. 2235 |
| 5-150 | Var. 2236 |
| 5-125 | Var. 2237 |
| 5-100 | Var. 2238 |
| 5-75 | Var. 2239 |
| 5-50 | Var. 2240 |
| 5-40 | Var. 2241 |
| 5-30 | Var. 2242 |
| 5-25 | Var. 2243 |
| 5-20 | Var. 2244 |
| 5-15 | Var. 2245 |
| 5-10 | Var. 2246 |
| 5-7.5 | Var. 2247 |
| 7.5-200 | Var. 2248 |
| 7.5-175 | Var. 2249 |
| 7.5-150 | Var. 2250 |
| 7.5-125 | Var. 2251 |
| 7.5-100 | Var. 2252 |
| 7.5-75 | Var. 2253 |
| 7.5-50 | Var. 2254 |
| 7.5-40 | Var. 2255 |
| 7.5-30 | Var. 2256 |
| 7.5-25 | Var. 2257 |
| 7.5-20 | Var. 2258 |
| 7.5-15 | Var. 2259 |
| 7.5-10 | Var. 2260 |
| 10-200 | Var. 2261 |
| 10-175 | Var. 2262 |
| 10-150 | Var. 2263 |
| 10-125 | Var. 2264 |
| 10-100 | Var. 2265 |
| 10-75 | Var. 2266 |
| 10-50 | Var. 2267 |
| 10-40 | Var. 2268 |
| 10-30 | Var. 2269 |
| 10-25 | Var. 2270 |
| 10-20 | Var. 2271 |
| 10-15 | Var. 2272 |
| 15-200 | Var. 2273 |
| 15-175 | Var. 2274 |
| 15-150 | Var. 2275 |
| 15-125 | Var. 2276 |
| 15-100 | Var. 2277 |
| 15-75 | Var. 2278 |
| 15-50 | Var. 2279 |
| 15-40 | Var. 2280 |
| 15-30 | Var. 2281 |
| 15-25 | Var. 2282 |
| 15-20 | Var. 2283 |
| 20-200 | Var. 2284 |
| 20-175 | Var. 2285 |
| 20-150 | Var. 2286 |
| 20-125 | Var. 2287 |
| 20-100 | Var. 2288 |
| 20-75 | Var. 2289 |
| 20-50 | Var. 2290 |
| 20-40 | Var. 2291 |
| 20-30 | Var. 2292 |
| 20-25 | Var. 2293 |
| 25-200 | Var. 2294 |
| 25-175 | Var. 2295 |
| 25-150 | Var. 2296 |
| 25-125 | Var. 2297 |
| 25-100 | Var. 2298 |
| 25-75 | Var. 2299 |
| 25-50 | Var. 2300 |
| 25-40 | Var. 2301 |
| 25-30 | Var. 2302 |
| 30-200 | Var. 2303 |
| 30-175 | Var. 2304 |
| 30-150 | Var. 2305 |
| 30-125 | Var. 2306 |
| 30-100 | Var. 2307 |
| 30-75 | Var. 2308 |
| 30-50 | Var. 2309 |
| 30-40 | Var. 2310 |
| 40-200 | Var. 2311 |
| 40-175 | Var. 2312 |
| 40-150 | Var. 2313 |
| 40-125 | Var. 2314 |
| 40-100 | Var. 2315 |
| 40-75 | Var. 2316 |
| 40-50 | Var. 2317 |
| 50-200 | Var. 2318 |
| 50-175 | Var. 2319 |
| 50-150 | Var. 2320 |
| 50-125 | Var. 2321 |
| 50-100 | Var. 2322 |
| 50-75 | Var. 2323 |
| 75-200 | Var. 2324 |
| 75-175 | Var. 2325 |
| 75-150 | Var. 2326 |
| 75-125 | Var. 2327 |
| 75-100 | Var. 2328 |
| 100-200 | Var. 2329 |
| 100-175 | Var. 2330 |
| 100-150 | Var. 2331 |
| 100-125 | Var. 2332 |
| 125-200 | Var. 2333 |
| 125-175 | Var. 2334 |
| 125-150 | Var. 2335 |
| 150-200 | Var. 2336 |
| 150-200 | Var. 2337 |
| 175-200 | Var. 2338 |

Var. = Variation

In still further embodiments, rVWF is administered at a dose such that it increases half-life of plasma FVIII by about 1.0-4.5, 1.5-4.0, 2.0-3.5, 2.5-3.0 fold. In still further embodiments, the dose and/or frequency of rVWF administration is such that the increase in FVIII half-life is maintained at least 10, 20, 30, 40, 50, 60, 70, 80, 90, 100 hours after administration of rVWF. In yet further embodiments, the dose and/or frequency of rVWF administration is such that the increase in FVIII half-life is maintained at least 5-125, 10-115, 15-105, 20-95, 25-85, 30-75, 35-65, 40-55 hours after administration of rVWF. In one embodiment, rVWF is administered at a dose such that it increases the half-life of plasma FVIII by a value selected from variations 1046 to 1089 found in Table 7.

As discussed above, the rVWF of the invention shows an increased effect on the stability of FVIII as compared to the effect of pdVWF. In certain aspects, rVWF is administered at a dose and/or with a frequency such that it increases average FVIII half-life by about 1-15, 2-14, 3-13, 4-12, 5-11, 6-10, 5-9, 6-8 hours. In still further embodiments, rVWF is administered at a dose and/or frequency such that it increases FVIII half-life by about 10% to about 75% as compared to pdVWF. In yet further embodiments, rVWF increases FVIII half-life by about 10-80%, 15-65%, 20-60%, 25-55%, 30-50%, 35-45% as compared to pdVWF. In yet further embodiments, the average or percentage increase in FVIII half-life is maintained at least 10, 20, 30, 40, 50, 60, 70, 80, 90, 100 hours after administration of rVWF. In yet further embodiments, the increase in FVIII half-life is maintained at least 5-125, 10-115, 15-105, 20-95, 25-85, 30-75, 35-65, 40-55 hours after administration of rVWF. As will be appreciated, the increase in FVIII stability, half-life and/or activity can be assessed using methods known in the art, including without limitation coagulation assays. In other embodiments, administration of rVWF increases the half-life of FVIII by an amount selected from variations 1300 to 1643 found in Table 9, as compared to administration of plasma-derived VWF.

As discussed herein, the stabilization of FVIII activity by rVWF as compared to pdVWF can be measured by metrics in addition to FVIII half-life, including mean residence time (MRT) and area under curve (AUC). In exemplary embodiments, rVWF is administered at a dose and/or frequency such that it increases MRT by about 1-15 hours as compared to pdVWF. In further embodiments, rVWF increases MRT by about 1-25, 2-20, 3-15, 4-10, 5-9, 6-8 hours as compared to pdVWF. In still further embodiments, rVWF increases FVIII MRT by about 10-80%, 15-65%, 20-60%, 25-55%, 30-50%, 35-45% as compared to pdVWF. In yet further embodiments, the average or percentage increase in FVIII half-life is maintained at least 10, 20, 30, 40, 50, 60, 70, 80, 90, 100 hours after administration of rVWF. In yet further embodiments, the increase in MRT is maintained at least 5-125, 10-115, 15-105, 20-95, 25-85, 30-75, 35-65, 40-55 hours after administration of rVWF. In other embodiments, administration of rVWF increases the MRT of FVIII by an amount selected from variations 1300 to 1643 found in Table 9, as compared to administration of plasma-derived VWF.

In further aspects, the doses of rVWF administered to patients are comparable to doses used in administration of pdVWF/pdFVIII.

Compositions of rVWF with or without FVIII can be contained in pharmaceutical formulations, as described herein. Such formulations can be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The route of administration can be, but is not limited to, by intravenous, intraperitoneal, subcutaneous, or intramuscular administration. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed., 1990, Mack Publishing Co., Easton, Pa. 18042 pages 1435-1712, the disclosure of which is hereby incorporated by reference in its entirety for all purposes and in particular for all teachings related to formulations, routes of administration and dosages for pharmaceutical products. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of a recombinant VWF of the present invention is approximately 50 U/kg, equal to 500 µg/kg. As studies are conducted, further information will emerge regarding the appropriate dosage levels and duration of treatment for various diseases and conditions.

In some embodiments, rVWF is administered to a subject alone. In some embodiments, rVWF is administered to a subject in combination with one or more coagulation factors. In further embodiments, the coagulation factor administered with rVWF is FVIII. In still further embodiments rVWF is administered prior to, subsequent to, or simultaneously with a coagulation factor such as FVIII. In certain embodiments, rVWF and FVIII are administered together in a single composition. As will be appreciated, the FVIII that is co-administered with rVWF can be either recombinant FVIII or plasma derived.

In further embodiments, rVWF (with or without FVIII) is administered to a subject no more than once daily. In further embodiments, rVWF (with or without FVIII) is administered to a subject: no more than once every other day, no more than once every third day, no more than once every fourth day, no more than once every fifth day, no more than once a week, no more than once every two weeks, no more than once a month. In still further embodiments, rVWF (with or without FVIII) is administered to a subject no more than twice a day.

In further embodiments, rVWF and FVIII are administered together to a subject in an initial dose, and then subsequent re-dosing is conducted with rVWF alone. In other embodiments, re-dosing is conducted with both rVWF and FVIII.

In still further embodiments, rVWF (with or without rFVIII) is administered at a dose such that plasma FVIII activity is stabilized for about 10 to about 90 hours. In further embodiments, plasma FVIII activity is stabilized for at least 12, 24, 36, 48 or 72 hours. As will be appreciated, the stabilized plasma FVIII activity may be that of endogenous FVIII, co-administered FVIII (plasma-derived or recombinant) or a combination of both endogenous and co-administered FVIII.

In some embodiments, rVWF and FVIII are administered together at a dose such that extension of in vivo half-life of plasma FVIII activity is stabilized for at least 12, 24, 36, 48 or 72 hours. In further embodiments, the plasma FVIII activity is stabilized for about 10 to about 90 hours. In still further embodiments, the increase in half-life of plasma FVIII is maintained for at least 24, 36, 48, 72, 90, 120, or 168 hours in a patient. The co-administered FVIII can be rFVIII or pdFVIII. In some embodiments, plasma FVIII activity is stabilized for a time selected from variations 1090 to 1299 found in Table 8, after co-administration of rVWF and FVIII.

In preferred aspects, the present invention provides methods for treating coagulation disease, including hemophilia and von Willebrand Disease (VWD).

As used herein, the terms "hemophilia" or "haemophilia" refer to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Common treatments for hemophilia include both prophylactic and on-demand administration of clotting factors, such as FVIII, FIX, including Bebulin®-VH, and FXI, as well as FEIBA-VH, desmopressin, and plasma infusions.

As used herein "von Willebrand Disease" refers to the group of diseases caused by a deficiency of von Willebrand factor. Von Willebrand factor helps blood platelets clump together and stick to the blood vessel wall, which is necessary for normal blood clotting. There are several types of Von Willebrand disease. The following table summarizes the characteristics of different types of VWD:

| Type | Characteristics |
| --- | --- |
| | Quantitative forms of VWD |
| Type 1 | Partial quantitative deficiencies of VWF |
| | VWF plasma levels that are 5% to 30% of normal |
| | approximately 60% to 80% of patients |
| Type 3 | Virtually complete deficiency of VWF |
| | Approximately 1% to 5% of patients |
| | Qualitative forms of VWD |
| Type 2 | Approximately 10% to 30% of patients |
| Type 2A | Decreased VWF-dependent platelet adhesion |
| | Selective deficiency of HMW-VMF multimers |
| | Platelet binding functions of VWF are impaired |
| Type 2B | Gain of function mutation with increased VWF binding to platelets |
| | Loss of HMW-VWF multimers from plasma, but not from platelets |
| | Loss of both VWF and platelets through a clearance mechanism |
| Type 2M | Decreased VWF-dependent platelet adhesion without selective deficiency of HMW-VWF multimers |
| Type 2N | Markedly decreased binding affinity for factor VIII |

Adopted from Sadler, J Thromb Haemost 2006; 4, 2103

Methods for treating coagulation disease include administering rVWF or a combination of rVWF rFVIII to subjects in need thereof in accordance with any of the methods of administration described herein and known in the art. Such subjects may be suffering from any coagulation disease, including without limitation von Willebrand Disease or hemophilia. As will be appreciated, any type of von Willebrand Disease, including any of the types listed in the above table, can be treated in accordance with any of the methods and compositions described herein.

In some embodiments, rVWF (with or without rFVIII) is administered to a subject such that the level of Factor VIII procoagulant activity (FVIII:C) in the plasma of the subject 24, 36, 48 or more hours post-administration is at least 90% of the level of FVIII:C activity present in the plasma 1 hour post-administration. In further embodiments, the level of the FVIII:C in the plasma of the subject 24, 36, 48 or more hours post-administration is at least between 50% and 100% of the level of FVIII:C activity present in the plasma 1 hour post-administration. In still further embodiments, the level of the FVIII:C in the plasma of the subject 24, 36, 48 or more hours post-administration is at least 50%, 55%, 60%, 65%. 70%, 75%, 80%, 85%, 90%, 95%, 96%, 97%, 98%. 99%, 100% of the level of FVIII:C activity present in the plasma 1 hour post-administration.

Administration of rVWF

In one aspect, the present disclosure provides method for treating Von Willebrand Disease (VWD) or Hemophilia A in a subject in need thereof, which includes administering a composition of recombinant Von Willebrand Factor (rVWF) such that Factor VIII (FVIII) stability is increased, as compared to FVIII half-life in a subject administered a composition of plasma derived Von Willebrand Factor (pdVWF). In one embodiment, the composition of rVWF administered to the subject is a composition of high molecular weight rVWF multimers. In one embodiment, the composition of rVWF administered to the subject has a higher specific activity than a composition of pdVWF. In yet another embodiment, the composition of rVWF administered to the subject is a composition of high molecular weight rVWF multimers with a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF such that FVIII stability is extended by at least 10%, 20%, 30%, 2 hr, 4 hr, 6 hr, or by an amount selected from variations 1300 to 1643 found in Table 9, as compared to FVIII stability in a subject administered a composition of pdVWF. In one embodiment, the composition of rVWF administered to the subject is a composition of high molecular weight rVWF multimers. In one embodiment, the composition of rVWF administered to the subject has a higher specific activity than a composition of pdVWF. In yet another embodiment, the composition of rVWF administered to the subject is a composition of high molecular weight rVWF multimers with a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF such that FVIII stability is extended by at least 10% as compared to FVIII stability in a subject administered a composition of pdVWF, wherein the composition of rVWF administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF such that FVIII stability is extended by at least 20% as compared to FVIII stability in a subject administered a composition of pdVWF, wherein the composition of rVWF administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF such that FVIII stability is extended by at least 30% as compared to FVIII stability in a subject administered a composition of pdVWF, wherein the composition of rVWF administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF. wherein the combination of rVWF specific activity in the composition and increase in FVIII stability, as compared to FVIII stability in a subject administered a composition of pdVWF, is selected from variations 2339 to 4868 in Table 13 to Table 19. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

TABLE 13

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | at least 1 hr | at least 2 hr | at least 3 hr | at least 4 hr | at least 5 hr | at least 6 hr | at least 7 hr | at least 8 hr |
| (mU/µg) | at least 20 | Var. 2339 | Var. 2385 | Var. 2431 | Var. 2477 | Var. 2523 | Var. 2569 | Var. 2615 | Var. 2661 |
| | at least 30 | Var. 2340 | Var. 2386 | Var. 2432 | Var. 2478 | Var. 2524 | Var. 2570 | Var. 2616 | Var. 2662 |
| | at least 40 | Var. 2341 | Var. 2387 | Var. 2433 | Var. 2479 | Var. 2525 | Var. 2571 | Var. 2617 | Var. 2663 |
| | at least 50 | Var. 2342 | Var. 2388 | Var. 2434 | Var. 2480 | Var. 2526 | Var. 2572 | Var. 2618 | Var. 2664 |
| | at least 60 | Var. 2343 | Var. 2389 | Var. 2435 | Var. 2481 | Var. 2527 | Var. 2573 | Var. 2619 | Var. 2665 |
| | at least 70 | Var. 2344 | Var. 2390 | Var. 2436 | Var. 2482 | Var. 2528 | Var. 2574 | Var. 2620 | Var. 2666 |
| | at least 80 | Var. 2345 | Var. 2391 | Var. 2437 | Var. 2483 | Var. 2529 | Var. 2575 | Var. 2621 | Var. 2667 |
| | at least 90 | Var. 2346 | Var. 2392 | Var. 2438 | Var. 2484 | Var. 2530 | Var. 2576 | Var. 2622 | Var. 2668 |
| | at least 100 | Var. 2347 | Var. 2393 | Var. 2439 | Var. 2485 | Var. 2531 | Var. 2577 | Var. 2623 | Var. 2669 |
| | at least 125 | Var. 2348 | Var. 2394 | Var. 2440 | Var. 2486 | Var. 2532 | Var. 2578 | Var. 2624 | Var. 2670 |
| | at least 150 | Var. 2349 | Var. 2395 | Var. 2441 | Var. 2487 | Var. 2533 | Var. 2579 | Var. 2625 | Var. 2671 |
| | 20-150 | Var. 2350 | Var. 2396 | Var. 2442 | Var. 2488 | Var. 2534 | Var. 2580 | Var. 2626 | Var. 2672 |
| | 20-125 | Var. 2351 | Var. 2397 | Var. 2443 | Var. 2489 | Var. 2535 | Var. 2581 | Var. 2627 | Var. 2673 |
| | 20-100 | Var. 2352 | Var. 2398 | Var. 2444 | Var. 2490 | Var. 2536 | Var. 2582 | Var. 2628 | Var. 2674 |
| | 20-90 | Var. 2353 | Var. 2399 | Var. 2445 | Var. 2491 | Var. 2537 | Var. 2583 | Var. 2629 | Var. 2675 |
| | 20-80 | Var. 2354 | Var. 2400 | Var. 2446 | Var. 2492 | Var. 2538 | Var. 2584 | Var. 2630 | Var. 2676 |
| | 20-70 | Var. 2355 | Var. 2401 | Var. 2447 | Var. 2493 | Var. 2539 | Var. 2585 | Var. 2631 | Var. 2677 |
| | 20-60 | Var. 2356 | Var. 2402 | Var. 2448 | Var. 2494 | Var. 2540 | Var. 2586 | Var. 2632 | Var. 2678 |
| | 20-50 | Var. 2357 | Var. 2403 | Var. 2449 | Var. 2495 | Var. 2541 | Var. 2587 | Var. 2633 | Var. 2679 |

TABLE 13-continued

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | at least 1 hr | at least 2 hr | at least 3 hr | at least 4 hr | at least 5 hr | at least 6 hr | at least 7 hr | at least 8 hr |
| | 20-40 | Var. 2358 | Var. 2404 | Var. 2450 | Var. 2496 | Var. 2542 | Var. 2588 | Var. 2634 | Var. 2680 |
| | 40-150 | Var. 2359 | Var. 2405 | Var. 2451 | Var. 2497 | Var. 2543 | Var. 2589 | Var. 2635 | Var. 2681 |
| | 40-125 | Var. 2360 | Var. 2406 | Var. 2452 | Var. 2498 | Var. 2544 | Var. 2590 | Var. 2636 | Var. 2682 |
| | 40-100 | Var. 2361 | Var. 2407 | Var. 2453 | Var. 2499 | Var. 2545 | Var. 2591 | Var. 2637 | Var. 2683 |
| | 40-90 | Var. 2362 | Var. 2408 | Var. 2454 | Var. 2500 | Var. 2546 | Var. 2592 | Var. 2638 | Var. 2684 |
| | 40-80 | Var. 2363 | Var. 2409 | Var. 2455 | Var. 2501 | Var. 2547 | Var. 2593 | Var. 2639 | Var. 2685 |
| | 40-70 | Var. 2364 | Var. 2410 | Var. 2456 | Var. 2502 | Var. 2548 | Var. 2594 | Var. 2640 | Var. 2686 |
| | 40-60 | Var. 2365 | Var. 2411 | Var. 2457 | Var. 2503 | Var. 2549 | Var. 2595 | Var. 2641 | Var. 2687 |
| | 40-50 | Var. 2366 | Var. 2412 | Var. 2458 | Var. 2504 | Var. 2550 | Var. 2596 | Var. 2642 | Var. 2688 |
| | 60-150 | Var. 2367 | Var. 2413 | Var. 2459 | Var. 2505 | Var. 2551 | Var. 2597 | Var. 2643 | Var. 2689 |
| | 60-125 | Var. 2368 | Var. 2414 | Var. 2460 | Var. 2506 | Var. 2552 | Var. 2598 | Var. 2644 | Var. 2690 |
| | 60-100 | Var. 2369 | Var. 2415 | Var. 2461 | Var. 2507 | Var. 2553 | Var. 2599 | Var. 2645 | Var. 2691 |
| | 60-90 | Var. 2370 | Var. 2416 | Var. 2462 | Var. 2508 | Var. 2554 | Var. 2600 | Var. 2646 | Var. 2692 |
| | 60-80 | Var. 2371 | Var. 2417 | Var. 2463 | Var. 2509 | Var. 2555 | Var. 2601 | Var. 2647 | Var. 2693 |
| | 60-70 | Var. 2372 | Var. 2418 | Var. 2464 | Var. 2510 | Var. 2556 | Var. 2602 | Var. 2648 | Var. 2694 |
| | 70-150 | Var. 2373 | Var. 2419 | Var. 2465 | Var. 2511 | Var. 2557 | Var. 2603 | Var. 2649 | Var. 2695 |
| | 70-125 | Var. 2374 | Var. 2420 | Var. 2466 | Var. 2512 | Var. 2558 | Var. 2604 | Var. 2651 | Var. 2696 |
| | 70-100 | Var. 2375 | Var. 2421 | Var. 2467 | Var. 2513 | Var. 2559 | Var. 2605 | Var. 2651 | Var. 2697 |
| | 70-90 | Var. 2376 | Var. 2422 | Var. 2468 | Var. 2514 | Var. 2560 | Var. 2606 | Var. 2652 | Var. 2698 |
| | 70-80 | Var. 2377 | Var. 2423 | Var. 2469 | Var. 2515 | Var. 2561 | Var. 2607 | Var. 2653 | Var. 2699 |
| | 80-150 | Var. 2378 | Var. 2424 | Var. 2470 | Var. 2516 | Var. 2562 | Var. 2608 | Var. 2654 | Var. 2700 |
| | 80-125 | Var. 2379 | Var. 2425 | Var. 2471 | Var. 2517 | Var. 2563 | Var. 2609 | Var. 2655 | Var. 2701 |
| | 80-100 | Var. 2380 | Var. 2426 | Var. 2472 | Var. 2518 | Var. 2564 | Var. 2610 | Var. 2656 | Var. 2702 |
| | 80-90 | Var. 2381 | Var. 2427 | Var. 2473 | Var. 2519 | Var. 2565 | Var. 2611 | Var. 2657 | Var. 2703 |
| | 90-150 | Var. 2382 | Var. 2428 | Var. 2474 | Var. 2520 | Var. 2566 | Var. 2612 | Var. 2658 | Var. 2704 |
| | 90-125 | Var. 2383 | Var. 2429 | Var. 2475 | Var. 2521 | Var. 2567 | Var. 2613 | Var. 2659 | Var. 2705 |
| | 90-100 | Var. 2384 | Var. 2430 | Var. 2476 | Var. 2522 | Var. 2568 | Var. 2614 | Var. 2660 | Var. 2706 |

Var. = Variation

TABLE 14

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | 1-8 hr | 1-7 hr | 1-6 hr | 1-5 hr | 1-4 hr | 1-3 hr | 1-2 hr | 2-8 hr |
| (mU/µg) | at least 20 | Var. 2707 | Var. 2753 | Var. 2799 | Var. 2845 | Var. 2891 | Var. 2937 | Var. 2983 | Var. 3029 |
| | at least 30 | Var. 2708 | Var. 2754 | Var. 2800 | Var. 2846 | Var. 2892 | Var. 2938 | Var. 2984 | Var. 3030 |

TABLE 14-continued

Exemplary embodiments for the combination of rVWF specific activity in a
composition used herein and increase in FVIII stability achieved, as compared
to FVIII stability in a subject administered a composition of pdVWF.

| | Increased Stability (Hours) | | | | | | | |
|---|---|---|---|---|---|---|---|---|
| | 1-8 hr | 1-7 hr | 1-6 hr | 1-5 hr | 1-4 hr | 1-3 hr | 1-2 hr | 2-8 hr |
| at least 40 | Var. 2709 | Var. 2755 | Var. 2801 | Var. 2847 | Var. 7893 | Var. 2939 | Var. 2985 | Var. 3031 |
| at least 50 | Var. 2710 | Var. 2756 | Var. 2802 | Var. 2848 | Var. 2894 | Var. 2940 | Var. 2986 | Var. 3032 |
| at least 60 | Var. 2711 | Var. 2757 | Var. 2803 | Var. 2849 | Var. 2895 | Var. 2941 | Var. 2987 | Var. 3033 |
| at least 70 | Var. 2712 | Var. 2758 | Var. 2804 | Var. 2850 | Var. 2896 | Var. 2942 | Var. 2988 | Var. 3034 |
| at least 80 | Var. 2713 | Var. 2759 | Var. 2805 | Var. 2851 | Var. 2897 | Var. 2943 | Var. 2989 | Var. 3035 |
| at least 90 | Var. 2714 | Var. 2760 | Var. 2806 | Var. 2852 | Var. 2898 | Var. 2944 | Var. 2990 | Var. 3036 |
| at least 100 | Var. 2715 | Var. 2761 | Var. 2807 | Var. 2853 | Var. 2899 | Var. 2945 | Var. 2991 | Var. 3037 |
| at least 125 | Var. 2716 | Var. 2762 | Var. 2808 | Var. 2854 | Var. 2900 | Var. 2946 | Var. 2992 | Var. 3038 |
| at least 150 | Var. 2717 | Var. 2763 | Var. 2809 | Var. 2855 | Var. 2901 | Var. 2947 | Var. 2993 | Var. 3039 |
| 20-150 | Var. 2718 | Var. 2764 | Var. 2810 | Var. 2856 | Var. 2902 | Var. 2948 | Var. 2994 | Var. 3040 |
| 20-125 | Var. 2719 | Var. 2765 | Var. 2811 | Var. 2857 | Var. 2903 | Var. 2949 | Var. 2995 | Var. 3041 |
| 20-100 | Var. 2720 | Var. 2766 | Var. 2812 | Var. 2858 | Var. 2904 | Var. 2950 | Var. 2996 | Var. 3042 |
| 20-90 | Var. 2721 | Var. 2767 | Var. 2813 | Var. 2859 | Var. 2905 | Var. 2951 | Var. 2997 | Var. 3043 |
| 20-80 | Var. 2722 | Var. 2768 | Var. 2814 | Var. 2860 | Var. 2906 | Var. 2952 | Var. 2998 | Var. 3044 |
| 20-70 | Var. 2723 | Var. 2769 | Var. 2815 | Var. 2861 | Var. 2907 | Var. 2953 | Var. 2999 | Var. 3045 |
| 20-60 | Var. 2724 | Var. 2770 | Var. 2816 | Var. 2862 | Var. 2908 | Var. 2954 | Var. 3000 | Var. 3046 |
| 20-50 | Var. 2725 | Var. 2771 | Var. 2817 | Var. 2863 | Var. 2909 | Var. 2955 | Var. 3001 | Var. 3047 |
| 20-40 | Var. 2726 | Var. 2772 | Var. 2818 | Var. 2864 | Var. 2910 | Var. 2956 | Var. 3002 | Var. 3048 |
| 40-150 | Var. 2727 | Var. 2773 | Var. 2819 | Var. 2865 | Var. 2911 | Var. 2957 | Var. 3003 | Var. 3049 |
| 40-125 | Var. 2728 | Var. 2774 | Var. 2820 | Var. 2866 | Var. 2912 | Var. 2958 | Var. 3004 | Var. 3050 |
| 40-100 | Var. 2779 | Var. 2775 | Var. 2821 | Var. 2867 | Var. 2913 | Var. 2959 | Var. 3005 | Var. 3051 |
| 40-90 | Var. 2730 | Var. 2776 | Var. 2822 | Var. 2868 | Var. 2914 | Var. 2960 | Var. 3006 | Var. 3052 |
| 40-80 | Var. 2731 | Var. 2777 | Var. 2823 | Var. 2869 | Var. 2915 | Var. 2961 | Var. 3007 | Var. 3053 |
| 40-70 | Var. 2732 | Var. 2778 | Var. 2824 | Var. 2870 | Var. 2916 | Var. 2962 | Var. 3008 | Var. 3054 |
| 40-60 | Var. 2733 | Var. 2779 | Var. 2825 | Var. 2871 | Var. 2917 | Var. 2963 | Var. 3009 | Var. 3055 |
| 40-50 | Var. 2734 | Var. 2780 | Var. 2826 | Var. 2872 | Var. 2918 | Var. 2964 | Var. 3010 | Var. 3056 |
| 60-150 | Var. 2735 | Var. 2781 | Var. 2827 | Var. 2873 | Var. 2919 | Var. 2965 | Var. 3011 | Var. 3057 |
| 60-125 | Var. 2736 | Var. 2782 | Var. 2828 | Var. 2874 | Var. 2920 | Var. 2966 | Var. 3012 | Var. 3058 |
| 60-100 | Var. 2737 | Var. 2783 | Var. 2829 | Var. 2875 | Var. 2921 | Var. 2967 | Var. 3013 | Var. 3059 |
| 60-90 | Var. 2738 | Var. 2784 | Var. 2830 | Var. 7876 | Var. 2922 | Var. 2968 | Var. 3014 | Var. 3060 |
| 60-80 | Var. 2739 | Var. 2785 | Var. 2831 | Var. 2877 | Var. 2923 | Var. 2969 | Var. 3015 | Var. 3061 |
| 60-70 | Var. 2740 | Var. 2786 | Var. 2832 | Var. 2878 | Var. 2924 | Var. 2970 | Var. 3016 | Var. 3062 |
| 70-150 | Var. 2741 | Var. 2787 | Var. 2833 | Var. 2879 | Var. 2925 | Var. 2971 | Var. 3017 | Var. 3063 |
| 70-125 | Var. 2742 | Var. 2788 | Var. 2834 | Var. 2880 | Var. 2926 | Var. 2972 | Var. 3018 | Var. 3064 |
| 70-100 | Var. 2743 | Var. 2789 | Var. 2835 | Var. 2881 | Var. 2927 | Var. 2973 | Var. 3019 | Var. 3065 |
| 70-90 | Var. 2744 | Var. 2790 | Var. 2836 | Var. 2887 | Var. 2928 | Var. 2974 | Var. 3020 | Var. 3066 |

TABLE 14-continued

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | 1-8 hr | 1-7 hr | 1-6 hr | 1-5 hr | 1-4 hr | 1-3 hr | 1-2 hr | 2-8 hr |
| | 70-80 | Var. 2745 | Var. 7791 | Var. 2837 | Var. 2883 | Var. 2929 | Var. 2975 | Var. 3021 | Var. 3067 |
| | 80-150 | Var. 2746 | Var. 2792 | Var. 2838 | Var. 2884 | Var. 2930 | Var. 2976 | Var. 3022 | Var. 3068 |
| | 80-125 | Var. 2747 | Var. 2793 | Var. 2839 | Var. 2885 | Var. 2931 | Var. 2977 | Var. 3023 | Var. 3069 |
| | 80-100 | Var. 2748 | Var. 2794 | Var. 2840 | Var. 2886 | Var. 2932 | Var. 2978 | Var. 3024 | Var. 3070 |
| | 80-90 | Var. 2749 | Var. 2795 | Var. 2841 | Var. 2887 | Var. 2933 | Var. 2979 | Var. 3025 | Var. 3071 |
| | 90-150 | Var. 2750 | Var. 2796 | Var. 2842 | Var. 2888 | Var. 2934 | Var. 2980 | Var. 3026 | Var. 3072 |
| | 90-125 | Var. 2751 | Var. 2797 | Var. 2843 | Var. 2889 | Var. 2935 | Var. 2981 | Var. 3027 | Var. 3073 |
| | 90-100 | Var. 2752 | Var. 2798 | Var. 2844 | Var. 2890 | Var. 2936 | Var. 2982 | Var. 3028 | Var. 3074 |

Var. = Variation

TABLE 15

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | 2-7 hr | 2-6 hr | 2-5 hr | 2-4 hr | 2-3 hr | 3-8 hr | 3-7 hr | 3-6 hr |
| (mU/µg) | at least 20 | Var. 3075 | Var. 3121 | Var. 3167 | Var. 3213 | Var. 3259 | Var. 3305 | Var. 3351 | Var. 3397 |
| | at least 30 | Var. 3076 | Var. 3122 | Var. 3168 | Var. 3214 | Var. 3260 | Var. 3306 | Var. 3352 | Var. 3398 |
| | at least 40 | Var. 3077 | Var. 3123 | Var. 3169 | Var. 3215 | Var. 3261 | Var. 3307 | Var. 3353 | Var. 3399 |
| | at least 50 | Var. 3078 | Var. 3124 | Var. 3170 | Var. 3216 | Var. 3262 | Var. 3308 | Var. 3354 | Var. 3400 |
| | at least 60 | Var. 3079 | Var. 3125 | Var. 3171 | Var. 3217 | Var. 3263 | Var. 3309 | Var. 3355 | Var. 3401 |
| | at least 70 | Var. 3080 | Var. 3126 | 1177 | Var. 3218 | Var. 3264 | Var. 3310 | Var. 3356 | Var. 3402 |
| | at least 80 | Var. 3081 | Var. 3127 | Var. 3173 | Var. 3219 | Var. 3265 | Var. 3311 | Var. 3357 | Var. 3403 |
| | at least 90 | Var. 3082 | Var. 3128 | Var. 3174 | Var. 3220 | Var. 3266 | Var. 3312 | Var. 3358 | Var. 3404 |
| | at least 100 | Var. 3083 | Var. 3129 | Var. 3175 | Var. 3221 | Var. 3267 | Var. 3313 | Var. 3359 | Var. 3405 |
| | at least 125 | Var. 3084 | Var. 3130 | Var. 3176 | Var. 3222 | Var. 3268 | Var. 3314 | Var. 3360 | Var. 3406 |
| | at least 150 | Var. 3085 | Var. 3131 | Var. 3177 | Var. 3223 | Var. 3269 | Var. 3315 | Var. 3361 | Var. 3407 |
| | 20-150 | Var. 3086 | Var. 3132 | Var. 3178 | Var. 3224 | Var. 3270 | Var. 3316 | Var. 3362 | Var. 3408 |
| | 20-125 | Var. 3087 | Var. 3133 | Var. 3179 | Var. 3225 | Var. 3271 | Var. 3317 | Var. 3363 | Var. 3409 |
| | 20-100 | Var. 3088 | Var. 3134 | Var. 3180 | Var. 3226 | Var. 3272 | Var. 3318 | Var. 3364 | Var. 3410 |
| | 20-90 | Var. 3089 | Var. 3135 | Var. 3181 | Var. 3227 | Var. 3273 | Var. 3319 | Var. 3365 | Var. 3411 |
| | 20-80 | Var. 3090 | Var. 3136 | Var. 3182 | Var. 3228 | Var. 3274 | Var. 3320 | Var. 3366 | Var. 3412 |
| | 20-70 | Var. 3091 | Var. 3137 | Var. 3183 | Var. 3229 | Var. 3275 | Var. 3321 | Var. 3367 | Var. 3413 |
| | 20-60 | Var. 3092 | Var. 3138 | Var. 3184 | Var. 3230 | Var. 3276 | Var. 3322 | Var. 3368 | Var. 3414 |
| | 20-50 | Var. 3093 | Var. 3139 | Var. 3185 | Var. 3231 | Var. 3277 | Var. 3323 | Var. 3369 | Var. 3415 |
| | 20-40 | Var. 3094 | Var. 3140 | Var. 3186 | Var. 3232 | Var. 3278 | Var. 3324 | Var. 3370 | Var. 3416 |

TABLE 15-continued

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | 2-7 hr | 2-6 hr | 2-5 hr | 2-4 hr | 2-3 hr | 3-8 hr | 3-7 hr | 3-6 hr |
| | 40-150 | Var. 3095 | Var. 3141 | Var. 3187 | Var. 3233 | Var. 3279 | Var. 3325 | Var. 3371 | Var. 3417 |
| | 40-125 | Var. 3096 | Var. 3142 | Var. 3188 | Var. 3234 | Var. 3280 | Var. 3326 | Var. 3372 | Var. 3418 |
| | 40-100 | Var. 3097 | Var. 3143 | Var. 3189 | Var. 3235 | Var. 3281 | Var. 3327 | Var. 3373 | Var. 3419 |
| | 40-90 | Var. 3098 | Var. 3144 | Var. 3190 | Var. 3236 | Var. 3282 | Var. 3328 | Var. 3374 | Var. 3420 |
| | 40-80 | Var. 3099 | Var. 3145 | Var. 3191 | Var. 3237 | Var. 3283 | Var. 3329 | Var. 3375 | Var. 3421 |
| | 40-70 | Var. 3100 | Var. 3146 | Var. 3192 | Var. 3238 | Var. 3284 | Var. 3330 | Var. 3376 | Var. 3422 |
| | 40-60 | Var. 3101 | Var. 3147 | Var. 3193 | Var. 3239 | Var. 3285 | Var. 3331 | Var. 3377 | Var. 3423 |
| | 40-50 | Var. 3102 | Var. 3148 | Var. 3194 | Var. 3240 | Var. 3286 | Var. 3332 | Var. 3378 | Var. 3424 |
| | 60-150 | Var. 3103 | Var. 3149 | Var. 3195 | Var. 3241 | Var. 3287 | Var. 3333 | Var. 3379 | Var. 3425 |
| | 60-125 | Var. 3104 | Var. 3150 | Var. 3196 | Var. 3242 | Var. 3288 | Var. 3334 | Var. 3380 | Var. 3426 |
| | 60-100 | Var. 3105 | Var. 3151 | Var. 3197 | Var. 3243 | Var. 3289 | Var. 3335 | Var. 3381 | Var. 3427 |
| | 60-90 | Var. 3106 | Var. 3152 | Var. 3198 | Var. 3244 | Var. 3290 | Var. 3336 | Var. 3382 | Var. 3428 |
| | 60-80 | Var. 3107 | Var. 3153 | Var. 3199 | Var. 3245 | Var. 3291 | Var. 3337 | Var. 3383 | Var. 3429 |
| | 60-70 | Var. 3108 | Var. 3154 | Var. 3200 | Var. 3246 | Var. 3292 | Var. 3338 | Var. 3384 | Var. 3430 |
| | 70-150 | Var. 3109 | Var. 3155 | Var. 3201 | Var. 3247 | Var. 3293 | Var. 3339 | Var. 3385 | Var. 3431 |
| | 70-125 | Var. 3110 | Var. 3156 | Var. 3202 | Var. 3248 | Var. 3294 | Var. 3340 | Var. 3386 | Var. 3432 |
| | 70-100 | Var. 3111 | Var. 3157 | Var. 3203 | Var. 3249 | Var. 3295 | Var. 3341 | Var. 3387 | Var. 3433 |
| | 70-90 | Var. 3112 | Var. 3158 | Var. 3204 | Var. 3250 | Var. 3296 | Var. 3342 | Var. 3388 | Var. 3434 |
| | 70-80 | Var. 3113 | Var. 3159 | Var. 3205 | Var. 3251 | Var. 3297 | Var. 3343 | Var. 3389 | Var. 3435 |
| | 80-150 | Var. 3114 | Var. 3160 | Var. 3206 | Var. 3252 | Var. 3298 | Var. 3344 | Var. 3390 | Var. 3436 |
| | 80-125 | Var. 3115 | Var. 3161 | Var. 3207 | Var. 3253 | Var. 3299 | Var. 3345 | Var. 3391 | Var. 3437 |
| | 80-100 | Var. 3116 | Var. 3162 | Var. 3208 | Var. 3254 | Var. 3300 | Var. 3346 | Var. 3392 | Var. 3438 |
| | 80-90 | Var. 3117 | Var. 3163 | Var. 3209 | Var. 3255 | Var. 3301 | Var. 3347 | Var. 3393 | Var. 3439 |
| | 90-150 | Var. 3118 | Var. 3164 | Var. 3210 | Var. 3256 | Var. 3302 | Var. 3348 | Var. 3394 | Var. 3440 |
| | 90-125 | Var. 3119 | Var. 3165 | Var. 3211 | Var. 3257 | Var. 3303 | Var. 3349 | Var. 3395 | Var. 3441 |
| | 90-100 | Var. 3120 | Var. 3166 | Var. 3212 | Var. 3258 | Var. 3304 | Var. 3350 | Var. 3396 | Var. 3442 |

Var. = Variation

TABLE 16

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | 3-5 hr | 3-4 hr | 4-8 hr | 4-7 hr | 4-6 hr | 4-5 hr | 5-8 hr | 5-7 hr |
| (mU/µg) | at least 20 | Var. 3443 | Var. 3489 | Var. 3535 | Var. 3581 | Var. 3627 | Var. 3673 | Var. 3719 | Var. 3765 |
| | at least 30 | Var. 3444 | Var. 3490 | Var. 3536 | Var. 3582 | Var. 3628 | Var. 3674 | Var. 3720 | Var. 3766 |

TABLE 16-continued

Exemplary embodiments for the combination of rVWF specific activity in a composition used herein and increase in FVIII stability achieved, as compared to FVIII stability in a subject administered a composition of pdVWF.

| | Increased Stability (Hours) | | | | | | | |
|---|---|---|---|---|---|---|---|---|
| | 3-5 hr | 3-4 hr | 4-8 hr | 4-7 hr | 4-6 hr | 4-5 hr | 5-8 hr | 5-7 hr |
| at least 40 | Var. 3445 | Var. 3491 | Var. 3537 | Var. 3583 | Var. 3629 | Var. 3675 | Var. 3721 | Var. 3767 |
| at least 50 | Var. 3446 | Var. 3492 | Var. 3538 | Var. 3584 | Var. 3630 | Var. 3676 | Var. 3722 | Var. 3768 |
| at least 60 | Var. 3447 | Var. 3493 | Var. 3539 | Var. 3585 | Var. 3631 | Var. 3677 | Var. 3723 | Var. 3769 |
| at least 70 | Var. 3448 | Var. 3494 | Var. 3540 | Var. 3586 | Var. 3632 | Var. 3678 | Var. 3724 | Var. 3770 |
| at least 80 | Var. 3449 | Var. 3495 | Var. 3541 | Var. 3587 | Var. 3633 | Var. 3679 | Var. 3725 | Var. 3771 |
| at least 90 | Var. 3450 | Var. 3496 | Var. 3542 | Var. 3588 | Var. 3634 | Var. 3680 | Var. 3726 | Var. 3772 |
| at least 100 | Var. 3451 | Var. 3497 | Var. 3543 | Var. 3589 | Var. 3635 | Var. 3681 | Var. 3727 | Var. 3773 |
| at least 125 | Var. 3452 | Var. 3498 | Var. 3544 | Var. 3590 | Var. 3636 | Var. 3682 | Var. 3728 | Var. 3774 |
| at least 150 | Var. 3453 | Var. 3499 | Var. 3545 | Var. 3591 | Var. 3637 | Var. 3683 | Var. 3729 | Var. 3775 |
| 20-150 | Var. 3454 | Var. 3500 | Var. 3546 | Var. 3592 | Var. 3638 | Var. 3684 | Var. 3730 | Var. 3776 |
| 20-125 | Var. 3455 | Var. 3501 | Var. 3547 | Var. 3593 | Var. 3639 | Var. 3685 | Var. 3731 | Var. 3777 |
| 20-100 | Var. 3456 | Var. 3502 | Var. 3548 | Var. 3594 | Var. 3640 | Var. 3686 | Var. 3732 | Var. 3778 |
| 20-90 | Var. 3457 | Var. 3503 | Var. 3549 | Var. 3595 | Var. 3641 | Var. 3687 | Var. 3733 | Var. 3779 |
| 20-80 | Var. 3458 | Var. 3504 | Var. 3550 | Var. 3596 | Var. 3642 | Var. 3688 | Var. 3734 | Var. 3780 |
| 20-70 | Var. 3459 | Var. 3505 | Var. 3551 | Var. 3597 | Var. 3643 | Var. 3689 | Var. 3735 | Var. 3781 |
| 20-60 | Var. 3460 | Var. 3506 | Var. 3552 | Var. 3598 | Var. 3644 | Var. 3690 | Var. 3736 | Var. 3782 |
| 20-50 | Var. 3461 | Var. 3507 | Var. 3553 | Var. 3599 | Var. 3645 | Var. 3691 | Var. 3737 | Var. 3783 |
| 20-40 | Var. 3462 | Var. 3508 | Var. 3554 | Var. 3600 | Var. 3646 | Var. 3692 | Var. 3738 | Var. 3784 |
| 40-150 | Var. 3463 | Var. 3509 | Var. 3555 | Var. 3601 | Var. 3647 | Var. 3693 | Var. 3739 | Var. 3785 |
| 40-125 | Var. 3464 | Var. 3510 | Var. 3556 | Var. 3602 | Var. 3648 | Var. 3694 | Var. 3740 | Var. 3786 |
| 40-100 | Var. 3465 | Var. 3511 | Var. 3557 | Var. 3603 | Var. 3649 | Var. 3695 | Var. 3741 | Var. 3787 |
| 40-90 | Var. 3466 | Var. 3512 | Var. 3558 | Var. 3604 | Var. 3650 | Var. 3696 | Var. 3742 | Var. 3788 |
| 40-80 | Var. 3467 | Var. 3513 | Var. 3559 | Var. 3605 | Var. 3651 | Var. 3697 | Var. 3743 | Var. 3789 |
| 40-70 | Var. 3468 | Var. 3514 | Var. 3560 | Var. 3606 | Var. 3652 | Var. 3698 | Var. 3744 | Var. 3790 |
| 40-60 | Var. 3469 | Var. 3515 | Var. 3561 | Var. 3607 | Var. 3653 | Var. 3699 | Var. 3745 | Var. 3791 |
| 40-50 | Var. 3470 | Var. 3516 | Var. 3562 | Var. 3608 | Var. 3654 | Var. 3700 | Var. 3746 | Var. 3792 |
| 60-150 | Var. 3471 | Var. 3517 | Var. 3563 | Var. 3609 | Var. 3655 | Var. 3701 | Var. 3747 | Var. 3793 |
| 60-125 | Var. 3472 | Var. 3518 | Var. 3564 | Var. 3610 | Var. 3656 | Var. 3702 | Var. 3748 | Var. 3794 |
| 60-100 | Var. 3473 | Var. 3519 | Var. 3565 | Var. 3611 | Var. 3657 | Var. 3703 | Var. 3749 | Var. 3795 |
| 60-90 | Var. 3474 | Var. 3520 | Var. 3566 | Var. 3612 | Var. 3658 | Var. 3704 | Var. 3750 | Var. 3796 |
| 60-80 | Var. 3475 | Var. 3521 | Var. 3567 | Var. 3613 | Var. 3659 | Var. 3705 | Var. 3751 | Var. 3797 |
| 60-70 | Var. 3476 | Var. 3522 | Var. 3568 | Var. 3614 | Var. 3660 | Var. 3706 | Var. 3752 | Var. 3798 |
| 70-150 | Var. 3477 | Var. 3523 | Var. 3569 | Var. 3615 | Var. 3661 | Var. 3707 | Var. 3753 | Var. 3799 |
| 70-125 | Var. 3478 | Var. 3524 | Var. 3570 | Var. 3616 | Var. 3662 | Var. 3708 | Var. 3754 | Var. 3800 |
| 70-100 | Var. 3479 | Var. 3525 | Var. 3571 | Var. 3617 | Var. 3663 | Var. 3709 | Var. 3755 | Var. 3801 |
| 70-90 | Var. 3480 | Var. 3526 | Var. 3572 | Var. 3618 | Var. 3664 | Var. 3710 | Var. 3756 | Var. 3802 |

TABLE 16-continued

Exemplary embodiments for the combination of rVWF specific activity in a composition used herein and increase in FVIII stability achieved, as compared to FVIII stability in a subject administered a composition of pdVWF.

| | | Increased Stability (Hours) | | | | | | | |
|---|---|---|---|---|---|---|---|---|---|
| | | 3-5 hr | 3-4 hr | 4-8 hr | 4-7 hr | 4-6 hr | 4-5 hr | 5-8 hr | 5-7 hr |
| | 70-80 | Var. 3481 | Var. 3527 | Var. 3573 | Var. 3619 | Var. 3665 | Var. 3711 | Var. 3757 | Var. 3803 |
| | 80-150 | Var. 3482 | Var. 3528 | Var. 3574 | Var. 3620 | Var. 3666 | Var. 3712 | Var. 3758 | Var. 3804 |
| | 80-125 | Var. 3483 | Var. 3529 | Var. 3575 | Var. 3621 | Var. 3667 | Var. 3713 | Var. 3759 | Var. 3805 |
| | 80-100 | Var. 3484 | Var. 3530 | Var. 3576 | Var. 3622 | Var. 3668 | Var. 3714 | Var. 3760 | Var. 3806 |
| | 80-90 | Var. 3485 | Var. 3531 | Var. 3577 | Var. 3623 | Var. 3669 | Var. 3715 | Var. 3761 | Var. 3807 |
| | 90-150 | Var. 3486 | Var. 3532 | Var. 3578 | Var. 3624 | Var. 3670 | Var. 3716 | Var. 3762 | Var. 3808 |
| | 90-125 | Var. 3487 | Var. 3533 | Var. 3579 | Var. 3625 | Var. 3671 | Var. 3717 | Var. 3763 | Var. 3809 |
| | 90-100 | Var. 3488 | Var. 3534 | Var. 3580 | Var. 3626 | Var. 3672 | Var. 3718 | Var. 3764 | Var. 3810 |

Var. = Variation

TABLE 17

Exemplary embodiments for the combination of rVWF specific activity in a composition used herein and increase in FVIII stability achieved, as compared to FVIII stability in a subject administered a composition of pdVWF.

| | | Increased Stability (Hours) | | | | Increased Stability (Percent) | | | |
|---|---|---|---|---|---|---|---|---|---|
| | | 5-6 hr | 6-8 hr | 6-7 hr | 7-8 hr | at least 10% | at least 20% | at least 30% | at least 40% |
| (mU/μg) | at least 20 | Var. 3811 | Var. 3857 | Var. 3903 | Var. 3949 | Var. 3995 | Var. 4041 | Var. 4087 | Var. 4133 |
| | at least 30 | Var. 3812 | Var. 3858 | Var. 3904 | Var. 3950 | Var. 3996 | Var. 4042 | Var. 4088 | Var. 4134 |
| | at least 40 | Var. 3813 | Var. 3859 | Var. 3905 | Var. 3951 | Var. 3997 | Var. 4043 | Var. 4089 | Var. 4135 |
| | at least 50 | Var. 3814 | Var. 3860 | Var. 3906 | Var. 3952 | Var. 3998 | Var. 4044 | Var. 4090 | Var. 4136 |
| | at least 60 | Var. 3815 | Var. 3861 | Var. 3907 | Var. 3953 | Var. 3999 | Var. 4045 | Var. 4091 | Var. 4137 |
| | at least 70 | Var. 3816 | Var. 3862 | Var. 3908 | Var. 3954 | Var. 4000 | Var. 4046 | Var. 4092 | Var. 4138 |
| | at least 80 | Var. 3817 | Var. 3863 | Var. 3909 | Var. 3955 | Var. 4001 | Var. 4047 | Var. 4093 | Var. 4139 |
| | at least 90 | Var. 3818 | Var. 3864 | Var. 3910 | Var. 3956 | Var. 4002 | Var. 4048 | Var. 4094 | Var. 4140 |
| | at least 100 | Var. 3819 | Var. 3865 | Var. 3911 | Var. 3957 | Var. 4003 | Var. 4049 | Var. 4095 | Var. 4141 |
| | at least 125 | Var. 3820 | Var. 3866 | Var. 3912 | Var. 3958 | Var. 4004 | Var. 4050 | Var. 4096 | Var. 4142 |
| | at least 150 | Var. 3821 | Var. 3867 | Var. 3913 | Var. 3959 | Var. 4005 | Var. 4051 | Var. 4097 | Var. 4143 |
| | 20-150 | Var. 3822 | Var. 3868 | Var. 3914 | Var. 3960 | Var. 4006 | Var. 4052 | Var. 4098 | Var. 4144 |
| | 20-125 | Var. 3823 | Var. 3869 | Var. 3915 | Var. 3961 | Var. 4007 | Var. 4053 | Var. 4099 | Var. 4145 |
| | 20-100 | Var. 3824 | Var. 3870 | Var. 3916 | Var. 3962 | Var. 4008 | Var. 4054 | Var. 4100 | Var. 4146 |
| | 20-90 | Var. 3825 | Var. 3871 | Var. 3917 | Var. 3963 | Var. 4009 | Var. 4055 | Var. 4101 | Var. 4147 |
| | 20-80 | Var. 3826 | Var. 3872 | Var. 3918 | Var. 3964 | Var. 4010 | Var. 4056 | Var. 4102 | Var. 4148 |
| | 20-70 | Var. 3827 | Var. 3873 | Var. 3919 | Var. 3965 | Var. 4011 | Var. 4057 | Var. 4103 | Var. 4149 |
| | 20-60 | Var. 3828 | Var. 3874 | Var. 3920 | Var. 3966 | Var. 4012 | Var. 4058 | Var. 4104 | Var. 4150 |
| | 20-50 | Var. 3829 | Var. 3875 | Var. 3921 | Var. 3967 | Var. 4013 | Var. 4059 | Var. 4105 | Var. 4151 |

TABLE 17-continued

Exemplary embodiments for the combination of rVWF specific activity in a composition used herein and increase in FVIII stability achieved, as compared to FVIII stability in a subject administered a composition of pdVWF.

|  | Increased Stability (Hours) | | | | Increased Stability (Percent) | | | |
|---|---|---|---|---|---|---|---|---|
|  | 5-6 hr | 6-8 hr | 6-7 hr | 7-8 hr | at least 10% | at least 20% | at least 30% | at least 40% |
| 20-40 | Var. 3830 | Var. 3876 | Var. 3922 | Var. 3968 | Var. 4014 | Var. 4060 | Var. 4106 | Var. 4152 |
| 40-150 | Var. 3831 | Var. 3877 | Var. 3923 | Var. 3969 | Var. 4015 | Var. 4061 | Var. 4107 | Var. 4153 |
| 40-125 | Var. 3832 | Var. 3878 | Var. 3924 | Var. 3970 | Var. 4016 | Var. 4062 | Var. 4108 | Var. 4154 |
| 40-100 | Var. 3833 | Var. 3879 | Var. 3925 | Var. 3971 | Var. 4017 | Var. 4063 | Var. 4109 | Var. 4155 |
| 40-90 | Var. 3834 | Var. 3880 | Var. 3926 | Var. 3972 | Var. 4018 | Var. 4064 | Var. 4110 | Var. 4156 |
| 40-80 | Var. 3835 | Var. 3881 | Var. 3927 | Var. 3973 | Var. 4019 | Var. 4065 | Var. 4111 | Var. 4157 |
| 40-70 | Var. 3836 | Var. 3882 | Var. 3928 | Var. 3974 | Var. 4020 | Var. 4066 | Var. 4112 | Var. 4158 |
| 40-60 | Var. 3837 | Var. 3883 | Var. 3929 | Var. 3975 | Var. 4021 | Var. 4067 | Var. 4113 | Var. 4159 |
| 40-50 | Var. 3838 | Var. 3884 | Var. 3930 | Var. 3976 | Var. 4022 | Var. 4068 | Var. 4114 | Var. 4160 |
| 60-150 | Var. 3839 | Var. 3885 | Var. 3931 | Var. 3977 | Var. 4023 | Var. 4069 | Var. 4115 | Var. 4161 |
| 60-125 | Var. 3840 | Var. 3886 | Var. 3932 | Var. 3978 | Var. 4024 | Var. 4070 | Var. 4116 | Var. 4162 |
| 60-100 | Var. 3841 | Var. 3887 | Var. 3933 | Var. 3979 | Var. 4025 | Var. 4071 | Var. 4117 | Var. 4163 |
| 60-90 | Var. 3842 | Var. 3888 | Var. 3934 | Var. 3980 | Var. 4026 | Var. 4072 | Var. 4118 | Var. 4164 |
| 60-80 | Var. 3843 | Var. 3889 | Var. 3935 | Var. 3981 | Var. 4027 | Var. 4073 | Var. 4119 | Var. 4165 |
| 60-70 | Var. 3844 | Var. 3890 | Var. 3936 | Var. 3982 | Var. 4028 | Var. 4074 | Var. 4120 | Var. 4166 |
| 70-150 | Var. 3845 | Var. 3891 | Var. 3937 | Var. 3983 | Var. 4029 | Var. 4075 | Var. 4121 | Var. 4167 |
| 70-125 | Var. 3846 | Var. 3892 | Var. 3938 | Var. 3984 | Var. 4030 | Var. 4076 | Var. 4122 | Var. 4168 |
| 70-100 | Var. 3847 | Var. 3893 | Var. 3939 | Var. 3985 | Var. 4031 | Var. 4077 | Var. 4123 | Var. 4169 |
| 70-90 | Var. 3848 | Var. 3894 | Var. 3940 | Var. 3986 | Var. 4032 | Var. 4078 | Var. 4124 | Var. 4170 |
| 70-80 | Var. 3849 | Var. 3895 | Var. 3941 | Var. 3987 | Var. 4033 | Var. 4079 | Var. 4125 | Var. 4171 |
| 80-150 | Var. 3850 | Var. 3896 | Var. 3942 | Var. 3988 | Var. 4034 | Var. 4080 | Var. 4126 | Var. 4172 |
| 80-125 | Var. 3851 | Var. 3897 | Var. 3943 | Var. 3989 | Var. 4035 | Var. 4081 | Var. 4127 | Var. 4173 |
| 80-100 | Var. 3852 | Var. 3898 | Var. 3944 | Var. 3990 | Var. 4036 | Var. 4082 | Var. 4128 | Var. 4174 |
| 80-90 | Var. 3853 | Var. 3899 | Var. 3945 | Var. 3991 | Var. 4037 | Var. 4083 | Var. 4129 | Var. 4175 |
| 90-150 | Var. 3854 | Var. 3900 | Var. 3946 | Var. 3992 | Var. 4038 | Var. 4084 | Var. 4130 | Var. 4176 |
| 90-125 | Var. 3855 | Var. 3901 | Var. 3947 | Var. 3993 | Var. 4039 | Var. 4085 | Var. 4131 | Var. 4177 |
| 90-100 | Var. 3856 | Var. 3902 | Var. 3948 | Var. 3994 | Var. 4040 | Var. 4086 | Var. 4132 | Var. 4178 |

Var. = Variation

TABLE 18

Exemplary embodiments for the combination of rVWF specific activity in a composition used herein and increase in FVIII stability achieved, as compared to FVIII stability in a subject administered a composition of pdVWF.

|  |  | Increased Stability (Percent) | | | | | | |
|---|---|---|---|---|---|---|---|---|
|  |  | at least 50% | 10-50% | 10-40% | 10-30% | 10-20% | 15-50% | 15-40% | 15-30% |
| (mU/µg) | at least 20 | Var. 4179 | Var. 4225 | Var. 4271 | Var. 4317 | Var. 4363 | Var. 4409 | Var. 4455 | Var. 4501 |
|  | at least 30 | Var. 4180 | Var. 4226 | Var. 4272 | Var. 4318 | Var. 4364 | Var. 4410 | Var. 4456 | Var. 4502 |
|  | at least 40 | Var. 4181 | Var. 4227 | Var. 4273 | Var. 4319 | Var. 4365 | Var. 4411 | Var. 4457 | Var. 4503 |
|  | at least 50 | Var. 4182 | Var. 4228 | Var. 4274 | Var. 4320 | Var. 4366 | Var. 4412 | Var. 4458 | Var. 4504 |
|  | at least 60 | Var. 4183 | Var. 4229 | Var. 4275 | Var. 4321 | Var. 4367 | Var. 4413 | Var. 4459 | Var. 4505 |
|  | at least 70 | Var. 4184 | Var. 4230 | Var. 4276 | Var. 4322 | Var. 4368 | Var. 4414 | Var. 4460 | Var. 4506 |
|  | at least 80 | Var. 4185 | Var. 4231 | Var. 4277 | Var. 4323 | Var. 4369 | Var. 4415 | Var. 4461 | Var. 4507 |
|  | at least 90 | Var. 4186 | Var. 4232 | Var. 4278 | Var. 4324 | Var. 4370 | Var. 4416 | Var. 4462 | Var. 4508 |
|  | at least 100 | Var. 4187 | Var. 4233 | Var. 4279 | Var. 4325 | Var. 4371 | Var. 4417 | Var. 4463 | Var. 4509 |
|  | at least 125 | Var. 4188 | Var. 4234 | Var. 4280 | Var. 4326 | Var. 4372 | Var. 4418 | Var. 4464 | Var. 4510 |
|  | at least 150 | Var. 4189 | Var. 4235 | Var. 4281 | Var. 4327 | Var. 4373 | Var. 4419 | Var. 4465 | Var. 4511 |
|  | 20-150 | Var. 4190 | Var. 4236 | Var. 4282 | Var. 4328 | Var. 4374 | Var. 4420 | Var. 4466 | Var. 4512 |
|  | 20-125 | Var. 4191 | Var. 4237 | Var. 4283 | Var. 4329 | Var. 4375 | Var. 4421 | Var. 4467 | Var. 4513 |
|  | 20-100 | Var. 4192 | Var. 4238 | Var. 4284 | Var. 4330 | Var. 4376 | Var. 4422 | Var. 4468 | Var. 4514 |
|  | 20-90 | Var. 4193 | Var. 4239 | Var. 4285 | Var. 4331 | Var. 4377 | Var. 4423 | Var. 4469 | Var. 4515 |
|  | 20-80 | Var. 4194 | Var. 4240 | Var. 4286 | Var. 4332 | Var. 4378 | Var. 4424 | Var. 4470 | Var. 4516 |
|  | 20-70 | Var. 4195 | Var. 4241 | Var. 4287 | Var. 4333 | Var. 4379 | Var. 4425 | Var. 4471 | Var. 4517 |
|  | 20-60 | Var. 4196 | Var. 4242 | Var. 4288 | Var. 4334 | Var. 4380 | Var. 4426 | Var. 4472 | Var. 4518 |
|  | 20-50 | Var. 4197 | Var. 4243 | Var. 4289 | Var. 4335 | Var. 4381 | Var. 4427 | Var. 4473 | Var. 4519 |
|  | 20-40 | Var. 4198 | Var. 4244 | Var. 4290 | Var. 4336 | Var. 4382 | Var. 4428 | Var. 4474 | Var. 4520 |
|  | 40-150 | Var. 4199 | Var. 4245 | Var. 4291 | Var. 4337 | Var. 4383 | Var. 4429 | Var. 4475 | Var. 4521 |
|  | 40-125 | Var. 4200 | Var. 4246 | Var. 4292 | Var. 4338 | Var. 4384 | Var. 4430 | Var. 4476 | Var. 4522 |
|  | 40-100 | Var. 4201 | Var. 4247 | Var. 4293 | Var. 4339 | Var. 4385 | Var. 4431 | Var. 4477 | Var. 4523 |
|  | 40-90 | Var. 4202 | Var. 4248 | Var. 4294 | Var. 4340 | Var. 4386 | Var. 4432 | Var. 4478 | Var. 4524 |
|  | 40-80 | Var. 4203 | Var. 4249 | Var. 4295 | Var. 4341 | Var. 4387 | Var. 4433 | Var. 4479 | Var. 4525 |
|  | 40-70 | Var. 4204 | Var. 4250 | Var. 4296 | Var. 4342 | Var. 4388 | Var. 4434 | Var. 4480 | Var. 4526 |
|  | 40-60 | Var. 4205 | Var. 4251 | Var. 4297 | Var. 4343 | Var. 4389 | Var. 4435 | Var. 4481 | Var. 4527 |
|  | 40-50 | Var. 4206 | Var. 4252 | Var. 4298 | Var. 4344 | Var. 4390 | Var. 4436 | Var. 4482 | Var. 4528 |
|  | 60-150 | Var. 4207 | Var. 4253 | Var. 4299 | Var. 4345 | Var. 4391 | Var. 4437 | Var. 4483 | Var. 4529 |
|  | 60-125 | Var. 4208 | Var. 4254 | Var. 4300 | Var. 4346 | Var. 4392 | Var. 4438 | Var. 4484 | Var. 4530 |
|  | 60-100 | Var. 4209 | Var. 4255 | Var. 4301 | Var. 4347 | Var. 4393 | Var. 4439 | Var. 4485 | Var. 4531 |
|  | 60-90 | Var. 4210 | Var. 4256 | Var. 4302 | Var. 4348 | Var. 4394 | Var. 4440 | Var. 4486 | Var. 4532 |
|  | 60-80 | Var. 4211 | Var. 4257 | Var. 4303 | Var. 4349 | Var. 4395 | Var. 4441 | Var. 4487 | Var. 4533 |
|  | 60-70 | Var. 4212 | Var. 4258 | Var. 4304 | Var. 4350 | Var. 4396 | Var. 4442 | Var. 4488 | Var. 4534 |
|  | 70-150 | Var. 4213 | Var. 4259 | Var. 4305 | Var. 4351 | Var. 4397 | Var. 4443 | Var. 4489 | Var. 4535 |
|  | 70-125 | Var. 4214 | Var. 4260 | Var. 4306 | Var. 4352 | Var. 4398 | Var. 4444 | Var. 4490 | Var. 4536 |

TABLE 18-continued

Exemplary embodiments for the combination of rVWF specific activity in a composition used herein and increase in FVIII stability achieved, as compared to FVIII stability in a subject administered a composition of pdVWF.

| | Increased Stability (Percent) | | | | | | | |
|---|---|---|---|---|---|---|---|---|
| | at least 50% | 10-50% | 10-40% | 10-30% | 10-20% | 15-50% | 15-40% | 15-30% |
| 70-100 | Var. 4215 | Var. 4261 | Var. 4307 | Var. 4353 | Var. 4399 | Var. 4445 | Var. 4491 | Var. 4537 |
| 70-90 | Var. 4216 | Var. 4262 | Var. 4308 | Var. 4354 | Var. 4400 | Var. 4446 | Var. 4492 | Var. 4538 |
| 70-80 | Var. 4217 | Var. 4263 | Var. 4309 | Var. 4355 | Var. 4401 | Var. 4447 | Var. 4493 | Var. 4539 |
| 80-150 | Var. 4218 | Var. 4264 | Var. 4310 | Var. 4356 | Var. 4402 | Var. 4448 | Var. 4494 | Var. 4540 |
| 80-125 | Var. 4219 | Var. 4265 | Var. 4311 | Var. 4357 | Var. 4403 | Var. 4449 | Var. 4495 | Var. 4541 |
| 80-100 | Var. 4220 | Var. 4266 | Var. 4312 | Var. 4358 | Var. 4404 | Var. 4450 | Var. 4496 | Var. 4542 |
| 80-90 | Var. 4221 | Var. 4267 | Var. 4313 | Var. 4359 | Var. 4405 | Var. 4451 | Var. 4497 | Var. 4543 |
| 90-150 | Var. 4222 | Var. 4268 | Var. 4314 | Var. 4360 | Var. 4406 | Var. 4452 | Var. 4498 | Var. 4544 |
| 90-125 | Var. 4223 | Var. 4269 | Var. 4315 | Var. 4361 | Var. 4407 | Var. 4453 | Var. 4499 | Var. 4545 |
| 90-100 | Var. 4224 | Var. 4270 | Var. 4316 | Var. 4362 | Var. 4408 | Var. 4454 | Var. 4500 | Var. 4546 |

Var. = Variation

TABLE 19

Exemplary embodiments for the combination of rVWF specific activity in a composition used herein and increase in FVIII stability achieved, as compared to FVIII stability in a subject administered a composition of pdVWF.

| | | Increased Stability (Percent) | | | | | | |
|---|---|---|---|---|---|---|---|---|
| | | 15-20% | 20-50% | 20-40% | 20-30% | 30-50% | 30-40% | 40-50% |
| (mU/µg) | at least 20 | Var. 4547 | Var. 4593 | Var. 4639 | Var. 4685 | Var. 4731 | Var. 4777 | Var. 4823 |
| | at least 30 | Var. 4548 | Var. 4594 | Var. 4640 | Var. 4686 | Var. 4732 | Var. 4778 | Var. 4824 |
| | at least 40 | Var. 4549 | Var. 4595 | Var. 4641 | Var. 4687 | Var. 4733 | Var. 4779 | Var. 4825 |
| | at least 50 | Var. 4550 | Var. 4596 | Var. 4642 | Var. 4688 | Var. 4734 | Var. 4780 | Var. 4826 |
| | at least 60 | Var. 4551 | Var. 4597 | Var. 4643 | Var. 4689 | Var. 4735 | Var. 4781 | Var. 4827 |
| | at least 70 | Var. 4552 | Var. 4598 | Var. 4644 | Var. 4690 | Var. 4736 | Var. 4782 | Var. 4828 |
| | at least 80 | Var. 4553 | Var. 4599 | Var. 4645 | Var. 4691 | Var. 4737 | Var. 4783 | Var. 4829 |
| | at least 90 | Var. 4554 | Var. 4600 | Var. 4646 | Var. 4692 | Var. 4738 | Var. 4784 | Var. 4830 |
| | at least 100 | Var. 4555 | Var. 4601 | Var. 4647 | Var. 4693 | Var. 4739 | Var. 4785 | Var. 4831 |
| | at least 125 | Var. 4556 | Var. 4602 | Var. 4648 | Var. 4694 | Var. 4740 | Var. 4786 | Var. 4832 |
| | at least 150 | Var. 4557 | Var. 4603 | Var. 4649 | Var. 4695 | Var. 4741 | Var. 4787 | Var. 4833 |
| | 20-150 | Var. 4558 | Var. 4604 | Var. 4650 | Var. 4696 | Var. 4742 | Var. 4788 | Var. 4834 |
| | 20-125 | Var. 4559 | Var. 4605 | Var. 4651 | Var. 4697 | Var. 4743 | Var. 4789 | Var. 4835 |
| | 20-100 | Var. 4560 | Var. 4606 | Var. 4652 | Var. 4698 | Var. 4744 | Var. 4790 | Var. 4836 |
| | 20-90 | Var. 4561 | Var. 4607 | Var. 4653 | Var. 4699 | Var. 4745 | Var. 4791 | Var. 4837 |
| | 20-80 | Var. 4562 | Var. 4608 | Var. 4654 | Var. 4700 | Var. 4746 | Var. 4792 | Var. 4838 |
| | 20-70 | Var. 4563 | Var. 4609 | Var. 4655 | Var. 4701 | Var. 4747 | Var. 4793 | Var. 4839 |
| | 20-60 | Var. 4564 | Var. 4610 | Var. 4656 | Var. 4702 | Var. 4748 | Var. 4794 | Var. 4840 |
| | 20-50 | Var. 4565 | Var. 4611 | Var. 4657 | Var. 4703 | Var. 4749 | Var. 4795 | Var. 4841 |
| | 20-40 | Var. 4566 | Var. 4612 | Var. 4658 | Var. 4704 | Var. 4750 | Var. 4796 | Var. 4842 |
| | 40-150 | Var. 4567 | Var. 4613 | Var. 4659 | Var. 4705 | Var. 4751 | Var. 4797 | Var. 4843 |
| | 40-125 | Var. 4568 | Var. 4614 | Var. 4660 | Var. 4706 | Var. 4752 | Var. 4798 | Var. 4844 |
| | 40-100 | Var. 4569 | Var. 4615 | Var. 4661 | Var. 4707 | Var. 4753 | Var. 4799 | Var. 4845 |
| | 40-90 | Var. 4570 | Var. 4616 | Var. 4662 | Var. 4708 | Var. 4754 | Var. 4800 | Var. 4846 |
| | 40-80 | Var. 4571 | Var. 4617 | Var. 4663 | Var. 4709 | Var. 4755 | Var. 4801 | Var. 4847 |
| | 40-70 | Var. 4572 | Var. 4618 | Var. 4664 | Var. 4710 | Var. 4756 | Var. 4802 | Var. 4848 |
| | 40-60 | Var. 4573 | Var. 4619 | Var. 4665 | Var. 4711 | Var. 4757 | Var. 4803 | Var. 4849 |
| | 40-50 | Var. 4574 | Var. 4620 | Var. 4666 | Var. 4712 | Var. 4758 | Var. 4804 | Var. 4850 |
| | 60-150 | Var. 4575 | Var. 4621 | Var. 4667 | Var. 4713 | Var. 4759 | Var. 4805 | Var. 4851 |
| | 60-125 | Var. 4576 | Var. 4622 | Var. 4668 | Var. 4714 | Var. 4760 | Var. 4806 | Var. 4852 |
| | 60-100 | Var. 4577 | Var. 4623 | Var. 4669 | Var. 4715 | Var. 4761 | Var. 4807 | Var. 4853 |
| | 60-90 | Var. 4578 | Var. 4624 | Var. 4670 | Var. 4716 | Var. 4762 | Var. 4808 | Var. 4854 |
| | 60-80 | Var. 4579 | Var. 4625 | Var. 4671 | Var. 4717 | Var. 4763 | Var. 4809 | Var. 4855 |
| | 60-70 | Var. 4580 | Var. 4626 | Var. 4672 | Var. 4718 | Var. 4764 | Var. 4810 | Var. 4856 |
| | 70-150 | Var. 4581 | Var. 4627 | Var. 4673 | Var. 4719 | Var. 4765 | Var. 4811 | Var. 4857 |
| | 70-125 | Var. 4582 | Var. 4628 | Var. 4674 | Var. 4720 | Var. 4766 | Var. 4812 | Var. 4858 |
| | 70-100 | Var. 4583 | Var. 4629 | Var. 4675 | Var. 4721 | Var. 4767 | Var. 4813 | Var. 4859 |

TABLE 19-continued

Exemplary embodiments for the combination of rVWF specific activity in a
composition used herein and increase in FVIII stability achieved, as compared
to FVIII stability in a subject administered a composition of pdVWF.

| | Increased Stability (Percent) | | | | | | |
|---|---|---|---|---|---|---|---|
| | 15-20% | 20-50% | 20-40% | 20-30% | 30-50% | 30-40% | 40-50% |
| 70-90 | Var. 4584 | Var. 4630 | Var. 4676 | Var. 4722 | Var. 4768 | Var. 4814 | Var. 4860 |
| 70-80 | Var. 4585 | Var. 4631 | Var. 4677 | Var. 4723 | Var. 4769 | Var. 4815 | Var. 4861 |
| 80-150 | Var. 4586 | Var. 4632 | Var. 4678 | Var. 4724 | Var. 4770 | Var. 4816 | Var. 4862 |
| 80-125 | Var. 4587 | Var. 4633 | Var. 4679 | Var. 4725 | Var. 4771 | Var. 4817 | Var. 4863 |
| 80-100 | Var. 4588 | Var. 4634 | Var. 4680 | Var. 4726 | Var. 4772 | Var. 4818 | Var. 4864 |
| 80-90 | Var. 4589 | Var. 4635 | Var. 4681 | Var. 4727 | Var. 4773 | Var. 4819 | Var. 4865 |
| 90-150 | Var. 4590 | Var. 4636 | Var. 4682 | Var. 4728 | Var. 4774 | Var. 4820 | Var. 4866 |
| 90-125 | Var. 4591 | Var. 4637 | Var. 4683 | Var. 4729 | Var. 4775 | Var. 4821 | Var. 4867 |
| 90-100 | Var. 4592 | Var. 4638 | Var. 4684 | Var. 4730 | Var. 4776 | Var. 4822 | Var. 4868 |

Var. = Variation

In one embodiment, the method comprises administering a composition of rVWF, wherein the composition of rVWF administered to the subject is a composition of high molecular weight rVWF multimers in which at least 30% of rVWF molecules in the composition are present in a multimer of at least 10 subunits, and wherein the combination of rVWF specific activity in the composition and increase in FVIII stability, as compared to FVIII stability in a subject administered a composition of pdVWF, is selected from variations 2339 to 4868 in Table 13 to Table 19. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers in which at least 50% of rVWF molecules in the composition are present in a multimer of at least 10 subunits, and wherein the combination of rVWF specific activity in the composition and increase in FVIII stability, as compared to FVIII stability in a subject administered a composition of pdVWF, is selected from variations 2339 to 4868 in Table 13 to Table 19. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers in which at least 70% of rVWF molecules in the composition are present in a multimer of at least 10 subunits, and wherein the combination of rVWF specific activity in the composition and increase in FVIII stability, as compared to FVIII stability in a subject administered a composition of pdVWF, is selected from variations 2339 to 4868 in Table 13 to Table 19. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers having a minimal percentage of rVWF molecules present in a particular higher-order rVWF multimer or larger multimer according to any one of variations 134 to 457 found in Table 3 to Table 5, and wherein the combination of rVWF specific activity in the composition and increase in FVIII stability, as compared to FVIII stability in a subject administered a composition of pdVWF, is selected from variations 2339 to 4868 in Table 13 to Table 19. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a dosage of a rVWF composition containing from 10 IU/kg to 40 IU/kg rVWF:RCo activity, wherein the combination of rVWF specific activity in the composition and increase in FVIII stability, as compared to FVIII stability in a subject administered a composition of pdVWF, is selected from variations 2339 to 4868 in Table 13 to Table 19. In a specific embodiment, the composition contains from 20 IU/kg to 30 IU/kg rVWF:RCo activity. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a dosage of a rVWF composition containing from 25 IU/kg to 75 IU/kg rVWF:RCo activity, wherein the combination of rVWF specific activity in the composition and increase in FVIII stability, as compared to FVIII stability in a subject administered a composition of pdVWF, is selected from variations 2339 to 4868 in Table 13 to Table 19. In a specific embodiment, the composition contains from 40 IU/kg to 60 IU/kg rVWF:RCo activity. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a dosage of a rVWF composition containing from 75 IU/kg to 125 IU/kg rVWF:RCo activity, wherein the combination of rVWF specific activity in the composition and increase in FVIII stability, as compared to FVIII stability in a subject administered a composition of pdVWF, is selected from variations 2339 to 4868 in Table 13 to Table 19. In a specific embodiment, the composition contains from 75 IU/kg to 100 IU/kg rVWF:RCo activity. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the subject is administered a dose of rVWF selected from variations 2141 to 2338 in Table 12, and wherein the combination of rVWF specific activity in the composition and increase in FVIII stability, as compared to FVIII stability in a subject administered a composition of pdVWF, is selected from variations 2339 to 4868 in Table 13 to Table 19. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject is a composition of high molecular weight rVWF multimers. In one embodiment, the composition of rVWF administered to the subject has a higher specific activity than a composition of pdVWF. In yet another embodiment, the composition of rVWF administered to the subject is a composition of high molecular weight rVWF multimers with a higher specific activity than a composition of pdVWF. In one embodiment. FVIII stability is characterized by the half life of FVIII. In another embodiment, FVIII stability is characterized by mean residence time (MRT) of FVIII. In a further embodiment, the method is for treating any type of VWD. In a specific emobidment, the method is for treating Type 3 VWD.

TABLE 20

Exemplary embodiments for the combination of rVWF dosage and increase in FVIII stability achieved, as compared to FVIII stability in a subject administered a composition of pdVWF.

| | | Increased Stability (Hours) | | | | | | |
|---|---|---|---|---|---|---|---|---|
| | | at least 1 hr | at least 2 hr | at least 3 hr | at least 4 hr | at least 5 hr | at least 6 hr | at least 7 hr |
| Dosage (IU/kg rVWF: RCo activity) | 0.5-200 | Var. 4869 | Var. 4926 | Var. 4983 | Var. 5040 | Var. 5097 | Var. 5154 | Var. 5211 |
| | 0.5-150 | Var. 4870 | Var. 4927 | Var. 4984 | Var. 5041 | Var. 5098 | Var. 5155 | Var. 5212 |
| | 0.5-100 | Var. 4871 | Var. 4928 | Var. 4985 | Var. 5042 | Var. 5099 | Var. 5156 | Var. 5213 |
| | 0.5-75 | Var. 4872 | Var. 4929 | Var. 4986 | Var. 5043 | Var. 5100 | Var. 5157 | Var. 5214 |
| | 0.5-50 | Var. 4873 | Var. 4930 | Var. 4987 | Var. 5044 | Var. 5101 | Var. 5158 | Var. 5215 |
| | 0.5-25 | Var. 4874 | Var. 4931 | Var. 4988 | Var. 5045 | Var. 5102 | Var. 5159 | Var. 5216 |
| | 0.5-10 | Var. 4875 | Var. 4932 | Var. 4989 | Var. 5046 | Var. 5103 | Var. 5160 | Var. 5217 |
| | 0.5-5 | Var. 4876 | Var. 4933 | Var. 4990 | Var. 5047 | Var. 5104 | Var. 5161 | Var. 5218 |
| | 0.5-2.5 | Var. 4877 | Var. 4934 | Var. 4991 | Var. 5048 | Var. 5105 | Var. 5162 | Var. 5219 |
| | 0.5-1 | Var. 4878 | Var. 4935 | Var. 4992 | Var. 5049 | Var. 5106 | Var. 5163 | Var. 5220 |
| | 2.5-200 | Var. 4879 | Var. 4936 | Var. 4993 | Var. 5050 | Var. 5107 | Var. 5164 | Var. 5221 |
| | 2.5-150 | Var. 4880 | Var. 4937 | Var. 4994 | Var. 5051 | Var. 5108 | Var. 5165 | Var. 5222 |
| | 2.5-100 | Var. 4881 | Var. 4938 | Var. 4995 | Var. 5052 | Var. 5109 | Var. 5166 | Var. 5223 |
| | 2.5-75 | Var. 4882 | Var. 4939 | Var. 4996 | Var. 5053 | Var. 5110 | Var. 5167 | Var. 5224 |
| | 2.5-50 | Var. 4883 | Var. 4940 | Var. 4997 | Var. 5054 | Var. 5111 | Var. 5168 | Var. 5225 |
| | 2.5-25 | Var. 4884 | Var. 4941 | Var. 4998 | Var. 5055 | Var. 5112 | Var. 5169 | Var. 5226 |
| | 2.5-10 | Var. 4885 | Var. 4942 | Var. 4999 | Var. 5056 | Var. 5113 | Var. 5170 | Var. 5227 |
| | 2.5-5 | Var. 4886 | Var. 4943 | Var. 5000 | Var. 5057 | Var. 5114 | Var. 5171 | Var. 5228 |
| | 5-200 | Var. 4887 | Var. 4944 | Var. 5001 | Var. 5058 | Var. 5115 | Var. 5172 | Var. 5229 |
| | 5-175 | Var. 4888 | Var. 4945 | Var. 5002 | Var. 5059 | Var. 5116 | Var. 5173 | Var. 5230 |
| | 5-150 | Var. 4889 | Var. 4946 | Var. 5003 | Var. 5060 | Var. 5117 | Var. 5174 | Var. 5231 |
| | 5-125 | Var. 4890 | Var. 4947 | Var. 5004 | Var. 5061 | Var. 5118 | Var. 5175 | Var. 5232 |
| | 5-100 | Var. 4891 | Var. 4948 | Var. 5005 | Var. 5062 | Var. 5119 | Var. 5176 | Var. 5233 |
| | 5-75 | Var. 4892 | Var. 4949 | Var. 5006 | Var. 5063 | Var. 5120 | Var. 5177 | Var. 5234 |
| | 5-50 | Var. 4893 | Var. 4950 | Var. 5007 | Var. 5064 | Var. 5121 | Var. 5178 | Var. 5235 |
| | 5-25 | Var. 4894 | Var. 4951 | Var. 5008 | Var. 5065 | Var. 5122 | Var. 5179 | Var. 5236 |
| | 5-10 | Var. 4895 | Var. 4952 | Var. 5009 | Var. 5066 | Var. 5123 | Var. 5180 | Var. 5237 |
| | 10-200 | Var. 4896 | Var. 4953 | Var. 5010 | Var. 5067 | Var. 5124 | Var. 5181 | Var. 5238 |
| | 10-150 | Var. 4897 | Var. 4954 | Var. 5011 | Var. 5068 | Var. 5125 | Var. 5182 | Var. 5239 |
| | 10-100 | Var. 4898 | Var. 4955 | Var. 5012 | Var. 5069 | Var. 5126 | Var. 5183 | Var. 5240 |
| | 10-75 | Var. 4899 | Var. 4956 | Var. 5013 | Var. 5070 | Var. 5127 | Var. 5184 | Var. 5241 |
| | 10-50 | Var. 4900 | Var. 4957 | Var. 5014 | Var. 5071 | Var. 5128 | Var. 5185 | Var. 5242 |
| | 10-25 | Var. 4901 | Var. 4958 | Var. 5015 | Var. 5072 | Var. 5129 | Var. 5186 | Var. 5243 |
| | 25-200 | Var. 4902 | Var. 4959 | Var. 5016 | Var. 5073 | Var. 5130 | Var. 5187 | Var. 5244 |
| | 25-150 | Var. 4903 | Var. 4960 | Var. 5017 | Var. 5074 | Var. 5131 | Var. 5188 | Var. 5245 |

TABLE 20-continued

Exemplary embodiments for the combination of rVWF dosage and increase in FVIII stability achieved, as compared to FVIII stability in a subject administered a composition of pdVWF.

| | Increased Stability (Hours) | | | | | | |
|---|---|---|---|---|---|---|---|
| | at least 1 hr | at least 2 hr | at least 3 hr | at least 4 hr | at least 5 hr | at least 6 hr | at least 7 hr |
| 25-100 | Var. 4904 | Var. 4961 | Var. 5018 | Var. 5075 | Var. 5132 | Var. 5189 | Var. 5246 |
| 25-75 | Var. 4905 | Var. 4962 | Var. 5019 | Var. 5076 | Var. 5133 | Var. 5190 | Var. 5247 |
| 25-50 | Var. 4906 | Var. 4963 | Var. 5020 | Var. 5077 | Var. 5134 | Var. 5191 | Var. 5248 |
| 50-200 | Var. 4907 | Var. 4964 | Var. 5021 | Var. 5078 | Var. 5135 | Var. 5192 | Var. 5249 |
| 50-150 | Var. 4908 | Var. 4965 | Var. 5022 | Var. 5079 | Var. 5136 | Var. 5193 | Var. 5250 |
| 50-100 | Var. 4909 | Var. 4966 | Var. 5023 | Var. 5080 | Var. 5137 | Var. 5194 | Var. 5251 |
| 50-75 | Var. 4910 | Var. 4967 | Var. 5024 | Var. 5081 | Var. 5138 | Var. 5195 | Var. 5252 |
| 75-200 | Var. 4911 | Var. 4968 | Var. 5025 | Var. 5082 | Var. 5139 | Var. 5196 | Var. 5253 |
| 75-175 | Var. 4912 | Var. 4969 | Var. 5026 | Var. 5083 | Var. 5140 | Var. 5197 | Var. 5254 |
| 75-150 | Var. 4913 | Var. 4970 | Var. 5027 | Var. 5084 | Var. 5141 | Var. 5198 | Var. 5255 |
| 75-125 | Var. 4914 | Var. 4971 | Var. 5028 | Var. 5085 | Var. 5142 | Var. 5199 | Var. 5256 |
| 75-100 | Var. 4915 | Var. 4972 | Var. 5029 | Var. 5086 | Var. 5143 | Var. 5200 | Var. 5257 |
| 100-200 | Var. 4916 | Var. 4973 | Var. 5030 | Var. 5087 | Var. 5144 | Var. 5201 | Var. 5258 |
| 100-175 | Var. 4917 | Var. 4974 | Var. 5031 | Var. 5088 | Var. 5145 | Var. 5202 | Var. 5259 |
| 100-150 | Var. 4918 | Var. 4975 | Var. 5032 | Var. 5089 | Var. 5146 | Var. 5203 | Var. 5260 |
| 100-125 | Var. 4919 | Var. 4976 | Var. 5033 | Var. 5090 | Var. 5147 | Var. 5204 | Var. 5261 |
| 125-200 | Var. 4920 | Var. 4977 | Var. 5034 | Var. 5091 | Var. 5148 | Var. 5205 | Var. 5262 |
| 125-175 | Var. 4921 | Var. 4978 | Var. 5035 | Var. 5092 | Var. 5149 | Var. 5206 | Var. 5263 |
| 125-150 | Var. 4922 | Var. 4979 | Var. 5036 | Var. 5093 | Var. 5150 | Var. 5207 | Var. 5264 |
| 150-200 | Var. 4923 | Var. 4980 | Var. 5037 | Var. 5094 | Var. 5151 | Var. 5208 | Var. 5265 |
| 150-200 | Var. 4924 | Var. 4981 | Var. 5038 | Var. 5095 | Var. 5152 | Var. 5209 | Var. 5266 |
| 175-200 | Var. 4925 | Var. 4982 | Var. 5039 | Var. 5096 | Var. 5153 | Var. 5210 | Var. 5267 |

Var. = Variation

TABLE 21

Exemplary embodiments for the combination of rVWF dosage and increase in FVIII stability achieved, as compared to FVIII stability in a subject administered a composition of pdVWF.

| | | Increased Stability (Hours) | | | | | | |
|---|---|---|---|---|---|---|---|---|
| | | at least 8 hr | 1-8 hr | 1-7 hr | 1-6 hr | 1-5 hr | 1-4 hr | 1-3 hr |
| Dosage (IU/kg rVWF: RCo activity) | 0.5-200 | Var. 5268 | Var. 5325 | Var. 5382 | Var. 5439 | Var. 5496 | Var. 5553 | Var. 5610 |
| | 0.5-150 | Var. 5269 | Var. 5326 | Var. 5383 | Var. 5440 | Var. 5497 | Var. 5554 | Var. 5611 |
| | 0.5-100 | Var. 5270 | Var. 5327 | Var. 5384 | Var. 5441 | Var. 5498 | Var. 5555 | Var. 5612 |
| | 0.5-75 | Var. 5271 | Var. 5328 | Var. 5385 | Var. 5442 | Var. 5499 | Var. 5556 | Var. 5613 |
| | 0.5-50 | Var. 5272 | Var. 5329 | Var. 5386 | Var. 5443 | Var. 5500 | Var. 5557 | Var. 5614 |
| | 0.5-25 | Var. 5273 | Var. 5330 | Var. 5387 | Var. 5444 | Var. 5501 | Var. 5558 | Var. 5615 |
| | 0.5-10 | Var. 5274 | Var. 5331 | Var. 5388 | Var. 5445 | Var. 5502 | Var. 5559 | Var. 5616 |
| | 0.5-5 | Var. 5275 | Var. 5332 | Var. 5389 | Var. 5446 | Var. 5503 | Var. 5560 | Var. 5617 |
| | 0.5-2.5 | Var. 5276 | Var. 5333 | Var. 5390 | Var. 5447 | Var. 5504 | Var. 5561 | Var. 5618 |
| | 0.5-1 | Var. 5277 | Var. 5334 | Var. 5391 | Var. 5448 | Var. 5505 | Var. 5562 | Var. 5619 |
| | 2.5-200 | Var. 5278 | Var. 5335 | Var. 5392 | Var. 5449 | Var. 5506 | Var. 5563 | Var. 5620 |
| | 2.5-150 | Var. 5279 | Var. 5336 | Var. 5393 | Var. 5450 | Var. 5507 | Var. 5564 | Var. 5621 |
| | 2.5-100 | Var. 5280 | Var. 5337 | Var. 5394 | Var. 5451 | Var. 5508 | Var. 5565 | Var. 5622 |
| | 2.5-75 | Var. 5281 | Var. 5338 | Var. 5395 | Var. 5452 | Var. 5509 | Var. 5566 | Var. 5623 |
| | 2.5-50 | Var. 5282 | Var. 5339 | Var. 5396 | Var. 5453 | Var. 5510 | Var. 5567 | Var. 5624 |
| | 2.5-25 | Var. 5283 | Var. 5340 | Var. 5397 | Var. 5454 | Var. 5511 | Var. 5568 | Var. 5625 |
| | 2.5-10 | Var. 5284 | Var. 5341 | Var. 5398 | Var. 5455 | Var. 5512 | Var. 5569 | Var. 5626 |
| | 2.5-5 | Var. 5285 | Var. 5342 | Var. 5399 | Var. 5456 | Var. 5513 | Var. 5570 | Var. 5627 |
| | 5-200 | Var. 5286 | Var. 5343 | Var. 5400 | Var. 5457 | Var. 5514 | Var. 5571 | Var. 5628 |
| | 5-175 | Var. 5287 | Var. 5344 | Var. 5401 | Var. 5458 | Var. 5515 | Var. 5572 | Var. 5629 |
| | 5-150 | Var. 5288 | Var. 5345 | Var. 5402 | Var. 5459 | Var. 5516 | Var. 5573 | Var. 5630 |
| | 5-125 | Var. 5289 | Var. 5346 | Var. 5403 | Var. 5460 | Var. 5517 | Var. 5574 | Var. 5631 |
| | 5-100 | Var. 5290 | Var. 5347 | Var. 5404 | Var. 5461 | Var. 5518 | Var. 5575 | Var. 5632 |
| | 5-75 | Var. 5291 | Var. 5348 | Var. 5405 | Var. 5462 | Var. 5519 | Var. 5576 | Var. 5633 |
| | 5-50 | Var. 5292 | Var. 5349 | Var. 5406 | Var. 5463 | Var. 5520 | Var. 5577 | Var. 5634 |
| | 5-25 | Var. 5293 | Var. 5350 | Var. 5407 | Var. 5464 | Var. 5521 | Var. 5578 | Var. 5635 |
| | 5-10 | Var. 5294 | Var. 5351 | Var. 5408 | Var. 5465 | Var. 5522 | Var. 5579 | Var. 5636 |
| | 10-200 | Var. 5295 | Var. 5352 | Var. 5409 | Var. 5466 | Var. 5523 | Var. 5580 | Var. 5637 |
| | 10-150 | Var. 5296 | Var. 5353 | Var. 5410 | Var. 5467 | Var. 5524 | Var. 5581 | Var. 5638 |
| | 10-100 | Var. 5297 | Var. 5354 | Var. 5411 | Var. 5468 | Var. 5525 | Var. 5582 | Var. 5639 |
| | 10-75 | Var. 5298 | Var. 5355 | Var. 5412 | Var. 5469 | Var. 5526 | Var. 5583 | Var. 5640 |
| | 10-50 | Var. 5299 | Var. 5356 | Var. 5413 | Var. 5470 | Var. 5527 | Var. 5584 | Var. 5641 |
| | 10-25 | Var. 5300 | Var. 5357 | Var. 5414 | Var. 5471 | Var. 5528 | Var. 5585 | Var. 5642 |
| | 25-200 | Var. 5301 | Var. 5358 | Var. 5415 | Var. 5472 | Var. 5529 | Var. 5586 | Var. 5643 |
| | 25-150 | Var. 5302 | Var. 5359 | Var. 5416 | Var. 5473 | Var. 5530 | Var. 5587 | Var. 5644 |
| | 25-100 | Var. 5303 | Var. 5360 | Var. 5417 | Var. 5474 | Var. 5531 | Var. 5588 | Var. 5645 |
| | 25-75 | Var. 5304 | Var. 5361 | Var. 5418 | Var. 5475 | Var. 5532 | Var. 5589 | Var. 5646 |

TABLE 21-continued

Exemplary embodiments for the combination of rVWF dosage and increase in FVIII
stability achieved, as compared to FVIII stability in a subject administered a composition of pdVWF.

| | | Increased Stability (Hours) | | | | | | |
|---|---|---|---|---|---|---|---|---|
| | | at least 8 hr | 1-8 hr | 1-7 hr | 1-6 hr | 1-5 hr | 1-4 hr | 1-3 hr |
| | 25-50 | Var. 5305 | Var. 5362 | Var. 5419 | Var. 5476 | Var. 5533 | Var. 5590 | Var. 5647 |
| | 50-200 | Var. 5306 | Var. 5363 | Var. 5420 | Var. 5477 | Var. 5534 | Var. 5591 | Var. 5648 |
| | 50-150 | Var. 5307 | Var. 5364 | Var. 5421 | Var. 5478 | Var. 5535 | Var. 5592 | Var. 5649 |
| | 50-100 | Var. 5308 | Var. 5365 | Var. 5422 | Var. 5479 | Var. 5536 | Var. 5593 | Var. 5650 |
| | 50-75 | Var. 5309 | Var. 5366 | Var. 5423 | Var. 5480 | Var. 5537 | Var. 5594 | Var. 5651 |
| | 75-200 | Var. 5310 | Var. 5367 | Var. 5424 | Var. 5481 | Var. 5538 | Var. 5595 | Var. 5652 |
| | 75-175 | Var. 5311 | Var. 5368 | Var. 5425 | Var. 5482 | Var. 5539 | Var. 5596 | Var. 5653 |
| | 75-150 | Var. 5312 | Var. 5369 | Var. 5426 | Var. 5483 | Var. 5540 | Var. 5597 | Var. 5654 |
| | 75-125 | Var. 5313 | Var. 5370 | Var. 5427 | Var. 5484 | Var. 5541 | Var. 5598 | Var. 5655 |
| | 75-100 | Var. 5314 | Var. 5371 | Var. 5428 | Var. 5485 | Var. 5542 | Var. 5599 | Var. 5656 |
| | 100-200 | Var. 5315 | Var. 5372 | Var. 5429 | Var. 5486 | Var. 5543 | Var. 5600 | Var. 5657 |
| | 100-175 | Var. 5316 | Var. 5373 | Var. 5430 | Var. 5487 | Var. 5544 | Var. 5601 | Var. 5658 |
| | 100-150 | Var. 5317 | Var. 5374 | Var. 5431 | Var. 5488 | Var. 5545 | Var. 5602 | Var. 5659 |
| | 100-125 | Var. 5318 | Var. 5375 | Var. 5432 | Var. 5489 | Var. 5546 | Var. 5603 | Var. 5660 |
| | 125-200 | Var. 5319 | Var. 5376 | Var. 5433 | Var. 5490 | Var. 5547 | Var. 5604 | Var. 5661 |
| | 125-175 | Var. 5320 | Var. 5377 | Var. 5434 | Var. 5491 | Var. 5548 | Var. 5605 | Var. 5662 |
| | 125-150 | Var. 5321 | Var. 5378 | Var. 5435 | Var. 5492 | Var. 5549 | Var. 5606 | Var. 5663 |
| | 150-200 | Var. 5322 | Var. 5379 | Var. 5436 | Var. 5493 | Var. 5550 | Var. 5607 | Var. 5664 |
| | 150-200 | Var. 5323 | Var. 5380 | Var. 5437 | Var. 5494 | Var. 5551 | Var. 5608 | Var. 5665 |
| | 175-200 | Var. 5324 | Var. 5381 | Var. 5438 | Var. 5495 | Var. 5552 | Var. 5609 | Var. 5666 |

Var. = Variation

TABLE 22

Exemplary embodiments for the combination of rVWF dosage and increase in FVIII
stability achieved, as compared to FVIII stability in a subject administered a composition of pdVWF.

| | | Increased Stability (Hours) | | | | | | |
|---|---|---|---|---|---|---|---|---|
| | | 1-2 hr | 2-8 hr | 2-7 hr | 2-6 hr | 2-5 hr | 2-4 hr | 2-3 hr |
| Dosage (IU/kg rVWF: RCo activity) | 0.5-200 | Var. 5667 | Var. 5724 | Var. 5781 | Var. 5838 | Var. 5895 | Var. 5952 | Var. 6009 |
| | 0.5-150 | Var. 5668 | Var. 5725 | Var. 5782 | Var. 5839 | Var. 5896 | Var. 5953 | Var. 6010 |
| | 0.5-100 | Var. 5669 | Var. 5726 | Var. 5783 | Var. 5840 | Var. 5897 | Var. 5954 | Var. 6011 |
| | 0.5-75 | Var. 5670 | Var. 5727 | Var. 5784 | Var. 5841 | Var. 5898 | Var. 5955 | Var. 6012 |
| | 0.5-50 | Var. 5671 | Var. 5728 | Var. 5785 | Var. 5842 | Var. 5899 | Var. 5956 | Var. 6013 |
| | 0.5-25 | Var. 5672 | Var. 5729 | Var. 5786 | Var. 5843 | Var. 5900 | Var. 5957 | Var. 6014 |
| | 0.5-10 | Var. 5673 | Var. 5730 | Var. 5787 | Var. 5844 | Var. 5901 | Var. 5958 | Var. 6015 |
| | 0.5-5 | Var. 5674 | Var. 5731 | Var. 5788 | Var. 5845 | Var. 5902 | Var. 5959 | Var. 6016 |
| | 0.5-2.5 | Var. 5675 | Var. 5732 | Var. 5789 | Var. 5846 | Var. 5903 | Var. 5960 | Var. 6017 |
| | 0.5-1 | Var. 5676 | Var. 5733 | Var. 5790 | Var. 5847 | Var. 5904 | Var. 5961 | Var. 6018 |
| | 2.5-200 | Var. 5677 | Var. 5734 | Var. 5791 | Var. 5848 | Var. 5905 | Var. 5962 | Var. 6019 |
| | 2.5-150 | Var. 5678 | Var. 5735 | Var. 5792 | Var. 5849 | Var. 5906 | Var. 5963 | Var. 6020 |
| | 2.5-100 | Var. 5679 | Var. 5736 | Var. 5793 | Var. 5850 | Var. 5907 | Var. 5964 | Var. 6021 |
| | 2.5-75 | Var. 5680 | Var. 5737 | Var. 5794 | Var. 5851 | Var. 5908 | Var. 5965 | Var. 6022 |
| | 2.5-50 | Var. 5681 | Var. 5738 | Var. 5795 | Var. 5852 | Var. 5909 | Var. 5966 | Var. 6023 |
| | 2.5-25 | Var. 5682 | Var. 5739 | Var. 5796 | Var. 5853 | Var. 5910 | Var. 5967 | Var. 6024 |
| | 2.5-10 | Var. 5683 | Var. 5740 | Var. 5797 | Var. 5854 | Var. 5911 | Var. 5968 | Var. 6025 |
| | 2.5-5 | Var. 5684 | Var. 5741 | Var. 5798 | Var. 5855 | Var. 5912 | Var. 5969 | Var. 6026 |
| | 5-200 | Var. 5685 | Var. 5742 | Var. 5799 | Var. 5856 | Var. 5913 | Var. 5970 | Var. 6027 |
| | 5-175 | Var. 5686 | Var. 5743 | Var. 5800 | Var. 5857 | Var. 5914 | Var. 5971 | Var. 6028 |
| | 5-150 | Var. 5687 | Var. 5744 | Var. 5801 | Var. 5858 | Var. 5915 | Var. 5972 | Var. 6029 |
| | 5-125 | Var. 5688 | Var. 5745 | Var. 5802 | Var. 5859 | Var. 5916 | Var. 5973 | Var. 6030 |
| | 5-100 | Var. 5689 | Var. 5746 | Var. 5803 | Var. 5860 | Var. 5917 | Var. 5974 | Var. 6031 |
| | 5-75 | Var. 5690 | Var. 5747 | Var. 5804 | Var. 5861 | Var. 5918 | Var. 5975 | Var. 6032 |
| | 5-50 | Var. 5691 | Var. 5748 | Var. 5805 | Var. 5862 | Var. 5919 | Var. 5976 | Var. 6033 |
| | 5-25 | Var. 5692 | Var. 5749 | Var. 5806 | Var. 5863 | Var. 5920 | Var. 5977 | Var. 6034 |
| | 5-10 | Var. 5693 | Var. 5750 | Var. 5807 | Var. 5864 | Var. 5921 | Var. 5978 | Var. 6035 |
| | 10-200 | Var. 5694 | Var. 5751 | Var. 5808 | Var. 5865 | Var. 5922 | Var. 5979 | Var. 6036 |
| | 10-150 | Var. 5695 | Var. 5752 | Var. 5809 | Var. 5866 | Var. 5923 | Var. 5980 | Var. 6037 |
| | 10-100 | Var. 5696 | Var. 5753 | Var. 5810 | Var. 5867 | Var. 5924 | Var. 5981 | Var. 6038 |
| | 10-75 | Var. 5697 | Var. 5754 | Var. 5811 | Var. 5868 | Var. 5925 | Var. 5982 | Var. 6039 |
| | 10-50 | Var. 5698 | Var. 5755 | Var. 5812 | Var. 5869 | Var. 5926 | Var. 5983 | Var. 6040 |
| | 10-25 | Var. 5699 | Var. 5756 | Var. 5813 | Var. 5870 | Var. 5927 | Var. 5984 | Var. 6041 |
| | 25-200 | Var. 5700 | Var. 5757 | Var. 5814 | Var. 5871 | Var. 5928 | Var. 5985 | Var. 6042 |
| | 25-150 | Var. 5701 | Var. 5758 | Var. 5815 | Var. 5872 | Var. 5929 | Var. 5986 | Var. 6043 |
| | 25-100 | Var. 5702 | Var. 5759 | Var. 5816 | Var. 5873 | Var. 5930 | Var. 5987 | Var. 6044 |
| | 25-75 | Var. 5703 | Var. 5760 | Var. 5817 | Var. 5874 | Var. 5931 | Var. 5988 | Var. 6045 |
| | 25-50 | Var. 5704 | Var. 5761 | Var. 5818 | Var. 5875 | Var. 5932 | Var. 5989 | Var. 6046 |
| | 50-200 | Var. 5705 | Var. 5762 | Var. 5819 | Var. 5876 | Var. 5933 | Var. 5990 | Var. 6047 |

TABLE 22-continued

Exemplary embodiments for the combination of rVWF dosage and increase in FVIII stability achieved, as compared to FVIII stability in a subject administered a composition of pdVWF.

| | Increased Stability (Hours) | | | | | | |
|---|---|---|---|---|---|---|---|
| | 1-2 hr | 2-8 hr | 2-7 hr | 2-6 hr | 2-5 hr | 2-4 hr | 2-3 hr |
| 50-150 | Var. 5706 | Var. 5763 | Var. 5820 | Var. 5877 | Var. 5934 | Var. 5991 | Var. 6048 |
| 50-100 | Var. 5707 | Var. 5764 | Var. 5821 | Var. 5878 | Var. 5935 | Var. 5992 | Var. 6049 |
| 50-75 | Var. 5708 | Var. 5765 | Var. 5822 | Var. 5879 | Var. 5936 | Var. 5993 | Var. 6050 |
| 75-200 | Var. 5709 | Var. 5766 | Var. 5823 | Var. 5880 | Var. 5937 | Var. 5994 | Var. 6051 |
| 75-175 | Var. 5710 | Var. 5767 | Var. 5824 | Var. 5881 | Var. 5938 | Var. 5995 | Var. 6052 |
| 75-150 | Var. 5711 | Var. 5768 | Var. 5825 | Var. 5882 | Var. 5939 | Var. 5996 | Var. 6053 |
| 75-125 | Var. 5712 | Var. 5769 | Var. 5826 | Var. 5883 | Var. 5940 | Var. 5997 | Var. 6054 |
| 75-100 | Var. 5713 | Var. 5770 | Var. 5827 | Var. 5884 | Var. 5941 | Var. 5998 | Var. 6055 |
| 100-200 | Var. 5714 | Var. 5771 | Var. 5828 | Var. 5885 | Var. 5942 | Var. 5999 | Var. 6056 |
| 100-175 | Var. 5715 | Var. 5772 | Var. 5829 | Var. 5886 | Var. 5943 | Var. 6000 | Var. 6057 |
| 100-150 | Var. 5716 | Var. 5773 | Var. 5830 | Var. 5887 | Var. 5944 | Var. 6001 | Var. 6058 |
| 100-125 | Var. 5717 | Var. 5774 | Var. 5831 | Var. 5888 | Var. 5945 | Var. 6002 | Var. 6059 |
| 125-200 | Var. 5718 | Var. 5775 | Var. 5832 | Var. 5889 | Var. 5946 | Var. 6003 | Var. 6060 |
| 125-175 | Var. 5719 | Var. 5776 | Var. 5833 | Var. 5890 | Var. 5947 | Var. 6004 | Var. 6061 |
| 125-150 | Var. 5720 | Var. 5777 | Var. 5834 | Var. 5891 | Var. 5948 | Var. 6005 | Var. 6062 |
| 150-200 | Var. 5721 | Var. 5778 | Var. 5835 | Var. 5892 | Var. 5949 | Var. 6006 | Var. 6063 |
| 150-200 | Var. 5722 | Var. 5779 | Var. 5836 | Var. 5893 | Var. 5950 | Var. 6007 | Var. 6064 |
| 175-200 | Var. 5723 | Var. 5780 | Var. 5837 | Var. 5894 | Var. 5951 | Var. 6008 | Var. 6065 |

Var. = Variation

TABLE 23

Exemplary embodiments for the combination of rVWF dosage and increase in FVIII stability achieved, as compared to FVIII stability in a subject administered a composition of pdVWF.

| | | Increased Stability (Hours) | | | | | | |
|---|---|---|---|---|---|---|---|---|
| | | 3-8 hr | 3-7 hr | 3-6 hr | 3-5 hr | 3-4 hr | 4-8 hr | 4-7 hr |
| Dosage (IU/kg rVWF:RCo activity) | 0.5-200 | Var. 6066 | Var. 6123 | Var. 6180 | Var. 6237 | Var. 6294 | Var. 6351 | Var. 6408 |
| | 0.5-150 | Var. 6067 | Var. 6124 | Var. 6181 | Var. 6238 | Var. 6295 | Var. 6352 | Var. 6409 |
| | 0.5-100 | Var. 6068 | Var. 6125 | Var. 6182 | Var. 6239 | Var. 6296 | Var. 6353 | Var. 6410 |
| | 0.5-75 | Var. 6069 | Var. 6126 | Var. 6183 | Var. 6240 | Var. 6297 | Var. 6354 | Var. 6411 |
| | 0.5-50 | Var. 6070 | Var. 6127 | Var. 6184 | Var. 6241 | Var. 6298 | Var. 6355 | Var. 6412 |
| | 0.5-25 | Var. 6071 | Var. 6128 | Var. 6185 | Var. 6242 | Var. 6299 | Var. 6356 | Var. 6413 |
| | 0.5-10 | Var. 6072 | Var. 6129 | Var. 6186 | Var. 6243 | Var. 6300 | Var. 6357 | Var. 6414 |
| | 0.5-5 | Var. 6073 | Var. 6130 | Var. 6187 | Var. 6244 | Var. 6301 | Var. 6358 | Var. 6415 |
| | 0.5-2.5 | Var. 6074 | Var. 6131 | Var. 6188 | Var. 6245 | Var. 6302 | Var. 6359 | Var. 6416 |
| | 0.5-1 | Var. 6075 | Var. 6132 | Var. 6189 | Var. 6246 | Var. 6303 | Var. 6360 | Var. 6417 |
| | 2.5-200 | Var. 6076 | Var. 6133 | Var. 6190 | Var. 6247 | Var. 6304 | Var. 6361 | Var. 6418 |
| | 2.5-150 | Var. 6077 | Var. 6134 | Var. 6191 | Var. 6248 | Var. 6305 | Var. 6362 | Var. 6419 |
| | 2.5-100 | Var. 6078 | Var. 6135 | Var. 6192 | Var. 6249 | Var. 6306 | Var. 6363 | Var. 6420 |
| | 2.5-75 | Var. 6079 | Var. 6136 | Var. 6193 | Var. 6250 | Var. 6307 | Var. 6364 | Var. 6421 |
| | 2.5-50 | Var. 6080 | Var. 6137 | Var. 6194 | Var. 6251 | Var. 6308 | Var. 6365 | Var. 6422 |
| | 2.5-25 | Var. 6081 | Var. 6138 | Var. 6195 | Var. 6252 | Var. 6309 | Var. 6366 | Var. 6423 |
| | 2.5-10 | Var. 6082 | Var. 6139 | Var. 6196 | Var. 6253 | Var. 6310 | Var. 6367 | Var. 6424 |
| | 2.5-5 | Var. 6083 | Var. 6140 | Var. 6197 | Var. 6254 | Var. 6311 | Var. 6368 | Var. 6425 |
| | 5-200 | Var. 6084 | Var. 6141 | Var. 6198 | Var. 6255 | Var. 6312 | Var. 6369 | Var. 6426 |
| | 5-175 | Var. 6085 | Var. 6142 | Var. 6199 | Var. 6256 | Var. 6313 | Var. 6370 | Var. 6427 |
| | 5-150 | Var. 6086 | Var. 6143 | Var. 6200 | Var. 6257 | Var. 6314 | Var. 6371 | Var. 6428 |
| | 5-125 | Var. 6087 | Var. 6144 | Var. 6201 | Var. 6258 | Var. 6315 | Var. 6372 | Var. 6429 |
| | 5-100 | Var. 6088 | Var. 6145 | Var. 6202 | Var. 6259 | Var. 6316 | Var. 6373 | Var. 6430 |
| | 5-75 | Var. 6089 | Var. 6146 | Var. 6203 | Var. 6260 | Var. 6317 | Var. 6374 | Var. 6431 |
| | 5-50 | Var. 6090 | Var. 6147 | Var. 6204 | Var. 6261 | Var. 6318 | Var. 6375 | Var. 6432 |
| | 5-25 | Var. 6091 | Var. 6148 | Var. 6205 | Var. 6262 | Var. 6319 | Var. 6376 | Var. 6433 |
| | 5-10 | Var. 6092 | Var. 6149 | Var. 6206 | Var. 6263 | Var. 6320 | Var. 6377 | Var. 6434 |
| | 10-200 | Var. 6093 | Var. 6150 | Var. 6207 | Var. 6264 | Var. 6321 | Var. 6378 | Var. 6435 |
| | 10-150 | Var. 6094 | Var. 6151 | Var. 6208 | Var. 6265 | Var. 6322 | Var. 6379 | Var. 6436 |
| | 10-100 | Var. 6095 | Var. 6152 | Var. 6209 | Var. 6266 | Var. 6323 | Var. 6380 | Var. 6437 |
| | 10-75 | Var. 6096 | Var. 6153 | Var. 6210 | Var. 6267 | Var. 6324 | Var. 6381 | Var. 6438 |
| | 10-50 | Var. 6097 | Var. 6154 | Var. 6211 | Var. 6268 | Var. 6325 | Var. 6382 | Var. 6439 |
| | 10-25 | Var. 6098 | Var. 6155 | Var. 6212 | Var. 6269 | Var. 6326 | Var. 6383 | Var. 6440 |
| | 25-200 | Var. 6099 | Var. 6156 | Var. 6213 | Var. 6270 | Var. 6327 | Var. 6384 | Var. 6441 |
| | 25-150 | Var. 6100 | Var. 6157 | Var. 6214 | Var. 6271 | Var. 6328 | Var. 6385 | Var. 6442 |
| | 25-100 | Var. 6101 | Var. 6158 | Var. 6215 | Var. 6272 | Var. 6329 | Var. 6386 | Var. 6443 |
| | 25-75 | Var. 6102 | Var. 6159 | Var. 6216 | Var. 6273 | Var. 6330 | Var. 6387 | Var. 6444 |
| | 25-50 | Var. 6103 | Var. 6160 | Var. 6217 | Var. 6274 | Var. 6331 | Var. 6388 | Var. 6445 |
| | 50-200 | Var. 6104 | Var. 6161 | Var. 6218 | Var. 6275 | Var. 6332 | Var. 6389 | Var. 6446 |
| | 50-150 | Var. 6105 | Var. 6162 | Var. 6219 | Var. 6276 | Var. 6333 | Var. 6390 | Var. 6447 |
| | 50-100 | Var. 6106 | Var. 6163 | Var. 6220 | Var. 6277 | Var. 6334 | Var. 6391 | Var. 6448 |

TABLE 23-continued

Exemplary embodiments for the combination of rVWF dosage and increase in FVIII stability achieved, as compared to FVIII stability in a subject administered a composition of pdVWF.

| | | Increased Stability (Hours) | | | | | | |
|---|---|---|---|---|---|---|---|---|
| | | 3-8 hr | 3-7 hr | 3-6 hr | 3-5 hr | 3-4 hr | 4-8 hr | 4-7 hr |
| | 50-75 | Var. 6107 | Var. 6164 | Var. 6221 | Var. 6278 | Var. 6335 | Var. 6392 | Var. 6449 |
| | 75-200 | Var. 6108 | Var. 6165 | Var. 6222 | Var. 6279 | Var. 6336 | Var. 6393 | Var. 6450 |
| | 75-175 | Var. 6109 | Var. 6166 | Var. 6223 | Var. 6280 | Var. 6337 | Var. 6394 | Var. 6451 |
| | 75-150 | Var. 6110 | Var. 6167 | Var. 6224 | Var. 6281 | Var. 6338 | Var. 6395 | Var. 6452 |
| | 75-125 | Var. 6111 | Var. 6168 | Var. 6225 | Var. 6282 | Var. 6339 | Var. 6396 | Var. 6453 |
| | 75-100 | Var. 6112 | Var. 6169 | Var. 6226 | Var. 6283 | Var. 6340 | Var. 6397 | Var. 6454 |
| | 100-200 | Var. 6113 | Var. 6170 | Var. 6227 | Var. 6284 | Var. 6341 | Var. 6398 | Var. 6455 |
| | 100-175 | Var. 6114 | Var. 6171 | Var. 6228 | Var. 6285 | Var. 6342 | Var. 6399 | Var. 6456 |
| | 100-150 | Var. 6115 | Var. 6172 | Var. 6229 | Var. 6286 | Var. 6343 | Var. 6400 | Var. 6457 |
| | 100-125 | Var. 6116 | Var. 6173 | Var. 6230 | Var. 6287 | Var. 6344 | Var. 6401 | Var. 6458 |
| | 125-200 | Var. 6117 | Var. 6174 | Var. 6231 | Var. 6288 | Var. 6345 | Var. 6402 | Var. 6459 |
| | 125-175 | Var. 6118 | Var. 6175 | Var. 6232 | Var. 6289 | Var. 6346 | Var. 6403 | Var. 6460 |
| | 125-150 | Var. 6119 | Var. 6176 | Var. 6233 | Var. 6290 | Var. 6347 | Var. 6404 | Var. 6461 |
| | 150-200 | Var. 6120 | Var. 6177 | Var. 6234 | Var. 6291 | Var. 6348 | Var. 6405 | Var. 6462 |
| | 150-200 | Var. 6121 | Var. 6178 | Var. 6235 | Var. 6292 | Var. 6349 | Var. 6406 | Var. 6463 |
| | 175-200 | Var. 6122 | Var. 6179 | Var. 6236 | Var. 6293 | Var. 6350 | Var. 6407 | Var. 6464 |

Var. = Variation

TABLE 24

Exemplary embodiments for the combination of rVWF dosage and increase in FVIII stability achieved, as compared to FVIII stability in a subject administered a composition of pdVWF.

| | | Increased Stability (Hours) | | | | | | |
|---|---|---|---|---|---|---|---|---|
| | | 4-6 hr | 4-5 hr | 5-8 hr | 5-7 hr | 5-6 hr | 6-8 hr | 6-7 hr |
| Dosage | 0.5-200 | Var. 6465 | Var. 6522 | Var. 6579 | Var. 6636 | Var. 6693 | Var. 6750 | Var. 6807 |
| (IU/kg rVWF:RCo | 0.5-150 | Var. 6466 | Var. 6523 | Var. 6580 | Var. 6637 | Var. 6694 | Var. 6751 | Var. 6808 |
| activity) | 0.5-100 | Var. 6467 | Var. 6524 | Var. 6581 | Var. 6638 | Var. 6695 | Var. 6752 | Var. 6809 |
| | 0.5-75 | Var. 6468 | Var. 6525 | Var. 6582 | Var. 6639 | Var. 6696 | Var. 6753 | Var. 6810 |
| | 0.5-50 | Var. 6469 | Var. 6526 | Var. 6583 | Var. 6640 | Var. 6697 | Var. 6754 | Var. 6811 |
| | 0.5-25 | Var. 6470 | Var. 6527 | Var. 6584 | Var. 6641 | Var. 6698 | Var. 6755 | Var. 6812 |
| | 0.5-10 | Var. 6471 | Var. 6528 | Var. 6585 | Var. 6642 | Var. 6699 | Var. 6756 | Var. 6813 |
| | 0.5-5 | Var. 6472 | Var. 6529 | Var. 6586 | Var. 6643 | Var. 6700 | Var. 6757 | Var. 6814 |
| | 0.5-2.5 | Var. 6473 | Var. 6530 | Var. 6587 | Var. 6644 | Var. 6701 | Var. 6758 | Var. 6815 |
| | 0.5-1 | Var. 6474 | Var. 6531 | Var. 6588 | Var. 6645 | Var. 6702 | Var. 6759 | Var. 6816 |
| | 2.5-200 | Var. 6475 | Var. 6532 | Var. 6589 | Var. 6646 | Var. 6703 | Var. 6760 | Var. 6817 |
| | 2.5-150 | Var. 6476 | Var. 6533 | Var. 6590 | Var. 6647 | Var. 6704 | Var. 6761 | Var. 6818 |
| | 2.5-100 | Var. 6477 | Var. 6534 | Var. 6591 | Var. 6648 | Var. 6705 | Var. 6762 | Var. 6819 |
| | 2.5-75 | Var. 6478 | Var. 6535 | Var. 6592 | Var. 6649 | Var. 6706 | Var. 6763 | Var. 6820 |
| | 2.5-50 | Var. 6479 | Var. 6536 | Var. 6593 | Var. 6650 | Var. 6707 | Var. 6764 | Var. 6821 |
| | 2.5-25 | Var. 6480 | Var. 6537 | Var. 6594 | Var. 6651 | Var. 6708 | Var. 6765 | Var. 6822 |
| | 2.5-10 | Var. 6481 | Var. 6538 | Var. 6595 | Var. 6652 | Var. 6709 | Var. 6766 | Var. 6823 |
| | 2.5-5 | Var. 6482 | Var. 6539 | Var. 6596 | Var. 6653 | Var. 6710 | Var. 6767 | Var. 6824 |
| | 5-200 | Var. 6483 | Var. 6540 | Var. 6597 | Var. 6654 | Var. 6711 | Var. 6768 | Var. 6825 |
| | 5-175 | Var. 6484 | Var. 6541 | Var. 6598 | Var. 6655 | Var. 6712 | Var. 6769 | Var. 6826 |
| | 5-150 | Var. 6485 | Var. 6542 | Var. 6599 | Var. 6656 | Var. 6713 | Var. 6770 | Var. 6827 |
| | 5-125 | Var. 6486 | Var. 6543 | Var. 6600 | Var. 6657 | Var. 6714 | Var. 6771 | Var. 6828 |
| | 5-100 | Var. 6487 | Var. 6544 | Var. 6601 | Var. 6658 | Var. 6715 | Var. 6772 | Var. 6829 |
| | 5-75 | Var. 6488 | Var. 6545 | Var. 6602 | Var. 6659 | Var. 6716 | Var. 6773 | Var. 6830 |
| | 5-50 | Var. 6489 | Var. 6546 | Var. 6603 | Var. 6660 | Var. 6717 | Var. 6774 | Var. 6831 |
| | 5-25 | Var. 6490 | Var. 6547 | Var. 6604 | Var. 6661 | Var. 6718 | Var. 6775 | Var. 6832 |
| | 5-10 | Var. 6491 | Var. 6548 | Var. 6605 | Var. 6662 | Var. 6719 | Var. 6776 | Var. 6833 |
| | 10-200 | Var. 6492 | Var. 6549 | Var. 6606 | Var. 6663 | Var. 6720 | Var. 6777 | Var. 6834 |
| | 10-150 | Var. 6493 | Var. 6550 | Var. 6607 | Var. 6664 | Var. 6721 | Var. 6778 | Var. 6835 |
| | 10-100 | Var. 6494 | Var. 6551 | Var. 6608 | Var. 6665 | Var. 6722 | Var. 6779 | Var. 6836 |
| | 10-75 | Var. 6495 | Var. 6552 | Var. 6609 | Var. 6666 | Var. 6723 | Var. 6780 | Var. 6837 |
| | 10-50 | Var. 6496 | Var. 6553 | Var. 6610 | Var. 6667 | Var. 6724 | Var. 6781 | Var. 6838 |
| | 10-25 | Var. 6497 | Var. 6554 | Var. 6611 | Var. 6668 | Var. 6725 | Var. 6782 | Var. 6839 |
| | 25-200 | Var. 6498 | Var. 6555 | Var. 6612 | Var. 6669 | Var. 6726 | Var. 6783 | Var. 6840 |
| | 25-150 | Var. 6499 | Var. 6556 | Var. 6613 | Var. 6670 | Var. 6727 | Var. 6784 | Var. 6841 |
| | 25-100 | Var. 6500 | Var. 6557 | Var. 6614 | Var. 6671 | Var. 6728 | Var. 6785 | Var. 6842 |
| | 25-75 | Var. 6501 | Var. 6558 | Var. 6615 | Var. 6672 | Var. 6729 | Var. 6786 | Var. 6843 |
| | 25-50 | Var. 6502 | Var. 6559 | Var. 6616 | Var. 6673 | Var. 6730 | Var. 6787 | Var. 6844 |
| | 50-200 | Var. 6503 | Var. 6560 | Var. 6617 | Var. 6674 | Var. 6731 | Var. 6788 | Var. 6845 |
| | 50-150 | Var. 6504 | Var. 6561 | Var. 6618 | Var. 6675 | Var. 6732 | Var. 6789 | Var. 6846 |
| | 50-100 | Var. 6505 | Var. 6562 | Var. 6619 | Var. 6676 | Var. 6733 | Var. 6790 | Var. 6847 |
| | 50-75 | Var. 6506 | Var. 6563 | Var. 6620 | Var. 6677 | Var. 6734 | Var. 6791 | Var. 6848 |
| | 75-200 | Var. 6507 | Var. 6564 | Var. 6621 | Var. 6678 | Var. 6735 | Var. 6792 | Var. 6849 |

TABLE 24-continued

Exemplary embodiments for the combination of rVWF dosage and increase in FVIII stability achieved, as compared to FVIII stability in a subject administered a composition of pdVWF.

| | | Increased Stability (Hours) | | | | | | |
|---|---|---|---|---|---|---|---|---|
| | | 4-6 hr | 4-5 hr | 5-8 hr | 5-7 hr | 5-6 hr | 6-8 hr | 6-7 hr |
| | 75-175 | Var. 6508 | Var. 6565 | Var. 6622 | Var. 6679 | Var. 6736 | Var. 6793 | Var. 6850 |
| | 75-150 | Var. 6509 | Var. 6566 | Var. 6623 | Var. 6680 | Var. 6737 | Var. 6794 | Var. 6851 |
| | 75-125 | Var. 6510 | Var. 6567 | Var. 6624 | Var. 6681 | Var. 6738 | Var. 6795 | Var. 6852 |
| | 75-100 | Var. 6511 | Var. 6568 | Var. 6625 | Var. 6682 | Var. 6739 | Var. 6796 | Var. 6853 |
| | 100-200 | Var. 6512 | Var. 6569 | Var. 6626 | Var. 6683 | Var. 6740 | Var. 6797 | Var. 6854 |
| | 100-175 | Var. 6513 | Var. 6570 | Var. 6627 | Var. 6684 | Var. 6741 | Var. 6798 | Var. 6855 |
| | 100-150 | Var. 6514 | Var. 6571 | Var. 6628 | Var. 6685 | Var. 6742 | Var. 6799 | Var. 6856 |
| | 100-125 | Var. 6515 | Var. 6572 | Var. 6629 | Var. 6686 | Var. 6743 | Var. 6800 | Var. 6857 |
| | 125-200 | Var. 6516 | Var. 6573 | Var. 6630 | Var. 6687 | Var. 6744 | Var. 6801 | Var. 6858 |
| | 125-175 | Var. 6517 | Var. 6574 | Var. 6631 | Var. 6688 | Var. 6745 | Var. 6802 | Var. 6859 |
| | 125-150 | Var. 6518 | Var. 6575 | Var. 6632 | Var. 6689 | Var. 6746 | Var. 6803 | Var. 6860 |
| | 150-200 | Var. 6519 | Var. 6576 | Var. 6633 | Var. 6690 | Var. 6747 | Var. 6804 | Var. 6861 |
| | 150-200 | Var. 6520 | Var. 6577 | Var. 6634 | Var. 6691 | Var. 6748 | Var. 6805 | Var. 6862 |
| | 175-200 | Var. 6521 | Var. 6578 | Var. 6635 | Var. 6692 | Var. 6749 | Var. 6806 | Var. 6863 |

Var. = Variation

TABLE 25

Exemplary embodiments for the combination of rVWF dosage and increase in FVIII stability achieved, as compared to FVIII stability in a subject administered a composition of pdVWF.

| | | Increased Stability (Hours/Percent) | | | | | | |
|---|---|---|---|---|---|---|---|---|
| | | 7-8 hr | at least 10% | at least 20% | at least 30% | at least 40% | at least 50% | 10-50% |
| Dosage (IU/kg rVWF:RCo activity) | 0.5-200 | Var. 6864 | Var. 6921 | Var. 6978 | Var. 7035 | Var. 7092 | Var. 7149 | Var. 7206 |
| | 0.5-150 | Var. 6865 | Var. 6922 | Var. 6979 | Var. 7036 | Var. 7093 | Var. 7150 | Var. 7207 |
| | 0.5-100 | Var. 6866 | Var. 6923 | Var. 6980 | Var. 7037 | Var. 7094 | Var. 7151 | Var. 7208 |
| | 0.5-75 | Var. 6867 | Var. 6924 | Var. 6981 | Var. 7038 | Var. 7095 | Var. 7152 | Var. 7209 |
| | 0.5-50 | Var. 6868 | Var. 6925 | Var. 6982 | Var. 7039 | Var. 7096 | Var. 7153 | Var. 7210 |
| | 0.5-25 | Var. 6869 | Var. 6926 | Var. 6983 | Var. 7040 | Var. 7097 | Var. 7154 | Var. 7211 |
| | 0.5-10 | Var. 6870 | Var. 6927 | Var. 6984 | Var. 7041 | Var. 7098 | Var. 7155 | Var. 7212 |
| | 0.5-5 | Var. 6871 | Var. 6928 | Var. 6985 | Var. 7042 | Var. 7099 | Var. 7156 | Var. 7213 |
| | 0.5-2.5 | Var. 6872 | Var. 6929 | Var. 6986 | Var. 7043 | Var. 7100 | Var. 7157 | Var. 7214 |
| | 0.5-1 | Var. 6873 | Var. 6930 | Var. 6987 | Var. 7044 | Var. 7101 | Var. 7158 | Var. 7215 |
| | 2.5-200 | Var. 6874 | Var. 6931 | Var. 6988 | Var. 7045 | Var. 7102 | Var. 7159 | Var. 7216 |
| | 2.5-150 | Var. 6875 | Var. 6932 | Var. 6989 | Var. 7046 | Var. 7103 | Var. 7160 | Var. 7217 |
| | 2.5-100 | Var. 6876 | Var. 6933 | Var. 6990 | Var. 7047 | Var. 7104 | Var. 7161 | Var. 7218 |
| | 2.5-75 | Var. 6877 | Var. 6934 | Var. 6991 | Var. 7048 | Var. 7105 | Var. 7162 | Var. 7219 |
| | 2.5-50 | Var. 6878 | Var. 6935 | Var. 6992 | Var. 7049 | Var. 7106 | Var. 7163 | Var. 7220 |
| | 2.5-25 | Var. 6879 | Var. 6936 | Var. 6993 | Var. 7050 | Var. 7107 | Var. 7164 | Var. 7221 |
| | 2.5-10 | Var. 6880 | Var. 6937 | Var. 6994 | Var. 7051 | Var. 7108 | Var. 7165 | Var. 7222 |
| | 2.5-5 | Var. 6881 | Var. 6938 | Var. 6995 | Var. 7052 | Var. 7109 | Var. 7166 | Var. 7223 |
| | 5-200 | Var. 6882 | Var. 6939 | Var. 6996 | Var. 7053 | Var. 7110 | Var. 7167 | Var. 7224 |
| | 5-175 | Var. 6883 | Var. 6940 | Var. 6997 | Var. 7054 | Var. 7111 | Var. 7168 | Var. 7225 |
| | 5-150 | Var. 6884 | Var. 6941 | Var. 6998 | Var. 7055 | Var. 7112 | Var. 7169 | Var. 7226 |
| | 5-125 | Var. 6885 | Var. 6942 | Var. 6999 | Var. 7056 | Var. 7113 | Var. 7170 | Var. 7227 |
| | 5-100 | Var. 6886 | Var. 6943 | Var. 7000 | Var. 7057 | Var. 7114 | Var. 7171 | Var. 7228 |
| | 5-75 | Var. 6887 | Var. 6944 | Var. 7001 | Var. 7058 | Var. 7115 | Var. 7172 | Var. 7229 |
| | 5-50 | Var. 6888 | Var. 6945 | Var. 7002 | Var. 7059 | Var. 7116 | Var. 7173 | Var. 7230 |
| | 5-25 | Var. 6889 | Var. 6946 | Var. 7003 | Var. 7060 | Var. 7117 | Var. 7174 | Var. 7231 |
| | 5-10 | Var. 6890 | Var. 6947 | Var. 7004 | Var. 7061 | Var. 7118 | Var. 7175 | Var. 7232 |
| | 10-200 | Var. 6891 | Var. 6948 | Var. 7005 | Var. 7062 | Var. 7119 | Var. 7176 | Var. 7233 |
| | 10-150 | Var. 6892 | Var. 6949 | Var. 7006 | Var. 7063 | Var. 7120 | Var. 7177 | Var. 7234 |
| | 10-100 | Var. 6893 | Var. 6950 | Var. 7007 | Var. 7064 | Var. 7121 | Var. 7178 | Var. 7235 |
| | 10-75 | Var. 6894 | Var. 6951 | Var. 7008 | Var. 7065 | Var. 7122 | Var. 7179 | Var. 7236 |
| | 10-50 | Var. 6895 | Var. 6952 | Var. 7009 | Var. 7066 | Var. 7123 | Var. 7180 | Var. 7237 |
| | 10-25 | Var. 6896 | Var. 6953 | Var. 7010 | Var. 7067 | Var. 7124 | Var. 7181 | Var. 7238 |
| | 25-200 | Var. 6897 | Var. 6954 | Var. 7011 | Var. 7068 | Var. 7125 | Var. 7182 | Var. 7239 |
| | 25-150 | Var. 6898 | Var. 6955 | Var. 7012 | Var. 7069 | Var. 7126 | Var. 7183 | Var. 7240 |
| | 25-100 | Var. 6899 | Var. 6956 | Var. 7013 | Var. 7070 | Var. 7127 | Var. 7184 | Var. 7241 |
| | 25-75 | Var. 6900 | Var. 6957 | Var. 7014 | Var. 7071 | Var. 7128 | Var. 7185 | Var. 7242 |
| | 25-50 | Var. 6901 | Var. 6958 | Var. 7015 | Var. 7072 | Var. 7129 | Var. 7186 | Var. 7243 |
| | 50-200 | Var. 6902 | Var. 6959 | Var. 7016 | Var. 7073 | Var. 7130 | Var. 7187 | Var. 7244 |
| | 50-150 | Var. 6903 | Var. 6960 | Var. 7017 | Var. 7074 | Var. 7131 | Var. 7188 | Var. 7245 |
| | 50-100 | Var. 6904 | Var. 6961 | Var. 7018 | Var. 7075 | Var. 7132 | Var. 7189 | Var. 7246 |
| | 50-75 | Var. 6905 | Var. 6962 | Var. 7019 | Var. 7076 | Var. 7133 | Var. 7190 | Var. 7247 |
| | 75-200 | Var. 6906 | Var. 6963 | Var. 7020 | Var. 7077 | Var. 7134 | Var. 7191 | Var. 7248 |
| | 75-175 | Var. 6907 | Var. 6964 | Var. 7021 | Var. 7078 | Var. 7135 | Var. 7192 | Var. 7249 |

TABLE 25-continued

Exemplary embodiments for the combination of rVWF dosage and increase in FVIII stability achieved, as compared to FVIII stability in a subject administered a composition of pdVWF.

| | | Increased Stability (Hours/Percent) | | | | | |
|---|---|---|---|---|---|---|---|
| | | 7-8 hr | at least 10% | at least 20% | at least 30% | at least 40% | at least 50% | 10-50% |
| | 75-150 | Var. 6908 | Var. 6965 | Var. 7022 | Var. 7079 | Var. 7136 | Var. 7193 | Var. 7250 |
| | 75-125 | Var. 6909 | Var. 6966 | Var. 7023 | Var. 7080 | Var. 7137 | Var. 7194 | Var. 7251 |
| | 75-100 | Var. 6910 | Var. 6967 | Var. 7024 | Var. 7081 | Var. 7138 | Var. 7195 | Var. 7252 |
| | 100-200 | Var. 6911 | Var. 6968 | Var. 7025 | Var. 7082 | Var. 7139 | Var. 7196 | Var. 7253 |
| | 100-175 | Var. 6912 | Var. 6969 | Var. 7026 | Var. 7083 | Var. 7140 | Var. 7197 | Var. 7254 |
| | 100-150 | Var. 6913 | Var. 6970 | Var. 7027 | Var. 7084 | Var. 7141 | Var. 7198 | Var. 7255 |
| | 100-125 | Var. 6914 | Var. 6971 | Var. 7028 | Var. 7085 | Var. 7142 | Var. 7199 | Var. 7256 |
| | 125-200 | Var. 6915 | Var. 6972 | Var. 7029 | Var. 7086 | Var. 7143 | Var. 7200 | Var. 7257 |
| | 125-175 | Var. 6916 | Var. 6973 | Var. 7030 | Var. 7087 | Var. 7144 | Var. 7201 | Var. 7258 |
| | 125-150 | Var. 6917 | Var. 6974 | Var. 7031 | Var. 7088 | Var. 7145 | Var. 7202 | Var. 7259 |
| | 150-200 | Var. 6918 | Var. 6975 | Var. 7032 | Var. 7089 | Var. 7146 | Var. 7203 | Var. 7260 |
| | 150-200 | Var. 6919 | Var. 6976 | Var. 7033 | Var. 7090 | Var. 7147 | Var. 7204 | Var. 7261 |
| | 175-200 | Var. 6920 | Var. 6977 | Var. 7034 | Var. 7091 | Var. 7148 | Var. 7205 | Var. 7262 |

Var. = Variation

TABLE 26

Exemplary embodiments for the combination of rVWF dosage and increase in FVIII stability achieved, as compared to FVIII stability in a subject administered a composition of pdVWF.

| | | Increased Stability (Percent) | | | | | | |
|---|---|---|---|---|---|---|---|---|
| | | 10-40% | 10-30% | 10-20% | 15-50% | 15-40% | 15-30% | 15-20% |
| Dosage (IU/kg rVWF:RCo activity) | 0.5-200 | Var. 7263 | Var. 7320 | Var. 7377 | Var. 7434 | Var. 7491 | Var. 7548 | Var. 7605 |
| | 0.5-150 | Var. 7264 | Var. 7321 | Var. 7378 | Var. 7435 | Var. 7492 | Var. 7549 | Var. 7606 |
| | 0.5-100 | Var. 7265 | Var. 7322 | Var. 7379 | Var. 7436 | Var. 7493 | Var. 7550 | Var. 7607 |
| | 0.5-75 | Var. 7266 | Var. 7323 | Var. 7380 | Var. 7437 | Var. 7494 | Var. 7551 | Var. 7608 |
| | 0.5-50 | Var. 7267 | Var. 7324 | Var. 7381 | Var. 7438 | Var. 7495 | Var. 7552 | Var. 7609 |
| | 0.5-25 | Var. 7268 | Var. 7325 | Var. 7382 | Var. 7439 | Var. 7496 | Var. 7553 | Var. 7610 |
| | 0.5-10 | Var. 7269 | Var. 7326 | Var. 7383 | Var. 7440 | Var. 7497 | Var. 7554 | Var. 7611 |
| | 0.5-5 | Var. 7270 | Var. 7327 | Var. 7384 | Var. 7441 | Var. 7498 | Var. 7555 | Var. 7612 |
| | 0.5-2.5 | Var. 7271 | Var. 7328 | Var. 7385 | Var. 7442 | Var. 7499 | Var. 7556 | Var. 7613 |
| | 0.5-1 | Var. 7272 | Var. 7329 | Var. 7386 | Var. 7443 | Var. 7500 | Var. 7557 | Var. 7614 |
| | 2.5-200 | Var. 7273 | Var. 7330 | Var. 7387 | Var. 7444 | Var. 7501 | Var. 7558 | Var. 7615 |
| | 2.5-150 | Var. 7274 | Var. 7331 | Var. 7388 | Var. 7445 | Var. 7502 | Var. 7559 | Var. 7616 |
| | 2.5-100 | Var. 7275 | Var. 7332 | Var. 7389 | Var. 7446 | Var. 7503 | Var. 7560 | Var. 7617 |
| | 2.5-75 | Var. 7276 | Var. 7333 | Var. 7390 | Var. 7447 | Var. 7504 | Var. 7561 | Var. 7618 |
| | 2.5-50 | Var. 7277 | Var. 7334 | Var. 7391 | Var. 7448 | Var. 7505 | Var. 7562 | Var. 7619 |
| | 2.5-25 | Var. 7278 | Var. 7335 | Var. 7392 | Var. 7449 | Var. 7506 | Var. 7563 | Var. 7620 |
| | 2.5-10 | Var. 7279 | Var. 7336 | Var. 7393 | Var. 7450 | Var. 7507 | Var. 7564 | Var. 7621 |
| | 2.5-5 | Var. 7280 | Var. 7337 | Var. 7394 | Var. 7451 | Var. 7508 | Var. 7565 | Var. 7622 |
| | 5-200 | Var. 7281 | Var. 7338 | Var. 7395 | Var. 7452 | Var. 7509 | Var. 7566 | Var. 7623 |
| | 5-175 | Var. 7282 | Var. 7339 | Var. 7396 | Var. 7453 | Var. 7510 | Var. 7567 | Var. 7624 |
| | 5-150 | Var. 7283 | Var. 7340 | Var. 7397 | Var. 7454 | Var. 7511 | Var. 7568 | Var. 7625 |
| | 5-125 | Var. 7284 | Var. 7341 | Var. 7398 | Var. 7455 | Var. 7512 | Var. 7569 | Var. 7626 |
| | 5-100 | Var. 7285 | Var. 7342 | Var. 7399 | Var. 7456 | Var. 7513 | Var. 7570 | Var. 7627 |
| | 5-75 | Var. 7286 | Var. 7343 | Var. 7400 | Var. 7457 | Var. 7514 | Var. 7571 | Var. 7628 |
| | 5-50 | Var. 7287 | Var. 7344 | Var. 7401 | Var. 7458 | Var. 7515 | Var. 7572 | Var. 7629 |
| | 5-25 | Var. 7288 | Var. 7345 | Var. 7402 | Var. 7459 | Var. 7516 | Var. 7573 | Var. 7630 |
| | 5-10 | Var. 7289 | Var. 7346 | Var. 7403 | Var. 7460 | Var. 7517 | Var. 7574 | Var. 7631 |
| | 10-200 | Var. 7290 | Var. 7347 | Var. 7404 | Var. 7461 | Var. 7518 | Var. 7575 | Var. 7632 |
| | 10-150 | Var. 7291 | Var. 7348 | Var. 7405 | Var. 7462 | Var. 7519 | Var. 7576 | Var. 7633 |
| | 10-100 | Var. 7292 | Var. 7349 | Var. 7406 | Var. 7463 | Var. 7520 | Var. 7577 | Var. 7634 |
| | 10-75 | Var. 7293 | Var. 7350 | Var. 7407 | Var. 7464 | Var. 7521 | Var. 7578 | Var. 7635 |
| | 10-50 | Var. 7294 | Var. 7351 | Var. 7408 | Var. 7465 | Var. 7522 | Var. 7579 | Var. 7636 |
| | 10-25 | Var. 7295 | Var. 7352 | Var. 7409 | Var. 7466 | Var. 7523 | Var. 7580 | Var. 7637 |
| | 25-200 | Var. 7296 | Var. 7353 | Var. 7410 | Var. 7467 | Var. 7524 | Var. 7581 | Var. 7638 |
| | 25-150 | Var. 7297 | Var. 7354 | Var. 7411 | Var. 7468 | Var. 7525 | Var. 7582 | Var. 7639 |
| | 25-100 | Var. 7298 | Var. 7355 | Var. 7412 | Var. 7469 | Var. 7526 | Var. 7583 | Var. 7640 |
| | 25-75 | Var. 7299 | Var. 7356 | Var. 7413 | Var. 7470 | Var. 7527 | Var. 7584 | Var. 7641 |
| | 25-50 | Var. 7300 | Var. 7357 | Var. 7414 | Var. 7471 | Var. 7528 | Var. 7585 | Var. 7642 |
| | 50-200 | Var. 7301 | Var. 7358 | Var. 7415 | Var. 7472 | Var. 7529 | Var. 7586 | Var. 7643 |
| | 50-150 | Var. 7302 | Var. 7359 | Var. 7416 | Var. 7473 | Var. 7530 | Var. 7587 | Var. 7644 |
| | 50-100 | Var. 7303 | Var. 7360 | Var. 7417 | Var. 7474 | Var. 7531 | Var. 7588 | Var. 7645 |
| | 50-75 | Var. 7304 | Var. 7361 | Var. 7418 | Var. 7475 | Var. 7532 | Var. 7589 | Var. 7646 |
| | 75-200 | Var. 7305 | Var. 7362 | Var. 7419 | Var. 7476 | Var. 7533 | Var. 7590 | Var. 7647 |
| | 75-175 | Var. 7306 | Var. 7363 | Var. 7420 | Var. 7477 | Var. 7534 | Var. 7591 | Var. 7648 |
| | 75-150 | Var. 7307 | Var. 7364 | Var. 7421 | Var. 7478 | Var. 7535 | Var. 7592 | Var. 7649 |

TABLE 26-continued

Exemplary embodiments for the combination of rVWF dosage and increase in FVIII stability achieved, as compared to FVIII stability in a subject administered a composition of pdVWF.

| | | Increased Stability (Percent) | | | | | | |
|---|---|---|---|---|---|---|---|---|
| | | 10-40% | 10-30% | 10-20% | 15-50% | 15-40% | 15-30% | 15-20% |
| | 75-125 | Var. 7308 | Var. 7365 | Var. 7422 | Var. 7479 | Var. 7536 | Var. 7593 | Var. 7650 |
| | 75-100 | Var. 7309 | Var. 7366 | Var. 7423 | Var. 7480 | Var. 7537 | Var. 7594 | Var. 7651 |
| | 100-200 | Var. 7310 | Var. 7367 | Var. 7424 | Var. 7481 | Var. 7538 | Var. 7595 | Var. 7652 |
| | 100-175 | Var. 7311 | Var. 7368 | Var. 7425 | Var. 7482 | Var. 7539 | Var. 7596 | Var. 7653 |
| | 100-150 | Var. 7312 | Var. 7369 | Var. 7426 | Var. 7483 | Var. 7540 | Var. 7597 | Var. 7654 |
| | 100-125 | Var. 7313 | Var. 7370 | Var. 7427 | Var. 7484 | Var. 7541 | Var. 7598. | Var. 7655 |
| | 125-200 | Var. 7314 | Var. 7371 | Var. 7428 | Var. 7485 | Var. 7542 | Var. 7599 | Var. 7656 |
| | 125-175 | Var. 7315 | Var. 7372 | Var. 7429 | Var. 7486 | Var. 7543 | Var. 7600 | Var. 7657 |
| | 125-150 | Var. 7316 | Var. 7373 | Var. 7430 | Var. 7487 | Var. 7544 | Var. 7601 | Var. 7658 |
| | 150-200 | Var. 7317 | Var. 7374 | Var. 7431 | Var. 7488 | Var. 7545 | Var. 7602 | Var. 7659 |
| | 150-200 | Var. 7318 | Var. 7375 | Var. 7432 | Var. 7489 | Var. 7546 | Var. 7603 | Var. 7660 |
| | 175-200 | Var. 7319 | Var. 7376 | Var. 7433 | Var. 7490 | Var. 7547 | Var. 7604 | Var. 7661 |

Var. = Variation

TABLE 27

Exemplary embodiments for the combination of rVWF dosage and increase in FVIII stability achieved, as compared to FVIII stability in a subject administered a composition of pdVWF.

| | | Increased Stability (Percent) | | | | | |
|---|---|---|---|---|---|---|---|
| | | 20-50% | 20-40% | 20-30% | 30-50% | 30-40% | 40-50% |
| Dosage | 0.5-200 | Var. 7662 | Var. 7719 | Var. 7776 | Var. 7833 | Var. 7890 | Var. 7947 |
| (IU/kg rVWF:RCo | 0.5-150 | Var. 7663 | Var. 7720 | Var. 7777 | Var. 7834 | Var. 7891 | Var. 7948 |
| activity) | 0.5-100 | Var. 7664 | Var. 7721 | Var. 7778 | Var. 7835 | Var. 7892 | Var. 7949 |
| | 0.5-75 | Var. 7665 | Var. 7722 | Var. 7779 | Var. 7836 | Var. 7893 | Var. 7950 |
| | 0.5-50 | Var. 7666 | Var. 7723 | Var. 7780 | Var. 7837 | Var. 7894 | Var. 7951 |
| | 0.5-25 | Var. 7667 | Var. 7724 | Var. 7781 | Var. 7838 | Var. 7895 | Var. 7952 |
| | 0.5-10 | Var. 7668 | Var. 7725 | Var. 7782 | Var. 7839 | Var. 7896 | Var. 7953 |
| | 0.5-5 | Var. 7669 | Var. 7726 | Var. 7783 | Var. 7840 | Var. 7897 | Var. 7954 |
| | 0.5-2.5 | Var. 7670 | Var. 7727 | Var. 7784 | Var. 7841 | Var. 7898 | Var. 7955 |
| | 0.5-1 | Var. 7671 | Var. 7728 | Var. 7785 | Var. 7842 | Var. 7899 | Var. 7956 |
| | 2.5-200 | Var. 7672 | Var. 7729 | Var. 7786 | Var. 7843 | Var. 7900 | Var. 7957 |
| | 2.5-150 | Var. 7673 | Var. 7730 | Var. 7787 | Var. 7844 | Var. 7901 | Var. 7958 |
| | 2.5-100 | Var. 7674 | Var. 7731 | Var. 7788 | Var. 7845 | Var. 7902 | Var. 7959 |
| | 2.5-75 | Var. 7675 | Var. 7732 | Var. 7789 | Var. 7846 | Var. 7903 | Var. 7960 |
| | 2.5-50 | Var. 7676 | Var. 7733 | Var. 7790 | Var. 7847 | Var. 7904 | Var. 7961 |
| | 2.5-25 | Var. 7677 | Var. 7734 | Var. 7791 | Var. 7848 | Var. 7905 | Var. 7962 |
| | 2.5-10 | Var. 7678 | Var. 7735 | Var. 7792 | Var. 7849 | Var. 7906 | Var. 7963 |
| | 2.5-5 | Var. 7679 | Var. 7736 | Var. 7793 | Var. 7850 | Var. 7907 | Var. 7964 |
| | 5-200 | Var. 7680 | Var. 7737 | Var. 7794 | Var. 7851 | Var. 7908 | Var. 7965 |
| | 5-175 | Var. 7681 | Var. 7738 | Var. 7795 | Var. 7852 | Var. 7909 | Var. 7966 |
| | 5-150 | Var. 7682 | Var. 7739 | Var. 7796 | Var. 7853 | Var. 7910 | Var. 7967 |
| | 5-125 | Var. 7683 | Var. 7740 | Var. 7797 | Var. 7854 | Var. 7911 | Var. 7968 |
| | 5-100 | Var. 7684 | Var. 7741 | Var. 7798 | Var. 7855 | Var. 7912 | Var. 7969 |
| | 5-75 | Var. 7685 | Var. 7742 | Var. 7799 | Var. 7856 | Var. 7913 | Var. 7970 |
| | 5-50 | Var. 7686 | Var. 7743 | Var. 7800 | Var. 7857 | Var. 7914 | Var. 7971 |
| | 5-25 | Var. 7687 | Var. 7744 | Var. 7801 | Var. 7858 | Var. 7915 | Var. 7972 |
| | 5-10 | Var. 7688 | Var. 7745 | Var. 7802 | Var. 7859 | Var. 7916 | Var. 7973 |
| | 10-200 | Var. 7689 | Var. 7746 | Var. 7803 | Var. 7860 | Var. 7917 | Var. 7974 |
| | 10-150 | Var. 7690 | Var. 7747 | Var. 7804 | Var. 7861 | Var. 7918 | Var. 7975 |
| | 10-100 | Var. 7691 | Var. 7748 | Var. 7805 | Var. 7862 | Var. 7919 | Var. 7976 |
| | 10-75 | Var. 7692 | Var. 7749 | Var. 7806 | Var. 7863 | Var. 7920 | Var. 7977 |
| | 10-50 | Var. 7693 | Var. 7750 | Var. 7807 | Var. 7864 | Var. 7921 | Var. 7978 |
| | 10-25 | Var. 7694 | Var. 7751 | Var. 7808 | Var. 7865 | Var. 7922 | Var. 7979 |
| | 25-200 | Var. 7695 | Var. 7752 | Var. 7809 | Var. 7866 | Var. 7923 | Var. 7980 |
| | 25-150 | Var. 7696 | Var. 7753 | Var. 7810 | Var. 7867 | Var. 7924 | Var. 7981 |
| | 25-100 | Var. 7697 | Var. 7754 | Var. 7811 | Var. 7868 | Var. 7925 | Var. 7982 |
| | 25-75 | Var. 7698 | Var. 7755 | Var. 7812 | Var. 7869 | Var. 7926 | Var. 7983 |
| | 25-50 | Var. 7699 | Var. 7756 | Var. 7813 | Var. 7870 | Var. 7927 | Var. 7984 |
| | 50-200 | Var. 7700 | Var. 7757 | Var. 7814 | Var. 7871 | Var. 7928 | Var. 7985 |
| | 50-150 | Var. 7701 | Var. 7758 | Var. 7815 | Var. 7872 | Var. 7929 | Var. 7986 |
| | 50-100 | Var. 7702 | Var. 7759 | Var. 7816 | Var. 7873 | Var. 7930 | Var. 7987 |
| | 50-75 | Var. 7703 | Var. 7760 | Var. 7817 | Var. 7874 | Var. 7931 | Var. 7988 |
| | 75-200 | Var. 7704 | Var. 7761 | Var. 7818 | Var. 7875 | Var. 7932 | Var. 7989 |
| | 75-175 | Var. 7705 | Var. 7762 | Var. 7819 | Var. 7876 | Var. 7933 | Var. 7990 |
| | 75-150 | Var. 7706 | Var. 7763 | Var. 7820 | Var. 7877 | Var. 7934 | Var. 7991 |
| | 75-125 | Var. 7707 | Var. 7764 | Var. 7821 | Var. 7878 | Var. 7935 | Var. 7992 |
| | 75-100 | Var. 7708 | Var. 7765 | Var. 7822 | Var. 7879 | Var. 7936 | Var. 7993 |

TABLE 27-continued

Exemplary embodiments for the combination of rVWF dosage and increase in FVIII stability achieved, as compared to FVIII stability in a subject administered a composition of pdVWF.

| | Increased Stability (Percent) | | | | | |
|---|---|---|---|---|---|---|
| | 20-50% | 20-40% | 20-30% | 30-50% | 30-40% | 40-50% |
| 100-200 | Var. 7709 | Var. 7766 | Var. 7823 | Var. 7880 | Var. 7937 | Var. 7994 |
| 100-175 | Var. 7710 | Var. 7767 | Var. 7824 | Var. 7881 | Var. 7938 | Var. 7995 |
| 100-150 | Var. 7711 | Var. 7768 | Var. 7825 | Var. 7882 | Var. 7939 | Var. 7996 |
| 100-125 | Var. 7712 | Var. 7769 | Var. 7826 | Var. 7883 | Var. 7940 | Var. 7997 |
| 125-200 | Var. 7713 | Var. 7770 | Var. 7827 | Var. 7884 | Var. 7941 | Var. 7998 |
| 125-175 | Var. 7714 | Var. 7771 | Var. 7828 | Var. 7885 | Var. 7942 | Var. 7999 |
| 125-150 | Var. 7715 | Var. 7772 | Var. 7829 | Var. 7886 | Var. 7943 | Var. 8000 |
| 150-200 | Var. 7716 | Var. 7773 | Var. 7830 | Var. 7887 | Var. 7944 | Var. 8001 |
| 150-200 | Var. 7717 | Var. 7774 | Var. 7831 | Var. 7888 | Var. 7945 | Var. 8002 |
| 175-200 | Var. 7718 | Var. 7775 | Var. 7832 | Var. 7889 | Var. 7946 | Var. 8003 |

Var. = Variation

In one embodiment, the method comprises administering a composition of rVWF, wherein the composition of rVWF administered to the subject is a composition of high molecular weight rVWF multimers in which at least 30% of rVWF molecules in the composition are present in a multimer of at least 10 subunits, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers in which at least 50% of rVWF molecules in the composition are present in a multimer of at least 10 subunits, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers in which at least 70% of rVWF molecules in the composition are present in a multimer of at least 10 subunits, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers having a minimal percentage of rVWF molecules present in a particular higher-order rVWF multimer or larger multimer according to any one of variations 134 to 457 found in Table 3 to Table 5, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the rVWF in the composition has a specific activity of from 40 mU/µg to 60 mU/µg, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the rVWF in the composition has a specific activity of at least 60 mU/µg, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the rVWF in the composition has a specific activity of at least 80 mU/µg, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the rVWF in the composition has a specific activity selected from variations 1 to 133 found in Table 1, and wherein the dose of rVWF and increase in FVIII stability, as compared to FVIII stability in a subject administered a composition of pdVWF, is selected from variations 4869 to 8003 in Table 20 to Table 27. In one embodiment, the composition of rVWF administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the dose of rVWF and specific activity of rVWF in the composition is selected from variations 8004 to 10625 in Table 28 to Table 34. In one embodiment, the composition of rVWF administered to the subject is a composition of high molecular weight rVWF multimers. In one embodiment, the composition of rVWF administered to the subject has a higher specific activity than a composition of pdVWF. In yet another embodiment, the composition of rVWF administered to the subject is a composition of high molecular weight rVWF multimers with a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

TABLE 28

Exemplary embodiments for the combination of rVWF dosage and rVWF specific activity useful in the methods described herein.

| | | Specific Activity (mU/µg) | | | | | | |
|---|---|---|---|---|---|---|---|---|
| | | at least 20 | at least 30 | at least 40 | at least 50 | at least 60 | at least 70 | at least 80 |
| Dosage (IU/kg rVWF:RCo activity) | 0.5-200 | Var. 8004 | Var. 8061 | Var. 8118 | Var. 8175 | Var. 8232 | Var. 8289 | Var. 8346 |
| | 0.5-150 | Var. 8005 | Var. 8062 | Var. 8119 | Var. 8176 | Var. 8233 | Var. 8290 | Var. 8347 |
| | 0.5-100 | Var. 8006 | Var. 8063 | Var. 8120 | Var. 8177 | Var. 8234 | Var. 8291 | Var. 8348 |
| | 0.5-75 | Var. 8007 | Var. 8064 | Var. 8121 | Var. 8178 | Var. 8235 | Var. 8292 | Var. 8349 |
| | 0.5-50 | Var. 8008 | Var. 8065 | Var. 8122 | Var. 8179 | Var. 8236 | Var. 8293 | Var. 8350 |
| | 0.5-25 | Var. 8009 | Var. 8066 | Var. 8123 | Var. 8180 | Var. 8237 | Var. 8294 | Var. 8351 |
| | 0.5-10 | Var. 8010 | Var. 8067 | Var. 8124 | Var. 8181 | Var. 8238 | Var. 8295 | Var. 8352 |
| | 0.5-5 | Var. 8011 | Var. 8068 | Var. 8125 | Var. 8182 | Var. 8239 | Var. 8296 | Var. 8353 |
| | 0.5-2.5 | Var. 8012 | Var. 8069 | Var. 8126 | Var. 8183 | Var. 8240 | Var. 8297 | Var. 8354 |
| | 0.5-1 | Var. 8013 | Var. 8070 | Var. 8127 | Var. 8184 | Var. 8241 | Var. 8298 | Var. 8355 |
| | 2.5-200 | Var. 8014 | Var. 8071 | Var. 8128 | Var. 8185 | Var. 8242 | Var. 8299 | Var. 8356 |
| | 2.5-150 | Var. 8015 | Var. 8072 | Var. 8129 | Var. 8186 | Var. 8243 | Var. 8300 | Var. 8357 |
| | 2.5-100 | Var. 8016 | Var. 8073 | Var. 8130 | Var. 8187 | Var. 8244 | Var. 8301 | Var. 8358 |
| | 2.5-75 | Var. 8017 | Var. 8074 | Var. 8131 | Var. 8188 | Var. 8245 | Var. 8302 | Var. 8359 |
| | 2.5-50 | Var. 8018 | Var. 8075 | Var. 8132 | Var. 8189 | Var. 8246 | Var. 8303 | Var. 8360 |
| | 2.5-25 | Var. 8019 | Var. 8076 | Var. 8133 | Var. 8190 | Var. 8247 | Var. 8304 | Var. 8361 |
| | 2.5-10 | Var. 8020 | Var. 8077 | Var. 8134 | Var. 8191 | Var. 8248 | Var. 8305 | Var. 8362 |
| | 2.5-5 | Var. 8021 | Var. 8078 | Var. 8135 | Var. 8192 | Var. 8249 | Var. 8306 | Var. 8363 |
| | 5-200 | Var. 8022 | Var. 8079 | Var. 8136 | Var. 8193 | Var. 8250 | Var. 8307 | Var. 8364 |
| | 5-175 | Var. 8023 | Var. 8080 | Var. 8137 | Var. 8194 | Var. 8251 | Var. 8308 | Var. 8365 |
| | 5-150 | Var. 8024 | Var. 8081 | Var. 8138 | Var. 8195 | Var. 8252 | Var. 8309 | Var. 8366 |
| | 5-125 | Var. 8025 | Var. 8082 | Var. 8139 | Var. 8196 | Var. 8253 | Var. 8310 | Var. 8367 |
| | 5-100 | Var. 8026 | Var. 8083 | Var. 8140 | Var. 8197 | Var. 8254 | Var. 8311 | Var. 8368 |
| | 5-75 | Var. 8027 | Var. 8084 | Var. 8141 | Var. 8198 | Var. 8255 | Var. 8312 | Var. 8369 |
| | 5-50 | Var. 8028 | Var. 8085 | Var. 8142 | Var. 8199 | Var. 8256 | Var. 8313 | Var. 8370 |
| | 5-25 | Var. 8029 | Var. 8086 | Var. 8143 | Var. 8200 | Var. 8257 | Var. 8314 | Var. 8371 |
| | 5-10 | Var. 8030 | Var. 8087 | Var. 8144 | Var. 8201 | Var. 8258 | Var. 8315 | Var. 8372 |
| | 10-200 | Var. 8031 | Var. 8088 | Var. 8145 | Var. 8202 | Var. 8259 | Var. 8316 | Var. 8373 |
| | 10-150 | Var. 8032 | Var. 8089 | Var. 8146 | Var. 8203 | Var. 8260 | Var. 8317 | Var. 8374 |
| | 10-100 | Var. 8033 | Var. 8090 | Var. 8147 | Var. 8204 | Var. 8261 | Var. 8318 | Var. 8375 |
| | 10-75 | Var. 8034 | Var. 8091 | Var. 8148 | Var. 8205 | Var. 8262 | Var. 8319 | Var. 8376 |
| | 10-50 | Var. 8035 | Var. 8092 | Var. 8149 | Var. 8206 | Var. 8263 | Var. 8320 | Var. 8377 |
| | 10-25 | Var. 8036 | Var. 8093 | Var. 8150 | Var. 8207 | Var. 8264 | Var. 8321 | Var. 8378 |
| | 25-200 | Var. 8037 | Var. 8094 | Var. 8151 | Var. 8208 | Var. 8265 | Var. 8322 | Var. 8379 |
| | 25-150 | Var. 8038 | Var. 8095 | Var. 8152 | Var. 8209 | Var. 8266 | Var. 8323 | Var. 8380 |
| | 25-100 | Var. 8039 | Var. 8096 | Var. 8153 | Var. 8210 | Var. 8267 | Var. 8324 | Var. 8381 |
| | 25-75 | Var. 8040 | Var. 8097 | Var. 8154 | Var. 8211 | Var. 8268 | Var. 8325 | Var. 8382 |
| | 25-50 | Var. 8041 | Var. 8098 | Var. 8155 | Var. 8212 | Var. 8269 | Var. 8326 | Var. 8383 |
| | 50-200 | Var. 8042 | Var. 8099 | Var. 8156 | Var. 8213 | Var. 8270 | Var. 8327 | Var. 8384 |
| | 50-150 | Var. 8043 | Var. 8100 | Var. 8157 | Var. 8214 | Var. 8271 | Var. 8328 | Var. 8385 |
| | 50-100 | Var. 8044 | Var. 8101 | Var. 8158 | Var. 8215 | Var. 8272 | Var. 8329 | Var. 8386 |

TABLE 28-continued

Exemplary embodiments for the combination of rVWF dosage and rVWF specific activity useful in the methods described herein.

| | | Specific Activity (mU/µg) | | | | | | |
|---|---|---|---|---|---|---|---|---|
| | | at least 20 | at least 30 | at least 40 | at least 50 | at least 60 | at least 70 | at least 80 |
| | 50-75 | Var. 8045 | Var. 8102 | Var. 8159 | Var. 8216 | Var. 8273 | Var. 8330 | Var. 8387 |
| | 75-200 | Var. 8046 | Var. 8103 | Var. 8160 | Var. 8217 | Var. 8274 | Var. 8331 | Var. 8388 |
| | 75-175 | Var. 8047 | Var. 8104 | Var. 8161 | Var. 8218 | Var. 8275 | Var. 8332 | Var. 8389 |
| | 75-150 | Var. 8048 | Var. 8105 | Var. 8162 | Var. 8219 | Var. 8276 | Var. 8333 | Var. 8390 |
| | 75-125 | Var. 8049 | Var. 8106 | Var. 8163 | Var. 8220 | Var. 8277 | Var. 8334 | Var. 8391 |
| | 75-100 | Var. 8050 | Var. 8107 | Var. 8164 | Var. 8221 | Var. 8278 | Var. 8335 | Var. 8392 |
| | 100-200 | Var. 8051 | Var. 8108 | Var. 8165 | Var. 8222 | Var. 8279 | Var. 8336 | Var. 8393 |
| | 100-175 | Var. 8052 | Var. 8109 | Var. 8166 | Var. 8223 | Var. 8280 | Var. 8337 | Var. 8394 |
| | 100-150 | Var. 8053 | Var. 8110 | Var. 8167 | Var. 8224 | Var. 8281 | Var. 8338 | Var. 8395 |
| | 100-125 | Var. 8054 | Var. 8111 | Var. 8168 | Var. 8225 | Var. 8282 | Var. 8339 | Var. 8396 |
| | 125-200 | Var. 8055 | Var. 8112 | Var. 8169 | Var. 8226 | Var. 8283 | Var. 8340 | Var. 8397 |
| | 125-175 | Var. 8056 | Var. 8113 | Var. 8170 | Var. 8227 | Var. 8284 | Var. 8341 | Var. 8398 |
| | 125-150 | Var. 8057 | Var. 8114 | Var. 8171 | Var. 8228 | Var. 8285 | Var. 8342 | Var. 8399 |
| | 150-200 | Var. 8058 | Var. 8115 | Var. 8172 | Var. 8229 | Var. 8286 | Var. 8343 | Var. 8400 |
| | 150-200 | Var. 8059 | Var. 8116 | Var. 8173 | Var. 8230 | Var. 8287 | Var. 8344 | Var. 8401 |
| | 175-200 | Var. 8060 | Var. 8117 | Var. 8174 | Var. 8231 | Var. 8288 | Var. 8345 | Var. 8402 |

Var. = Variation

TABLE 29

Exemplary embodiments for the combination of rVWF dosage and rVWF specific activity useful in the methods described herein.

| | | Specific Activity (mU/µg) | | | | | | |
|---|---|---|---|---|---|---|---|---|
| | | at least 90 | at least 100 | at least 125 | at least 150 | 20-150 | 20-125 | 20-100 |
| Dosage (IU/kg rVWF:RCo activity) | 0.5-200 | Var. 8403 | Var. 8460 | Var. 8517 | Var. 8574 | Var. 8631 | Var. 8688 | Var. 8745 |
| | 0.5-150 | Var. 8404 | Var. 8461 | Var. 8518 | Var. 8575 | Var. 8632 | Var. 8689 | Var. 8746 |
| | 0.5-100 | Var. 8405 | Var. 8462 | Var. 8519 | Var. 8576 | Var. 8633 | Var. 8690 | Var. 8747 |
| | 0.5-75 | Var. 8406 | Var. 8463 | Var. 8520 | Var. 8577 | Var. 8634 | Var. 8691 | Var. 8748 |
| | 0.5-50 | Var. 8407 | Var. 8464 | Var. 8521 | Var. 8578 | Var. 8635 | Var. 8692 | Var. 8749 |
| | 0.5-25 | Var. 8408 | Var. 8465 | Var. 8522 | Var. 8579 | Var. 8636 | Var. 8693 | Var. 8750 |
| | 0.5-10 | Var. 8409 | Var. 8466 | Var. 8523 | Var. 8580 | Var. 8637 | Var. 8694 | Var. 8751 |
| | 0.5-5 | Var. 8410 | Var. 8467 | Var. 8524 | Var. 8581 | Var. 8638 | Var. 8695 | Var. 8752 |
| | 0.5-2.5 | Var. 8411 | Var. 8468 | Var. 8525 | Var. 8582 | Var. 8639 | Var. 8696 | Var. 8753 |
| | 0.5-1 | Var. 8412 | Var. 8469 | Var. 8526 | Var. 8583 | Var. 8640 | Var. 8697 | Var. 8754 |
| | 2.5-200 | Var. 8413 | Var. 8470 | Var. 8527 | Var. 8584 | Var. 8641 | Var. 8698 | Var. 8755 |
| | 2.5-150 | Var. 8414 | Var. 8471 | Var. 8528 | Var. 8585 | Var. 8642 | Var. 8699 | Var. 8756 |
| | 2.5-100 | Var. 8415 | Var. 8472 | Var. 8529 | Var. 8586 | Var. 8643 | Var. 8700 | Var. 8757 |
| | 2.5-75 | Var. 8416 | Var. 8473 | Var. 8530 | Var. 8587 | Var. 8644 | Var. 8701 | Var. 8758 |
| | 2.5-50 | Var. 8417 | Var. 8474 | Var. 8531 | Var. 8588 | Var. 8645 | Var. 8702 | Var. 8759 |
| | 2.5-25 | Var. 8418 | Var. 8475 | Var. 8532 | Var. 8589 | Var. 8646 | Var. 8703 | Var. 8760 |
| | 2.5-10 | Var. 8419 | Var. 8476 | Var. 8533 | Var. 8590 | Var. 8647 | Var. 8704 | Var. 8761 |
| | 2.5-5 | Var. 8420 | Var. 8477 | Var. 8534 | Var. 8591 | Var. 8648 | Var. 8705 | Var. 8762 |
| | 5-200 | Var. 8421 | Var. 8478 | Var. 8535 | Var. 8592 | Var. 8649 | Var. 8706 | Var. 8763 |
| | 5-175 | Var. 8422 | Var. 8479 | Var. 8536 | Var. 8593 | Var. 8650 | Var. 8707 | Var. 8764 |
| | 5-150 | Var. 8423 | Var. 8480 | Var. 8537 | Var. 8594 | Var. 8651 | Var. 8708 | Var. 8765 |
| | 5-125 | Var. 8424 | Var. 8481 | Var. 8538 | Var. 8595 | Var. 8652 | Var. 8709 | Var. 8766 |
| | 5-100 | Var. 8425 | Var. 8482 | Var. 8539 | Var. 8596 | Var. 8653 | Var. 8710 | Var. 8767 |
| | 5-75 | Var. 8426 | Var. 8483 | Var. 8540 | Var. 8597 | Var. 8654 | Var. 8711 | Var. 8768 |
| | 5-50 | Var. 8427 | Var. 8484 | Var. 8541 | Var. 8598 | Var. 8655 | Var. 8712 | Var. 8769 |
| | 5-25 | Var. 8428 | Var. 8485 | Var. 8542 | Var. 8599 | Var. 8656 | Var. 8713 | Var. 8770 |
| | 5-10 | Var. 8429 | Var. 8486 | Var. 8543 | Var. 8600 | Var. 8657 | Var. 8714 | Var. 8771 |
| | 10-200 | Var. 8430 | Var. 8487 | Var. 8544 | Var. 8601 | Var. 8658 | Var. 8715 | Var. 8772 |
| | 10-150 | Var. 8431 | Var. 8488 | Var. 8545 | Var. 8602 | Var. 8659 | Var. 8716 | Var. 8773 |
| | 10-100 | Var. 8432 | Var. 8489 | Var. 8546 | Var. 8603 | Var. 8660 | Var. 8717 | Var. 8774 |
| | 10-75 | Var. 8433 | Var. 8490 | Var. 8547 | Var. 8604 | Var. 8661 | Var. 8718 | Var. 8775 |
| | 10-50 | Var. 8434 | Var. 8491 | Var. 8548 | Var. 8605 | Var. 8662 | Var. 8719 | Var. 8776 |
| | 10-25 | Var. 8435 | Var. 8492 | Var. 8549 | Var. 8606 | Var. 8663 | Var. 8720 | Var. 8777 |
| | 25-200 | Var. 8436 | Var. 8493 | Var. 8550 | Var. 8607 | Var. 8664 | Var. 8721 | Var. 8778 |
| | 25-150 | Var. 8437 | Var. 8494 | Var. 8551 | Var. 8608 | Var. 8665 | Var. 8722 | Var. 8779 |
| | 25-100 | Var. 8438 | Var. 8495 | Var. 8552 | Var. 8609 | Var. 8666 | Var. 8723 | Var. 8780 |
| | 25-75 | Var. 8439 | Var. 8496 | Var. 8553 | Var. 8610 | Var. 8667 | Var. 8724 | Var. 8781 |
| | 25-50 | Var. 8440 | Var. 8497 | Var. 8554 | Var. 8611 | Var. 8668 | Var. 8725 | Var. 8782 |
| | 50-200 | Var. 8441 | Var. 8498 | Var. 8555 | Var. 8612 | Var. 8669 | Var. 8726 | Var. 8783 |
| | 50-150 | Var. 8442 | Var. 8499 | Var. 8556 | Var. 8613 | Var. 8670 | Var. 8727 | Var. 8784 |
| | 50-100 | Var. 8443 | Var. 8500 | Var. 8557 | Var. 8614 | Var. 8671 | Var. 8728 | Var. 8785 |
| | 50-75 | Var. 8444 | Var. 8501 | Var. 8558 | Var. 8615 | Var. 8672 | Var. 8729 | Var. 8786 |
| | 75-200 | Var. 8445 | Var. 8502 | Var. 8559 | Var. 8616 | Var. 8673 | Var. 8730 | Var. 8787 |

TABLE 29-continued

Exemplary embodiments for the combination of rVWF dosage and rVWF specific activity useful in the methods described herein.

| | | Specific Activity (mU/µg) | | | | | | |
|---|---|---|---|---|---|---|---|---|
| | | at least 90 | at least 100 | at least 125 | at least 150 | 20-150 | 20-125 | 20-100 |
| | 75-175 | Var. 8446 | Var. 8503 | Var. 8560 | Var. 8617 | Var. 8674 | Var. 8731 | Var. 8788 |
| | 75-150 | Var. 8447 | Var. 8504 | Var. 8561 | Var. 8618 | Var. 8675 | Var. 8732 | Var. 8789 |
| | 75-125 | Var. 8448 | Var. 8505 | Var. 8562 | Var. 8619 | Var. 8676 | Var. 8733 | Var. 8790 |
| | 75-100 | Var. 8449 | Var. 8506 | Var. 8563 | Var. 8620 | Var. 8677 | Var. 8734 | Var. 8791 |
| | 100-200 | Var. 8450 | Var. 8507 | Var. 8564 | Var. 8621 | Var. 8678 | Var. 8735 | Var. 8792 |
| | 100-175 | Var. 8451 | Var. 8508 | Var. 8565 | Var. 8622 | Var. 8679 | Var. 8736 | Var. 8793 |
| | 100-150 | Var. 8452 | Var. 8509 | Var. 8566 | Var. 8623 | Var. 8680 | Var. 8737 | Var. 8794 |
| | 100-125 | Var. 8453 | Var. 8510 | Var. 8567 | Var. 8624 | Var. 8681 | Var. 8738 | Var. 8795 |
| | 125-200 | Var. 8454 | Var. 8511 | Var. 8568 | Var. 8625 | Var. 8682 | Var. 8739 | Var. 8796 |
| | 125-175 | Var. 8455 | Var. 8512 | Var. 8569 | Var. 8626 | Var. 8683 | Var. 8740 | Var. 8797 |
| | 125-150 | Var. 8456 | Var. 8513 | Var. 8570 | Var. 8627 | Var. 8684 | Var. 8741 | Var. 8798 |
| | 150-200 | Var. 8457 | Var. 8514 | Var. 8571 | Var. 8628 | Var. 8685 | Var. 8742 | Var. 8799 |
| | 150-200 | Var. 8458 | Var. 8515 | Var. 8572 | Var. 8629 | Var. 8686 | Var. 8743 | Var. 8800 |
| | 175-200 | Var. 8459 | Var. 8516 | Var. 8573 | Var. 8630 | Var. 8687 | Var. 8744 | Var. 8801 |

Var. = Variation

TABLE 30

Exemplary embodiments for the combination of rVWF dosage and rVWF specific activity useful in the methods described herein.

| | | Specific Activity (mU/µg) | | | | | | |
|---|---|---|---|---|---|---|---|---|
| | | 20-90 | 20-80 | 20-70 | 20-60 | 20-50 | 20-40 | 40-150 |
| Dosage (IU/kg rVWF:RCo activity) | 0.5-200 | Var. 8802 | Var. 8859 | Var. 8916 | Var. 8973 | Var. 9030 | Var. 9087 | Var. 9144 |
| | 0.5-150 | Var. 8803 | Var. 8860 | Var. 8917 | Var. 8974 | Var. 9031 | Var. 9088 | Var. 9145 |
| | 0.5-100 | Var. 8804 | Var. 8861 | Var. 8918 | Var. 8975 | Var. 9032 | Var. 9089 | Var. 9146 |
| | 0.5-75 | Var. 8805 | Var. 8862 | Var. 8919 | Var. 8976 | Var. 9033 | Var. 9090 | Var. 9147 |
| | 0.5-50 | Var. 8806 | Var. 8863 | Var. 8920 | Var. 8977 | Var. 9034 | Var. 9091 | Var. 9148 |
| | 0.5-25 | Var. 8807 | Var. 8864 | Var. 8921 | Var. 8978 | Var. 9035 | Var. 9092 | Var. 9149 |
| | 0.5-10 | Var. 8808 | Var. 8865 | Var. 8922 | Var. 8979 | Var. 9036 | Var. 9093 | Var. 9150 |
| | 0.5-5 | Var. 8809 | Var. 8866 | Var. 8923 | Var. 8980 | Var. 9037 | Var. 9094 | Var. 9151 |
| | 0.5-2.5 | Var. 8810 | Var. 8867 | Var. 8924 | Var. 8981 | Var. 9038 | Var. 9095 | Var. 9152 |
| | 0.5-1 | Var. 8811 | Var. 8868 | Var. 8925 | Var. 8982 | Var. 9039 | Var. 9096 | Var. 9153 |
| | 2.5-200 | Var. 8812 | Var. 8869 | Var. 8926 | Var. 8983 | Var. 9040 | Var. 9097 | Var. 9154 |
| | 2.5-150 | Var. 8813 | Var. 8870 | Var. 8927 | Var. 8984 | Var. 9041 | Var. 9098 | Var. 9155 |
| | 2.5-100 | Var. 8814 | Var. 8871 | Var. 8928 | Var. 8985 | Var. 9042 | Var. 9099 | Var. 9156 |
| | 2.5-75 | Var. 8815 | Var. 8872 | Var. 8929 | Var. 8986 | Var. 9043 | Var. 9100 | Var. 9157 |
| | 2.5-50 | Var. 8816 | Var. 8873 | Var. 8930 | Var. 8987 | Var. 9044 | Var. 9101 | Var. 9158 |
| | 2.5-25 | Var. 8817 | Var. 8874 | Var. 8931 | Var. 8988 | Var. 9045 | Var. 9102 | Var. 9159 |
| | 2.5-10 | Var. 8818 | Var. 8875 | Var. 8932 | Var. 8989 | Var. 9046 | Var. 9103 | Var. 9160 |
| | 2.5-5 | Var. 8819 | Var. 8876 | Var. 8933 | Var. 8990 | Var. 9047 | Var. 9104 | Var. 9161 |
| | 5-200 | Var. 8820 | Var. 8877 | Var. 8934 | Var. 8991 | Var. 9048 | Var. 9105 | Var. 9162 |
| | 5-175 | Var. 8821 | Var. 8878 | Var. 8935 | Var. 8992 | Var. 9049 | Var. 9106 | Var. 9163 |
| | 5-150 | Var. 8822 | Var. 8879 | Var. 8936 | Var. 8993 | Var. 9050 | Var. 9107 | Var. 9164 |
| | 5-125 | Var. 8823 | Var. 8880 | Var. 8937 | Var. 8994 | Var. 9051 | Var. 9108 | Var. 9165 |
| | 5-100 | Var. 8824 | Var. 8881 | Var. 8938 | Var. 8995 | Var. 9052 | Var. 9109 | Var. 9166 |
| | 5-75 | Var. 8825 | Var. 8882 | Var. 8939 | Var. 8996 | Var. 9053 | Var. 9110 | Var. 9167 |
| | 5-50 | Var. 8826 | Var. 8883 | Var. 8940 | Var. 8997 | Var. 9054 | Var. 9111 | Var. 9168 |
| | 5-25 | Var. 8827 | Var. 8884 | Var. 8941 | Var. 8998 | Var. 9055 | Var. 9112 | Var. 9169 |
| | 5-10 | Var. 8828 | Var. 8885 | Var. 8942 | Var. 8999 | Var. 9056 | Var. 9113 | Var. 9170 |
| | 10-200 | Var. 8829 | Var. 8886 | Var. 8943 | Var. 9000 | Var. 9057 | Var. 9114 | Var. 9171 |
| | 10-150 | Var. 8830 | Var. 8887 | Var. 8944 | Var. 9001 | Var. 9058 | Var. 9115 | Var. 9172 |
| | 10-100 | Var. 8831 | Var. 8888 | Var. 8945 | Var. 9002 | Var. 9059 | Var. 9116 | Var. 9173 |
| | 10-75 | Var. 8832 | Var. 8889 | Var. 8946 | Var. 9003 | Var. 9060 | Var. 9117 | Var. 9174 |
| | 10-50 | Var. 8833 | Var. 8890 | Var. 8947 | Var. 9004 | Var. 9061 | Var. 9118 | Var. 9175 |
| | 10-25 | Var. 8834 | Var. 8891 | Var. 8948 | Var. 9005 | Var. 9062 | Var. 9119 | Var. 9176 |
| | 25-200 | Var. 8835 | Var. 8892 | Var. 8949 | Var. 9006 | Var. 9063 | Var. 9120 | Var. 9177 |
| | 25-150 | Var. 8836 | Var. 8893 | Var. 8950 | Var. 9007 | Var. 9064 | Var. 9121 | Var. 9178 |
| | 25-100 | Var. 8837 | Var. 8894 | Var. 8951 | Var. 9008 | Var. 9065 | Var. 9122 | Var. 9179 |
| | 25-75 | Var. 8838 | Var. 8895 | Var. 8952 | Var. 9009 | Var. 9066 | Var. 9123 | Var. 9180 |
| | 25-50 | Var. 8839 | Var. 8896 | Var. 8953 | Var. 9010 | Var. 9067 | Var. 9124 | Var. 9181 |
| | 50-200 | Var. 8840 | Var. 8897 | Var. 8954 | Var. 9011 | Var. 9068 | Var. 9125 | Var. 9182 |
| | 50-150 | Var. 8841 | Var. 8898 | Var. 8955 | Var. 9012 | Var. 9069 | Var. 9126 | Var. 9183 |
| | 50-100 | Var. 8842 | Var. 8899 | Var. 8956 | Var. 9013 | Var. 9070 | Var. 9127 | Var. 9184 |
| | 50-75 | Var. 8843 | Var. 8900 | Var. 8957 | Var. 9014 | Var. 9071 | Var. 9128 | Var. 9185 |
| | 75-200 | Var. 8844 | Var. 8901 | Var. 8958 | Var. 9015 | Var. 9072 | Var. 9129 | Var. 9186 |
| | 75-175 | Var. 8845 | Var. 8902 | Var. 8959 | Var. 9016 | Var. 9073 | Var. 9130 | Var. 9187 |
| | 75-150 | Var. 8846 | Var. 8903 | Var. 8960 | Var. 9017 | Var. 9074 | Var. 9131 | Var. 9188 |

TABLE 30-continued

Exemplary embodiments for the combination of rVWF dosage and rVWF specific activity useful in the methods described herein.

| | | Specific Activity (mU/µg) | | | | | | |
|---|---|---|---|---|---|---|---|---|
| | | 20-90 | 20-80 | 20-70 | 20-60 | 20-50 | 20-40 | 40-150 |
| | 75-125 | Var. 8847 | Var. 8904 | Var. 8961 | Var. 9018 | Var. 9075 | Var. 9132 | Var. 9189 |
| | 75-100 | Var. 8848 | Var. 8905 | Var. 8962 | Var. 9019 | Var. 9076 | Var. 9133 | Var. 9190 |
| | 100-200 | Var. 8849 | Var. 8906 | Var. 8963 | Var. 9020 | Var. 9077 | Var. 9134 | Var. 9191 |
| | 100-175 | Var. 8850 | Var. 8907 | Var. 8964 | Var. 9021 | Var. 9078 | Var. 9135 | Var. 9192 |
| | 100-150 | Var. 8851 | Var. 8908 | Var. 8965 | Var. 9022 | Var. 9079 | Var. 9136 | Var. 9193 |
| | 100-125 | Var. 8852 | Var. 8909 | Var. 8966 | Var. 9023 | Var. 9080 | Var. 9137 | Var. 9194 |
| | 125-200 | Var. 8853 | Var. 8910 | Var. 8967 | Var. 9024 | Var. 9081 | Var. 9138 | Var. 9195 |
| | 125-175 | Var. 8854 | Var. 8911 | Var. 8968 | Var. 9025 | Var. 9082 | Var. 9139 | Var. 9196 |
| | 125-150 | Var. 8855 | Var. 8912 | Var. 8969 | Var. 9026 | Var. 9083 | Var. 9140 | Var. 9197 |
| | 150-200 | Var. 8856 | Var. 8913 | Var. 8970 | Var. 9027 | Var. 9084 | Var. 9141 | Var. 9198 |
| | 150-200 | Var. 8857 | Var. 8914 | Var. 8971 | Var. 9028 | Var. 9085 | Var. 9142 | Var. 9199 |
| | 175-200 | Var. 8858 | Var. 8915 | Var. 8972 | Var. 9029 | Var. 9086 | Var. 9143 | Var. 9200 |

Var. = Variation

TABLE 31

Exemplary embodiments for the combination of rVWF dosage and rVWF specific activity useful in the methods described herein.

| | | Specific Activity (mU/µg) | | | | | | |
|---|---|---|---|---|---|---|---|---|
| | | 40-125 | 40-100 | 40-90 | 40-80 | 40-70 | 40-60 | 40-50 |
| Dosage | 0.5-200 | Var. 9201 | Var. 9258 | Var. 9315 | Var. 9372 | Var. 9429 | Var. 9486 | Var. 9543 |
| (IU/kg rVWF:RCo | 0.5-150 | Var. 9202 | Var. 9259 | Var. 9316 | Var. 9373 | Var. 9430 | Var. 9487 | Var. 9544 |
| activity) | 0.5-100 | Var. 9203 | Var. 9260 | Var. 9317 | Var. 9374 | Var. 9431 | Var. 9488 | Var. 9545 |
| | 0.5-75 | Var. 9204 | Var. 9261 | Var. 9318 | Var. 9375 | Var. 9432 | Var. 9489 | Var. 9546 |
| | 0.5-50 | Var. 9205 | Var. 9262 | Var. 9319 | Var. 9376 | Var. 9433 | Var. 9490 | Var. 9547 |
| | 0.5-25 | Var. 9206 | Var. 9263 | Var. 9320 | Var. 9377 | Var. 9434 | Var. 9491 | Var. 9548 |
| | 0.5-10 | Var. 9207 | Var. 9264 | Var. 9321 | Var. 9378 | Var. 9435 | Var. 9492 | Var. 9549 |
| | 0.5-5 | Var. 9208 | Var. 9265 | Var. 9322 | Var. 9379 | Var. 9436 | Var. 9493 | Var. 9550 |
| | 0.5-2.5 | Var. 9209 | Var. 9266 | Var. 9323 | Var. 9380 | Var. 9437 | Var. 9494 | Var. 9551 |
| | 0.5-1 | Var. 9210 | Var. 9267 | Var. 9324 | Var. 9381 | Var. 9438 | Var. 9495 | Var. 9552 |
| | 2.5-200 | Var. 9211 | Var. 9268 | Var. 9325 | Var. 9382 | Var. 9439 | Var. 9496 | Var. 9553 |
| | 2.5-150 | Var. 9212 | Var. 9269 | Var. 9326 | Var. 9383 | Var. 9440 | Var. 9497 | Var. 9554 |
| | 2.5-100 | Var. 9213 | Var. 9270 | Var. 9327 | Var. 9384 | Var. 9441 | Var. 9498 | Var. 9555 |
| | 2.5-75 | Var. 9214 | Var. 9271 | Var. 9328 | Var. 9385 | Var. 9442 | Var. 9499 | Var. 9556 |
| | 2.5-50 | Var. 9215 | Var. 9272 | Var. 9329 | Var. 9386 | Var. 9443 | Var. 9500 | Var. 9557 |
| | 2.5-25 | Var. 9216 | Var. 9273 | Var. 9330 | Var. 9387 | Var. 9444 | Var. 9501 | Var. 9558 |
| | 2.5-10 | Var. 9217 | Var. 9274 | Var. 9331 | Var. 9388 | Var. 9445 | Var. 9502 | Var. 9559 |
| | 2.5-5 | Var. 9218 | Var. 9275 | Var. 9332 | Var. 9389 | Var. 9446 | Var. 9503 | Var. 9560 |
| | 5-200 | Var. 9219 | Var. 9276 | Var. 9333 | Var. 9390 | Var. 9447 | Var. 9504 | Var. 9561 |
| | 5-175 | Var. 9220 | Var. 9277 | Var. 9334 | Var. 9391 | Var. 9448 | Var. 9505 | Var. 9562 |
| | 5-150 | Var. 9221 | Var. 9278 | Var. 9335 | Var. 9392 | Var. 9449 | Var. 9506 | Var. 9563 |
| | 5-125 | Var. 9222 | Var. 9279 | Var. 9336 | Var. 9393 | Var. 9450 | Var. 9507 | Var. 9564 |
| | 5-100 | Var. 9223 | Var. 9280 | Var. 9337 | Var. 9394 | Var. 9451 | Var. 9508 | Var. 9565 |
| | 5-75 | Var. 9224 | Var. 9281 | Var. 9338 | Var. 9395 | Var. 9452 | Var. 9509 | Var. 9566 |
| | 5-50 | Var. 9225 | Var. 9282 | Var. 9339 | Var. 9396 | Var. 9453 | Var. 9510 | Var. 9567 |
| | 5-25 | Var. 9226 | Var. 9283 | Var. 9340 | Var. 9397 | Var. 9454 | Var. 9511 | Var. 9568 |
| | 5-10 | Var. 9227 | Var. 9284 | Var. 9341 | Var. 9398 | Var. 9455 | Var. 9512 | Var. 9569 |
| | 10-200 | Var. 9228 | Var. 9285 | Var. 9342 | Var. 9399 | Var. 9456 | Var. 9513 | Var. 9570 |
| | 10-150 | Var. 9229 | Var. 9286 | Var. 9343 | Var. 9400 | Var. 9457 | Var. 9514 | Var. 9571 |
| | 10-100 | Var. 9230 | Var. 9287 | Var. 9344 | Var. 9401 | Var. 9458 | Var. 9515 | Var. 9572 |
| | 10-75 | Var. 9231 | Var. 9288 | Var. 9345 | Var. 9402 | Var. 9459 | Var. 9516 | Var. 9573 |
| | 10-50 | Var. 9232 | Var. 9289 | Var. 9346 | Var. 9403 | Var. 9460 | Var. 9517 | Var. 9574 |
| | 10-25 | Var. 9233 | Var. 9290 | Var. 9347 | Var. 9404 | Var. 9461 | Var. 9518 | Var. 9575 |
| | 25-200 | Var. 9234 | Var. 9291 | Var. 9348 | Var. 9405 | Var. 9462 | Var. 9519 | Var. 9576 |
| | 25-150 | Var. 9235 | Var. 9292 | Var. 9349 | Var. 9406 | Var. 9463 | Var. 9520 | Var. 9577 |
| | 25-100 | Var. 9236 | Var. 9293 | Var. 9350 | Var. 9407 | Var. 9464 | Var. 9521 | Var. 9578 |
| | 25-75 | Var. 9237 | Var. 9294 | Var. 9351 | Var. 9408 | Var. 9465 | Var. 9522 | Var. 9579 |
| | 25-50 | Var. 9238 | Var. 9295 | Var. 9352 | Var. 9409 | Var. 9466 | Var. 9523 | Var. 9580 |
| | 50-200 | Var. 9239 | Var. 9296 | Var. 9353 | Var. 9410 | Var. 9467 | Var. 9524 | Var. 9581 |
| | 50-150 | Var. 9240 | Var. 9297 | Var. 9354 | Var. 9411 | Var. 9468 | Var. 9525 | Var. 9582 |
| | 50-100 | Var. 9241 | Var. 9298 | Var. 9355 | Var. 9412 | Var. 9469 | Var. 9526 | Var. 9583 |
| | 50-75 | Var. 9242 | Var. 9299 | Var. 9356 | Var. 9413 | Var. 9470 | Var. 9527 | Var. 9584 |
| | 75-200 | Var. 9243 | Var. 9300 | Var. 9357 | Var. 9414 | Var. 9471 | Var. 9528 | Var. 9585 |
| | 75-175 | Var. 9244 | Var. 9301 | Var. 9358 | Var. 9415 | Var. 9472 | Var. 9529 | Var. 9586 |
| | 75-150 | Var. 9245 | Var. 9302 | Var. 9359 | Var. 9416 | Var. 9473 | Var. 9530 | Var. 9587 |
| | 75-125 | Var. 9246 | Var. 9303 | Var. 9360 | Var. 9417 | Var. 9474 | Var. 9531 | Var. 9588 |
| | 75-100 | Var. 9247 | Var. 9304 | Var. 9361 | Var. 9418 | Var. 9475 | Var. 9532 | Var. 9589 |

TABLE 31-continued

Exemplary embodiments for the combination of rVWF dosage and rVWF specific activity useful in the methods described herein.

| | | Specific Activity (mU/µg) | | | | | | |
|---|---|---|---|---|---|---|---|---|
| | | 40-125 | 40-100 | 40-90 | 40-80 | 40-70 | 40-60 | 40-50 |
| | 100-200 | Var. 9248 | Var. 9305 | Var. 9362 | Var. 9419 | Var. 9476 | Var. 9533 | Var. 9590 |
| | 100-175 | Var. 9249 | Var. 9306 | Var. 9363 | Var. 9420 | Var. 9477 | Var. 9534 | Var. 9591 |
| | 100-150 | Var. 9250 | Var. 9307 | Var. 9364 | Var. 9421 | Var. 9478 | Var. 9535 | Var. 9592 |
| | 100-125 | Var. 9251 | Var. 9308 | Var. 9365 | Var. 9422 | Var. 9479 | Var. 9536 | Var. 9593 |
| | 125-200 | Var. 9252 | Var. 9309 | Var. 9366 | Var. 9423 | Var. 9480 | Var. 9537 | Var. 9594 |
| | 125-175 | Var. 9253 | Var. 9310 | Var. 9367 | Var. 9424 | Var. 9481 | Var. 9538 | Var. 9595 |
| | 125-150 | Var. 9254 | Var. 9311 | Var. 9368 | Var. 9425 | Var. 9482 | Var. 9539 | Var. 9596 |
| | 150-200 | Var. 9255 | Var. 9312 | Var. 9369 | Var. 9426 | Var. 9483 | Var. 9540 | Var. 9597 |
| | 150-200 | Var. 9256 | Var. 9313 | Var. 9370 | Var. 9427 | Var. 9484 | Var. 9541 | Var. 9598 |
| | 175-200 | Var. 9257 | Var. 9314 | Var. 9371 | Var. 9428 | Var. 9485 | Var. 9542 | Var. 9599 |

Var. = Variation

TABLE 32

Exemplary embodiments for the combination of rVWF dosage and rVWF specific activity useful in the methods described herein.

| | | Specific Activity (mU/µg) | | | | | |
|---|---|---|---|---|---|---|---|
| | | 60-150 | 60-125 | 60-100 | 60-90 | 60-80 | 60-70 |
| Dosage (IU/kg rVWF:RCo activity) | 0.5-200 | Var. 9600 | Var. 9657 | Var. 9714 | Var. 9771 | Var. 9828 | Var. 9885 |
| | 0.5-150 | Var. 9601 | Var. 9658 | Var. 9715 | Var. 9772 | Var. 9829 | Var. 9886 |
| | 0.5-100 | Var. 9602 | Var. 9659 | Var. 9716 | Var. 9773 | Var. 9830 | Var. 9887 |
| | 0.5-75 | Var. 9603 | Var. 9660 | Var. 9717 | Var. 9774 | Var. 9831 | Var. 9888 |
| | 0.5-50 | Var. 9604 | Var. 9661 | Var. 9718 | Var. 9775 | Var. 9832 | Var. 9889 |
| | 0.5-25 | Var. 9605 | Var. 9662 | Var. 9719 | Var. 9776 | Var. 9833 | Var. 9890 |
| | 0.5-10 | Var. 9606 | Var. 9663 | Var. 9720 | Var. 9777 | Var. 9834 | Var. 9891 |
| | 0.5-5 | Var. 9607 | Var. 9664 | Var. 9721 | Var. 9778 | Var. 9835 | Var. 9892 |
| | 0.5-2.5 | Var. 9608 | Var. 9665 | Var. 9722 | Var. 9779 | Var. 9836 | Var. 9893 |
| | 0.5-1 | Var. 9609 | Var. 9666 | Var. 9723 | Var. 9780 | Var. 9837 | Var. 9894 |
| | 2.5-200 | Var. 9610 | Var. 9667 | Var. 9724 | Var. 9781 | Var. 9838 | Var. 9895 |
| | 2.5-150 | Var. 9611 | Var. 9668 | Var. 9725 | Var. 9782 | Var. 9839 | Var. 9896 |
| | 2.5-100 | Var. 9612 | Var. 9669 | Var. 9726 | Var. 9783 | Var. 9840 | Var. 9897 |
| | 2.5-75 | Var. 9613 | Var. 9670 | Var. 9727 | Var. 9784 | Var. 9841 | Var. 9898 |
| | 2.5-50 | Var. 9614 | Var. 9671 | Var. 9728 | Var. 9785 | Var. 9842 | Var. 9899 |
| | 2.5-25 | Var. 9615 | Var. 9672 | Var. 9729 | Var. 9786 | Var. 9843 | Var. 9900 |
| | 2.5-10 | Var. 9616 | Var. 9673 | Var. 9730 | Var. 9787 | Var. 9844 | Var. 9901 |
| | 2.5-5 | Var. 9617 | Var. 9674 | Var. 9731 | Var. 9788 | Var. 9845 | Var. 9902 |
| | 5-200 | Var. 9618 | Var. 9675 | Var. 9732 | Var. 9789 | Var. 9846 | Var. 9903 |
| | 5-175 | Var. 9619 | Var. 9676 | Var. 9733 | Var. 9790 | Var. 9847 | Var. 9904 |
| | 5-150 | Var. 9620 | Var. 9677 | Var. 9734 | Var. 9791 | Var. 9848 | Var. 9905 |
| | 5-125 | Var. 9621 | Var. 9678 | Var. 9735 | Var. 9792 | Var. 9849 | Var. 9906 |
| | 5-100 | Var. 9622 | Var. 9679 | Var. 9736 | Var. 9793 | Var. 9850 | Var. 9907 |
| | 5-75 | Var. 9623 | Var. 9680 | Var. 9737 | Var. 9794 | Var. 9851 | Var. 9908 |
| | 5-50 | Var. 9624 | Var. 9681 | Var. 9738 | Var. 9795 | Var. 9852 | Var. 9909 |
| | 5-25 | Var. 9625 | Var. 9682 | Var. 9739 | Var. 9796 | Var. 9853 | Var. 9910 |
| | 5-10 | Var. 9626 | Var. 9683 | Var. 9740 | Var. 9797 | Var. 9854 | Var. 9911 |
| | 10-200 | Var. 9627 | Var. 9684 | Var. 9741 | Var. 9798 | Var. 9855 | Var. 9912 |
| | 10-150 | Var. 9628 | Var. 9685 | Var. 9742 | Var. 9799 | Var. 9856 | Var. 9913 |
| | 10-100 | Var. 9629 | Var. 9686 | Var. 9743 | Var. 9800 | Var. 9857 | Var. 9914 |
| | 10-75 | Var. 9630 | Var. 9687 | Var. 9744 | Var. 9801 | Var. 9858 | Var. 9915 |
| | 10-50 | Var. 9631 | Var. 9688 | Var. 9745 | Var. 9802 | Var. 9859 | Var. 9916 |
| | 10-25 | Var. 9632 | Var. 9689 | Var. 9746 | Var. 9803 | Var. 9860 | Var. 9917 |
| | 25-200 | Var. 9633 | Var. 9690 | Var. 9747 | Var. 9804 | Var. 9861 | Var. 9918 |
| | 25-150 | Var. 9634 | Var. 9691 | Var. 9748 | Var. 9805 | Var. 9862 | Var. 9919 |
| | 25-100 | Var. 9635 | Var. 9692 | Var. 9749 | Var. 9806 | Var. 9863 | Var. 9920 |
| | 25-75 | Var. 9636 | Var. 9693 | Var. 9750 | Var. 9807 | Var. 9864 | Var. 9921 |
| | 25-50 | Var. 9637 | Var. 9694 | Var. 9751 | Var. 9808 | Var. 9865 | Var. 9922 |
| | 50-200 | Var. 9638 | Var. 9695 | Var. 9752 | Var. 9809 | Var. 9866 | Var. 9923 |
| | 50-150 | Var. 9639 | Var. 9696 | Var. 9753 | Var. 9810 | Var. 9867 | Var. 9924 |
| | 50-100 | Var. 9640 | Var. 9697 | Var. 9754 | Var. 9811 | Var. 9868 | Var. 9925 |
| | 50-75 | Var. 9641 | Var. 9698 | Var. 9755 | Var. 9812 | Var. 9869 | Var. 9926 |
| | 75-200 | Var. 9642 | Var. 9699 | Var. 9756 | Var. 9813 | Var. 9870 | Var. 9927 |
| | 75-175 | Var. 9643 | Var. 9700 | Var. 9757 | Var. 9814 | Var. 9871 | Var. 9928 |
| | 75-150 | Var. 9644 | Var. 9701 | Var. 9758 | Var. 9815 | Var. 9872 | Var. 9929 |
| | 75-125 | Var. 9645 | Var. 9702 | Var. 9759 | Var. 9816 | Var. 9873 | Var. 9930 |
| | 75-100 | Var. 9646 | Var. 9703 | Var. 9760 | Var. 9817 | Var. 9874 | Var. 9931 |
| | 100-200 | Var. 9647 | Var. 9704 | Var. 9761 | Var. 9818 | Var. 9875 | Var. 9932 |
| | 100-175 | Var. 9648 | Var. 9705 | Var. 9762 | Var. 9819 | Var. 9876 | Var. 9933 |

TABLE 32-continued

Exemplary embodiments for the combination of rVWF dosage and rVWF specific activity useful in the methods described herein.

|  |  | Specific Activity (mU/μg) | | | | | |
|---|---|---|---|---|---|---|---|
|  |  | 60-150 | 60-125 | 60-100 | 60-90 | 60-80 | 60-70 |
|  | 100-150 | Var. 9649 | Var. 9706 | Var. 9763 | Var. 9820 | Var. 9877 | Var. 9934 |
|  | 100-125 | Var. 9650 | Var. 9707 | Var. 9764 | Var. 9821 | Var. 9878 | Var. 9935 |
|  | 125-200 | Var. 9651 | Var. 9708 | Var. 9765 | Var. 9822 | Var. 9879 | Var. 9936 |
|  | 125-175 | Var. 9652 | Var. 9709 | Var. 9766 | Var. 9823 | Var. 9880 | Var. 9937 |
|  | 125-150 | Var. 9653 | Var. 9710 | Var. 9767 | Var. 9824 | Var. 9881 | Var. 9938 |
|  | 150-200 | Var. 9654 | Var. 9711 | Var. 9768 | Var. 9825 | Var. 9882 | Var. 9939 |
|  | 150-200 | Var. 9655 | Var. 9712 | Var. 9769 | Var. 9826 | Var. 9883 | Var. 9940 |
|  | 175-200 | Var. 9656 | Var. 9713 | Var. 9770 | Var. 9827 | Var. 9884 | Var. 9941 |

Var. = Variation

TABLE 33

Exemplary embodiments for the combination of rVWF dosage and rVWF specific activity useful in the methods described herein.

|  |  | Specific Activity (mU/μg) | | | | | |
|---|---|---|---|---|---|---|---|
|  |  | 70-150 | 70-125 | 70-100 | 70-90 | 70-80 | 80-150 |
| Dosage (IU/kg rVWF: RCo activity) | 0.5-200 | Var. 9942 | Var. 9999 | Var. 10056 | Var. 10113 | Var. 10170 | Var. 10227 |
| | 0.5-150 | Var. 9943 | Var. 10000 | Var. 10057 | Var. 10114 | Var. 10171 | Var. 10228 |
| | 0.5-100 | Var. 9944 | Var. 10001 | Var. 10058 | Var. 10115 | Var. 10172 | Var. 10229 |
| | 0.5-75 | Var. 9945 | Var. 10002 | Var. 10059 | Var. 10116 | Var. 10173 | Var. 10230 |
| | 0.5-50 | Var. 9946 | Var. 10003 | Var. 10060 | Var. 10117 | Var. 10174 | Var. 10231 |
| | 0.5-25 | Var. 9947 | Var. 10004 | Var. 10061 | Var. 10118 | Var. 10175 | Var. 10232 |
| | 0.5-10 | Var. 9948 | Var. 10005 | Var. 10062 | Var. 10119 | Var. 10176 | Var. 10233 |
| | 0.5-5 | Var. 9949 | Var. 10006 | Var. 10063 | Var. 10120 | Var. 10177 | Var. 10234 |
| | 0.5-2.5 | Var. 9950 | Var. 10007 | Var. 10064 | Var. 10121 | Var. 10178 | Var. 10235 |
| | 0.5-1 | Var. 9951 | Var. 10008 | Var. 10065 | Var. 10122 | Var. 10179 | Var. 10236 |
| | 2.5-200 | Var. 9952 | Var. 10009 | Var. 10066 | Var. 10123 | Var. 10180 | Var. 10237 |
| | 2.5-150 | Var. 9953 | Var. 10010 | Var. 10067 | Var. 10124 | Var. 10181 | Var. 10238 |
| | 2.5-100 | Var. 9954 | Var. 10011 | Var. 10068 | Var. 10125 | Var. 10182 | Var. 10239 |
| | 2.5-75 | Var. 9955 | Var. 10012 | Var. 10069 | Var. 10126 | Var. 10183 | Var. 10240 |
| | 2.5-50 | Var. 9956 | Var. 10013 | Var. 10070 | Var. 10127 | Var. 10184 | Var. 10241 |
| | 2.5-25 | Var. 9957 | Var. 10014 | Var. 10071 | Var. 10128 | Var. 10185 | Var. 10242 |
| | 2.5-10 | Var. 9958 | Var. 10015 | Var. 10072 | Var. 10129 | Var. 10186 | Var. 10243 |
| | 2.5-5 | Var. 9959 | Var. 10016 | Var. 10073 | Var. 10130 | Var. 10187 | Var. 10244 |
| | 5-200 | Var. 9960 | Var. 10017 | Var. 10074 | Var. 10131 | Var. 10188 | Var. 10245 |
| | 5-175 | Var. 9961 | Var. 10018 | Var. 10075 | Var. 10132 | Var. 10189 | Var. 10246 |
| | 5-150 | Var. 9962 | Var. 10019 | Var. 10076 | Var. 10133 | Var. 10190 | Var. 10247 |
| | 5-125 | Var. 9963 | Var. 10020 | Var. 10077 | Var. 10134 | Var. 10191 | Var. 10248 |
| | 5-100 | Var. 9964 | Var. 10021 | Var. 10078 | Var. 10135 | Var. 10192 | Var. 10249 |
| | 5-75 | Var. 9965 | Var. 10022 | Var. 10079 | Var. 10136 | Var. 10193 | Var. 10250 |
| | 5-50 | Var. 9966 | Var. 10023 | Var. 10080 | Var. 10137 | Var. 10194 | Var. 10251 |
| | 5-25 | Var. 9967 | Var. 10024 | Var. 10081 | Var. 10138 | Var. 10195 | Var. 10252 |
| | 5-10 | Var. 9968 | Var. 10025 | Var. 10082 | Var. 10139 | Var. 10196 | Var. 10253 |
| | 10-200 | Var. 9969 | Var. 10026 | Var. 10083 | Var. 10140 | Var. 10197 | Var. 10254 |
| | 10-150 | Var. 9970 | Var. 10027 | Var. 10084 | Var. 10141 | Var. 10198 | Var. 10255 |
| | 10-100 | Var. 9971 | Var. 10028 | Var. 10085 | Var. 10142 | Var. 10199 | Var. 10256 |
| | 10-75 | Var. 9972 | Var. 10029 | Var. 10086 | Var. 10143 | Var. 10200 | Var. 10257 |
| | 10-50 | Var. 9973 | Var. 10030 | Var. 10087 | Var. 10144 | Var. 10201 | Var. 10258 |
| | 10-25 | Var. 9974 | Var. 10031 | Var. 10088 | Var. 10145 | Var. 10202 | Var. 10259 |
| | 25-200 | Var. 9975 | Var. 10032 | Var. 10089 | Var. 10146 | Var. 10203 | Var. 10260 |
| | 25-150 | Var. 9976 | Var. 10033 | Var. 10090 | Var. 10147 | Var. 10204 | Var. 10261 |
| | 25-100 | Var. 9977 | Var. 10034 | Var. 10091 | Var. 10148 | Var. 10205 | Var. 10262 |
| | 25-75 | Var. 9978 | Var. 10035 | Var. 10092 | Var. 10149 | Var. 10206 | Var. 10263 |
| | 25-50 | Var. 9979 | Var. 10036 | Var. 10093 | Var. 10150 | Var. 10207 | Var. 10264 |
| | 50-200 | Var. 9980 | Var. 10037 | Var. 10094 | Var. 10151 | Var. 10208 | Var. 10265 |
| | 50-150 | Var. 9981 | Var. 10038 | Var. 10095 | Var. 10152 | Var. 10209 | Var. 10266 |
| | 50-100 | Var. 9982 | Var. 10039 | Var. 10096 | Var. 10153 | Var. 10210 | Var. 10267 |
| | 50-75 | Var. 9983 | Var. 10040 | Var. 10097 | Var. 10154 | Var. 10211 | Var. 10268 |
| | 75-200 | Var. 9984 | Var. 10041 | Var. 10098 | Var. 10155 | Var. 10212 | Var. 10269 |
| | 75-175 | Var. 9985 | Var. 10042 | Var. 10099 | Var. 10156 | Var. 10213 | Var. 10270 |
| | 75-150 | Var. 9986 | Var. 10043 | Var. 10100 | Var. 10157 | Var. 10214 | Var. 10271 |
| | 75-125 | Var. 9987 | Var. 10044 | Var. 10101 | Var. 10158 | Var. 10215 | Var. 10272 |
| | 75-100 | Var. 9988 | Var. 10045 | Var. 10102 | Var. 10159 | Var. 10216 | Var. 10273 |
| | 100-200 | Var. 9989 | Var. 10046 | Var. 10103 | Var. 10160 | Var. 10217 | Var. 10274 |
| | 100-175 | Var. 9990 | Var. 10047 | Var. 10104 | Var. 10161 | Var. 10218 | Var. 10275 |
| | 100-150 | Var. 9991 | Var. 10048 | Var. 10105 | Var. 10162 | Var. 10219 | Var. 10276 |
| | 100-125 | Var. 9992 | Var. 10049 | Var. 10106 | Var. 10163 | Var. 10220 | Var. 10277 |

TABLE 33-continued

Exemplary embodiments for the combination of rVWF dosage and rVWF specific activity useful in the methods described herein.

| | | Specific Activity (mU/µg) | | | | | |
|---|---|---|---|---|---|---|---|
| | | 70-150 | 70-125 | 70-100 | 70-90 | 70-80 | 80-150 |
| | 125-200 | Var. 9993 | Var. 10050 | Var. 10107 | Var. 10164 | Var. 10221 | Var. 10278 |
| | 125-175 | Var. 9994 | Var. 10051 | Var. 10108 | Var. 10165 | Var. 10222 | Var. 10279 |
| | 125-150 | Var. 9995 | Var. 10052 | Var. 10109 | Var. 10166 | Var. 10223 | Var. 10280 |
| | 150-200 | Var. 9996 | Var. 10053 | Var. 10110 | Var. 10167 | Var. 10224 | Var. 10281 |
| | 150-200 | Var. 9997 | Var. 10054 | Var. 10111 | Var. 10168 | Var. 10225 | Var. 10282 |
| | 175-200 | Var. 9998 | Var. 10055 | Var. 10112 | Var. 10169 | Var. 10226 | Var. 10283 |

Var. = Variation

TABLE 34

Exemplary embodiments for the combination of rVWF dosage and rVWF specific activity useful in the methods described herein.

| | | Specific Activity (mU/µg) | | | | | |
|---|---|---|---|---|---|---|---|
| | | 80-125 | 80-100 | 80-90 | 90-150 | 90-125 | 90-100 |
| Dosage (IU/kg rVWF:RCo activity) | 0.5-200 | Var. 10284 | Var. 10341 | Var. 10398 | Var. 10455 | Var. 10512 | Var. 10569 |
| | 0.5-150 | Var. 10285 | Var. 10342 | Var. 10399 | Var. 10456 | Var. 10513 | Var. 10570 |
| | 0.5-100 | Var. 10286 | Var. 10343 | Var. 10400 | Var. 10457 | Var. 10514 | Var. 10571 |
| | 0.5-75 | Var. 10287 | Var. 10344 | Var. 10401 | Var. 10458 | Var. 10515 | Var. 10572 |
| | 0.5-50 | Var. 10288 | Var. 10345 | Var. 10402 | Var. 10459 | Var. 10516 | Var. 10573 |
| | 0.5-25 | Var. 10289 | Var. 10346 | Var. 10403 | Var. 10460 | Var. 10517 | Var. 10574 |
| | 0.5-10 | Var. 10290 | Var. 10347 | Var. 10404 | Var. 10461 | Var. 10518 | Var. 10575 |
| | 0.5-5 | Var. 10291 | Var. 10348 | Var. 10405 | Var. 10462 | Var. 10519 | Var. 10576 |
| | 0.5-2.5 | Var. 10292 | Var. 10349 | Var. 10406 | Var. 10463 | Var. 10520 | Var. 10577 |
| | 0.5-1 | Var. 10293 | Var. 10350 | Var. 10407 | Var. 10464 | Var. 10521 | Var. 10578 |
| | 2.5-200 | Var. 10294 | Var. 10351 | Var. 10408 | Var. 10465 | Var. 10522 | Var. 10579 |
| | 2.5-150 | Var. 10295 | Var. 10352 | Var. 10409 | Var. 10466 | Var. 10523 | Var. 10580 |
| | 2.5-100 | Var. 10296 | Var. 10353 | Var. 10410 | Var. 10467 | Var. 10524 | Var. 10581 |
| | 2.5-75 | Var. 10297 | Var. 10354 | Var. 10411 | Var. 10468 | Var. 10525 | Var. 10582 |
| | 2.5-50 | Var. 10298 | Var. 10355 | Var. 10412 | Var. 10469 | Var. 10526 | Var. 10583 |
| | 2.5-25 | Var. 10299 | Var. 10356 | Var. 10413 | Var. 10470 | Var. 10527 | Var. 10584 |
| | 2.5-10 | Var. 10300 | Var. 10357 | Var. 10414 | Var. 10471 | Var. 10528 | Var. 10585 |
| | 23-5 | Var. 10301 | Var. 10358 | Var. 10415 | Var. 10472 | Var. 10529 | Var. 10586 |
| | 5-200 | Var. 10302 | Var. 10359 | Var. 10416 | Var. 10473 | Var. 10530 | Var. 10587 |
| | 5-175 | Var. 10303 | Var. 10360 | Var. 10417 | Var. 10474 | Var. 10531 | Var. 10588 |
| | 5-150 | Var. 10304 | Var. 10361 | Var. 10418 | Var. 10475 | Var. 10532 | Var. 10589 |
| | 5-125 | Var. 10305 | Var. 10362 | Var. 10419 | Var. 10476 | Var. 10533 | Var. 10590 |
| | 5-100 | Var. 10306 | Var. 10363 | Var. 10420 | Var. 10477 | Var. 10534 | Var. 10591 |
| | 5-75 | Var. 10307 | Var. 10364 | Var. 10421 | Var. 10478 | Var. 10535 | Var. 10592 |
| | 5-50 | Var. 10308 | Var. 10365 | Var. 10422 | Var. 10479 | Var. 10536 | Var. 10593 |
| | 5-25 | Var. 10309 | Var. 10366 | Var. 10423 | Var. 10480 | Var. 10537 | Var. 10594 |
| | 5-10 | Var. 10310 | Var. 10367 | Var. 10424 | Var. 10481 | Var. 10538 | Var. 10595 |
| | 10-200 | Var. 10311 | Var. 10368 | Var. 10425 | Var. 10482 | Var. 10539 | Var. 10596 |
| | 10-150 | Var. 10312 | Var. 10369 | Var. 10426 | Var. 10483 | Var. 10540 | Var. 10597 |
| | 10-100 | Var. 10313 | Var. 10370 | Var. 10427 | Var. 10484 | Var. 10541 | Var. 10598 |
| | 10-75 | Var. 10314 | Var. 10371 | Var. 10428 | Var. 10485 | Var. 10542 | Var. 10599 |
| | 10-50 | Var. 10315 | Var. 10372 | Var. 10429 | Var. 10486 | Var. 10543 | Var. 10600 |
| | 10-25 | Var. 10316 | Var. 10373 | Var. 10430 | Var. 10487 | Var. 10544 | Var. 10601 |
| | 25-200 | Var. 10317 | Var. 10374 | Var. 10431 | Var. 10488 | Var. 10545 | Var. 10602 |
| | 25-150 | Var. 10318 | Var. 10375 | Var. 10432 | Var. 10489 | Var. 10546 | Var. 10603 |
| | 25-100 | Var. 10319 | Var. 10376 | Var. 10433 | Var. 10490 | Var. 10547 | Var. 10604 |
| | 25-75 | Var. 10320 | Var. 10377 | Var. 10434 | Var. 10491 | Var. 10548 | Var. 10605 |
| | 25-50 | Var. 10321 | Var. 10378 | Var. 10435 | Var. 10492 | Var. 10549 | Var. 10606 |
| | 50-200 | Var. 10322 | Var. 10379 | Var. 10436 | Var. 10493 | Var. 10550 | Var. 10607 |
| | 50-150 | Var. 10323 | Var. 10380 | Var. 10437 | Var. 10494 | Var. 10551 | Var. 10608 |
| | 50-100 | Var. 10324 | Var. 10381 | Var. 10438 | Var. 10495 | Var. 10552 | Var. 10609 |
| | 50-75 | Var. 10325 | Var. 10382 | Var. 10439 | Var. 10496 | Var. 10553 | Var. 10610 |
| | 75-200 | Var. 10326 | Var. 10383 | Var. 10440 | Var. 10497 | Var. 10554 | Var. 10611 |
| | 75-175 | Var. 10327 | Var. 10384 | Var. 10441 | Var. 10498 | Var. 10555 | Var. 10612 |
| | 75-150 | Var. 10328 | Var. 10385 | Var. 10442 | Var. 10499 | Var. 10556 | Var. 10613 |
| | 75-125 | Var. 10329 | Var. 10386 | Var. 10443 | Var. 10500 | Var. 10557 | Var. 10614 |
| | 75-100 | Var. 10330 | Var. 10387 | Var. 10444 | Var. 10501 | Var. 10558 | Var. 10615 |
| | 100-200 | Var. 10331 | Var. 10388 | Var. 10445 | Var. 10502 | Var. 10559 | Var. 10616 |
| | 100-175 | Var. 10332 | Var. 10389 | Var. 10446 | Var. 10503 | Var. 10560 | Var. 10617 |
| | 100-150 | Var. 10333 | Var. 10390 | Var. 10447 | Var. 10504 | Var. 10561 | Var. 10618 |
| | 100-125 | Var. 10334 | Var. 10391 | Var. 10448 | Var. 10505 | Var. 10562 | Var. 10619 |
| | 125-200 | Var. 10335 | Var. 10392 | Var. 10449 | Var. 10506 | Var. 10563 | Var. 10620 |
| | 125-175 | Var. 10336 | Var. 10393 | Var. 10450 | Var. 10507 | Var. 10564 | Var. 10621 |

TABLE 34-continued

Exemplary embodiments for the combination of rVWF dosage and
rVWF specific activity useful in the methods described herein.

| | Specific Activity (mU/µg) | | | | | |
|---|---|---|---|---|---|---|
| | 80-125 | 80-100 | 80-90 | 90-150 | 90-125 | 90-100 |
| 125-150 | Var. 10337 | Var. 10394 | Var. 10451 | Var. 10508 | Var. 10565 | Var. 10622 |
| 150-200 | Var. 10338 | Var. 10395 | Var. 10452 | Var. 10509 | Var. 10566 | Var. 10623 |
| 150-200 | Var. 10339 | Var. 10396 | Var. 10453 | Var. 10510 | Var. 10567 | Var. 10624 |
| 175-200 | Var. 10340 | Var. 10397 | Var. 10454 | Var. 10511 | Var. 10568 | Var. 10625 |

Var. = Variation

In one embodiment, the method comprises administering a composition of rVWF, wherein the composition of rVWF administered to the subject is a composition of high molecular weight rVWF multimers in which at least 30% of rVWF molecules in the composition are present in a multimer of at least 10 subunits, and wherein the dose of rVWF and specific activity of rVWF in the composition is selected from variations 8004 to 10625 in Table 28 to Table 34. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers in which at least 50% of rVWF molecules in the composition are present in a multimer of at least 10 subunits, and wherein the dose of rVWF and specific activity of rVWF in the composition is selected from variations 8004 to 10625 in Table 28 to Table 34. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers in which at least 70% of rVWF molecules in the composition are present in a multimer of at least 10 subunits, and wherein the dose of rVWF and specific activity of rVWF in the composition is selected from variations 8004 to 10625 in Table 28 to Table 34. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein the composition of rVWF administered to the subject is a composition of high molecular weight rVWF multimers having a minimal percentage of rVWF molecules present in a particular higher-order rVWF multimer or larger multimer according to any one of variations 134 to 457 found in Table 3 to Table 5, and wherein the dose of rVWF and specific activity of rVWF in the composition is selected from variations 8004 to 10625 in Table 28 to Table 34. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein FVIII in the subject is stabilized for at least 18 hours post-administration, and wherein the dose of rVWF and specific activity of rVWF in the composition is selected from variations 8004 to 10625 in Table 28 to Table 34. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein FVIII in the subject is stabilized for at least 24 hours post-administration, and wherein the dose of rVWF and specific activity of rVWF in the composition is selected from variations 8004 to 10625 in Table 28 to Table 34. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF, wherein FVIII in the subject is stabilized for at least 30 hours post-administration, and wherein the dose of rVWF and specific activity of rVWF in the composition is selected from variations 8004 to 10625 in Table 28 to Table 34. In one embodiment, the composition of rVWF administered to the subject has a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

Administration of rVWF/rFVIII

In one aspect, the present disclosure provides method for treating Von Willebrand Disease (VWD) or Hemophilia A in a subject in need thereof, which includes administering a composition of recombinant Von Willebrand Factor (rVWF) and recombinant FVIII (rFVIII) such that Factor VIII (FVIII) stability is increased, as compared to FVIII half-life in a subject administered a composition of plasma derived Von Willebrand Factor (pdVWF). In one embodiment, the composition of rVWF/rFVIII administered to the subject is a composition of high molecular weight rVWF multimers. In one embodiment, the composition of rVWF/rFVIII administered to the subject has a higher VWF specific activity than a composition of pdVWF. In yet another embodiment, the composition of rVWF/rFVIII administered to the subject is a composition of high molecular weight rVWF multimers with a higher VWF specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII such that FVIII stability is extended by at least 10%, 20%, 30%, 2 hr, 4 hr, 6 hr, or by an amount selected from variations 1300 to 1643 found in Table 9, as compared to FVIII stability in a subject administered a composition of pdVWF/FVIII. In one embodiment, the composition of rVWF/rFVIII administered to the subject is a composition of high molecular weight rVWF multimers. In one embodiment, the composition of rVWF/rFVIII administered to the subject has a higher VWF specific activity than a composition of pdVWF/FVIII. In yet another embodiment, the composition of rVWF/rFVIII administered to the subject is a composition of high molecular weight rVWF multimers with a higher specific activity than a composition of pdVWF. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII such that FVIII stability is extended by at least 10% as compared to FVIII stability in a subject administered a composition of pdVWF/FVIII, wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII such that FVIII stability is extended by at least 20% as compared to FVIII stability in a subject administered a composition of pdVWF/FVIII, wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII such that FVIII stability is extended by at least 30% as compared to FVIII stability in a subject administered a composition of pdVWF/FVIII, wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the combination of rVWF specific activity in the composition and increase in FVIII stability, as compared to FVIII stability in a subject administered a composition of pdVWF/FVIII, is selected from variations 2339 to 4868 in Table 13 to Table 19. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 30% of rVWF molecules in the composition are present in a multimer of at least 10 subunits, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 50% of rVWF molecules in the composition are present in a multimer of at least 10 subunits, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 70% of rVWF molecules in the composition are present in a multimer of at least 10 subunits, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a dosage of a rVWF/rFVIII composition containing from 10 IU/kg to 40 IU/kg rVWF:RCo activity, wherein the combination of rVWF specific activity in the composition and increase in FVIII stability, as compared to FVIII stability in a subject administered a composition of pdVWF/FVIII, is selected from variations 2339 to 4868 in Table 13 to Table 19. In a specific embodiment, the composition contains from 20 IU/kg to 30 IU/kg rVWF:RCo activity. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a dosage of a rVWF/rFVIII composition containing from 25 IU/kg to 75 IU/kg rVWF:RCo activity, wherein the combination of rVWF specific activity in the composition and increase in FVIII stability, as compared to FVIII stability in a subject administered a composition of pdVWF/FVIII, is selected from variations 2339 to 4868 in Table 13 to Table 19. In a specific embodiment, the composition contains from 40 IU/kg to 60 IU/kg rVWF:RCo activity. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a dosage of a rVWF/rFVIII composition containing from 75 IU/kg to 125 IU/kg rVWF:RCo activity, wherein the combination of rVWF specific activity in the composition and increase in FVIII stability, as compared to FVIII stability in a subject administered a composition of pdVWF/FVIII, is selected from variations 2339 to 4868 in Table 13 to Table 19. In a specific embodiment, the composition contains from 75 IU/kg to 100 IU/kg rVWF:RCo activity. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the subject is administered a dose of rVWF selected from variations 2141 to 2338 in Table 12, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject is a composition of high molecular weight rVWF multimers. In one embodiment, the composition of rVWF/rFVIII administered to the subject has a higher specific activity than a composition of pdVWF. In yet another embodiment, the composition of rVWF/rFVIII administered to the subject is a composition of high molecular weight rVWF multimers with a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 30% of rVWF molecules in the composition are present in a multimer of at least 10 subunits, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 50% of rVWF molecules in the composition are present in a multimer of at least 10 subunits, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 70% of rVWF molecules in the composition are present in a multimer of at least 10 subunits, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the rVWF in the composition has a specific activity of from 40 mU/μg to 60 mU/μg, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the rVWF in the composition has a specific activity of at least 60 mU/μg, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the rVWF in the composition has a specific activity of at least 80 mU/μg, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the rVWF in the composition has a specific activity selected from variations 1 to 133 found in Table 1, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the dose of rVWF and specific activity of rVWF in the composition is selected from variations 8004 to 10625 in Table 28 to Table 34. In one embodiment, the composition of rVWF/rFVIII administered to the subject is a composition of high molecular weight rVWF multimers. In one embodiment, the composition of rVWF/rFVIII administered to the subject has a higher specific activity than a composition of pdVWF/FVIII. In yet another embodiment, the composition of rVWF/rFVIII administered to the subject is a composition of high molecular weight rVWF multimers with a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 30% of rVWF molecules in the composition are present in a multimer of at least 10 subunits, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 50% of rVWF molecules in the composition are present in a multimer of at least 10 subunits, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers in which at least 70% of rVWF molecules in the composition are present in a multimer of at least 10 subunits, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein FVIII in the subject is stabilized for at least 18 hours post-administration, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein FVIII in the subject is stabilized for at least 24 hours post-administration, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein FVIII in the subject is stabilized for at least 30 hours post-administration, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 4:1-3:2, and wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In a specific embodiment, the ratio of rFVIII procoagulant activity (IU rFVIII:C) to rVWF Ristocetin cofactor activity (IU rVWF:RCo) in the composition is from 3:1-3:2. In one embodiment, the composition of rVWF/rFVIII administered to the subject has a higher VWF specific activity than a composition of pdVWF/FVIII. In one embodiment. FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:1-1:2, and wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In a specific embodiment, the ratio of rFVIII procoagulant activity (IU rFVIII:C) to rVWF Ristocetin cofactor activity (IU rVWF:RCo) in the composition is from 3:2-2:3. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:3-1:6, and wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In a specific embodiment, the ratio of rFVIII procoagulant activity (IU rFVIII:C) to rVWF Ristocetin cofactor activity (IU rVWF:RCo) in the composition is from 2:3-1:5. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is selected from variations 1988 to 2140 found in Table 11, and wherein the composition of rVWF/rFVIII administered to the subject is a composition of high molecular weight rVWF multimers having a minimal percentage of rVWF molecules present in a particular higher-order rVWF multimer or larger multimer according to any one of variations 134 to 457 found in Table 3 to Table 5. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is selected from variations 1988 to 2140 found in Table 11. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 4:1-3:2, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In a specific embodiment, the ratio of rFVIII procoagulant activity (IU rFVIII:C) to rVWF Ristocetin cofactor activity (IU rVWF:RCo) in the composition is from 3:1-3:2. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:1-1:2, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In a specific embodiment, the ratio of rFVIII procoagulant activity (IU rFVIII:C) to rVWF Ristocetin cofactor activity (IU rVWF:RCo) in the composition is from 3:2-2:3. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:3-1:6, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In a specific embodiment, the ratio of rFVIII procoagulant activity (IU rFVIII:C) to rVWF Ristocetin cofactor activity (IU rVWF:RCo) in the composition is from 2:3-1:5. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is selected from variations 1988 to 2140 found in Table 11, and wherein the combination of rVWF specific activity in the composition and increase in FVIII stability, as compared to FVIII stability in a subject administered a composition of pdVWF/FVIII, is selected from variations 2339 to 4868 in Table 13 to Table 19. In one embodiment, the composition of rVWF/rFVIII administered to the subject is a composition of high molecular weight rVWF multimers. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 4:1-3:2, and wherein the dose of rVWF and increase in FVIII stability, as compared to FVIII stability in a subject administered a composition of pdVWF/FVIII, is selected from variations 4869 to 8003 in Table 20 to Table 27. In a specific embodiment, the ratio of rFVIII procoagulant activity (IU rFVIII:C) to rVWF Ristocetin cofactor activity (IU rVWF:RCo) in the composition is from 3:1-3:2. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:1-1:2, and wherein the dose of rVWF and increase in FVIII stability, as compared to FVIII stability in a subject administered a composition of pdVWF/FVIII, is selected from variations 4869 to 8003 in Table 20 to Table 27. In a specific embodiment, the ratio of rFVIII procoagulant activity (IU rFVIII:C) to rVWF Ristocetin cofactor activity (IU rVWF:RCo) in the composition is from 3:2-2:3. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:3-1:6, and wherein the dose of rVWF and increase in FVIII stability, as compared to FVIII stability in a subject administered a composition of pdVWF/FVIII, is selected from variations 4869 to 8003 in Table 20 to Table 27. In a specific embodiment, the ratio of rFVIII procoagulant activity (IU rFVIII:C) to rVWF Ristocetin cofactor activity (IU rVWF:RCo) in the composition is from 2:3-1:5. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is selected from variations 1988 to 2140 found in Table 11, and wherein the dose of rVWF and increase in FVIII stability, as compared to FVIII stability in a subject administered a composition of pdVWF/FVIII, is selected from variations 4869 to 8003 in Table 20 to Table 27. In one embodiment, the composition of rVWF/rFVIII administered to the subject has a higher specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 4:1-3:2, and wherein the dose of rVWF and specific activity of rVWF in the composition is selected from variations 8004 to 10625 in Table 28 to Table 34. In a specific embodiment, the ratio of rFVIII procoagulant activity (IU rFVIII:C) to rVWF Ristocetin cofactor activity (IU rVWF:RCo) in the composition is from 3:1-3:2. In one embodiment, the composition of rVWF/rFVIII administered to the subject has a higher VWF specific activity than a composition of pdVWF/FVIII. In one embodiment, FVIII stability is characterized by the half life of FVIII. In another embodiment. FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:1-1:2, and wherein the dose of rVWF and specific activity of rVWF in the composition is selected from variations 8004 to 10625 in Table 28 to Table 34. In a specific embodiment, the ratio of rFVIII procoagulant activity (IU rFVIII:C) to rVWF Ristocetin cofactor activity (IU rVWF:RCo) in the composition is from 3:2-2:3. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is from 2:3-1:6, and wherein the dose of rVWF and specific activity of rVWF in the composition is selected from variations 8004 to 10625 in Table 28 to Table 34. In a specific embodiment, the ratio of rFVIII procoagulant activity (IU rFVIII:C) to rVWF Ristocetin cofactor activity (IU rVWF:RCo) in the composition is from 2:3-1:5. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

In one embodiment, the method comprises administering a composition of rVWF/rFVIII, wherein the ratio of rFVIII procoagulant activity (IU rFVIII:C) to rVWF Ristocetin cofactor activity (IU rVWF:RCo) in the composition is selected from variations 1988 to 2140 found in Table 11, and wherein the dose of rVWF and specific activity of rVWF in the composition is selected from variations 8004 to 10625 in Table 28 to Table 34. In one embodiment, the composition of rVWF/rFVIII administered to the subject has a higher VWF specific activity than a composition of pdVWF/FVIII. In one embodiment, FVIII stability is characterized by the half life of FVIII. In another embodiment, FVIII stability is characterized by mean residence time (MRT) of FVIII. In a further embodiment, the method is for treating any type of VWD. In a specific embodiment, the method is for treating Type 3 VWD.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, Highly stabilized York, Gait, "*Oligonucleotide Synthesis: A Practical Approach*" 1984, IRL Press, London, Nelson and Cox (2000), *Lehninger, Principles of Biochemistry* 3rd Ed., W. H. Freeman Pub., Highly stabilized York, N.Y. and Berg et al. (2002) *Biochemistry*, 5th Ed., W. H. Freeman Pub., Highly stabilized York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the above description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

EXAMPLES

Example 1

Study of rVWF:rFVIII Co-Administration.

Figure 1:
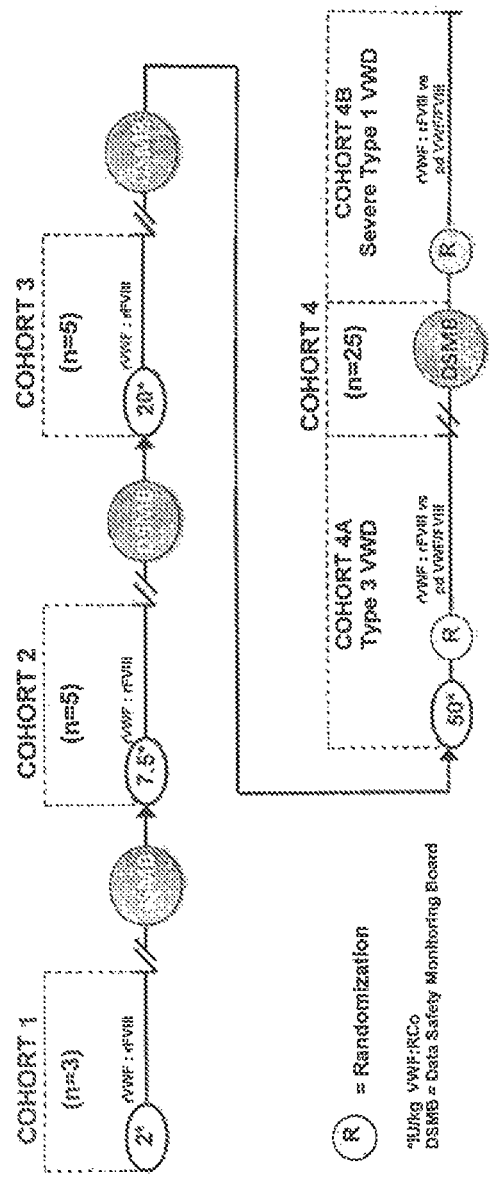
FIG. 1. A schematic of the study design assessing tolerability and safety after single doses of rVWF:rFVIII.

The immediate tolerability and safety after single doses of rVWF:rFVIII at 2 IU/kg, 7.5 IU/kg, 20 IU/kg and 50 IU/kg VWF:RCo was assessed as a primary endpoint of the study. Secondary endpoints included PK for VWF:RCo. VWF:CB, VWF:Ag, FVIII and multimeric composition of the VWF. An additional secondary endpoint was a PK comparison with pdVWF/pdFVIII [Cohort 4 (50 IU/kg VWF:RCo)]. See FIG. 1 for a schematic illustration of the study design.

Recombinant human Von Willebrand Factor (rVWF) was expressed in CHO cells. Propeptide removal was mediated in vitro through exposure of the pro-VWF to recombinant Furin. Fully glycosylated/ABO blood groups glycans were absent. The recombinant VWF has higher specific activity than plasma-derived VWF (pdVWF) and offers the therapeutic flexibility of dosing with or without rFVIII. The rVWF used in this study was not exposed to ADAMTS13, resulting in the presence of ultra-large VWF multimers and intact VWF subunits. ADAMTS13 results in subunit cleavage at $TYR^{1605}$-$MET^{1606}$.

Figure 2A:
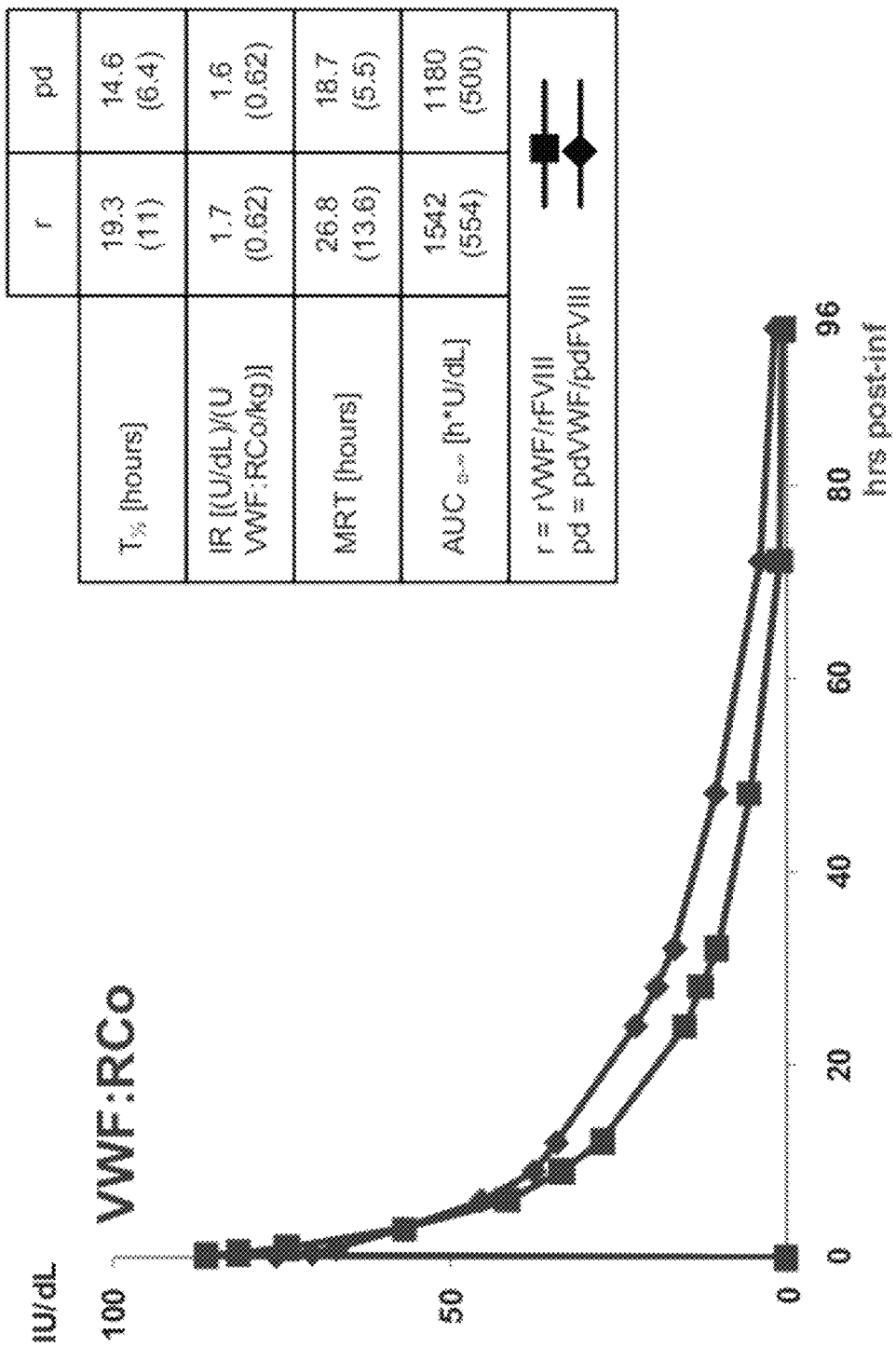
FIG. 2. Pharmacokinetic data. (A) provides PK data for rVWF/rFVIII and pdVWF/pdFVIII. (B) provides data on progressive loss of high molecular weight rVWF upon exposure to ADAMTS13.
Figure 2B:
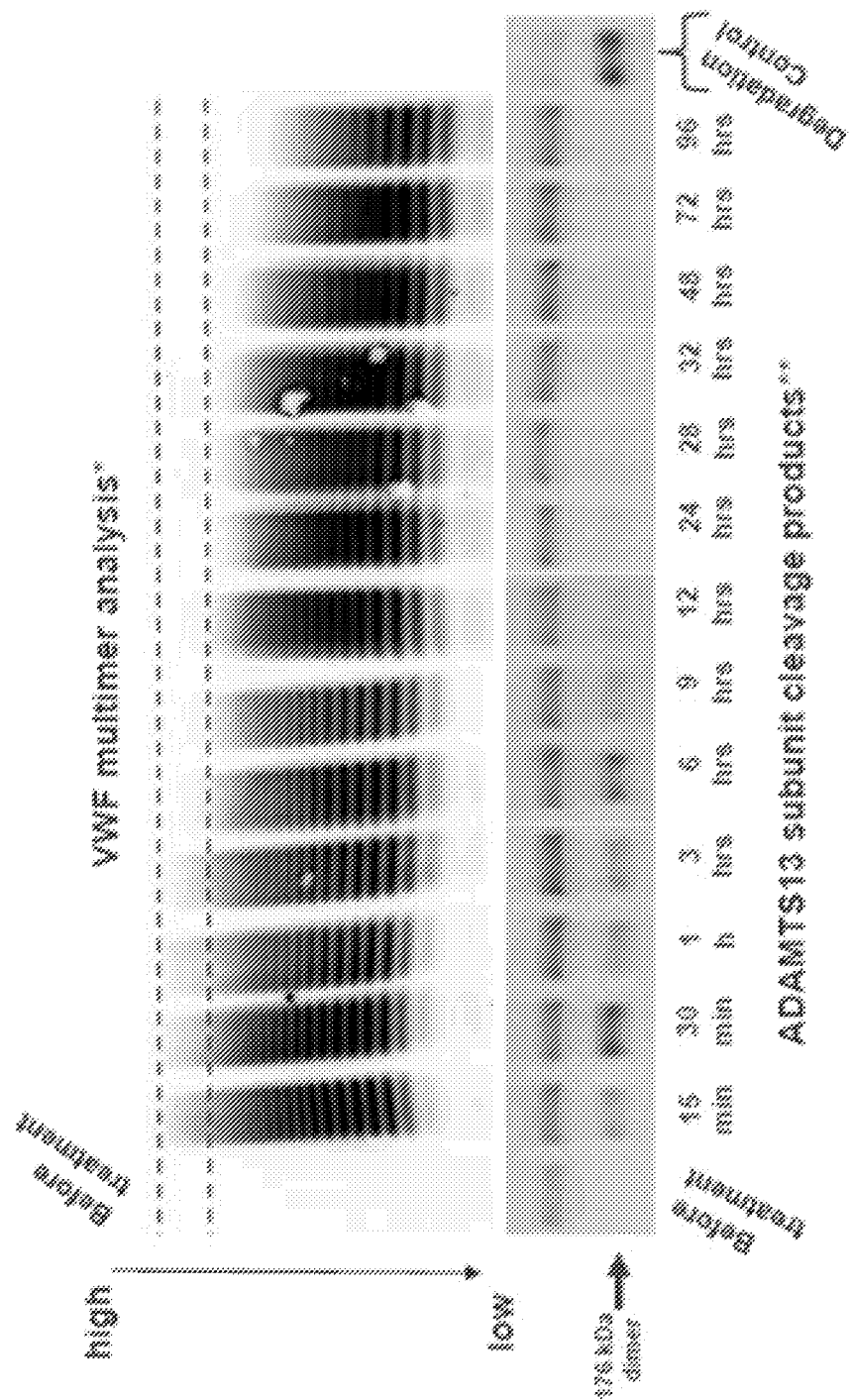

VWF:RCo PK/VWF multimer kinetics showed highly similar PK for VWF:RCo (VWF activity) between rVWF and Humate P (FIG. 2A). Humate P is human derived medium purity Factor VIII concentrates complexed to VWF. A surrogate marker was used for efficacy and dosing recommendations. The data in FIG. 2A show that rVWF shows similar activity to that of plasma derived VW. Progressive loss of high molecular weight rVWF was seen upon exposure to ADAMTS13 (FIG. 2B), showing that rVWF is present in high molecular weight multimers prior to the ADAMTS13 exposure.

Figure 3:
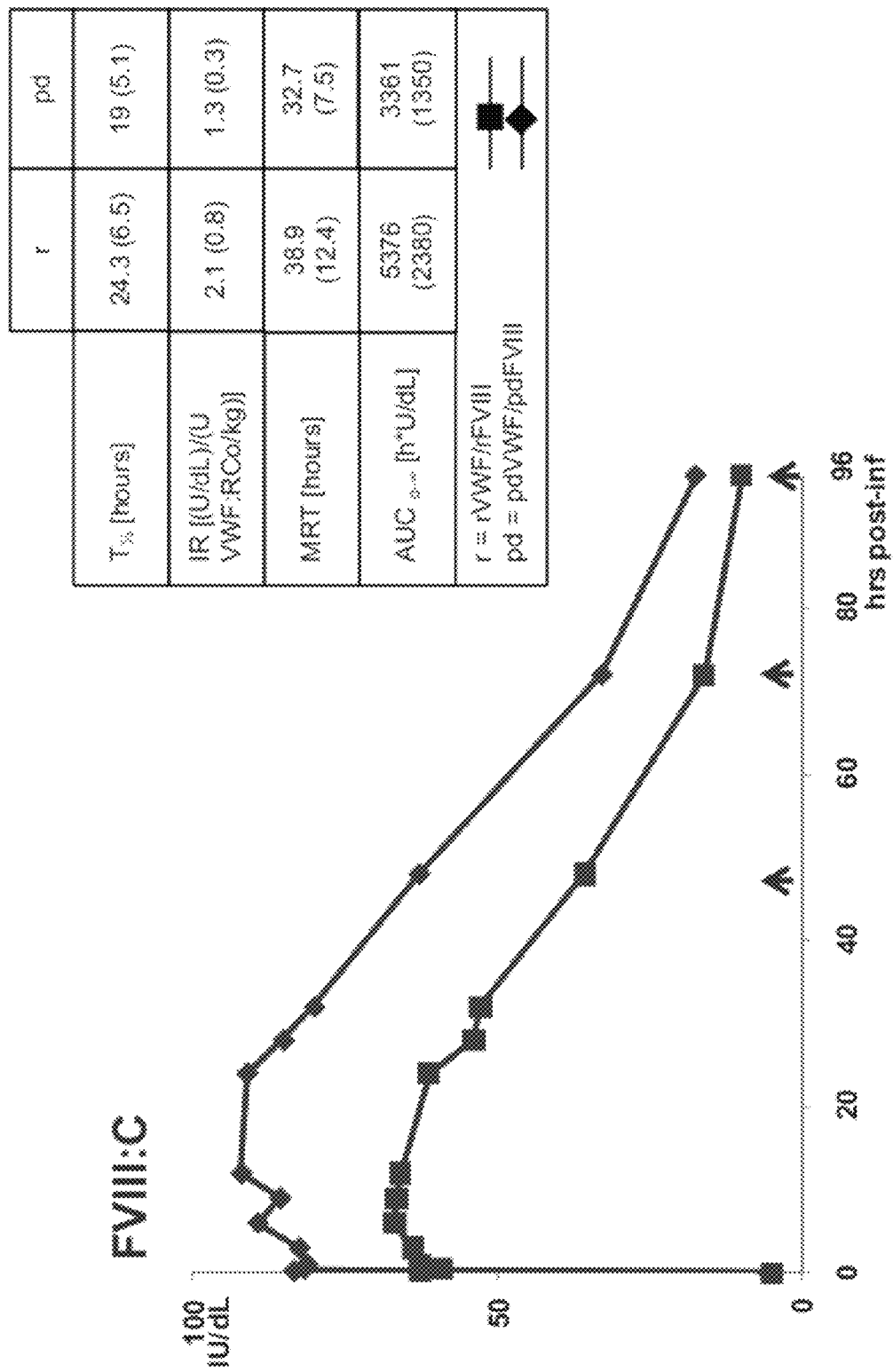
FIG. 3. Pharmacokinetic data showing FVIII PK for rVWF/rFVIII and pdVWF/pdFVIII.

Higher FVIII levels were observed in rVWF patients as compared to Humate (FIG. 3). These data show that rVWF stabilizes endogenous FVIII in vivo. There was a difference in effects seen with different VWF:FVIII ratios (1.3:1 vs. ~2.1 VWF/FVIII). These different ratios suggest that less rVWF can be used to stabilize FVIII than is needed when using plasma derived VWF. The study design provided a flexibility of re-dosing with rVWF alone (no rFVIII) after the initial dose.

Ultra-large molecular weight multimers are present with rVWF—these ultra-large molecular weight multimers rapidly disappear following infusion. ADAMTS13 mediated cleavage fragments were seen in all subjects. The pharmacokinetic profile of VWF:RCo was similar to that of pdVWF. There was sustained stabilization of endogenous FVIII with rVWF which was comparable to that observed with pdVWF. The adverse drug reaction profile with rVWF was similar to that of pdVWF/pdFVIII, and all related adverse events (AEs) were mild.

The overall safety and pharmacokinetic profile suggests that rVWF can be used for the treatment and preventing of bleeding episodes at doses comparable to pdVWF/pdFVIII, while enhancing the levels of FVIII as compared to the effect from the use of pdVWF. Without being limited by theory, it is possible that the high proportion of ultra-large multimers (decamers or higher) in the population of rVWF leads to the enhanced stabilization of FVIII seen with rVWF as compared to that by plasma derived VWF.

Example 2

In-Human Study Evaluating Pharmacokinetics Demonstrating Safety and Tolerability in Severe Von Willebrand Disease (VWD).

This study compared the effects of pdVWF and rVWF in patients with type 3 VWD or severe Type 1 VWD.

The pdVWF used in this study was synthesized in endothelial cells and megakaryocytes. Post-translational modification of propeptide removal occurred intracellularly during passage of the protein to the Golgi and post-Golgi compartments. Glycosylation/ABO blood group glycans were present. The pdVWF consisted of VWF subunits that had been exposed to plasma ADAMTS13. There were no ultra-large VWF multimers in the pdVWF population and subunits were cleaved at $TYR^{1605}$-$MET^{1606}$. pdVWF concentrates contained other proteins, including ADAMTS13 and hemagglutins.

The rVWF used in this study was expressed in CHO cells. Propeptide removal was mediated in vitro through exposure of the pro-VWF to recombinant Furin. Fully glycosylated/ABO blood group glycans were absent. The rVWF was not exposed to ADAMTS13. The subunits of the rVWF were intact and ultra-large VWF multimers were present. Subunit cleavage did occur upon ADAMTS13 exposure. The rVWF showed higher specific activity than pdVWF.

Figure 5:
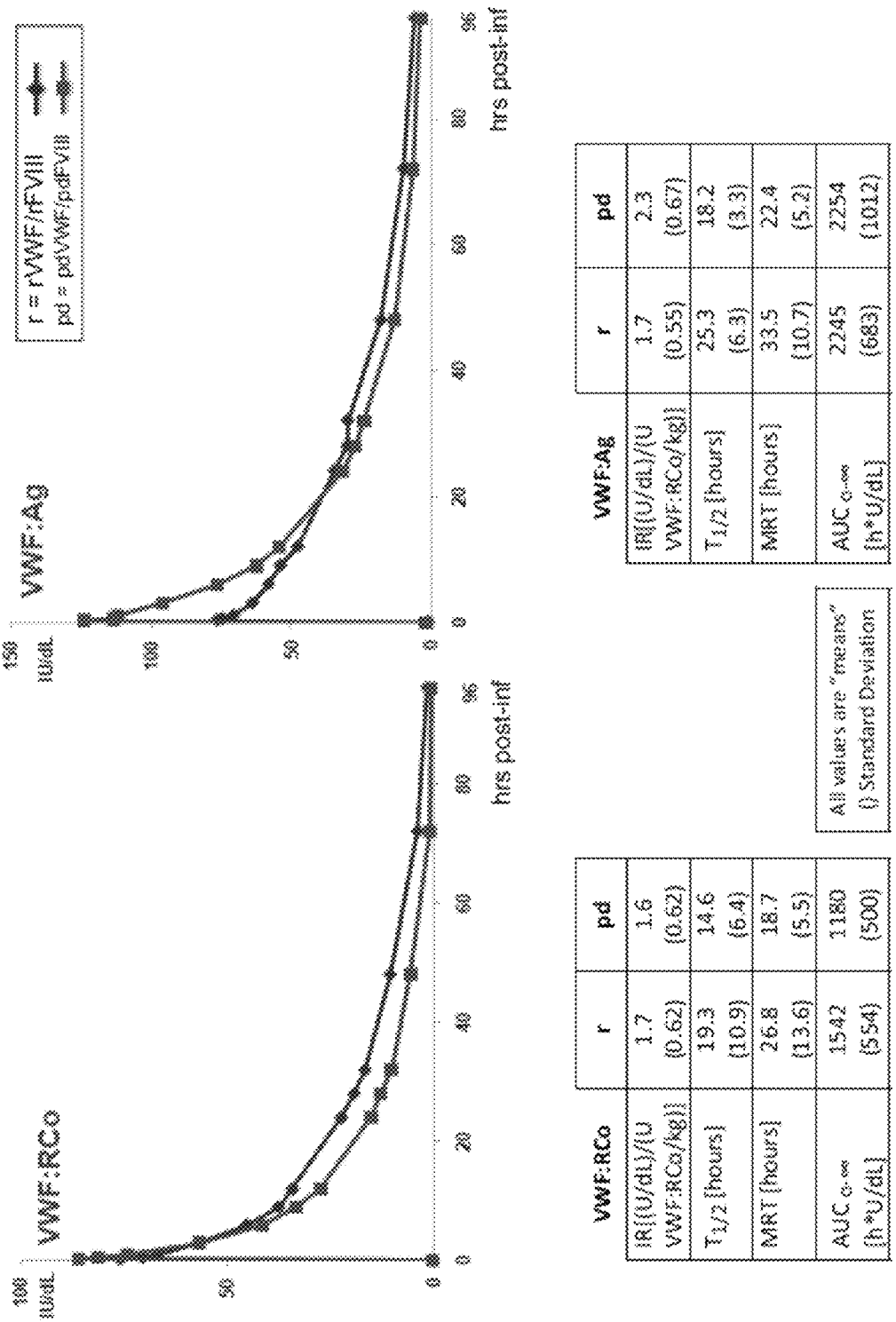
FIG. 5. Pharmacokinetic data of rVWF/rFVIII and pdVWF/pdFVIII treatment of Cohort 4A.
Figure 6:
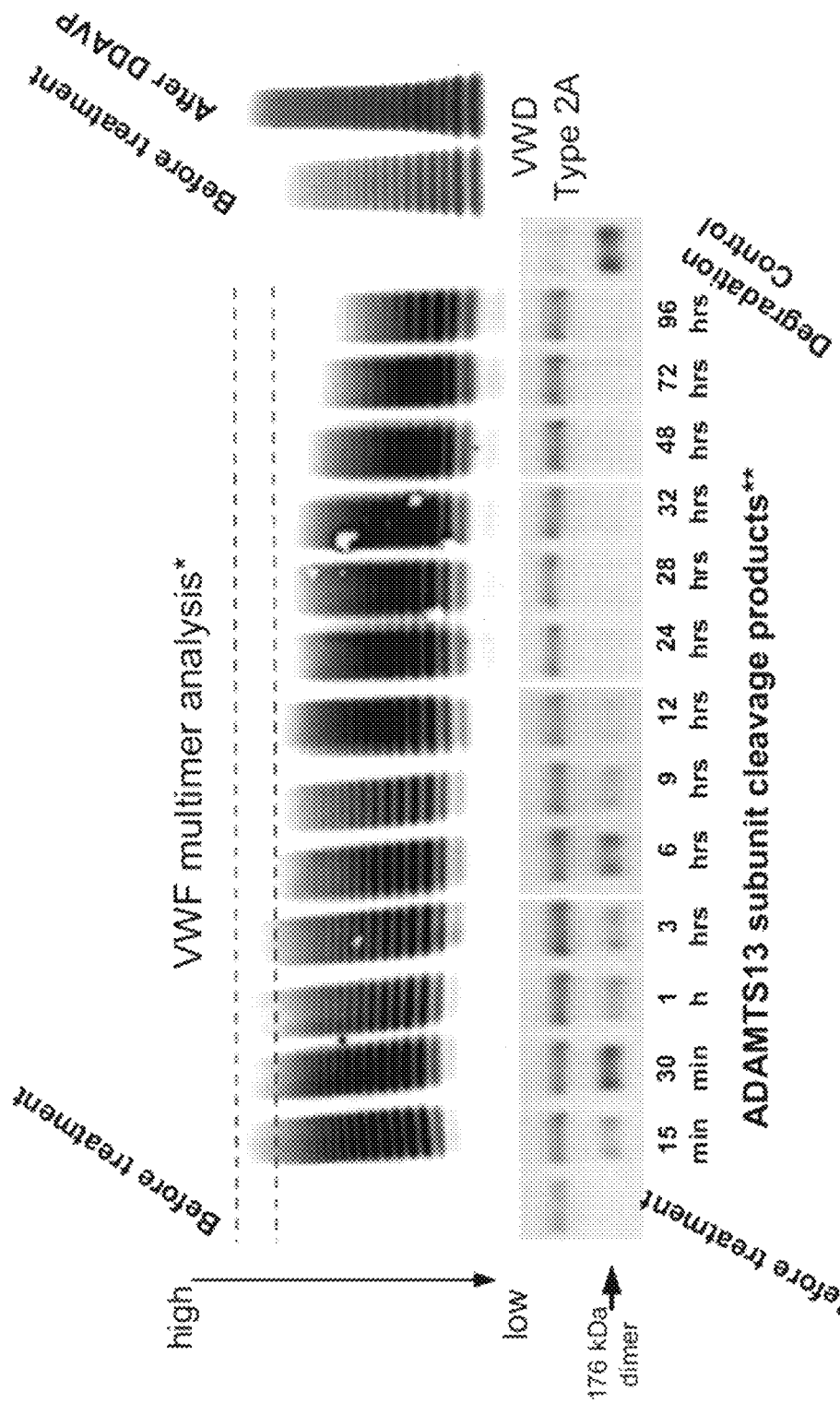
FIG. 6. SDS-PAGE data on VWF multimer cleavage by ADAMTS13.

The inclusion criteria for this study were:
Type 3 VWD (VWF:Ag≤3 IU/dL)
Severe Type 1 VWD (VWF:RCo≤10 IU/dL and FVIII:C<20 IU/dL)
18 to 60 years of age
Previous coagulation factor replacement therapy (≥25 ED)
Non-bleeding state The exclusion criteria for this study were:
Other coagulation disorders
History of VWF and/or FVIII inhibitors
Cardiovascular disease
Medical history of thromboembolic event
Medical history of other immunological disorders The immediate tolerability and safety after single doses of rVWF:rFVIII at 2 IU/kg, 7.5 IU/kg, 20 IU/kg and 50 IU/kg VWF:RCo was assessed as a primary endpoint of this study. Secondary endpoints included PK for VWF:RCo, VWF:CB, VWF:Ag, FVIII and multimeric composition of the VWF. An additional secondary endpoint was a PK comparison with pdVWF/pdFVIII [Cohort 4 (50 IU/kg VWF:RCo)]. Patient demographics for this study are shown in FIG. 4. Pharmacokinetic analysis of Cohort 4A (Type 3 VWD) VWF:RCo/VWF:Ag is shown in FIG. 5. These data show that the total activities of rVWF were comparable to those of pdVWF. Progressive loss of high molecular weight rVWF was seen upon exposure to ADAMTS13 (FIG. 6). Further pharmacokinetic analysis of Cohort 4A (Type 3 VWD) FVIII:C is shown in FIG. 7. The data in FIG. 7 suggests that rVWF was more effective at stabilizing the in vivo activity of FVIII than pdVWF, resulting in increased FVIII procoagulant activity after treatment with rVWF/rVWF as compared to treatment with pdVWF/pdFVIII.

Ultra-large molecular weight multimers were present in rVWF and rapidly disappeared following infusion. ADAMTS13 mediated cleavage fragments were seen in all subjects. The pharmacokinetic profile of VWF:RCo was similar to that of pdVWF. There was sustained stabilization of endogenous FVIII that was comparable to that observed with pdVWF. The adverse drug reaction profile was similar to that of pdVWF/pdFVIII, and all related adverse events were mild.

The overall safety and pharmacokinetic profile suggests that rVWF can be used for the treatment and preventing of bleeding episodes at doses comparable to pdVWF/pdFVIII.

Example 3

Clinical Study of rVWF:rFVIII Complex.

This study was a pharmacokinetics, immediate safety and tolerability study in congenital von Willebrand disease Type 3. FIG. 9 shows the rVWF PK parameters for three patients in the study.

Figure 10:
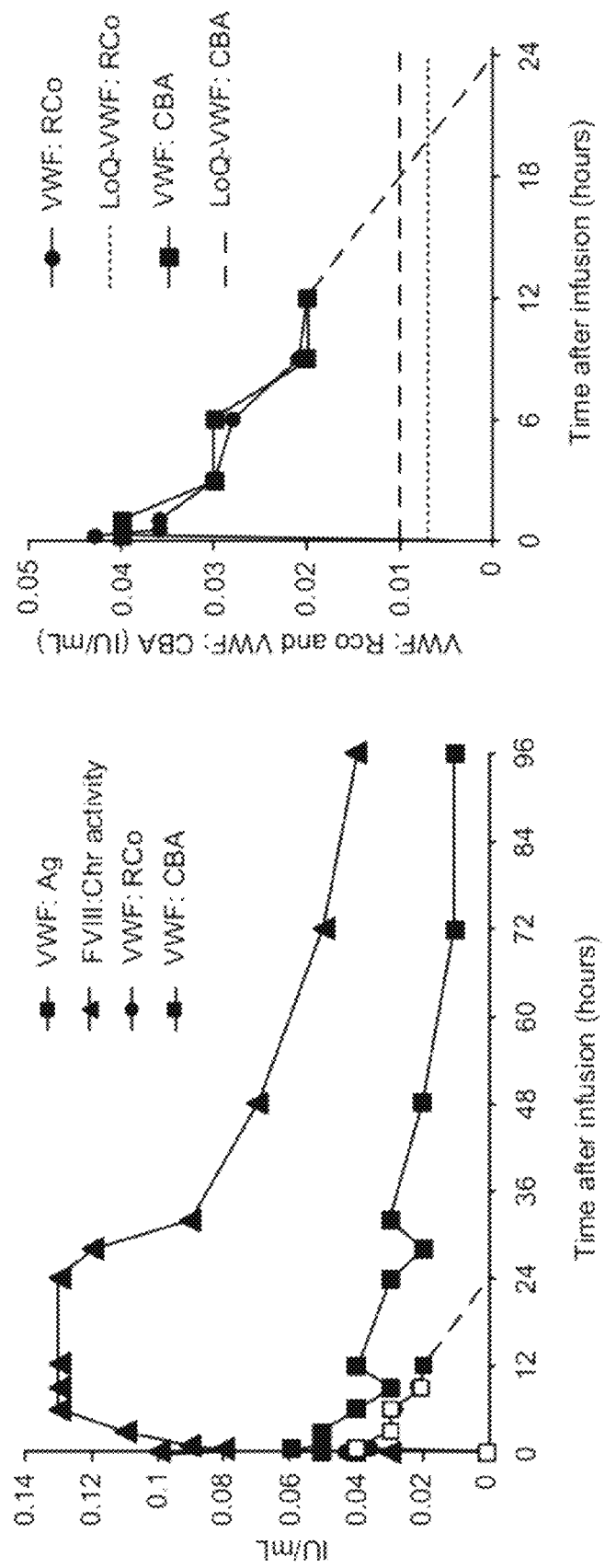
FIG. 10. rVWF PK data from Patient 1.

FIG. 10 shows PK data for Patient 1. There was a good correlation between VWF:RCo and VWF:CBA. Activities were measurable up to 12 hours (both were below the limit of quantification at 24 hours). VWF:Ag was still measurable at 96 hours. Endogenous FVIII activity increased to a maximum of 0.13 IU/mL.

Figure 11:
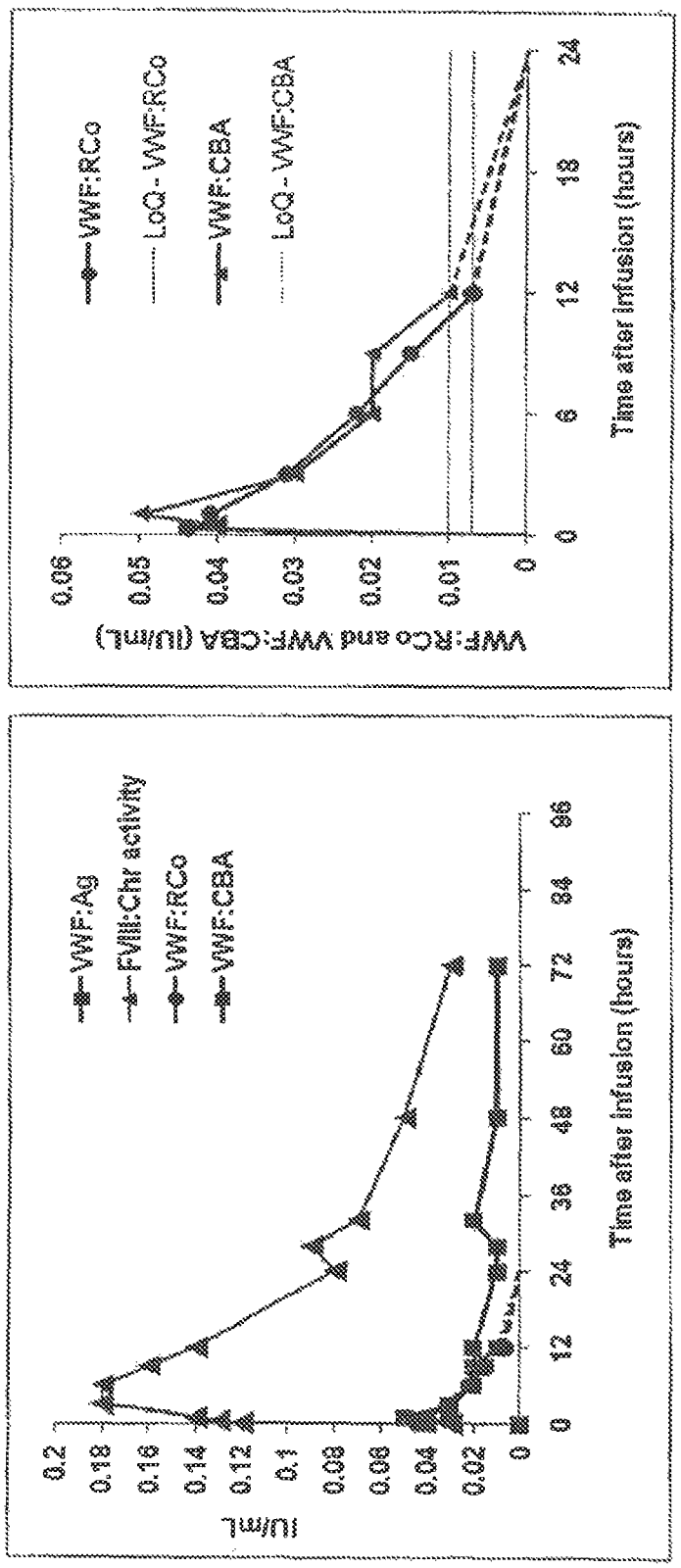
FIG. 11. rVWF PK data from Patient 2.

FIG. 11 shows PK data in Patient 2. As with Patient 1, there was a good correlation between VWF:RCo and VWF:CBA. Both activities were measurable (albeit at the limit of quantification) up to 12 hours. VWF:Ag was still measurable at 72 hours (the 96 hour sample was not tested). Endogenous FVIII activity increased to a maximum of 0.18 IU/mL for this patient.

Figure 12:
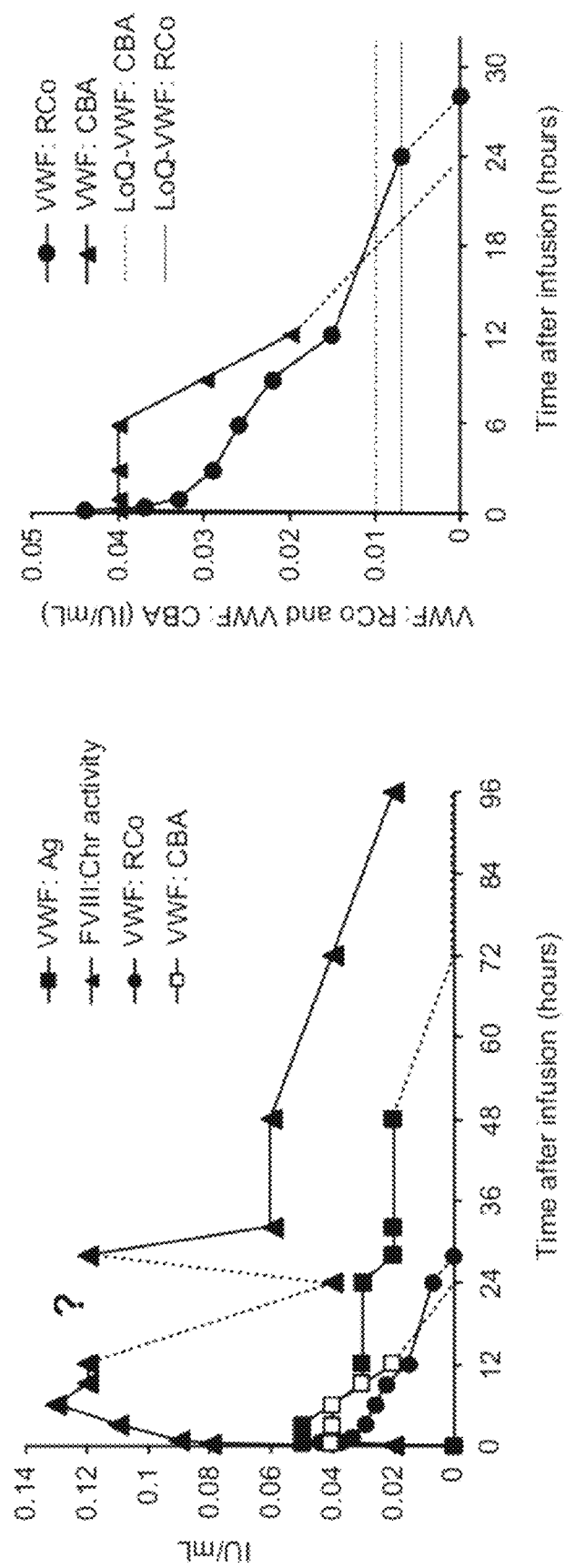
FIG. 12. rVWF PK data from Patient 3.

FIG. 12 shows PK data in Patient 3. VWF:RCo activity was measurable up to 24 hours (albeit at the limit of quantification), while VWF:CBA was below LoQ at 24 hours. VWF:Ag was still measurable up to 48 hours. Endogenous FVIII activity increased to a maximum of 0.13 IU/mL for this patient.

Figure 13:
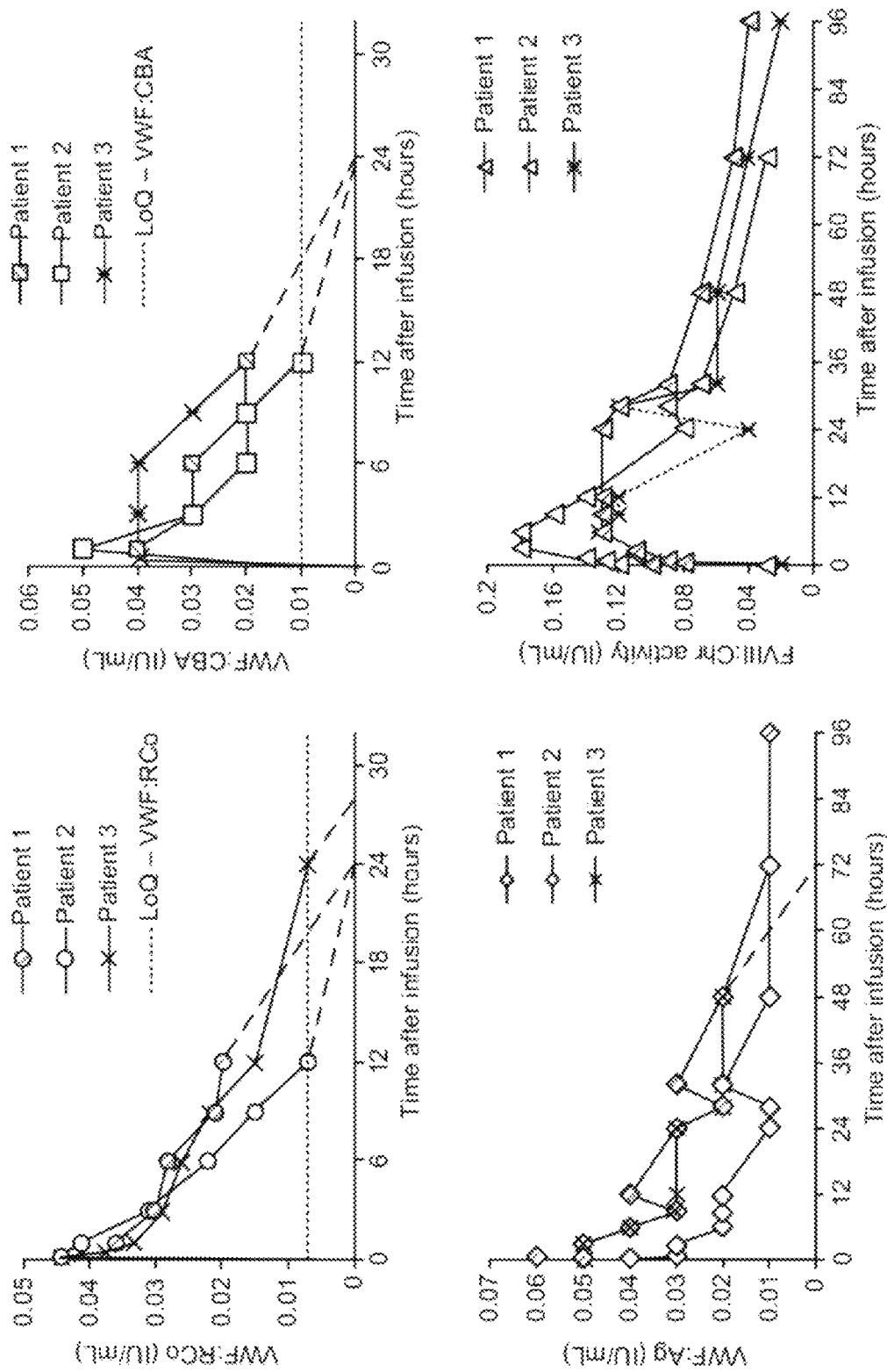
FIG. 13. Comparison of rVWF PK in Patients 1, 2 and 3—comparison of the VWF parameters and FVIII activity.

FIG. 13 shows data comparing the VWF parameters and FVIII activity for the three patients. There was a good correlation see in all three patients for all parameters tested (VWF:RCo, VWF:CBA, VWF:Ag, and FVII:Chr activity).

rVWF had ~100% recovery in all patients. The three patients showed slightly different rVWF PK. For VWF antigen, there was a maximum 0.06 IU/ml 30 minutes after application of 2 IU VWF:RCo/kg followed by a steady decline. For FVIII activity, the baseline FVIII activity increased to approximately 0.1 IU/ml 15 minutes after application of rVWF+rFVIII. Thereafter, activity further increased to 0.16 IU/ml, reached a plateau at 3-6 hours that stayed up to 28 hours followed by a steady decline. The delayed increase in FVIII indicates that the secondary rise was induced by rVWF.

Example 4 rVWF Study-FVII PK Assessment and TA Assessment.

Figure 14:
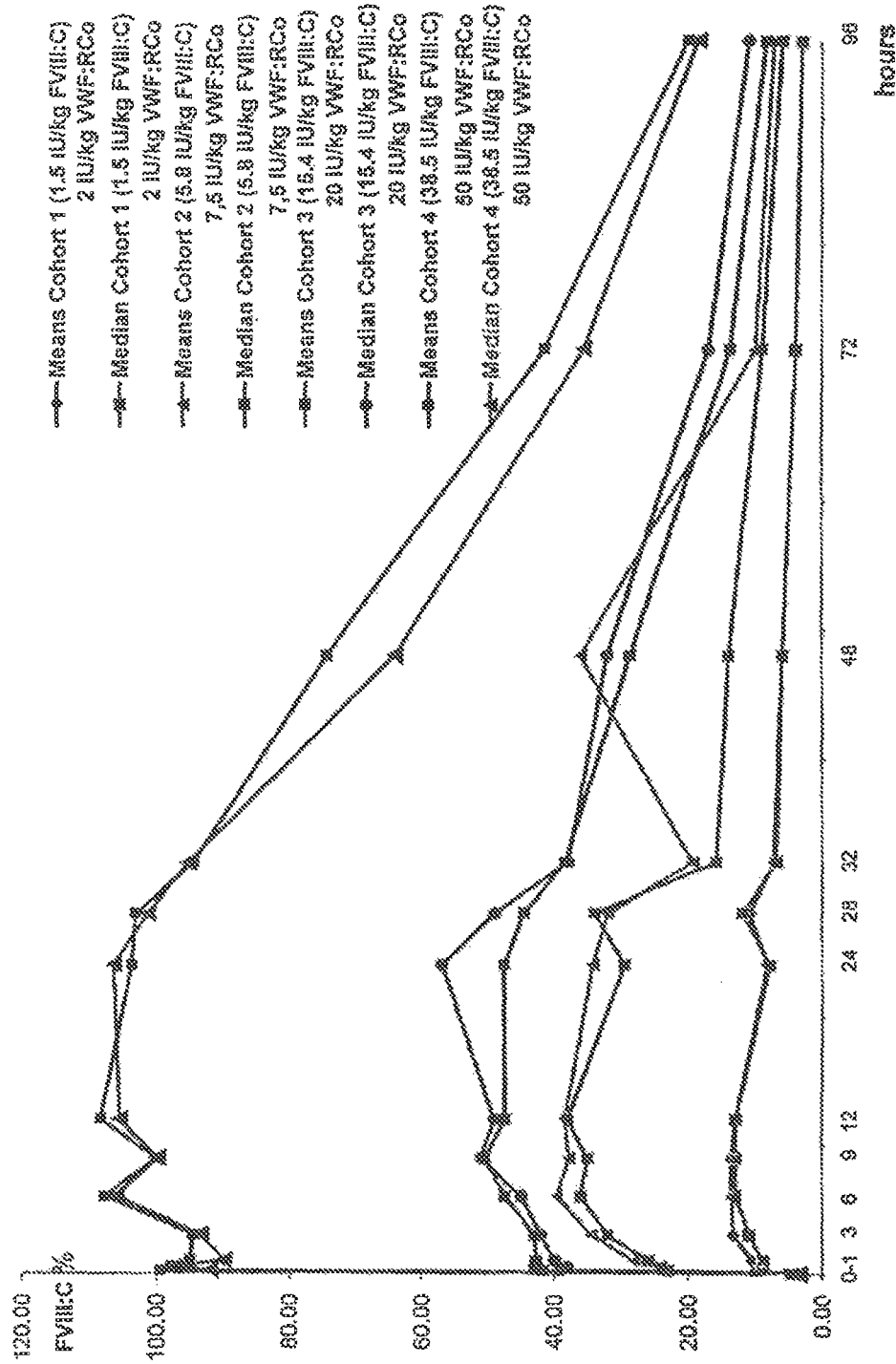
FIG. 14. FVIII activity across all cohorts in the study.
Figure 15:
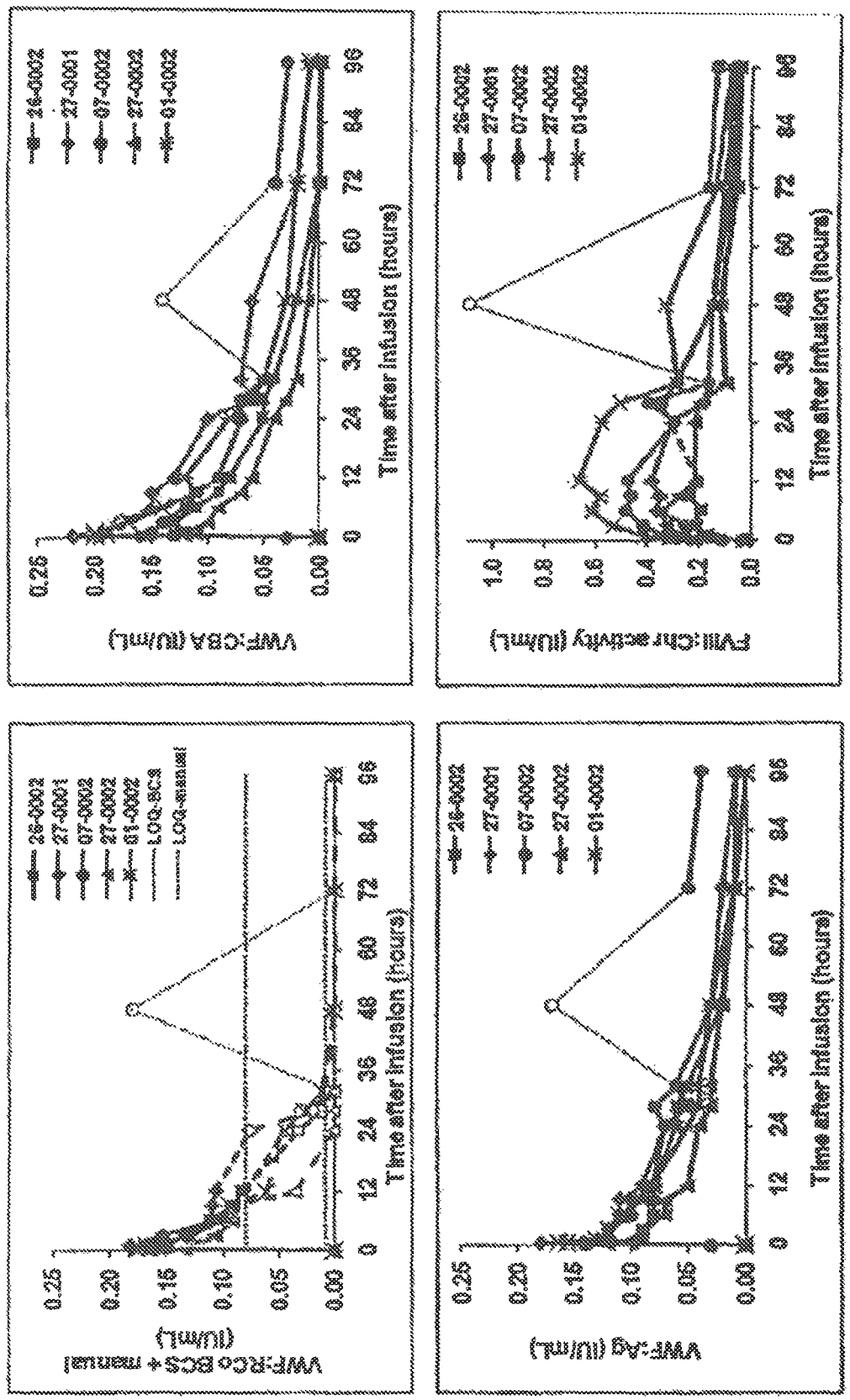
FIG. 15. rVWF PK in patients of Cohort 2—comparison of VWF parameters and FVIII activity.

FIG. 14 shows data for FVIII activity across all cohorts. FIG. 15 shows data from Cohort 1 (2 IU/kg VWF:RCo/1.5 IU/kg FVIII). There was good correlation for all three patients in this cohort for all parameters tested.

FIG. 15 shows data from Cohort 2 (7.5 IU/kg VWF:RCo/5.8 IU/kg FVIII). FIG. 16 shows the pharmacokinetics data for this cohort for FVIII:C.

Figure 17:
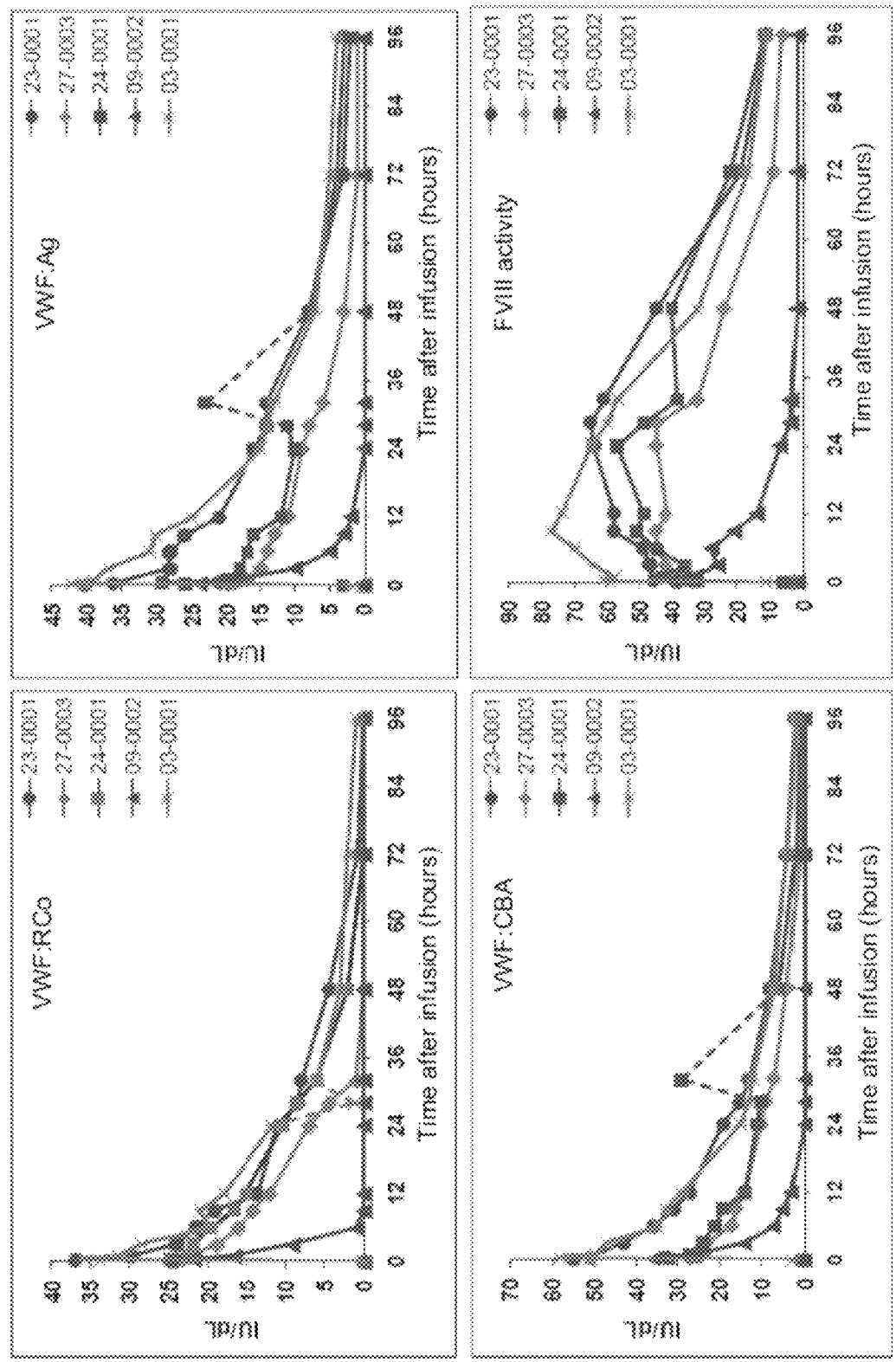
FIG. 17. rVWF PK in all patients of Cohort 3—comparison of plasma parameters for VWF and FVIII.

FIG. 17 shows data for Cohort 3 (20 IU/kg VWF:RCo/15.4 IU/kg FVIII). These data show a comparison of plasma parameters for VWF and FVIII. FIG. 18 shows the pharmacokinetics data for this cohort for FVIII:C.

Figure 19:
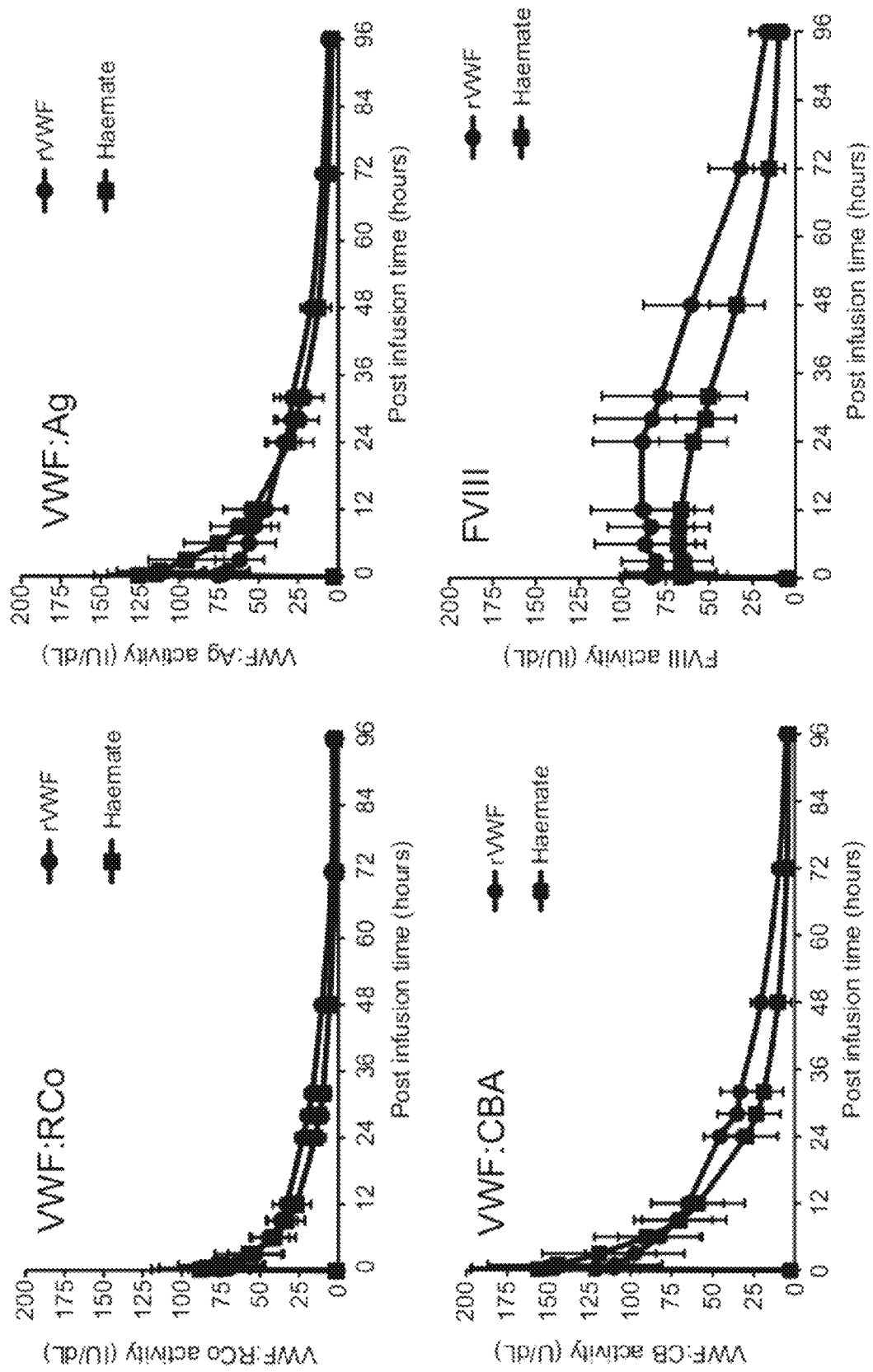
FIG. 19. Data from patients in Cohort 4.

FIG. 19 shows data for Cohort 4 (50 IU/kg VWF:RCo). FVIII dosing was 38.5 IU/kg rFVIII or 25 IU/kg pdFVIII. These data show that the parameters for rVWF are similar to those for pdVWF (Haemate), but that rVWF is more effective at stabilizing FVIII activity, resulting in an increase seen in FVIII activity as compared to that seen with pdVWF. FIG. 20 shows a summary of pharmacokinetics data for this cohort for FVIII:C. As can be seen in these data, the median and mean $T_{1/2}$ was increased for rVWF/FVIII as compared to pdVWF/FVIII, suggesting that rVWF is more effective at stabilizing in vivo FVIII than is pdVWF resulting in increased half-life.

Example 5

Clinical Study of rVWF Effect on rFVIII Half-Life in the Treatment of Hemophilia A.

This study evaluates the immediate tolerability and safety of rVWF after single doses of 50 IU/kg rFVIII (Advate) alone or in combination with rVWF at 10 or 50 IU/kg von Willebrand Factor:Ristocetin cofactor activity (VWF:RCo). This study also evaluates the pharmacokinetics after single doses of 50 IU/kg rFVIII (Advate) alone or in combination with rVWF at 10 or 50 IU/kg (VWF:RCo).

The population for the study is selected using the following criteria:
Inclusion Criteria:
Severe Hemophilia A (FVIII:C<1 IU/dL)
18 to 60 years of age
Previous coagulation factor replacement therapy (>150 ED)
Non-bleeding state
Exclusion Criteria:
Other coagulation disorders
History of VWF and/or FVIII inhibitors
Cardiovascular disease
Medical history of thromboembolic event
Medical history of other immunological disorders (exceptions)
Subject participation is for 16 weeks with an overall study duration of 7 months.

The design of the study is a multicenter, uncontrolled, non randomized, open-label clinical study to assess safety, immediate tolerability and pharmacokinetics of rFVIII:rVWF in subjects with hereditary severe hemophilia A (FVIII:C<1%).

Each subject (N=14) participating in the triple-period PK analysis receives in a non randomized fashion 50 IU/kg rFVIII (Advate) with no, 10 IU/kg VWF:RCo, or 50 IU/kg VWF:RCo rVWF, and is expected to participate for approximately 16 weeks.

The intra-individual pharmacokinetics are spaced at 5-14 days apart to ensure a "wash-out" period of at least 5 days and a timely completion of the study. Safety analyses are performed separately once 6 subjects have been dosed with 10 IU/KG VWF:RCo rVWF and once 6 subjects have been dosed with 50 IU/KG VWF:RCo rVWF.

Subjects should not have received cryoprecipitate, fresh frozen plasma or other drugs interfering with VWF or FVIII PK for at least 5 days before either of the infusions.

Dosage of rVWF is escalated when immediate tolerability and safety are demonstrated after a minimum of 6 subjects treated with 10 IU VWF:RCo rVWF. The effects of the investigational product on vital signs, hematology, and clinical chemistry parameters will determine short-term safety.

Samples for the determination of levels of FVIII activity (FVIII:C), VWF antigen (VWF:Ag), VWF activity (VWF:RCo), VWF:CB, (and VWF multimer distribution) are taken pre-infusion (within 30 minutes prior to the start of the infusion) and after the end of the infusion at 15 minutes (±5 minutes), 30 minutes (±5 minutes), 1 hour (±5 minutes), 3 hours (±10 minutes), 6 hours (±10 minutes), 9 hours (±15 minutes), 24 hours (±2 hours) and 48 hours (+2 hours), 72 hours (±2 hours), 96 hours (±2 hours), and 120 hours (±2 hours) (or at least every 24 hours thereafter until FVIII drops below <1%). FVIII activity is determined using both the chromogenic and one-stage a PTT-based assay methods performed at the local and central laboratory.

The effects of each infusion on vital signs and other symptoms indicative of an adverse event (AE), hematology, and clinical chemistry parameters are used as indicators of short-term safety. Vital signs, clinical chemistry, and hematology parameters are assessed pre-infusion and until 120 hours post-infusion. The occurrence of AEs are continuously monitored for up to 2 hours post-infusion (rVWF treated subjects) and at various time points during the follow-up period.

The presence of inhibitors to FVIII and VWF are assessed before investigational product infusion and at the study completion visit.

If at any time a serious AE related to the investigational product occurs, an independent data monitoring committee (DMC) will advise whether to continue the study.

Pharmacokinetic primary endpoints for the study include: $AUC_{0-\infty}$/Dose (area under the plasma concentration/time curve from time 0 to infinity); $AUC_{0-96h}$/Dose (area under the plasma concentration/time curve from time 0 to 96 hours); mean residence time (MRT); clearance (CL); T½ (elimination phase half-life); Volume of distribution at steady state (Vss) of VWF:RCo, VWF:Ag, VWF:CB, and FVIII.

Analysis for pharmacokinetic primary endpoints include $AUC_{0-96h}$/Dose, $AUC_{0-\infty}$/Dose, MRT, CL, $T_{1/2}$ and Vss summarized per treatment group (50 IU/kg rFVIII (Advate) alone, 50 IU/kg rFVIII (Advate) premixed with rVWF at 10 IU/kg VWF:RCo, 50 IU/kg rFVIII (Advate) premixed with rVWF at 50 IU/kg VWF:RCo) by median and two-sided 95% CIs for the median, mean, standard deviation, coefficient of variation and geometric mean. Descriptive statistics (medians and ranges) are used to summarize VWF:RCo, VWF:Ag, VWF:CB and FVIII levels over time.

Safety primary endpoint includes: occurrence of treatment related AEs. Analysis of the safety primary endpoint includes the number and percentage of subjects who experience a treatment related AE. The number and rate of treatment related AEs are tabulated.

Pharmacokinetic secondary endpoints include: In vivo recovery (IVR) and incremental recovery (IR) of FVIII, VWF:RCo, VWF:Ag and VWF:CB. Analysis of pharmacokinetic secondary endpoints includes determining IVR and IR of FVIII, VWF:RCo, VWF:Ag and VWF:CB by subject and summarizing by medians and ranges.

Safety secondary endpoints include: development of inhibitory and total binding anti-VWF antibodies, development of inhibitory antibodies to FVIII, development of antibodies to Chinese hamster ovary (CHO) proteins, mouse immunoglobulin G (IgG) and rFurin, occurrence of thrombotic events.

Safety secondary endpoints are analyzed by tabulating the number of subjects who experience an SAE and the number of SAEs. In addition, the number of subjects who experience a treatment related AE and the number and rate of treatment related AEs are subcategorized for thrombotic events, inhibitory and total binding anti-VWF antibodies, inhibitory antibodies to FVIII, antibodies to Chinese hamster ovary (CHO) proteins, antibodies to mouse immunoglobulin G (IgG) and antibodies to rFurin.

A listing of all AEs are presented by subject identifier, age, sex, preferred term and reported term of the AE, duration, severity, seriousness, action taken, outcome, causality assessment, onset date, stop date and medication or non-drug therapy to treat the AE. An overview table for AEs are provided, presenting the number of AEs, the number of subjects with AEs and the corresponding percent of subjects in total and by seriousness and relationship to treatment. An additional summary table presents the total number of (mild, moderate, severe) AEs by system organ class and preferred term with relationship to treatment.

No formal sample size calculation has been conducted for this study.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating Von Willebrand Disease or Hemophilia A in a subject in need thereof, the method comprising: intravenously administering to the subject a composition comprising recombinant Von Willebrand Factor (rVWF) wherein endogenous Factor VIII half-life is extended as compared to a subject administered plasma derived Von Willebrand Factor, wherein the rVWF is not modified with a water soluble polymer, wherein the composition is a high molecular weight VWF multimer composition comprising at least 20% VWF decamers or higher order multimers, and wherein the rVWF has a higher specific activity than plasma derived Von Willebrand Factor, and the higher order rVWF multimers are stable for at least 3 hours post-administration.

2. The method of claim 1, wherein the method comprises co-administering to the subject said composition comprising recombinant Von Willebrand Factor (rVWF) and a composition comprising recombinant Factor VIII (rFVIII).

3. The method of claim 2, wherein the rVWF and rFVIII are administered together in a single composition.

4. The method according to claim 1, wherein the subject is administered between 1.0 IU/kg VWF:RCo and 150 IU/kg VWF:RCo per dose.

5. The method of claim 4, wherein the subject is administered between 2 IU/kg VWF:RCo and 50 IU/kg VWF:RCo per dose.

6. The method of claim 4, wherein the subject is administered between 5 IU/kg VWF:RCo and 40 IU/kg VWF:RCo per dose.

7. The method of claim 4, wherein the subject is administered between 10 IU/kg VWF:RCo and 20 IU/kg VWF:RCo per dose.

8. The method according to claim 1, wherein the rVWF is matured in vitro by treatment with Furin.

9. The method according to claim 1, wherein the rVWF is produced through expression in a Chinese Hamster Ovary (CHO cell culture).

10. The method according to claim 2, wherein the rFVIII and rVWF are produced through expression in the same cell culture.

11. The method according to claim 1, wherein the subject is administered rVWF no more than once every other day.

12. The method of claim 11, wherein the subject is administered rVWF no more than twice a week.

13. The method according claim 1, wherein the Factor VIII half-life is extended by at least 5 hours.

14. The method of claim 13, wherein the Factor VIII half-life is extended by at least 12 hours.

15. The method of claim 13, wherein the Factor VIII half-life is extended by at least 24 hours.

16. The method of claim 13, wherein the Factor VIII half-life is extended by at least 36 hours.

17. The method of claim 13, wherein the Factor VIII half-life is extended by at least 48 or 72 hours.

18. The method of claim 2, wherein the ratio of procoagulant activity (IU FVIII:C) of the administered FVIII to Ristocetin cofactor activity (IU rVWF:RCo) of the administered rVWF is between 2:1 and 1:4.

19. The method of claim 18, wherein the ratio of FVIII procoagulant activity (IU FVIII:C) to rVWF Ristocetin cofactor activity (IU rVWF:RCo) is between 3:2 and 1:3.

20. The method of claim 18, wherein the ratio of FVIII procoagulant activity (IU FVIII:C) to rVWF Ristocetin cofactor activity (IU rVWF:RCo) is between 1:1 and 1:2.

21. The method of claim 18, wherein the ratio of FVIII procoagulant activity (IU FVIII:C) to rVWF Ristocetin cofactor activity (IU rVWF:RCo) is about 3:4.

22. The method of claim 1, wherein the rVWF has a specific activity of about 20-150 mU/µg.

23. The method of claim 1, wherein the high molecular weight VWF multimer composition comprises at least 30% VWF decamers or higher order multimers.

24. The method of claim 1, wherein the high molecular weight VWF multimer composition comprises at least 40% VWF decamers or higher order multimers.

25. The method of claim 1, wherein the high molecular weight VWF multimer composition comprises at least 50% VWF decamers or higher order multimers.

26. The method of claim 1, wherein the high molecular weight VWF multimer composition comprises at least 60% VWF decamers or higher order multimers.

27. The method of claim 1, wherein the high molecular weight VWF multimer composition comprises at least 70% VWF decamers or higher order multimers.

28. A method for treating Hemophilia A or Von Willebrand Disease in a subject in need thereof, the method comprising: administering to the subject a composition comprising recombinant Von Willebrand Factor (rVWF) wherein Factor VIII half-life is extended as compared to a subject administered plasma derived Von Willebrand Factor, wherein: (a) the rVWF has a higher specific activity than plasma derived Von Willebrand Factor, wherein the specific activity of rVWF is about 20-150 mU/g; (b) the FVIII half-life is at least 1.5 times higher as compared to FVIII half-life in a subject administered plasma derived Von Willebrand Factor; and (c) the rVWF is not modified with a water soluble polymer; and (d) the rVWF is a high molecular weight VWF multimer composition comprising at least 20% VWF decamers or higher order multimers, wherein the higher order rVWF multimers are stable for at least 3 hours post-administration.

29. A method for treating Hemophilia A or Von Willebrand Disease in a subject in need thereof, the method comprising: administering to the subject a composition comprising recombinant Von Willebrand Factor (rVWF) wherein Factor VIII half-life is extended as compared to a subject administered plasma derived Von Willebrand Factor, wherein: (a) the composition is a high molecular weight VWF multimer composition comprising at least 20% VWF decamers or higher order multimers, (b) the rVWF has a higher specific activity than plasma derived Von Willebrand Factor, wherein the specific activity of rVWF is at least about 20-150 mU/g; (c) the FVIII half-life is at least 1.5 times higher as compared to FVIII half-life in a subject administered plasma derived Von Willebrand Factor; and (d) the rVWF is not modified with a water soluble polymer; and (e) the rVWF is a high molecular weight VWF multimer composition comprising at least 20% VWF decamers or higher order multimers, wherein the higher order rVWF multimers are stable for at least 3 hours post-administration.

30. The method of claim 1, 28 or 29, wherein the method is a method for treating Von Willebrand Disease Type 3.

31. The method of claim 1, 28 or 29, wherein the level of Factor VIII procoagulant activity (FVIII:C) in the plasma of the subject 24 hours post-administration is at least 90% of the level of FVIII:C activity present in the plasma 1 hour post-administration.

32. The method of claim 1, 28 or 29 wherein said water soluble polymer is PEG.

* * * * *

UNITED STATES PATENT AND TRADEMARK OFFICE
CERTIFICATE OF CORRECTION

PATENT NO. : 9,272,021 B2  
APPLICATION NO. : 13/493926  
DATED : March 1, 2016  
INVENTOR(S) : Friedrich Scheiflinger et al.

Page 1 of 1

It is certified that error appears in the above-identified patent and that said Letters Patent is hereby corrected as shown below:

In the Claims:

Claim 28, column 137, line 6: replace "20-150 mU/g" with "20-150 mU/µg"

Claim 28, column 137, line 8: delete "and"

Claim 29, column 138, line 3: replace "20-150 mU/g" with "20-150 mU/µg"

Claim 29, column 138, line 6: delete "and"

Signed and Sealed this
Twenty-third Day of August, 2016

Michelle K. Lee
*Director of the United States Patent and Trademark Office*